US012254985B2

United States Patent
Choi et al.

(10) Patent No.: US 12,254,985 B2
(45) Date of Patent: *Mar. 18, 2025

(54) DIAGNOSIS ASSISTANCE METHOD AND CARDIOVASCULAR DISEASE DIAGNOSIS ASSISTANCE METHOD

(71) Applicant: MEDI WHALE INC., Seoul (KR)

(72) Inventors: Tae Geun Choi, Seoul (KR); Geun Yeong Lee, Seoul (KR); Hyung Taek Rim, Seoul (KR)

(73) Assignee: MEDI WHALE INC., Seoul (KR)

( * ) Notice: Subject to any disclaimer, the term of this patent is extended or adjusted under 35 U.S.C. 154(b) by 524 days.

This patent is subject to a terminal disclaimer.

(21) Appl. No.: 17/489,177

(22) Filed: Sep. 29, 2021

(65) Prior Publication Data

US 2022/0301709 A1    Sep. 22, 2022

Related U.S. Application Data

(63) Continuation-in-part of application No. 16/807,686, filed on Mar. 3, 2020, now Pat. No. 11,164,313,
(Continued)

(30) Foreign Application Priority Data

Dec. 20, 2017   (KR) .................. 10-2017-0175865
Dec. 7, 2018    (KR) .................. 10-2018-0157559
(Continued)

(51) Int. Cl.
*G16H 50/20*      (2018.01)
*A61B 3/12*       (2006.01)
(Continued)

(52) U.S. Cl.
CPC ............. *G16H 50/20* (2018.01); *A61B 3/12* (2013.01); *A61B 5/021* (2013.01); *A61B 5/7267* (2013.01);
(Continued)

(58) Field of Classification Search
None
See application file for complete search history.

(56) References Cited

U.S. PATENT DOCUMENTS 8,787,638 B2   7/2014   Zee et al.
9,462,945 B1   10/2016  Barriga et al.
(Continued)

FOREIGN PATENT DOCUMENTS

CN       1145213 A       3/1997
CN     101485569 A       7/2009
(Continued)

OTHER PUBLICATIONS

Gondal et al ("Weakly-Supervised Localization of Diabetic Retinopathy Lesions in Retinal Fundus Images", 2017 IEEE International Conference on Image Processing, Jun. 29, 2017) (Year: 2017).*
(Continued)

*Primary Examiner* — Leon Viet Q Nguyen
(74) *Attorney, Agent, or Firm* — BROADVIEW IP LAW, PC

(57) ABSTRACT

The present invention relates to a method of assisting in diagnosis of a target heart disease using a retinal image, the method including: obtaining a target retinal image which is obtained by imaging a retina of a testee; on the basis of the target retinal image, obtaining heart disease diagnosis assistance information of the testee according to the target retinal image, via a heart disease diagnosis assistance neural network model which obtains diagnosis assistance information that is used for diagnosis of the target heart disease according to the retinal image; and outputting the heart disease diagnosis assistance information of the testee.

8 Claims, 78 Drawing Sheets

Related U.S. Application Data which is a continuation of application No. PCT/KR2018/016388, filed on Dec. 20, 2018.

(60) Provisional application No. 62/776,345, filed on Dec. 6, 2018, provisional application No. 62/715,729, filed on Aug. 7, 2018, provisional application No. 62/694,901, filed on Jul. 6, 2018.

(30) Foreign Application Priority Data

| Dec. 7, 2018 | (KR) | 10-2018-0157560 |
|---|---|---|
| Dec. 7, 2018 | (KR) | 10-2018-0157561 |

(51) Int. Cl.

| A61B 5/00 | (2006.01) |
|---|---|
| A61B 5/021 | (2006.01) |
| G06T 7/00 | (2017.01) |
| G16H 30/40 | (2018.01) |
| G16H 50/30 | (2018.01) |

(52) U.S. Cl.
CPC .......... *A61B 5/7275* (2013.01); *G06T 7/0004* (2013.01); *G16H 30/40* (2018.01); *G16H 50/30* (2018.01); *G06T 2207/20084* (2013.01); *G06T 2207/30041* (2013.01)

(56) References Cited

U.S. PATENT DOCUMENTS

| 10,413,180 | B1* | 9/2019 | Barriga | A61B 3/0033 |
|---|---|---|---|---|
| 11,164,313 | B2* | 11/2021 | Choi | G06V 10/82 |
| 2003/0009107 | A1 | 1/2003 | Kawada et al. | |
| 2005/0249391 | A1 | 11/2005 | Kimmel et al. | |
| 2006/0036167 | A1 | 2/2006 | Shina | |
| 2007/0165916 | A1 | 7/2007 | Cloutier et al. | |
| 2012/0257164 | A1* | 10/2012 | Zee | A61B 3/12 |
| | | | | 351/246 |
| 2015/0110348 | A1 | 4/2015 | Solanki et al. | |
| 2015/0110368 | A1* | 4/2015 | Solanki | G06V 10/267 |
| | | | | 382/128 |
| 2016/0166142 | A1 | 6/2016 | Kobayashi | |
| 2016/0196488 | A1 | 7/2016 | Ahn | |
| 2016/0235373 | A1* | 8/2016 | Sharma | G16H 10/40 |
| 2016/0292856 | A1 | 10/2016 | Niemeijer et al. | |
| 2016/0331224 | A1 | 11/2016 | Uji et al. | |
| 2016/0367216 | A1 | 12/2016 | Yan et al. | |
| 2017/0011210 | A1* | 1/2017 | Cheong | A61B 5/681 |
| 2017/0049419 | A1 | 2/2017 | Park et al. | |
| 2017/0143211 | A1* | 5/2017 | Liu | A61B 5/015 |
| 2017/0270653 | A1 | 9/2017 | Garnavi et al. | |
| 2017/0281095 | A1 | 10/2017 | An et al. | |
| 2017/0290551 | A1 | 10/2017 | An et al. | |
| 2019/0278972 | A1 | 9/2019 | Anderson et al. | |
| 2020/0353250 | A1* | 11/2020 | Haddad | G16H 20/17 |

FOREIGN PATENT DOCUMENTS

| CN | 103458772 A | 12/2013 |
|---|---|---|
| CN | 105678066 A | 6/2016 |
| JP | 2003-052639 A | 2/2003 |
| JP | 2003-190094 A | 7/2003 |
| JP | 2003-299621 A | 10/2003 |
| JP | 2005-342284 A | 12/2005 |
| JP | 2007-512862 A | 5/2007 |
| JP | 2008-104762 A | 5/2008 |
| JP | 2009-502220 A | 1/2009 |
| JP | 2015-083276 A | 4/2015 |
| JP | 6076329 B2 | 1/2017 |
| JP | 2018-005841 A | 1/2018 |
| JP | 2018-014059 A | 1/2018 |
| JP | 2018-015189 A | 2/2018 |
| JP | 2018-061621 A | 4/2018 |
| KR | 10-0669625 B1 | 1/2007 |
| KR | 10-2012-0024842 A | 3/2012 |
| KR | 10-2013-0100384 A | 9/2013 |
| KR | 10-2015-0016089 A | 2/2015 |
| KR | 10-2016-0134585 A | 11/2016 |
| KR | 10-2017-0021558 A | 2/2017 |
| KR | 10-2017-0113251 A | 10/2017 |
| KR | 10-1828011 B1 | 2/2018 |
| KR | 10-1839789 B1 | 3/2018 |
| KR | 10-1848321 B1 | 4/2018 |
| KR | 10-2018-0045551 A | 5/2018 |
| KR | 10-1857624 B1 | 5/2018 |
| KR | 10-1889725 B1 | 8/2018 |

OTHER PUBLICATIONS

Office Action of Chinese Patent Application of 201880089339.X mailed on Jul. 1, 2023.

Gondal, W. M. et al., "Weakly-Supervised Localization of Diabetic Retinopathy Lesions in Retinal Fundus Images," arXiv preprint arXiv:1706.09634v1, Jun. 29, 2017, five pages.

Jun, T. J. et al., "2sRanking-CNN: A 2-stage ranking-CNN for diagnosis of glaucoma from fundus images using CAM-extracted ROI as an intermediate input," arXiv preprint arXiv:1805.05727, May 15, 2018, 11 pages.

Korean Intellectual Property Office, Grant of Patent, Korean Patent Application No. 10-2018-0157564, Apr. 21, 2021, six pages.

Korean Intellectual Property Office, Grant of Patent, Korean Patent Application No. 10-2017-0175865, Oct. 22, 2019, three pages.

Korean Intellectual Property Office, Notification of Reason for Refusal, Korean Patent Application No. 10-2020-0008919, Mar. 15, 2021, seven pages.

Korean Intellectual Property Office, Notification of Reason for Refusal, Korean Patent Application No. 10-2019-0056631, Feb. 27, 2021, 13 pages.

Korean Intellectual Property Office, Notification of Reason for Refusal, Korean Patent Application No. 10-2019-0086604, Feb. 23, 2021, 19 pages.

Korean Intellectual Property Office, Notification of Reason for Refusal, Korean Patent Application No. 10-2018-0157564, Aug. 25, 2020, 13 pages.

Korean Intellectual Property Office, Notification of Reason for Refusal, Korean Patent Application No. 10-2017-0175865, May 14, 2019, 11 pages.

Korean Intellectual Property Office, Office Action, Korean Patent Application No. 10-2018-0157563, Feb. 24, 2020, 12 pages.

PCT International Search Report, PCT Application No. PCT/KR2018/016388, Apr. 9, 2019, five pages.

PCT International Search Report, PCT Application No. PCT/KR2018/015577, Apr. 5, 2019, five pages.

PCT International Search Report, PCT Application No. PCT/KR2018/015576, Mar. 13, 2019, five pages.

Poplin, R. et al., "Predicting Cardiovascular Risk Factors from Retinal Fundus Photographs using Deep Learning," arXiv preprint arXiv: 1708.09843, Sep. 1, 2017, 21 pages, [Online] [Retrieved from the Internet on Apr. 5, 2019], Retrieved from the Internet<URL:http://arxiv.org/ftp/arxiv/papers/1708/1708.09843.pdf>.

Roseline, R. H. et al., "Retinal Based Disease Prediction using Deep Neural Networks and SVM Classification Techniques," International Journal of Engineering Trends and Technology (IJETT), Jul. 7, 2017, pp. 437-444, vol. 49, No. 7.

United States Office Action, U.S. Appl. No. 16/807,686, Aug. 12, 2020, 20 pages.

United States Office Action, U.S. Appl. No. 16/807,686, Apr. 29, 2020, 17 pages.

European Patent Office, Extended European Search Report, European Patent Application No. 18890528.5, Sep. 6, 2021, 12 pages.

PCT Written Opinion, PCT Application No. PCT/KR2018/015576, Mar. 13, 2019, 13 pages.

PCT Written Opinion, PCT Application No. PCT/KR2018/015577, Apr. 5, 2019, 24 pages.

(56) References Cited

OTHER PUBLICATIONS

Triwijoyo, B. K. et al. "The Classification of Hypertensive Retinopathy Using Convolutional Neural Network." Procedia Computer Science, ICCSCI, vol. 116, Oct. 13-14, 2017, pp. 166-173.

* cited by examiner

FIG. 32

| EXTENT OF RISK | NUMERICAL VALUE RANGE | INDICATION |
|---|---|---|
| NORMAL GROUP | 0~10 | NORMAL |
| RISK GROUP | HIGHER THAN 10 | RISK |

(a)

| GRADE | NUMERICAL VALUE RANGE | INDICATION |
|---|---|---|
| A | 0 | NORMAL |
| B | 1~10 | MILD RISK |
| C | 10~100 | MODERATE RISK |
| D | 100~400 | SERIOUS RISK |
| E | HIGHER THAN 400 | SEVERE RISK |

DIAGNOSIS ASSISTANCE METHOD AND CARDIOVASCULAR DISEASE DIAGNOSIS ASSISTANCE METHOD

CROSS-REFERENCE TO RELATED APPLICATIONS

This is a continuation-in-part application of U.S. patent application Ser. No. 16/807,686, filed on Mar. 3, 2020, which is a bypass continuation application of International Application No. PCT/KR2018/016388, filed on Dec. 20, 2018, which claims priority from a U.S. Provisional Patent Application No. 62/694,901, filed Jul. 6, 2018, U.S. Provisional Patent Application No. 62/715,729, filed Aug. 7, 2018, and U.S. Provisional Patent Application No. 62/776,345, filed Dec. 6, 2018, and also claims priority to Republic of Korea Patent Application No. 10-2017-0175865, filed Dec. 20, 2017, Republic of Korea Patent Application No. 10-2018-0157560, filed Dec. 7, 2018, Republic of Korea Patent Application No. 10-2018-0157561, filed Dec. 7, 2018, and Republic of Korea Patent Application No. 10-2018-0157559, filed Dec. 7, 2018, which are incorporated by reference in their entirety.

TECHNICAL FIELD

The present invention relates to a method and device for assisting in heart disease diagnosis, and more particularly, to a method and device for assisting in heart disease diagnosis using an artificial neural network model.

BACKGROUND ART

The fundus examination is a diagnosis assistance material frequently utilized in ophthalmology since it is able to observe the abnormalities of the retina, optic nerve, and macula and allows the results to be confirmed by relatively simple imaging. In recent years, the fundus examination has been increasingly used because, through the fundus examination, it is able to observe not only eye diseases but also a degree of blood vessel damage caused by chronic diseases such as hypertension and diabetes by a non-invasive method.

Meanwhile, due to the recent rapid development of deep learning technology, the development of diagnostic artificial intelligence has been actively carried out in the field of medical diagnosis, especially the field of image-based diagnosis. Global companies such as Google and IBM have invested heavily in the development of artificial intelligence for analyzing a variety of medical video data, including large-scale data input through collaborations with the medical community. Some companies have succeeded in developing an artificial intelligence diagnostic tool that outputs superior diagnostic results.

However, since it is able to non-invasively observe blood vessels in the body when fundus images are used, there has been a demand for expanding the application of diagnosis using fundus images not only for eye diseases but also for systemic diseases.

SUMMARY

Embodiments relate to assisting in heart disease diagnosis. Embodiments also relate to assisting in heart disease diagnosis using a neural network model on the basis of a fundus image.

According to an aspect of the present invention, there is provided a method of assisting in diagnosis of a target heart disease using a fundus image, the method including: obtaining a target fundus image which is obtained by imaging a fundus of a testee; on the basis of the target fundus image, obtaining heart disease diagnosis assistance information of the testee according to the target fundus image, via a heart disease diagnosis assistance neural network model which obtains diagnosis assistance information that is used for diagnosis of the target heart disease according to the fundus image; and outputting the heart disease diagnosis assistance information of the testee, wherein the heart disease diagnosis assistance information includes at least one of grade information which includes a grade selected from a plurality of grades indicating an extent of risk of the target heart disease, score information which is numerical value information for determining an extent of risk of the target heart disease, and risk information which indicates whether the testee belongs to a risk group for the target heart disease.

According to another aspect of the present invention, there is provided a method for assisting in diagnosis of a target heart disease using a fundus image, the method including: obtaining a target fundus image which is obtained by imaging a fundus of a testee; obtaining heart disease diagnosis assistance information of the testee, via a heart disease diagnosis assistance neural network model which obtains heart disease diagnosis assistance information on the basis of a fundus image based on a reconstructed target fundus image which is obtained by performing reconstruction by which a blood vessel element is highlighted in the target fundus image; and outputting the heart disease diagnosis assistance information of the testee, wherein the heart disease diagnosis assistance neural network model is trained using fundus image training data including a plurality of fundus images in which blood vessel elements are highlighted and a plurality of heart disease diagnosis assistance labels assigned to the plurality of fundus images.

According to still another aspect of the present invention, there is provided a heart disease diagnosis assistance device which is a diagnostic device for assisting in diagnosis of a target heart disease using a fundus image, the heart disease diagnosis assistance device including: a fundus image obtaining unit configured to obtain a target fundus image which is obtained by imaging a fundus of a testee; a heart disease diagnosis assistance information obtaining unit configured to, on the basis of the target fundus image, obtain heart disease diagnosis assistance information of the testee according to the target fundus image, via a heart disease diagnosis assistance neural network model which obtains diagnosis assistance information that is used for diagnosis of the target heart disease according to the fundus image; and a heart disease diagnosis assistance information output unit configured to output the obtained heart disease diagnosis assistance information, wherein the heart disease diagnosis assistance information includes at least one of grade information which includes a grade selected from a plurality of grades indicating an extent of risk of the target heart disease, score information which is numerical value information for determining an extent of risk of the target heart disease, and risk information which indicates whether the testee belongs to a risk group for the target heart disease.

Technical solutions of the present invention are not limited to those mentioned above, and other unmentioned technical solutions should be clearly understood by one of ordinary skill in the art to which the present invention pertains from the present specification and the accompanying drawings.

According to the present invention, information that may be used in heart disease diagnosis can be obtained on the basis of a fundus image.

According to the present invention, various pieces of information that may be used in heart disease diagnosis can be obtained on the basis of a fundus image.

According to the present invention, information that may be used in heart disease diagnosis can be obtained on the basis of left-eye and right-eye fundus images.

Advantageous effects of the present invention are not limited to those mentioned above, and other unmentioned advantageous effects should be clearly understood by one of ordinary skill in the art to which the present invention pertains from the present specification and the accompanying drawings.

BRIEF DESCRIPTION OF DRAWINGS

FIG. 32 is a view for describing heart disease diagnosis assistance information with which a fundus image is labeled.

FIG. 75 is a view for describing a graphical interface for displaying diagnosis assistance information according to an embodiment of the invention described herein.

DETAILED DESCRIPTION OF EMBODIMENTS

Figure 1:
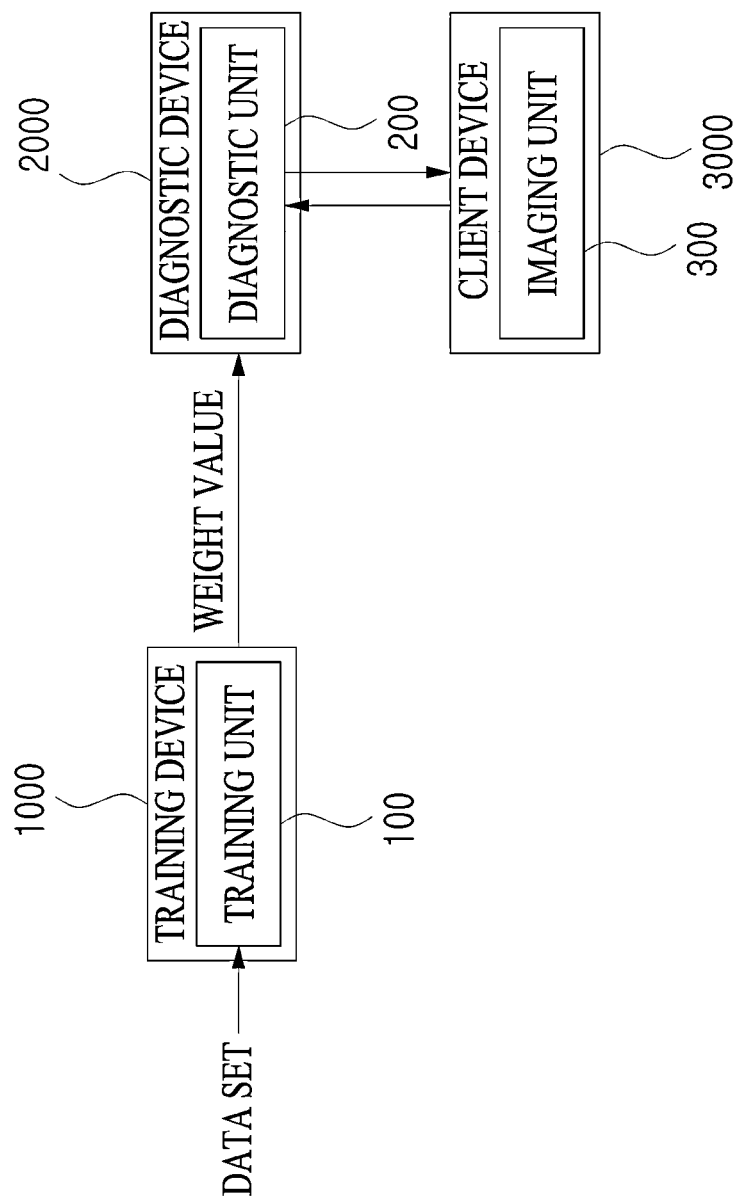
FIG. 1 illustrates a diagnosis assistance system according to an embodiment of the present invention.

The foregoing objects, features and advantages of the present invention will become more apparent from the following detailed description related to the accompanying drawings. It should be understood, however, that various modifications may be applied to the invention, and the invention may have various embodiments. Hereinafter, specific embodiments, which are illustrated in the drawings, will be described in detail.

In the drawings, the thicknesses of layers and regions are exaggerated for clarity. When it is indicated that an element or layer is "on" or "above" another element or layer, this includes a case in which another layer or element is interposed therebetween as well as a case in which the element or layer is directly above the other element or layer. In principle, like reference numerals designate like elements throughout the specification. In the following description, like reference numerals are used to designate elements which have the same function within the same idea illustrated in the drawings of each embodiment.

When detailed description of known functions or configurations related to the present invention is deemed to unnecessarily blur the gist of the invention, the detailed description thereof will be omitted. Also, numerals (e.g., first, second, etc.) used in the description herein are merely identifiers for distinguishing one element from another element.

In addition, the terms "module" and "unit" used to refer to elements in the following description are given or used in combination only in consideration of ease of writing the specification, and the terms themselves do not have distinct meanings or roles.

A method according to an embodiment may be implemented in the form of a program command that can be executed through various computer means and may be recorded in a computer-readable medium. The computer-readable medium may include program commands, data files, data structures, and the like alone or in combination. The program commands recorded in the medium may be those specially designed and configured for the embodiment or those known to those skilled in the art of computer software and usable. Examples of the computer-readable recording medium include magnetic media such as a hard disk, a floppy disk, and a magnetic tape, optical media such as compact disk-read only memory (CD-ROM), and a digital versatile disk (DVD), magneto-optical media such as a floptical disk, and hardware devices such as a read only memory (ROM), a random access memory (RAM), and a flash memory specially configured to store and execute a program command Examples of the program command include high-level language codes that may be executed by a computer using an interpreter or the like as well as machine language codes generated by a compiler. The above-mentioned hardware device may be configured to operate as one or more software modules to execute operations according to an embodiment, and vice versa.

1. Diagnosis Assistance Using Fundus Image

1.1 System and Process for Diagnosis Assistance

1.1.1 Purpose and Definition

Hereinafter, a system and method for diagnosis assistance for assisting in determination of the presence of a disease or illness on the basis of a fundus image or the presence of an abnormality which is a basis of the determination will be described. Particularly, a system or method for diagnosis assistance in which a neural network model for diagnosing a disease is constructed using a deep learning technique and detection of the presence of a disease or abnormal findings is assisted using the constructed model will be described.

According to an embodiment of the present invention, a system or method for diagnosis assistance in which diagnostic information related to the presence of a disease, findings information used in diagnosis of the presence of a disease, or the like are obtained on the basis of a fundus image and diagnosis is assisted using the obtained information may be provided.

According to an embodiment of the present invention, a system or method for diagnosis assistance in which diagnosis of an eye disease is assisted on the basis of a fundus image may be provided. For example, a system or method for diagnosis assistance in which diagnosis is assisted by obtaining diagnostic information related to the presence of glaucoma, cataract, macular degeneration, retinopathy of prematurity of a testee may be provided.

According to another embodiment of the present invention, a system or method for diagnosis assistance in which diagnosis of a disease other than an eye disease (for example, a systemic disease or a chronic disease) is assisted may be provided. For example, a system or method for diagnosis assistance in which diagnosis is assisted by obtaining diagnostic information on a systemic disease such as hypertension, diabetes, Alzheimer's, cytomegalovirus, stroke, heart disease, and arteriosclerosis may be provided.

According to still another embodiment of the present invention, a system or method for diagnosis assistance for detecting abnormal fundus findings that may be used in diagnosis of an eye disease or other diseases may be provided. For example, a system or method for diagnosis assistance for obtaining findings information such as abnormal color of the entire fundus, opacity of crystalline lens, abnormal cup-to-disc (C/D) ratio, macular abnormalities (e.g., macular hole), an abnormal diameter or course of a blood vessel, an abnormal diameter of the retinal artery, retinal hemorrhage, generation of exudate, and drusen may be provided.

In the specification, diagnosis assistance information may be understood as encompassing diagnostic information according to determination of the presence of a disease, findings information which is a basis of the determination, or the like.

1.1.2 Configuration of Diagnosis Assistance System

According to an embodiment of the present invention, a diagnosis assistance system may be provided.

FIG. 1 illustrates a diagnosis assistance system 10 according to an embodiment of the present invention. Referring to FIG. 1, the diagnosis assistance system 10 may include a training device 1000 configured to train a diagnostic model, a diagnostic device 2000 configured to perform diagnosis using the diagnostic model, and a client device 3000 configured to obtain a diagnosis request. The diagnosis assistance system 10 may include a plurality of training devices, a plurality of diagnostic devices, or a plurality of client devices.

The training device 1000 may include a training unit 100. The training unit 100 may perform training of a neural network model. For example, the training unit 100 may obtain a fundus image data set and perform training of a neural network model that detects a disease or abnormal findings from a fundus image.

The diagnostic device 2000 may include a diagnostic unit 200. The diagnostic unit 200 may perform diagnosis of a disease or obtain assistance information used for the diagnosis by using a neural network model. For example, the diagnostic unit 200 may obtain diagnosis assistance information by using a diagnostic model trained by the training unit.

The client device 3000 may include an imaging unit 300. The imaging unit 300 may capture a fundus image. The client device may be an ophthalmic fundus imaging device. Alternatively, the client device 3000 may be a handheld device such as a smartphone or a tablet personal computer (PC).

In the diagnosis assistance system 10 according to the present embodiment, the training device 1000 may obtain a data set and train a neural network model to determine a neural network model to be used in diagnosis assistance, the diagnostic device may obtain diagnosis assistance information according to a diagnosis target image by using the determined neural network model when an information request is obtained from the client device, and the client device may request the diagnostic device for information and obtain diagnosis assistance information transmitted in response to the request.

A diagnosis assistance system according to another embodiment may include a diagnostic device configured to train a diagnostic model and perform diagnosis using the same and may include a client device. A diagnosis assistance system according to still another embodiment may include a diagnostic device configured to train a diagnostic model, obtain a diagnosis request, and perform diagnosis. A diagnosis assistance system according to yet another embodiment may include a training device configured to train a diagnostic model and a diagnostic device configured to obtain a diagnosis request and perform diagnosis.

The diagnosis assistance system disclosed herein is not limited to the above-described embodiments and may be implemented in any form including a training unit configured to train a model, a diagnostic unit configured to obtain diagnosis assistance information according to the trained image, and an imaging unit configured to obtain a diagnosis target image.

Hereinafter, some embodiments of each device constituting the system will be described.

1.1.2.1 Training Device

A training device according to an embodiment of the present invention may train a neural network model that assists diagnosis.

Figure 2:
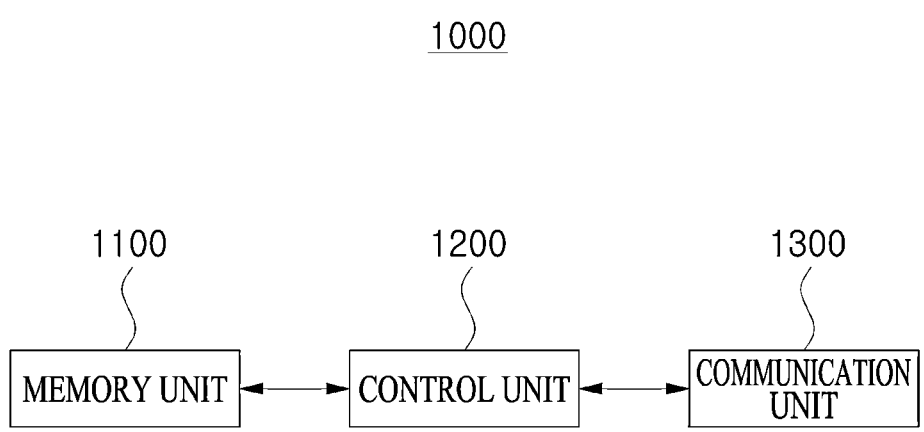
FIG. 2 is a block diagram for describing a training device according to an embodiment of the present invention.

FIG. 2 is a block diagram for describing a training device 1000 according to an embodiment of the present invention. Referring to FIG. 2, the training device 1000 may include a control unit 1200 and a memory unit 1100.

The training device 1000 may include the control unit 1200. The control unit 1200 may control operation of the training device 1000.

The control unit 1200 may include one or more of a central processing unit (CPU), a random access memory (RAM), a graphic processing unit (GPU), one or more microprocessors, and an electronic component capable of processing input data according to predetermined logic.

The control unit 1200 may read a system program and various processing programs stored in the memory unit 1100. For example, the control unit 1200 may develop a data processing process for performing diagnosis assistance which will be described below, a diagnostic process, and the like in a RAM and perform various processes according to a developed program. The control unit 1200 may perform training of a neural network model which will be described below.

The training device 1000 may include the memory unit 1100. The memory unit 1100 may store data required for training and a training model.

The memory unit 1100 may be implemented using a nonvolatile semiconductor memory, a hard disk, a flash memory, a RAM, a ROM, an electrically erasable programmable ROM (EEPROM), or other tangible nonvolatile recording media.

The memory unit 1100 may store various processing programs, parameters for processing programs, result data of such processing, or the like. For example, the memory unit 1100 may store a data processing process program for performing diagnosis assistance which will be described below, a diagnostic process program, parameters for executing each program, data obtained according to execution of such programs (for example, processed data or diagnosis result values), and the like.

The training device 1000 may include a separate training unit (or training module). The training unit may train a neural network model. The training will be described in more detail below in Section "2. Training process."

The training unit may be included in the above-described control unit 1200. The training unit may be stored in the above-described memory unit 1100. The training unit may be implemented by partial configurations of the above-described control unit 1200 and memory unit 1100. For example, the training unit may be stored in the memory unit 1100 and driven by the control unit 1200.

The training device 1000 may further include a communication unit 1300. The communication unit 1300 may communicate with an external device. For example, the communication unit 1300 may communicate with a diagnostic device, a server device, or a client device which will be described below. The communication unit 1300 may perform wired or wireless communication. The communication unit 1300 may perform bidirectional or unidirectional communication.

Figure 3:
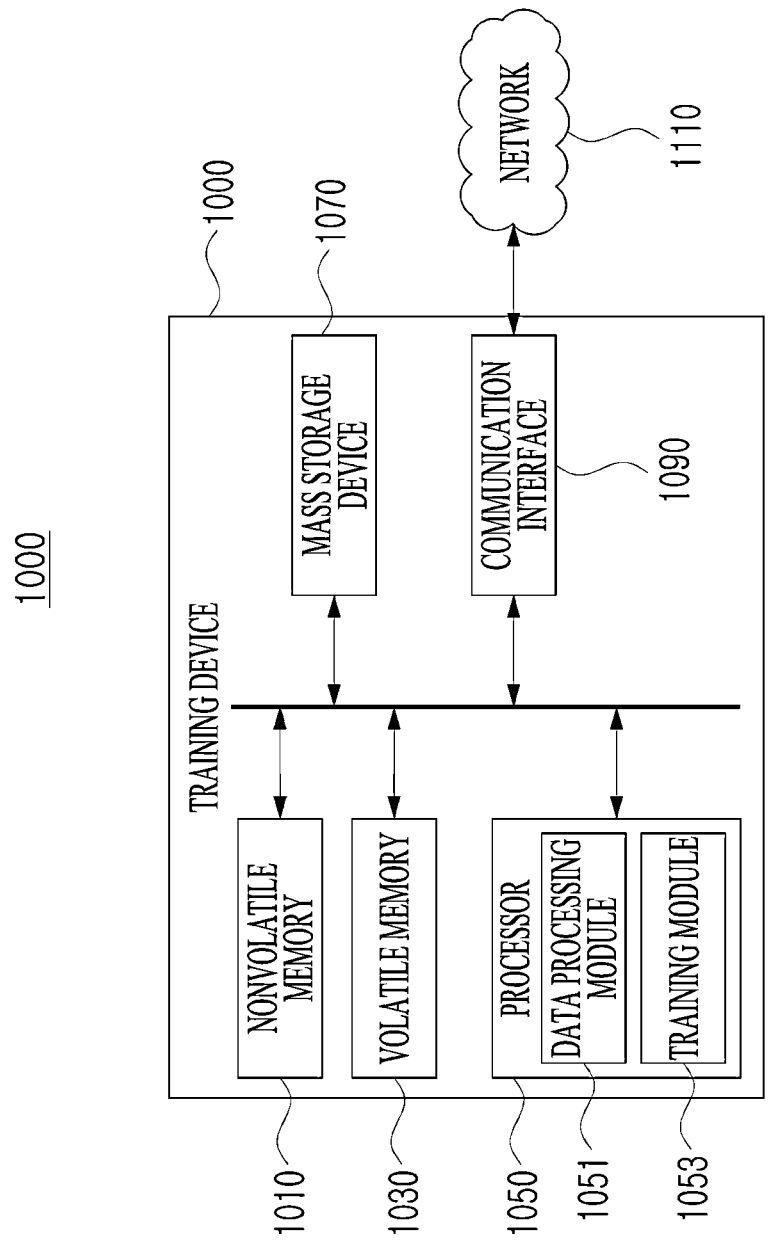
FIG. 3 is a block diagram for describing the training device in more detail according to another embodiment of the present invention.

FIG. 3 is a block diagram for describing the training device 1000 in more detail according to another embodiment of the present invention. Referring to FIG. 3, the training device 1000 may include a processor 1050, a volatile memory 1030, a nonvolatile memory 1010, a mass storage device 1070, and a communication interface 1090.

The processor 1050 of the training device 1000 may include a data processing module 1051 and a training module 1053. The processor 1050 may process a data set stored in the mass storage device or nonvolatile memory through the data processing module 1051. The processor 1050 may train a diagnosis assistance neural network model through the training module 1053. The processor 1050 may include a local memory. The communication interface 1090 may be connected to a network 1110.

However, the training device 1000 illustrated in FIG. 3 is merely an example, and the configuration of the training device 1000 according to the present invention is not limited thereto. Particularly, the data processing module or training module may be provided at locations different from those illustrated in FIG. 3.

1.1.2.2 Diagnostic Device

A diagnostic device may obtain diagnosis assistance information using a neural network model.

Figure 4:
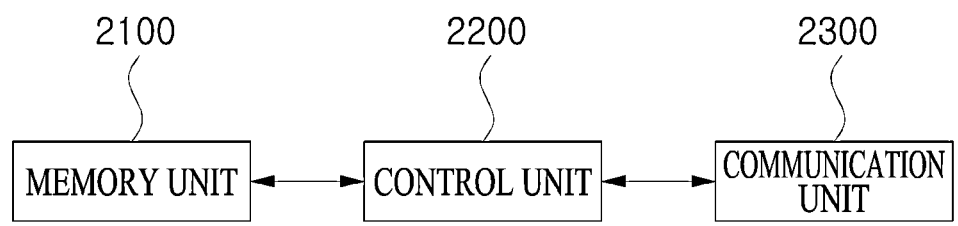
FIG. 4 is a block diagram for describing a diagnostic device according to an embodiment of the present invention.

FIG. 4 is a block diagram for describing a diagnostic device 2000 according to an embodiment of the present invention. Referring to FIG. 4, the diagnostic device 2000 may include a control unit 2200 and a memory unit 2100.

The control unit 2200 may generate diagnosis assistance information using a diagnosis assistance neural network model. The control unit 2200 may obtain diagnostic data for diagnosis (for example, fundus data of a testee) and obtain diagnosis assistance information predicted by the diagnostic data using a trained diagnosis assistance neural network model.

The memory unit 2100 may store a trained diagnosis assistance neural network model. The memory unit 2100 may store parameters, variables, and the like of a diagnosis assistance neural network model.

The diagnostic device 2000 may further include a communication unit 2300. The communication unit 2300 may communicate with a training device and/or a client device.

For example, the diagnostic device 2000 may be provided in the form of a server that communicates with a client device. This will be described in more detail below.

Figure 5:
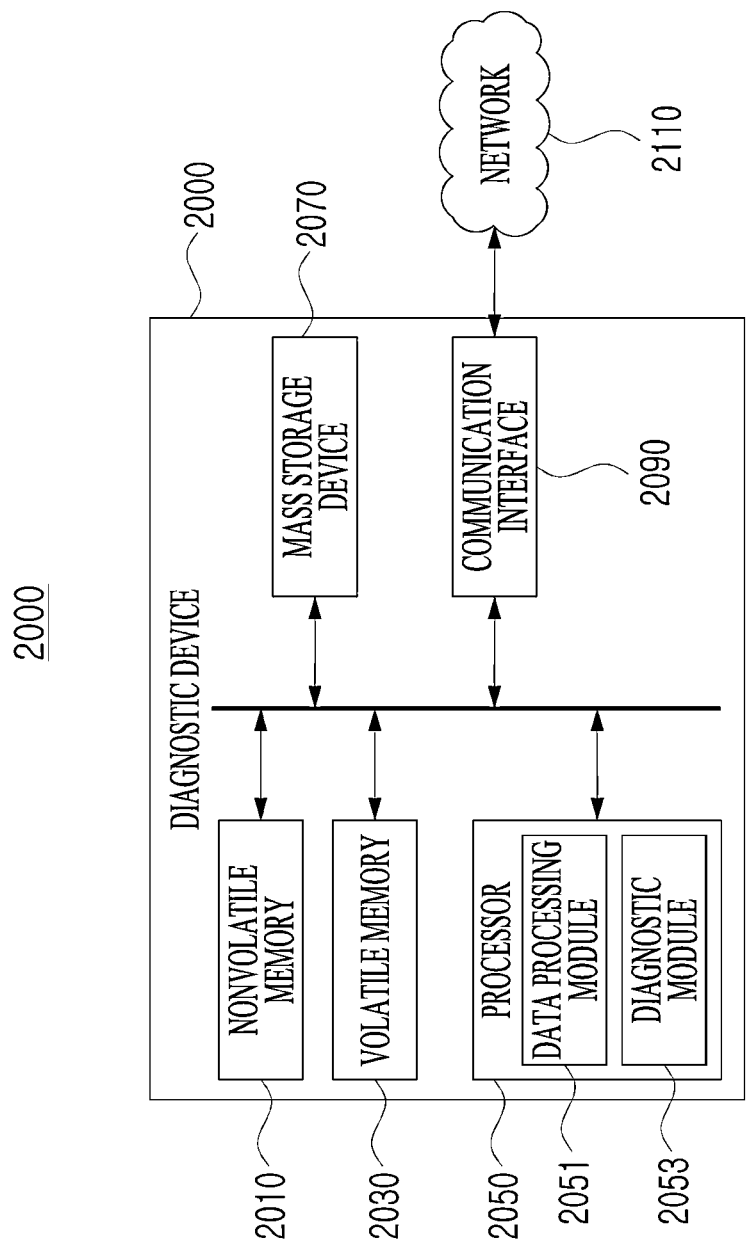
FIG. 5 is a view for describing the diagnostic device according to another embodiment of the present invention.

FIG. 5 is a view for describing the diagnostic device 2000 according to another embodiment of the present invention. Referring to FIG. 5, the diagnostic device 2000 according to an embodiment of the present invention may include a processor 2050, a volatile memory 2030, a nonvolatile memory 2010, a mass storage device 2070, and a communication interface 2090.

The processor 2050 of the diagnostic device may include a data processing module 2051 and a diagnostic module 2053. The processor 2050 may process diagnostic data through the data processing module 2051 and obtain diagnosis assistance information according to the diagnostic data through the diagnostic module 2053.

1.1.2.3 Server Device

According to an embodiment of the present invention, a diagnosis assistance system may include a server device. The diagnosis assistance system according to an embodiment of the present invention may also include a plurality of server devices.

The server device may store and/or drive a neural network model. The server device may store weights constituting a trained neural network model. The server device may collect or store data used in diagnosis assistance.

The server device may output a result of a diagnosis assistance process using a neural network model to a client device. The server device may obtain feedback from the client device. The server device may operate similar to the above-described diagnostic device.

Figure 6:
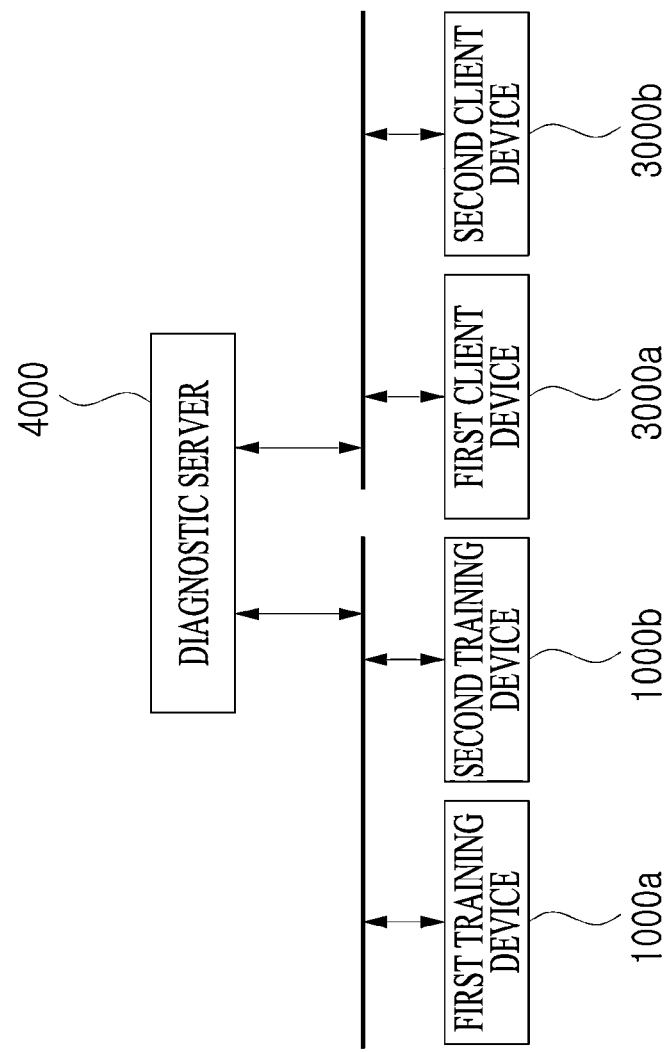
FIG. 6 illustrates a diagnosis assistance system according to an embodiment of the present invention.

FIG. 6 illustrates a diagnosis assistance system 20 according to an embodiment of the present invention. Referring to FIG. 6, the diagnosis assistance system 20 according to an embodiment of the present invention may include a diagnostic server 4000, a training device, and a client device.

The diagnostic server 4000, i.e., server device, may communicate with a plurality of training devices or a plurality of diagnostic devices. Referring to FIG. 6, the diagnostic server 4000 may communicate with a first training device 1000*a* and a second training device 1000*b*. Referring to FIG. 6, the diagnostic server 4000 may communicate with a first client device 3000*a* and a second client device 3000*b*.

For example, the diagnostic server 4000 may communicate with the first training device 1000*a* configured to train a first diagnosis assistance neural network model that obtains a first diagnosis assistance information and the second training device 1000*b* configured to train a second diagnosis assistance neural network model that obtains a second diagnosis assistance information.

The diagnostic server 4000 may store the first diagnosis assistance neural network model that obtains the first diagnosis assistance information and the second diagnosis assistance neural network model that obtains the second diagnosis assistance information, obtain diagnosis assistance information in response to a request for obtaining diagnosis assistance information from the first client device 3000*a* or the second client device 3000*b*, and transmit the obtained diagnosis assistance information to the first client device 3000*a* or the second client device 3000*b*.

Alternatively, the diagnostic server 4000 may communicate with the first client device 3000*a* that requests for the first diagnosis assistance information and the second client device 3000*b* that requests for the second diagnosis assistance information.

1.1.2.4 Client Device

A client device may request a diagnostic device or a server device for diagnosis assistance information. The client device may obtain data required for diagnosis and transmit the obtained data to the diagnostic device.

The client device may include a data obtaining unit. The data obtaining unit may obtain data required for diagnosis assistance. The data obtaining unit may be an imaging unit configured to obtain an image used in a diagnosis assistance model.

Figure 7:
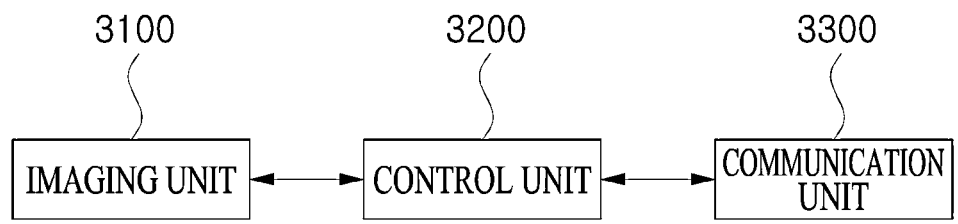
FIG. 7 is a block diagram for describing a client device according to an embodiment of the present invention.

FIG. 7 is a block diagram for describing the client device 3000 according to an embodiment of the present invention. Referring to FIG. 7, the client device 3000 according to an embodiment of the present invention may include an imaging unit 3100, a control unit 3200, and a communication unit 3300.

The imaging unit 3100 may obtain image or video data. The imaging unit 3100 may obtain a fundus image. However, in the client device 3000, the imaging unit 3100 may also be substituted with another form of data obtaining unit.

The communication unit 3300 may communicate with an external device, e.g., a diagnostic device or a server device. The communication unit 3300 may perform wired or wireless communication.

The control unit 3200 may control the imaging unit 3100 to obtain images or data. The control unit 3200 may control the imaging unit 3100 to obtain a fundus image. The control unit 3200 may transmit the obtained fundus image to the diagnostic device. The control unit may transmit an image obtained through the imaging unit 3100 to the server device through the communication unit 3300 and obtain diagnosis assistance information generated on the basis of the obtained image.

Although not illustrated, the client device may further include an output unit. The output unit may include a display configured to output a video or an image or may include a speaker configured to output sound. The output unit may output video or image data obtained by the imaging unit. The output unit may output diagnosis assistance information obtained from the diagnostic device.

Although not illustrated, the client device may further include an input unit. The input unit may obtain a user input. For example, the input unit may obtain a user input that requests for diagnosis assistance information. The input unit may obtain information on a user who evaluates diagnosis assistance information obtained from the diagnostic device.

In addition, although not illustrated, the client device may further include a memory unit. The memory unit may store an image obtained by the imaging unit.

1.1.3 Outline of Diagnosis Assistance Process

A diagnosis assistance process may be performed by a diagnosis assistance system or a diagnosis assistance device disclosed herein. The diagnosis assistance process may be taken into consideration by being mainly divided into a training process for training a diagnosis assistance model used in diagnosis assistance and a diagnostic process using the diagnosis assistance model.

Figure 8:
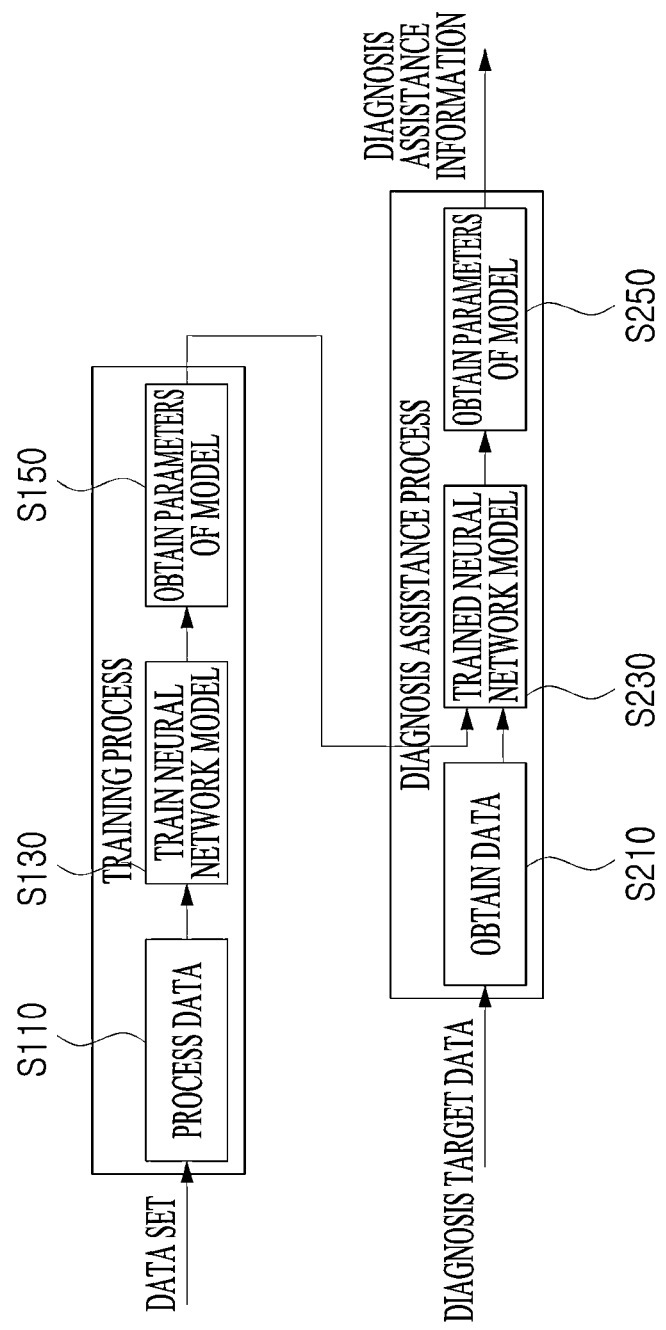
FIG. 8 is a view for describing a diagnosis assistance process according to an embodiment of the present invention.

FIG. 8 is a view for describing a diagnosis assistance process according to an embodiment of the present invention. Referring to FIG. 8, the diagnosis assistance process according to an embodiment of the present invention may include a training process including obtaining and processing data (S110), training a neural network model (S130), and obtaining variables of the trained neural network model (S150) and a diagnosis assistance process including obtaining diagnosis target data (S210), using a neural network model trained on the basis of the diagnosis target data (S230), and obtaining diagnosis assistance information using the trained neural network model (S250).

More specifically, the training process may include a data processing process in which input training image data is processed to a state in which the data may be used for model training and a training process in which a model is trained using the processed data. The training process may be performed by the above-described training device.

The diagnostic process may include a data processing process in which input examination target image data is processed to a state in which diagnosis using a neural network model may be performed and a diagnostic process in which diagnosis is performed using the processed data. The diagnostic process may be performed by the above-described diagnostic device or server device.

Hereinafter, each process will be described.

1.2 Training Process

According to an embodiment of the present invention, a process for training a neural network model may be provided. As a specific example, a process for training a neural network model that performs or assists diagnosis on the basis of a fundus image may be disclosed.

The training process which will be described below may be performed by the above-described training device.

1.2.1 Training Unit

According to an embodiment of the present invention, a training process may be performed by a training unit. The training unit may be provided in the above-described training device.

Figure 9:
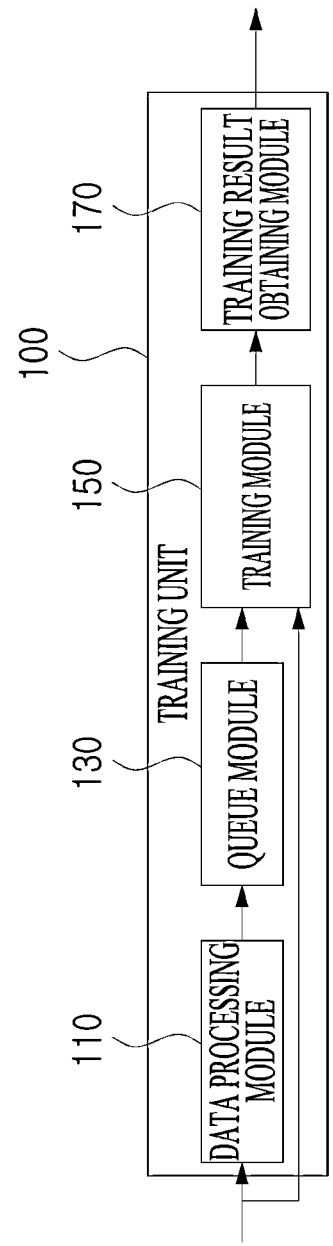
FIG. 9 is a view for describing a configuration of a training unit according to an embodiment of the present invention.

FIG. 9 is a view for describing a configuration of a training unit 100 according to an embodiment of the present invention. Referring to FIG. 9, the training unit 100 may include a data processing module 110, a queue module 130, a training module 150, and a training result obtaining module 170. As will be described below, the modules may perform individual steps of a data processing process and a training process. However, not all of the elements described with reference to FIG. 9 and functions performed by the elements are essential, and some elements may be added or omitted according to a form of training.

1.2.2 Data Processing Process

1.2.2.1 Obtaining Image Data

According to an embodiment of the present invention, a data set may be obtained. According to an embodiment of the present invention, a data processing module may obtain a data set.

The data set may be an image data set. Specifically, the data set may be a fundus image data set. The fundus image data set may be obtained using a general non-mydriatic fundus camera or the like. A fundus image may be a panorama image. The fundus image may be a red-free image. The fundus image may be an infrared image. The fundus image may be an autofluorescence image. The image data may be obtained in any one format among JPG, PNG, DCM (DICOM), BMP, GIF, and TIFF.

The data set may include a training data set. The data set may include a test data set. The data set may include a validation data set. In other words, the data set may be assigned as at least one of a training data set, a test data set, and a validation data set.

The data set may be determined in consideration of diagnosis assistance information that is desired to be obtained using a neural network model trained through the corresponding data set. For example, when it is desired to train a neural network model that obtains diagnosis assistance information related to cataract, an infrared fundus image data set may be determined as a data set to be obtained. Alternatively, when it is desired to train a neural network model that obtains diagnosis assistance information related to macular degeneration, an obtained data set may be an autofluorescence fundus image data set.

Individual data included in a data set may include a label. There may be a plurality of labels. In other words, individual data included in a data set may be labeled in relation to at least one feature. For example, a data set may be a fundus image data set including a plurality of fundus image data, and each fundus image data may include a label related to diagnostic information (for example, the presence of a specific disease) and/or a label related to findings information (for example, whether a specific site is abnormal) according to the corresponding image.

As another example, a data set may be a fundus image data set, and each fundus image data may include a label related to peripheral information on the corresponding image. For example, each fundus image data may include a label related to peripheral information including left eye/right eye information on whether the corresponding fundus image is an image of the left eye or an image of the right eye, gender information on whether the corresponding fundus image is a fundus image of a female or a fundus image of a male, age information on the age of a testee to which the corresponding fundus image belongs, and the like.

Figure 10:
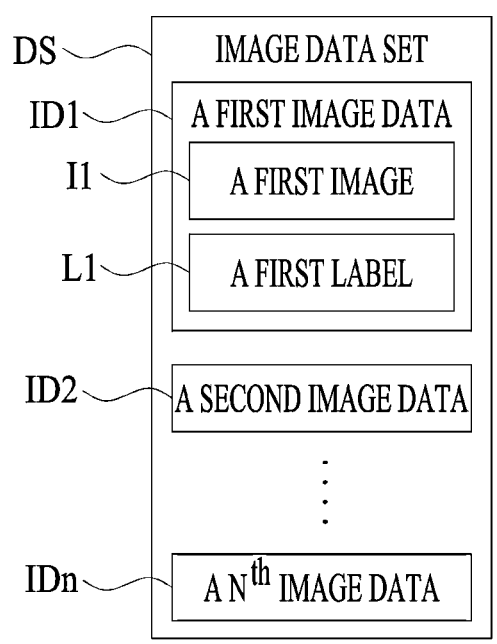
FIG. 10 is a conceptual diagram for describing an image data set according to an embodiment of the present invention.

FIG. 10 is a conceptual diagram for describing an image data set DS according to an embodiment of the present invention. Referring to FIG. 10, the image data set DS according to an embodiment of the present invention may include a plurality of image data ID. Each image data ID may include an image I and a label L assigned to the image. Referring to FIG. 10, the image data set DS may include a first image data ID1 and a second image data ID2. The first image data ID1 may include a first image I1 and a first label L1 corresponding to the first image.

Although the case in which a single image data includes a single label has been described above with reference to FIG. 10, a single image data may include a plurality of labels as described above.

1.2.2.2 Image Resizing

According to an embodiment of the present invention, the size of an obtained piece of image data may be adjusted. That is, images may be resized. According to an embodiment of the present invention, image resizing may be performed by the data processing module of the above-described training unit.

The size or aspect ratio of an image may be adjusted. Sizes of a plurality of obtained images may be adjusted so that the images have a certain size. Alternatively, the sizes of the images may be adjusted so that the images have a certain aspect ratio. Resizing an image may include applying an image conversion filter to an image.

When the sizes or capacities of obtained individual images are excessively large or small, the size or volume of an image may be adjusted to convert the image to an appropriate size. Alternatively, when the sizes or capacities of individual images vary, the sizes or capacities may be made uniform through resizing.

According to an embodiment, a volume of an image may be adjusted. For example, when a volume of an image exceeds an appropriate range, the image may be reduced through down-sampling. Alternatively, when a volume of an image is below an appropriate range, the image may be enlarged through up-sampling or interpolating.

According to another embodiment, an image may be cut or pixels may be added to an obtained image to adjust the size or aspect ratio of the image. For example, when a portion unnecessary for training is included in an image, a portion of the image may be cropped to remove the unnecessary portion. Alternatively, when a portion of the image is cut away and a set aspect ratio is not met, a column or row may be added to the image to adjust the aspect ratio of the image. In other words, a margin or padding may be added to the image to adjust the aspect ratio.

According to still another embodiment, the volume and the size or aspect ratio of the image may be adjusted together. For example, when a volume of an image is large, the image may be down-sampled to reduce the volume of the image, and an unnecessary portion included in the reduced image may be cropped to convert the image to appropriate image data.

According to another embodiment of the present invention, an orientation of image data may be changed.

As a specific example, when a fundus image data set is used as a data set, the volume or size of each fundus image may be adjusted. Cropping may be performed to remove a margin portion excluding a fundus portion of a fundus image, or padding may be performed to supplement a cut-away portion of a fundus image and adjust an aspect ratio thereof.

Figure 11:
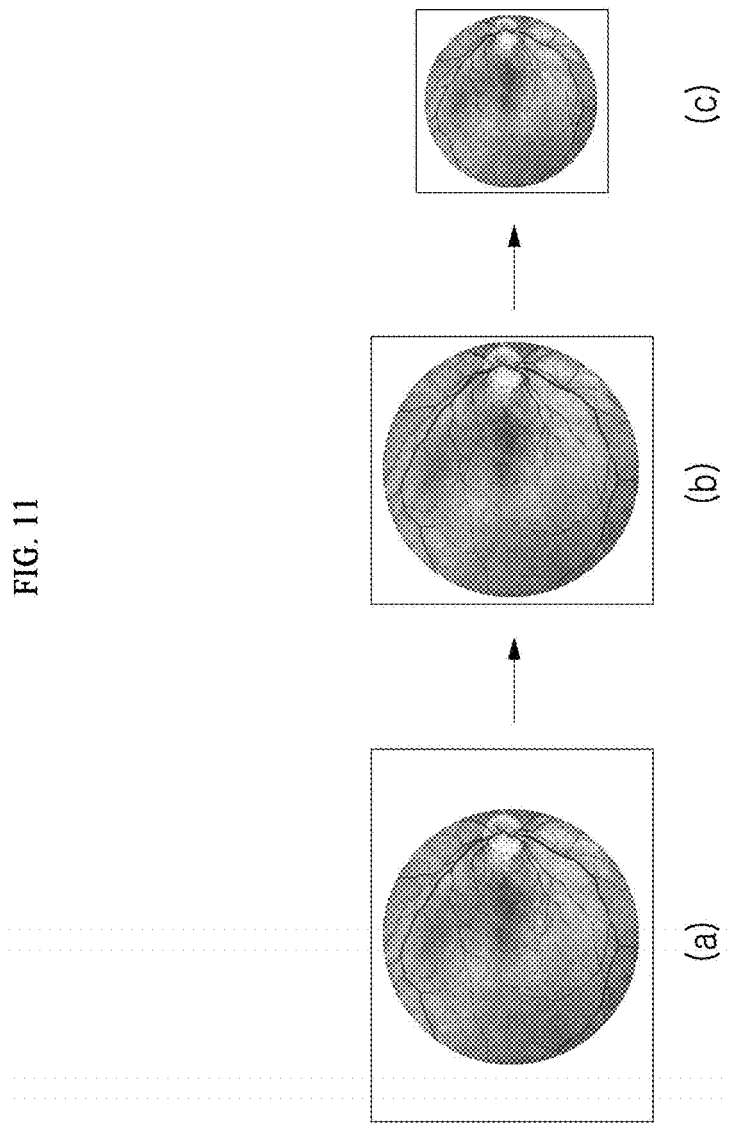
FIG. 11 is a view for describing image resizing according to an embodiment of the present invention.

FIG. 11 is a view for describing image resizing according to an embodiment of the present invention. Referring to FIG. 11, an obtained fundus image may be resized by an image resizing process according to an embodiment of the present invention.

Specifically, an original fundus image (a) may be cropped as shown in (b) so that a margin portion unnecessary for obtaining diagnostic information is removed or the size thereof may be reduced as shown in (c) for enhancing the training efficiency.

1.2.2.3 Image Pre-Processing

According to an embodiment of the present invention, image pre-processing may be performed. When an input image is used as it is in training, an overfitting phenomenon may occur as a result of a training for unnecessary characteristics, and the training efficiency may also be degraded.

To prevent this, image data may be appropriately pre-processed to serve a purpose of training, thereby improving the efficiency and performance of training. For example, pre-processing of a fundus image may be performed to facilitate detection of abnormal symptoms of an eye disease, or pre-processing of a fundus image may be performed so that changes in retinal vessels or blood flow are emphasized.

Image pre-processing may be performed by the data processing module of the above-described training unit. The data processing module may obtain a resized image and perform pre-processing required for training.

Image pre-processing may be performed on the above-mentioned resized image. However, content of the invention disclosed herein is not limited thereto, and image pre-processing may also be performed without the resizing process. Pre-processing an image may include applying a pre-processing filter to the image.

According to an embodiment, a blur filter may be applied to an image. A Gaussian filter may be applied to an image. A Gaussian blur filter may also be applied to an image. Alternatively, a deblur filter which sharpens an image may be applied to the image.

According to another embodiment, a filter that adjusts or modulates color of an image may be applied. For example, a filter that changes values of some components of RGB values constituting an image or binarizes the image may be applied.

According to still another embodiment, a filter that causes a specific element in an image to be emphasized may be applied to the image. For example, pre-processing that causes a blood vessel element to be emphasized from each image may be performed on fundus image data. In this case, the pre-processing that causes a blood vessel element to be emphasized may include applying one or more filters sequentially or in combination.

According to an embodiment of the present invention, image pre-processing may be performed in consideration of a characteristic of diagnosis assistance information that is desired to be obtained. For example, when it is desired to obtain diagnosis assistance information related to findings such as retinal hemorrhage, drusen, microaneurysms, and exudates, pre-processing that converts an obtained fundus image into a red-free fundus image may be performed.

1.2.2.4 Image Augmentation

According to an embodiment of the present invention, an image may be augmented or expanded. Image augmentation may be performed by the data processing module of the above-described training unit.

Augmented images may be used for improving performance of training a neural network model. For example, when an amount of data for training a neural network model is insufficient, existing training image data may be modulated to increase the number of data for training, and modulated (or modified) images may be used together with an original image, thereby increasing the number of training image data. Accordingly, overfitting may be suppressed, layers of a model may be formed deeper, and accuracy of prediction may be improved.

For example, expansion of image data may be performed by reversing the left and right of an image, cutting (cropping) a part of the image, correcting a color value of the image, or adding artificial noise to the image. As a specific example, cutting a part of the image may be performed by cutting a partial region of an element constituting an image or randomly cutting partial regions. In addition, image data may be expanded by reversing the left and right of the image data, reversing the top and bottom of the image data, rotating the image data, resizing the image data to a certain ratio, cropping the image data, padding the image data, adjusting color of the image data, or adjusting brightness of the image data.

For example, the above-described augmentation or expansion of image data may be generally applied to a training data set. However, the augmentation or expansion of image data may also be applied to other data sets, for example, a test data set, i.e., a data set for testing a model on which training using training data and validation using validation data have been completed.

As a specific example, when a fundus image data set is used as a data set, an augmented fundus image data set may be obtained by randomly applying one or more processes of reversing an image, cutting an image, adding noise to an image, and changing color of an image to increase the number of data.

Figure 12:
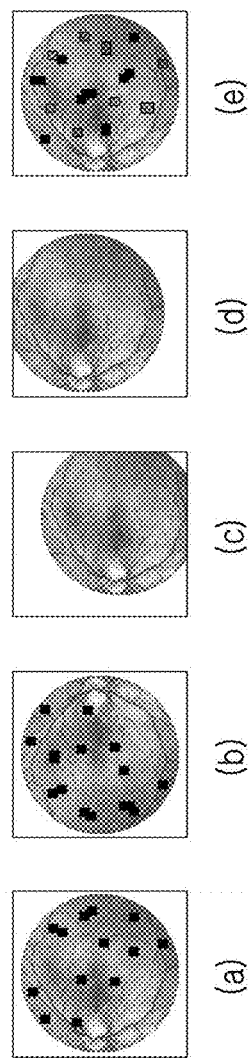
FIG. 12 is a view for describing expansion of an image data set according to an embodiment of the present invention.

FIG. 12 is a view for describing expansion of an image data set according to an embodiment of the present invention. Referring to FIG. 12, an image according to embodiments of the present invention may be deformed to improve prediction accuracy of a neural network model.

Specifically, referring to FIG. 12, partial regions may be dropped out from an image according to embodiments of the present invention as shown in (a), the left and right of the image may be reversed as shown in (b), a central point of the image may be moved as shown in (c) and (d), and color of partial regions of the image may be modulated as shown in (e).

1.2.2.5 Image Serialization

According to an embodiment of the present invention, image data may be serialized. An image may be serialized by the data processing module of the above-described training unit. A serializing module may serialize pre-processed image data and transmit the serialized image data to a queue module.

When image data is used as it is in training, since the image data has an image file format such as JPG, PNG, and DCM, decoding is necessary. However, when training is performed through decoding every time, performance of training a model may be degraded. Accordingly, training may be performed using an serialized image instead of using the image file as it is in training. Therefore, image data may be serialized to improve the performance and speed of training. The image data being serialized may be image data to which one or more steps of the above-described image resizing and image pre-processing are applied or may be image data on which neither the image resizing nor the image pre-processing has been processed.

Each piece of image data included in an image data set may be converted to a string format. Image data may be converted to a binarized data format. Particularly, image data may be converted to a data format suitable for use in training a neural network model. For example, image data may be converted to the TFRecord format for use in training a neural network model using Tensorflow.

As a specific example, when a fundus image set is used as a data set, the obtained fundus image set may be converted to the TFRecord format and used in training a neural network model.

1.2.2.6 Queue

A queue may be used for solving a data bottleneck phenomenon. The queue module of the above-described training unit may store image data in a queue and transmit the image data to a training module.

Particularly, when a training process is performed by using a CPU and a GPU together, a bottleneck phenomenon between the CPU and the GPU may be minimized, access to a database may be facilitated, and the memory usage efficiency may be enhanced by using a queue.

A queue may store data used in training a neural network model. The queue may store image data. The image data stored in the queue may be image data on which at least one of the above-described data processing processes (that is, resizing, pre-processing, and augmentation) are processed or may be image data that is unchanged after being obtained.

A queue may store image data, preferably, serialized image data as described above. The queue may store image data and supply the image data to a neural network model. The queue may transfer image data in batch size to a neural network model.

A queue may provide image data. The queue may provide data to a training module which will be described below. As data is extracted from the training module, the number of data accumulated in the queue may be decreased.

When the number of data stored in the queue is decreased to a reference number or lower as training of a neural network model is performed, the queue may request for supplementation of data. The queue may request for supplementation of a specific type of data. When the queue requests the training unit for supplementation of data, the training unit may supplement the queue with data.

A queue may be provided in a system memory of the training device. For example, the queue may be formed in a RAM of a CPU. In this case, the size, i.e., volume, of the queue may be set according to the capacity of the RAM of the CPU. A first-in-first-out (FIFO) queue, a primary queue, or a random queue may be used as the queue.

1.2.3 Training Process

According to an embodiment of the present invention, a training process of a neural network model may be disclosed.

According to an embodiment of the present invention, training of a neural network model may be performed by the above-described training device. A training process may be performed by the control unit of the training device. A training process may be performed by the training module of the above-described training unit.

Figure 13:
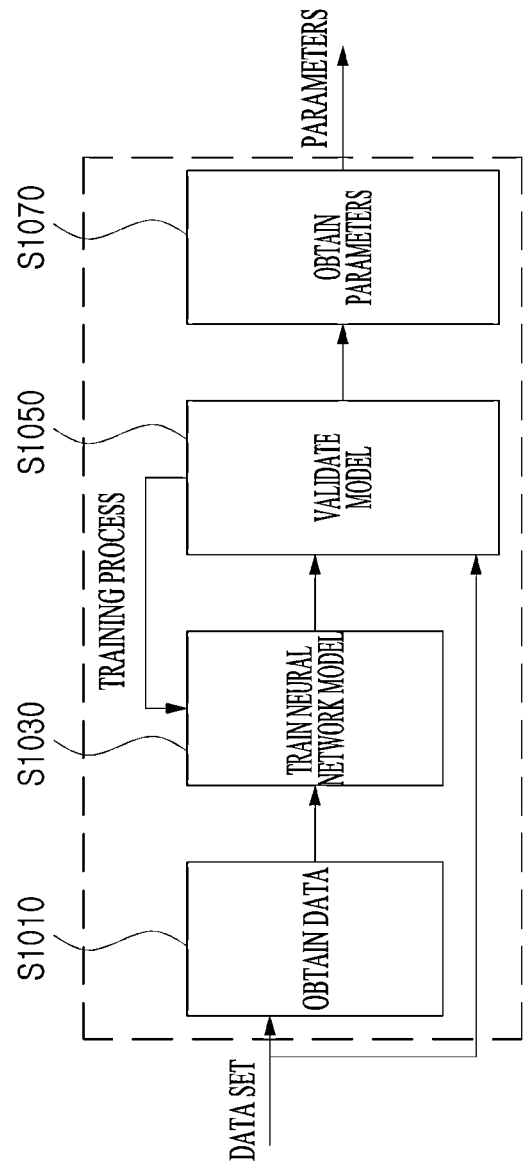
FIG. 13 is a block diagram for describing a training process of a neural network model according to an embodiment of the present invention.

FIG. 13 is a block diagram for describing a training process of a neural network model according to an embodiment of the present invention. Referring to FIG. 13, a training process of a neural network model according to an embodiment of the present invention may be performed by obtaining data (S1010), training a neural network model (S1030), validating the trained model (S1050), and obtaining variables of the trained model (S1070).

Hereinafter, some embodiments of a training process of a neural network model will be described with reference to FIG. 13.

1.2.3.1 Data Input

A data set for training a diagnosis assistance neural network model may be obtained.

Obtained data may be an image data set processed by the above-described data processing process. For example, a data set may include fundus image data which is adjusted in size, has a pre-processing filter applied thereto, is augmented and then serialized.

In training a neural network model, a training data set may be obtained and used. In validating the neural network model, a validation data set may be obtained and used. In testing the neural network model, a test data set may be obtained and used. Each data set may include fundus images and labels.

A data set may be obtained from a queue. The data set may be obtained in batches from the queue. For example, when sixty data sets are designated as the size of a batch, sixty data sets may be extracted at a time from the queue. The size of a batch may be limited by the capacity of a RAM of a GPU.

A data set may be randomly obtained from a queue by the training module. Data sets may also be obtained in order of being accumulated in the queue.

The training module may extract a data set by designating a configuration of a data set to be obtained from the queue. For example, the training module may extract fundus image data having a left eye label of a specific patient and fundus image data having a right eye label of the specific patient to be used together in training.

The training module may obtain a data set having a specific label from the queue. For example, the training module may obtain fundus image data in which a diagnostic information label is abnormal label from the queue. The training module may obtain a data set from the queue by designating a ratio between numbers of data according to certain labels. For example, the training module may obtain a fundus image data set from the queue so that the number of fundus image data in which a diagnostic information label is abnormal and the number of fundus image data in which the diagnostic information label is normal has a 1:1 ratio.

1.2.3.2 Model Design

A neural network model may be a diagnosis assistance model that outputs diagnosis assistance information on the basis of image data. A structure of a diagnosis assistance neural network model for obtaining diagnosis assistance information may have a predetermined form. The neural network model may include a plurality of layers.

A neural network model may be implemented in the form of a classifier that generates diagnosis assistance information. The classifier may perform binary classification or multiclass classification. For example, a neural network model may be a binary classification model that classifies input data as a normal or abnormal class in relation to target diagnosis assistance information such as a specific disease or abnormal symptoms. Alternatively, a neural network model may be a multiclass classification model that classifies input data into a plurality of classes in relation to a specific characteristic (for example, a degree of disease progression). Alternatively, a neural network model may be implemented as a regression model that outputs specific values related to a specific disease.

A neural network model may include a convolutional neural network (CNN). As a CNN structure, at least one of AlexNet, LENET, NIN, VGGNet, ResNet, WideResnet, GoogleNet, FractaNet, DenseNet, FitNet, RitResNet, HighwayNet, MobileNet, and DeeplySupervisedNet may be used. The neural network model may be implemented using a plurality of CNN structures.

For example, a neural network model may be implemented to include a plurality of VGGNet blocks. As a more specific example, a neural network model may be provided by coupling between a first structure in which a 3×3 CNN layer having 64 filters, a batch normalization (BN) layer, and a ReLu layer are sequentially coupled and a second block in which a 3×3 CNN layer having 128 filters, a ReLu layer, and a BN layer are sequentially coupled.

A neural network model may include a max pooling layer subsequent to each CNN block and include a global average pooling (GAP) layer, a fully connected (FC) layer, and an activation layer (for example, sigmoid, softmax, and the like) at an end.

1.2.3.3 Model Training

A neural network model may be trained using a training data set.

A neural network model may be trained using a labeled data set. However, a training process of a diagnosis assistance neural network model described herein is not limited thereto, and a neural network model may also be trained in an unsupervised form using unlabeled data.

Training of a neural network model may be performed by obtaining a result value using a neural network model to which arbitrary weights are assigned on the basis of training image data, comparing the obtained result value with a label value of the training data, and performing backpropagation according to an error therebetween to optimize the weights. Also, training of a neural network model may be affected by a result of validating the model, a result of testing the model, and/or feedback on the model received from the diagnosis step.

The above-described training of a neural network model may be performed using Tensorflow. However, the present invention is not limited thereto, and a framework such as Theano, Keras, Caffe, Torch, and Microsoft Cognitive Toolkit (CNTK) may also be used in training a neural network model.

1.2.3.4 Model Validation

A neural network model may be validated using a validation data set. Validation of a neural network model may be performed by obtaining a result value related to a validation data set from a neural network model which has been trained and comparing the result value with a label of the validation data set. The validation may be performed by measuring accuracy of the result value. Parameters of a neural network model (for example, weights and/or bias) or hyperparameters (for example, learning rate) of the neural network model may be adjusted according to a validation result.

For example, the training device according to an embodiment of the present invention may train a neural network model that predicts diagnosis assistance information on the basis of a fundus image and compare diagnosis assistance information on a validated fundus image of the trained model with a validation label corresponding to the validated fundus image to perform validation of the diagnosis assistance neural network model.

In validation of a neural network model, an external data set, that is, a data set having a distinguished factor not included in a training data set, may be used. For example, the external data set may be a data set in which factors such as race, environment, age, and gender are distinguished from the training data set.

1.2.3.5 Model Test

A neural network model may be tested using a test data set.

Although not illustrated in FIG. 13, according to the training process according to an embodiment of the present invention, a neural network model may be tested using a test data set which is differentiated from a training data set and a validation data set. Parameters of a neural network model (for example, weights and/or bias) or hyperparameters (for example, learning rate) of the neural network model may be adjusted according to a test result.

For example, the training device according to an embodiment of the present invention may obtain a result value which has test fundus image data, which has not been used in the training and validation, as input from the neural network model which has been trained to predict diagnosis assistance information on the basis of a fundus image and may perform testing of the diagnosis assistance neural network model which has been trained and validated.

In testing of the neural network model, an external data set, that is, a data set having a factor distinguished from the training data set and/or validation data set, may be used.

1.2.3.6 Output of Result

As a result of training a neural network model, optimized parameter values of the model may be obtained. As training of the model using a test data set as described above is repeatedly performed, more appropriate parameter (variable) values may be obtained. When the training is sufficiently performed, optimized values of weights and/or bias may be obtained.

According to an embodiment of the present invention, a trained neural network model and/or parameters or variables of the trained neural network model may be stored in the training device and/or diagnostic device (or server). The trained neural network model may be used in predicting diagnosis assistance information by the diagnostic device and/or client device. Also, the parameters or variables of the trained neural network model may be updated by feedback obtained from the diagnostic device or client device.

1.2.3.7 Model Ensemble

According to an embodiment of the present invention, in a process of training a single diagnosis assistance neural network model, a plurality of sub-models may be simultaneously trained. The plurality of sub-models may have different layer structures.

In this case, the diagnosis assistance neural network model according to an embodiment of the present invention may be implemented by combining a plurality of sub-neural network models. In other words, training of a neural network model may be performed using an ensemble technique in which a plurality of sub-neural network models are combined.

When a diagnosis assistance neural network model is configured by forming an ensemble, since prediction may be performed by synthesizing results predicted from various forms of sub-neural network models, accuracy of result prediction may be further improved.

Figure 14:
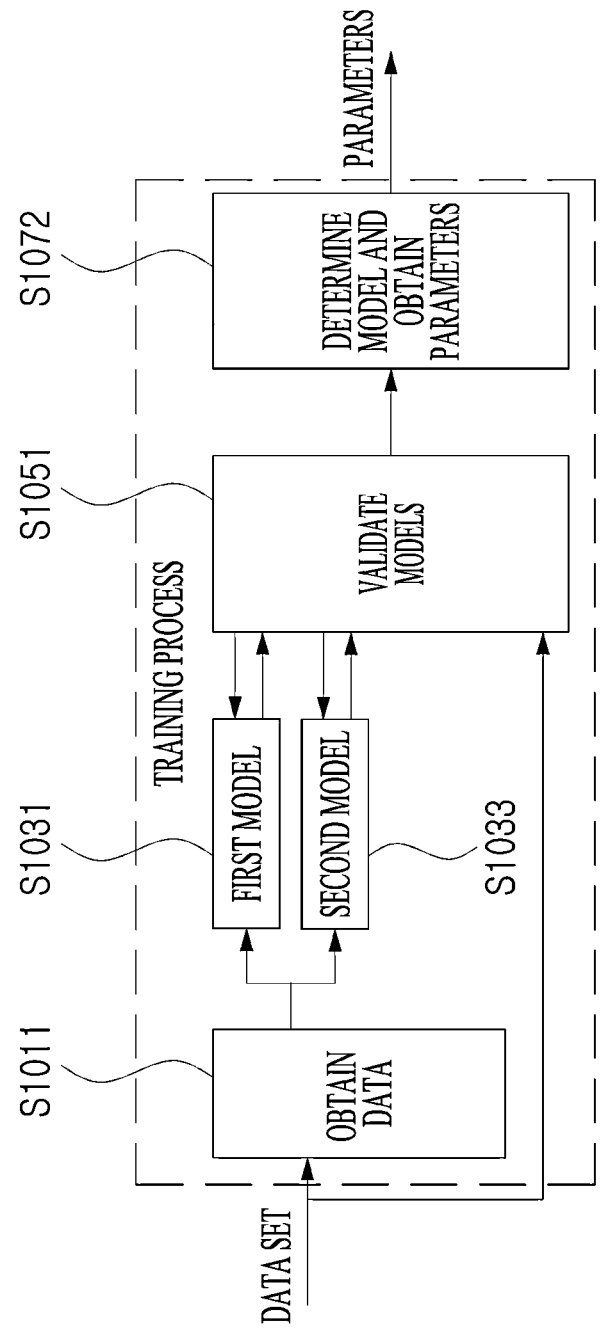
FIG. 14 is a block diagram for describing a training process of a neural network model according to an embodiment of the present invention.

FIG. 14 is a block diagram for describing a training process of a neural network model according to an embodiment of the present invention. Referring to FIG. 14, the training process of a neural network model according to an embodiment of the present invention may include obtaining a data set (S1011), training a first model (that is, first neural network model) and a second model (that is, second neural network model) using the obtained data (S1031, S1033), validating the trained first neural network model and second neural network model (S1051), and determining a final neural network model and obtaining parameters or variables thereof (S1072).

Hereinafter, some embodiments of the training process of a neural network model will be described with reference to FIG. 14.

According to an embodiment of the present invention, a plurality of sub-neural network models may obtain the same training data set and individually generate output values. In this case, an ensemble of the plurality of sub-neural network models may be determined as a final neural network model, and parameter values related to each of the plurality of sub-neural network models may be obtained as training results. An output value of the final neural network model may be set to an average value of the output values by the sub-neural network models. Alternatively, in consideration of accuracy obtained as a result of validating each of the sub-neural network models, the output value of the final neural network model may be set to a weighted average value of the output values of the sub-neural network models.

As a more specific example, when a neural network model includes a first sub-neural network model and a second sub-neural network model, optimized parameter values of the first sub-neural network model and optimized parameter values of the second sub-neural network model may be obtained by machine learning. In this case, an average value of output values (for example, probability values related to specific diagnosis assistance information) obtained from the first sub-neural network model and second sub-neural network model may be determined as an output value of the final neural network model.

According to another embodiment of the present invention, accuracy of individual sub-neural network models may be evaluated on the basis of output values by each of the plurality of sub-neural network models. In this case, any one of the plurality of sub-neural network models may be selected on the basis of the accuracy and determined as the final neural network model. A structure of the determined sub-neural network model and parameter values of the determined sub-neural network model obtained as a result of training may be stored.

As a more specific example, when a neural network model includes a first sub-neural network model and a second sub-neural network model, accuracies of the first sub-neural network model and second sub-neural network model may be obtained, and a more accurate sub-neural network model may be determined as the final neural network model.

According to still another embodiment of the present invention, one or more sub-neural network models among a plurality of neural network models may be combined, ensembles of the one or more combined sub-neural network models may be formed, and each ensemble may be evaluated, wherein a combination of sub-neural network models which forms the most accurate ensemble among the plurality of ensembles may be determined as a final neural network model. In this case, an ensemble may be formed for all possible cases of selecting one or more of the plurality of sub-neural network models, and a combination of sub-neural network models which is evaluated to be the most accurate may be determined as a final neural network model.

As a more specific example, when a neural network model includes a first sub-neural network model and a second sub-neural network model, accuracy of the first sub-neural network model, accuracy of the second sub-neural network model, and accuracy of an ensemble of the first and second sub-neural network models may be compared, and a sub-neural network model combination of the most accurate case may be determined as a final neural network model.

1.2.4 Embodiment 1—Control Method of Training Device

Figure 15:
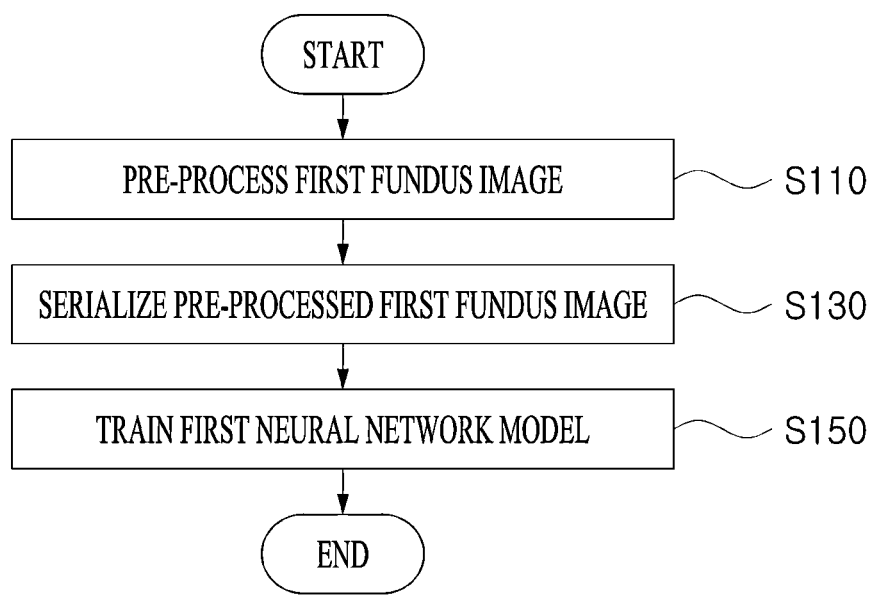
FIG. 15 is a view for describing a control method of a training device according to an embodiment of the present invention.

FIG. 15 is a view for describing a control method of a training device according to an embodiment of the present invention.

Referring to FIG. 15, the control method of a training device according to an embodiment of the present invention may include pre-processing a first fundus image (S110), serializing the pre-processed first fundus image (S130), and training a first neural network model (S150).

The control method of a training device according to an embodiment of the present invention may be a control method of a training device included in a system including a training device configured to obtain a first training data set including a plurality of fundus images, process the fundus images included in the first training data set, and train a first neural network model using the first training data set and a diagnostic device configured to obtain a target fundus image for obtaining diagnosis assistance information and obtain the diagnosis assistance information on the basis of the target fundus image by using the trained first neural network model.

The pre-processing of the first fundus image (S110) may further include pre-processing the first fundus image so that the first fundus image included in the first training data set is converted to a format suitable for training the first neural network model.

The control method of the training device according to an embodiment of the present invention may include the serializing of the pre-processed first fundus image (S130). The first fundus image may be serialized to a format that facilitates training of the neural network model.

In this case, the training of the first neural network model (S150) may further include training the first neural network model that classifies the target fundus image as a first label or a second label by using the serialized first fundus image.

The training device may obtain a second training data set which includes the plurality of fundus images and at least partially differs from the first training data set and may train a second neural network model using the second training data set.

According to an embodiment of the present invention, the control method of the training device may further include pre-processing a second fundus image so that the second fundus image included in the second data training set is suitable for training the second neural network model, serializing the pre-processed second fundus image, and training the second neural network model that classifies the target fundus image as a third label or a fourth label by using the serialized second fundus image.

Figure 16:
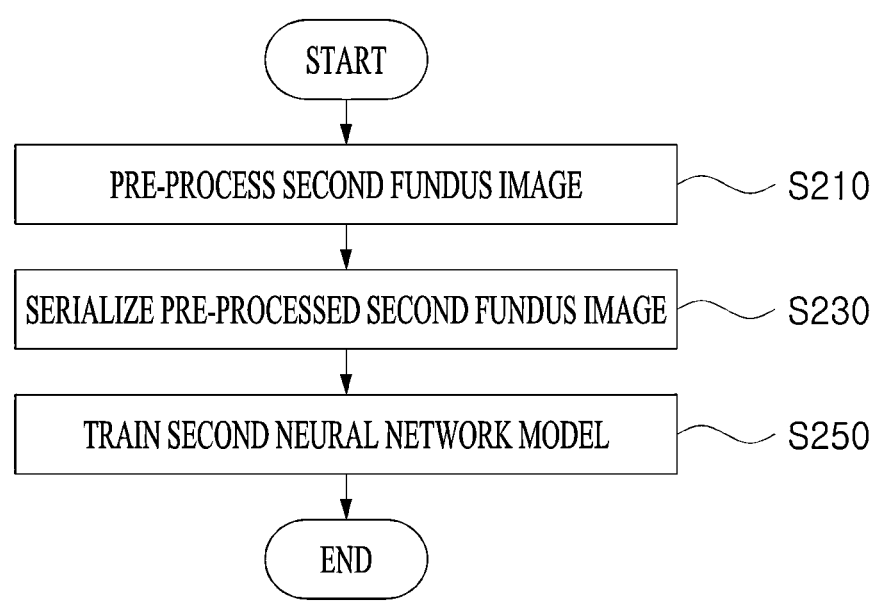
FIG. 16 is a view for describing a control method of a training device according to an embodiment of the present invention.

FIG. 16 is a view for describing a control method of a training device according to an embodiment of the present invention. Referring to FIG. 16, the control method of a training device according to an embodiment of the present invention may include pre-processing a second fundus image (S210), serializing the pre-processed second fundus image (S230), and training a second neural network model (S250).

Although, for convenience of description, it has been depicted in FIG. 16 that the pre-processing of the second fundus image, the serializing of the second fundus image, and the training using the second fundus image may be performed subsequent to the pre-processing of the first fundus image, the serializing of the first fundus image, and the training using the first fundus image, content of the invention is not limited thereto.

The pre-processing of the second fundus image included in the second training data set, the serializing of the second fundus image, and the training using the second fundus image may be performed independently of the above-described pre-processing of the first fundus image, serializing of the first fundus image, and training using the first fundus image. The pre-processing of the second fundus image included in the second training data set, the serializing of the second fundus image, and the training using the second fundus image may be performed in parallel with the above-described pre-processing of the first fundus image, serializing of the first fundus image, and training using the first fundus image. In other words, the pre-processing of the second fundus image included in the second training data set, the serializing of the second fundus image, and the training using the second fundus image are not necessarily performed subsequent or prior to the above-described pre-processing of the first fundus image, serializing of the first fundus image, and training using the first fundus image. The process related to the first fundus image and the process related to the second fundus image may be performed without dependence on each other.

First pre-processing performed in relation to the fundus image included in the first training data set may be distinguished from second pre-processing performed in relation to the fundus image included in the second training data set. For example, the first pre-processing may be pre-processing for emphasizing a blood vessel, and the second pre-processing may be pre-processing for modulating color. Each pre-processing may be determined in consideration of diagnosis assistance information desired to be obtained through each neural network model.

The control method of the training device according to an embodiment of the present invention may further include validating the first neural network model by evaluating accuracy of the trained first neural network model by using a first validation data set that is at least partially distinguished from the first training data set and validating the second neural network model by evaluating accuracy of the trained second neural network model by using a second validation data set that is at least partially distinguished from the second training data set. In this case, validation of the first neural network model and validation of the second neural network model may be performed independently of each other.

Serialized first fundus images may be sequentially stored in a first queue, and a predetermined unit volume of the serialized fundus images stored in the first queue may be used each time in training the first neural network model. Serialized second fundus images may be sequentially stored in a second queue distinguished from the first queue, and a predetermined unit volume of the serialized fundus images stored in the second queue may be used each time in training the second neural network model.

The first neural network model may include a first sub-neural network model and a second sub-neural network model. In this case, classifying a target fundus image as the first label or the second label may be performed by simultaneously taking into consideration a first predicted value predicted by the first sub-neural network model and a second predicted value predicted by the second sub-neural network model.

The second neural network model may include a third sub-neural network model and a fourth sub-neural network model. In this case, classifying a target fundus image as the third label or the fourth label may be performed by simultaneously taking into consideration a third predicted value predicted by the third sub-neural network model and a fourth predicted value predicted by the fourth sub-neural network model.

The first training data set may include at least some of fundus images labeled with the first label, and the second training data set may include at least some of fundus images labeled with the third label. In this case, the fundus images labeled with the first label may be the same as at least some of the fundus images labeled with the third label.

The first label may be a normal label indicating that a patient corresponding to the target fundus image is normal in relation to a first finding, and the second label may be an abnormal label indicating that the patient is abnormal in relation to a second finding.

The pre-processing of the first fundus image may include cropping the first fundus image so that a reference aspect ratio is satisfied and changing the size of the first fundus image.

The pre-processing of the first fundus image may further include, by a processing unit, applying a blood vessel emphasizing filter to the fundus image so that a blood vessel included in the first fundus image is emphasized.

Serialized first fundus images may be sequentially stored in a queue, and a predetermined number of the serialized first fundus images stored in the queue may be used each time in training the first neural network model. When the capacity of the serialized first fundus images which have not been used in the training of the first neural network model is reduced to a reference amount or lower, the queue may request for supplementation of the serialized first fundus images.

The first finding may be any one of a finding of retinal hemorrhage, a finding of generation of retinal exudates, a finding of opacity of crystalline lens, and a finding of diabetic retinopathy.

Figure 17:
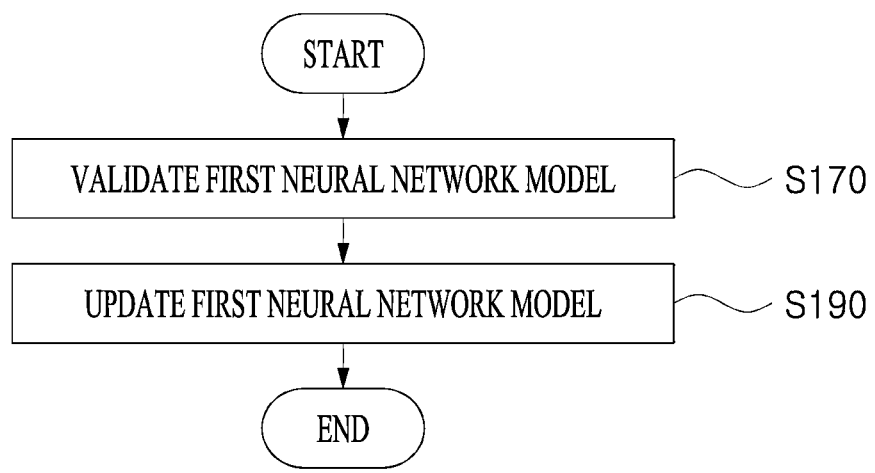
FIG. 17 is a view for describing a control method of a training device according to an embodiment of the present invention.

FIG. 17 is a view for describing a control method of a training device according to an embodiment of the present invention.

Referring to FIG. 17, the control method of the training device according to an embodiment of the present invention may further include validating the first neural network model (S170) and updating the first neural network model (S190).

The validating of the first neural network model (S170) may further include validating the first neural network model by evaluating accuracy of the trained first neural network model by using the first validation data set that is at least partially distinguished from the first training data set.

The updating of the first neural network model (S190) may further include updating the first neural network model by reflecting a validation result obtained from the validating of the first neural network model (S170).

Meanwhile, the first neural network model may include a first sub-neural network model and a second sub-neural network model. In this case, the training of the first neural network model may include validating the first sub-neural network model using the first validation data set to obtain accuracy of the first sub-neural network model, validating the second sub-neural network model using the first validation data set to obtain accuracy of the second sub-neural network model, and comparing the accuracy of the first sub-neural network model and the accuracy of the second sub-neural network model to determine a more accurate sub-neural network model as the final neural network model.

1.3. Diagnosis Assistance Process

According to an embodiment of the present invention, a diagnosis assistance process (or diagnostic process) in which diagnosis assistance information is obtained using a neural network model may be provided. As a specific example, by the diagnosis assistance process, diagnosis assistance information (for example, diagnostic information or findings information) may be predicted through a diagnosis assistance neural network model trained using a fundus image.

The diagnosis assistance process which will be described below may be performed by a diagnostic device.

1.3.1 Diagnostic Unit

According to an embodiment of the present invention, a diagnostic process may be performed by a diagnostic unit 200. The diagnostic unit 200 may be provided in the above-described diagnostic device.

Figure 18:
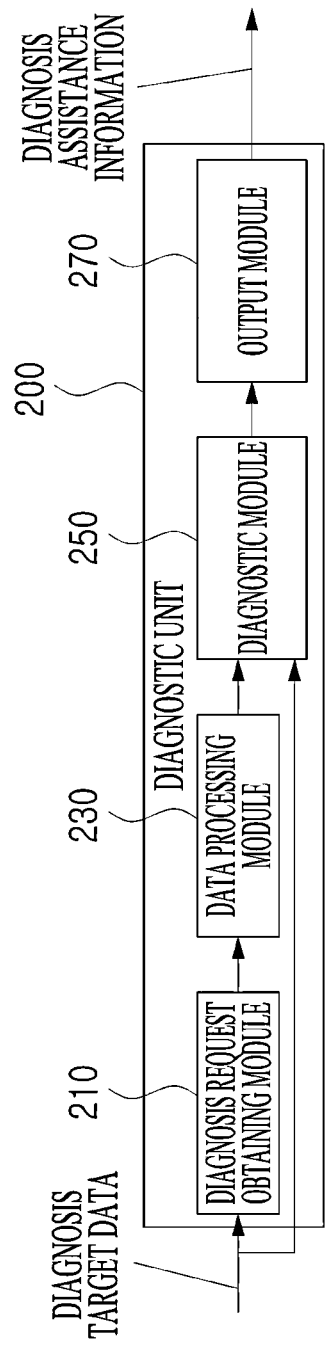
FIG. 18 is a view for describing a configuration of a diagnostic unit according to an embodiment of the present invention.

FIG. 18 is a view for describing a configuration of the diagnostic unit 200 according to an embodiment of the present invention. Referring to FIG. 18, the diagnostic unit 200 may include a diagnosis request obtaining module 210, a data processing module 230, a diagnostic module 250, and an output module 270.

As will be described below, the modules may perform individual steps of a data processing process and a training process. However, not all of the elements described with reference to FIG. 18 and functions performed by the elements are essential, and some elements may be added or omitted according to an aspect of diagnosis.

1.3.2 Obtaining Data and Diagnosis Request

The diagnostic device according to an embodiment of the present invention may obtain diagnosis target data and obtain diagnosis assistance information on the basis of the obtained diagnosis target data. The diagnosis target data may be image data. The obtaining of the data and obtaining of a diagnosis request may be performed by the diagnosis request obtaining module of the above-described diagnostic unit.

Figure 19:
FIG. 19 is a view for describing diagnosis target data according to an embodiment of the present invention.

FIG. 19 is a view for describing diagnosis target data TD according to an embodiment of the present invention. Referring to FIG. 19, the diagnosis target data TD may include a diagnosis target image TI and diagnosis target patient information PI.

The diagnosis target image TI may be an image for obtaining diagnosis assistance information on a diagnosis target patient. For example, the diagnosis target image may be a fundus image. The diagnosis target image TI may have any one format among JPG, PNG, DCM (DICOM), BMP, GIF, and TIFF.

The diagnosis patient information PI may be information for identifying a patient to be diagnosed. Alternatively, the diagnosis patient information PI may be characteristic information of a patient or an image to be diagnosed. For example, the diagnosis patient information PI may include information such as the date and time of imaging and imaging equipment of an image to be diagnosed or information such as an identification (ID) number, an ID, name, age, or weight of a patient to be diagnosed. When the image to be diagnosed is a fundus image, the diagnosis patient information PI may further include eye-related information such as left eye/right eye information on whether the corresponding fundus image is an image of the left eye or an image of the right eye.

The diagnostic device may obtain a diagnosis request. The diagnostic device may obtain diagnosis target data together with the diagnosis request. When the diagnosis request is obtained, the diagnostic device may obtain diagnosis assistance information using a trained diagnosis assistance neural network model. The diagnostic device may obtain a diagnosis request from a client device. Alternatively, the diagnostic device may obtain a diagnosis request from a user through a separately-provided input means.

1.3.3 Date Processing Process

Obtained data may be processed. Data processing may be performed by the data processing module of the above-described diagnostic unit.

Generally, a data processing process may be performed similar to the data processing process in the above-described training process. Hereinafter, the data processing process in the diagnostic process will be described focusing on differences from the data processing process in the training process.

In the diagnostic process, the diagnostic device may obtain data as in the training process. In this case, the obtained data may have the same format as the data obtained in the training process. For example, when the training device has trained a diagnosis assistance neural network model using image data in the DCM format in the training process, the diagnostic device may obtain the DCM image and obtain diagnosis assistance information using the trained neural network model.

In the diagnostic process, the obtained image to be diagnosed may be resized similar to the image data used in the training process. To efficiently perform prediction of diagnosis assistance information through the trained diagnosis assistance neural network model, the form of the image to be diagnosed may be adjusted to have a suitable volume, size, and/or aspect ratio.

For example, when an image to be diagnosed is a fundus image, resizing of the image such as removing an unnecessary portion of the image or reducing the size of the image may be performed to predict diagnostic information on the basis of the fundus image.

In the diagnostic process, similar to the image data used in the training process, a pre-processing filter may be applied to the obtained image to be diagnosed. A suitable filter may be applied to the image to be diagnosed so that accuracy of prediction of diagnosis assistance information through a trained diagnosis assistance neural network model is further improved.

For example, when an image to be diagnosed is a fundus image, pre-processing that facilitates prediction of correct diagnostic information, for example, image pre-processing that causes a blood vessel to be emphasized or image pre-processing that causes a specific color to be emphasized or weakened, may be applied to the image to be diagnosed.

In the diagnostic process, similar to the image data used in the training process, the obtained image to be diagnosed may be serialized. The image to be diagnosed may be converted to a form that facilitates driving of a diagnostic model in a specific work frame or may be serialized.

The serializing of the image to be diagnosed may be omitted. This may be because, in the diagnostic process, the number of data processed at one time by a processor is not large unlike in the training process, and thus the burden on data processing speed is relatively small.

In the diagnostic process, similar to the image data used in the training process, the obtained image to be diagnosed may be stored in a queue. However, since the number of data being processed is smaller in the diagnostic process in comparison to that in the training process, storing data in a queue may also be omitted.

Meanwhile, since an increase in the number of data is not required in the diagnostic process, it is preferable that, in order to obtain accurate diagnosis assistance information, the process of data augmentation or image augmentation is not used, unlike in the training process.

1.3.4 Diagnostic Process

According to an embodiment of the present invention, a diagnostic process using a trained neural network model may be disclosed. The diagnostic process may be performed by the above-described diagnostic device. The diagnostic process may be performed by the above-described diagnostic server. The diagnostic process may be performed by the control unit of the above-described diagnostic device. The diagnostic process may be performed by the diagnostic module of the above-described diagnostic unit.

Figure 20:
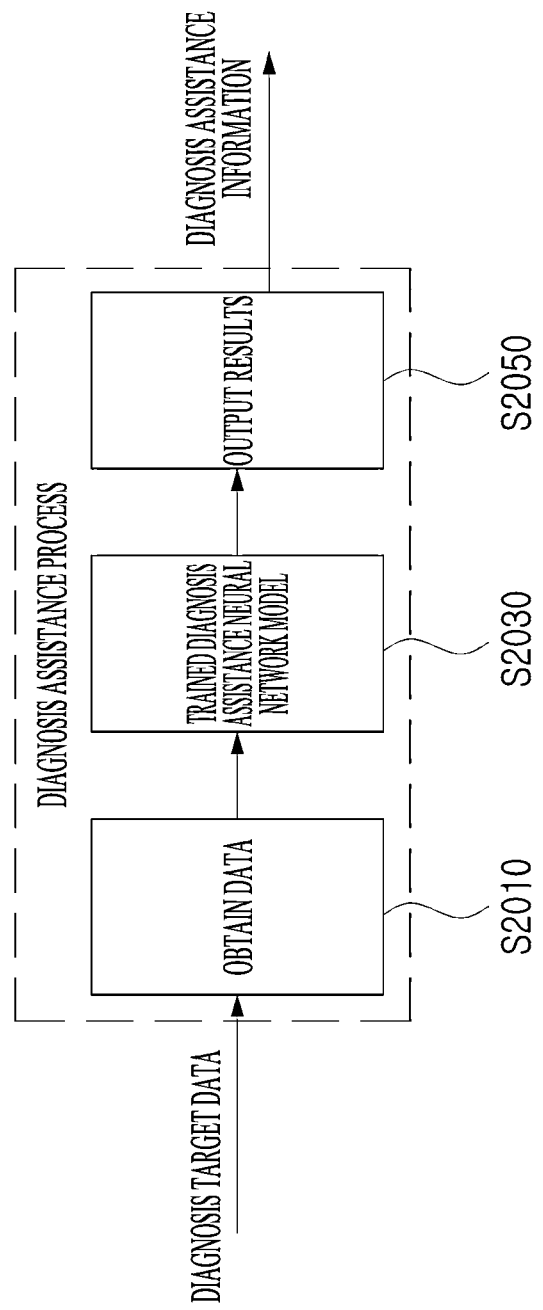
FIG. 20 is a view for describing a diagnostic process according to an embodiment of the present invention.

FIG. 20 is a view for describing a diagnostic process according to an embodiment of the present invention. Referring to FIG. 20, the diagnostic process may include obtaining diagnosis target data (S2010), using a trained neural network model (S2030), and obtaining and outputting a result corresponding to the obtained diagnosis target data (S2050). However, data processing may be selectively performed.

Hereinafter, each step of the diagnostic process will be described with reference to FIG. 20.

1.3.4.1 Data Input

According to an embodiment of the present invention, the diagnostic module may obtain diagnosis target data. The obtained data may be data processed as described above. For example, the obtained data may be a patient's fundus image data to which pre-processing that causes the size to be adjusted and a blood vessel to be emphasized is applied. According to an embodiment of the present invention, a left eye image and a right eye image of a single patient may be input together as diagnosis target data.

1.3.4.2 Data Classification

A diagnosis assistance neural network model provided in the form of a classifier may classify input diagnosis target images into a positive class or a negative class in relation to a predetermined label.

A trained diagnosis assistance neural network model may receive diagnosis target data and output a predicted label. The trained diagnosis assistance neural network model may output a predicted value of diagnosis assistance information. Diagnosis assistance information may be obtained using the trained diagnosis assistance neural network model. The diagnosis assistance information may be determined on the basis of the predicted label.

For example, the diagnosis assistance neural network model may predict diagnostic information (that is, information on the presence of a disease) or findings information (that is, information on the presence of abnormal findings) related to an eye disease or a systemic disease of the patient. In this case, the diagnostic information or findings information may be output in the form of a probability. For example, the probability that the patient has a specific disease or the probability that there may be a specific abnormal finding in the patient's fundus image may be output. When a diagnosis assistance neural network model provided in the form of a classifier is used, a predicted label may be determined in consideration of whether an output probability value (or predicted score) exceeds a threshold value.

As a specific example, a diagnosis assistance neural network model may output a probability value with respect to the presence of diabetic retinopathy in a patient with the patient's fundus image as a diagnosis target image. When a diagnosis assistance neural network model in the form of a classifier that assumes 1 as normal is used, a patient's fundus image may be input to the diagnosis assistance neural network model, and in relation to whether the patient has diabetic retinopathy, a normal:abnormal probability value may be obtained in the form of 0.74:0.26 or the like.

Although the case in which data is classified using the diagnosis assistance neural network model in the form of a classifier has been described herein, the present invention is not limited thereto, and a specific diagnosis assistance numerical value (for example, blood pressure or the like) may also be predicted using a diagnosis assistance neural network model implemented in the form of a regression model.

According to another embodiment of the present invention, suitability information on an image may be obtained. The suitability information may indicate whether a diagnosis target image is suitable for obtaining diagnosis assistance information using a diagnosis assistance neural network model.

The suitability information of an image may be quality information. The quality information or suitability information may indicate whether a diagnosis target image reaches a reference level.

For example, when a diagnosis target image has a defect due to a defect of imaging equipment or an influence of an illumination during imaging, a result indicating that the diagnosis target image is unsuitable may be output as suitability information of the corresponding diagnosis target image. When a diagnosis target image includes noise at a predetermined level or higher, the diagnosis target image may be determined as being unsuitable.

The suitability information may be a value predicted using a neural network model. Alternatively, the suitability information may be information obtained through a separate image analysis process.

According to an embodiment, even when an image is classified as unsuitable, diagnosis assistance information may be obtained on the basis of the unsuitable image.

According to an embodiment, an image classified as unsuitable may be reexamined by a diagnosis assistance neural network model.

In this case, the diagnosis assistance neural network model that performs the reexamination may differ from a diagnosis assistance neural network model that performs initial examination. For example, the diagnostic device may store a first diagnosis assistance neural network model and a second diagnosis assistance neural network model, and an image classified as unsuitable through the first diagnosis assistance neural network model may be examined through the second diagnosis assistance neural network model.

According to still another embodiment of the present invention, a class activation map (CAM) may be obtained from a trained neural network model. Diagnosis assistance information may include a CAM. The CAM may be obtained together with other diagnosis assistance information.

The CAM may be obtained optionally. For example, the CAM may be extracted and/or output when diagnostic information or findings information obtained by a diagnosis assistance model is classified into an abnormal class.

1.3.5 Output of Diagnosis Assistance Information

Diagnosis assistance information may be determined on the basis of a label predicted from a diagnosis assistance neural network model.

Output of diagnosis assistance information may be performed by the output module of the above-described diagnostic unit. Diagnosis assistance information may be output from the diagnostic device to a client device. Diagnosis assistance information may be output from the diagnostic device to a server device. Diagnosis assistance information may be stored in the diagnostic device or diagnostic server. Diagnosis assistance information may be stored in a separately-provided server device or the like.

Diagnosis assistance information may be managed by being formed into a database. For example, obtained diagnosis assistance information may be stored and managed together with a diagnosis target image of a subject according to an identification number of the corresponding subject. In this case, the diagnosis target image and diagnosis assistance information of the patient may be managed in chronological order. By managing the diagnosis assistance information and diagnosis target image in time series, tracking personal diagnostic information and managing history thereof may be facilitated.

Diagnosis assistance information may be provided to a user. The diagnosis assistance information may be provided to the user through an output means of a diagnostic device or client device. The diagnosis assistance information may be output through a visual or aural output means provided in the diagnostic device or client device so that the user may recognize the diagnosis assistance information.

According to an embodiment of the present invention, an interface for effectively providing diagnosis assistance information to a user may be provided. Such a user interface will be described in more detail below in Section "5. User interface."

When a CAM is obtained by a neural network model, an image of the CAM may be provided together. The image of the CAM may be selectively provided. For example, the CAM image may not be provided when diagnostic information obtained through a diagnosis assistance neural network model is normal findings information or normal diagnostic information, and the CAM image may be provided together for more accurate clinical diagnosis when the obtained diagnostic information is abnormal findings information or abnormal diagnostic information.

When an image is classified as unsuitable, suitability information of the image may be provided together. For example, when an image is classified as unsuitable, diagnosis assistance information and "unsuitable" judgment information obtained according to the corresponding image may be provided together.

A diagnosis target image that has been judged to be unsuitable may be classified as an image to be retaken. In this case, a retake guide for a target patient of the image classified as an image to be retaken may be provided together with the suitability information.

Meanwhile, in response to providing of diagnosis assistance information obtained through a neural network model, feedback related to training of the neural network model may be obtained. For example, feedback for adjusting a parameter or hyperparameter related to training of the neural network model may be obtained. The feedback may be obtained through a user input unit provided in the diagnostic device or client device.

According to an embodiment of the present invention, diagnosis assistance information corresponding to a diagnosis target image may include level information. The level information may be selected among a plurality of levels. The level information may be determined on the basis of diagnostic information and/or findings information obtained through a neural network model. The level information may be determined in consideration of suitability information or quality information of a diagnosis target image. When a neural network model is a classifier model that performs multiclass classification, the level information may be determined in consideration of a class into which a diagnosis target image is classified by the neural network model. When a neural network model is a regression model that outputs a numerical value related to a specific disease, the level information may be determined in consideration of the output numerical value.

For example, diagnosis assistance information obtained corresponding to a diagnosis target image may include any one level information selected from a first level information and a second level information. When abnormal findings information or abnormal diagnostic information is obtained through a neural network model, the first level information may be selected as the level information. When abnormal findings information or abnormal diagnostic information is not obtained through a neural network model, the second level information may be selected as the level information. Alternatively, the first level information may be selected as the level information when a numerical value obtained through a neural network model exceeds a reference numerical value, and the second level information may be selected as the level information when the obtained numerical value is less than the reference numerical value. The first level information may indicate that strong abnormal information is present in a diagnosis target image compared with the second level information.

Meanwhile, a third level information may be selected as the level information when the quality of a diagnosis target image is determined to a reference quality or lower using image analysis or a neural network model. Alternatively, diagnosis assistance information may include the third level information together with the first or second level information.

When diagnosis assistance information includes the first level information, a first user guide may be output through an output means. The first user guide may indicate that a more precise test is required for a testee (patient) corresponding to the diagnosis assistance information. For example, the first user guide may indicate that secondary diagnosis (for example, diagnosis in a separate medical institution or a hospital transfer procedure) is required for the patient. Alternatively, the first user guide may indicate treatment required for the patient. As a specific example, when abnormal information on macular degeneration of the patient is obtained by diagnosis assistance information, the first user guide may include injection prescription and a guide on a hospital transfer procedure (for example, a list of hospitals to which transfer is possible) related to the patient.

When diagnosis assistance information includes the second level information, a second user guide may be output through an output means. The second user guide may include future care plans related to the patient corresponding to the diagnosis assistance information. For example, the second user guide may indicate the time of next visit and the next medical course.

When diagnosis target information includes the third level information, a third user guide may be output through an output means. The third user guide may indicate that a diagnosis target image has to be retaken. The third user guide may include information on the quality of the diagnosis target image. For example, the third user guide may include information on an artifact present in a diagnosis target image (for example, whether the artifact is a bright artifact or a dark artifact, or the degree thereof).

1.4 Diagnosis Assistance System for Multiple Labels

According to an embodiment of the present invention, a diagnosis assistance system for performing prediction on a plurality of labels (for example, a plurality of diagnosis assistance information) may be provided. For this, a diagnosis assistance neural network of the above-mentioned diagnosis assistance system may be designed to perform prediction on a plurality of labels.

Alternatively, in the above-mentioned diagnosis assistance system, a plurality of diagnosis assistance neural networks that perform prediction on different labels may be used in parallel. Hereinafter, such a parallel diagnosis assistance system will be described.

1.4.1 Configuration of Parallel Diagnosis Assistance System

According to an embodiment of the present invention, a parallel diagnosis assistance system for obtaining a plurality of diagnosis assistance information may be provided. The parallel diagnosis assistance system may train a plurality of neural network models for obtaining a plurality of diagnosis assistance information and obtain the plurality of diagnosis assistance information using the trained plurality of neural network models.

For example, the parallel diagnosis assistance system may train, on the basis of fundus images, a first neural network model that obtains a first diagnosis assistance information related to the presence of an eye disease of a patient and a second neural network model that obtains a second diagnosis assistance information related to the presence of a systemic disease of the patient and may output the diagnosis assistance information related to the presence of an eye disease and the presence of a systemic disease of the patient by using the trained first neural network model and the second neural network model.

Figure 21:
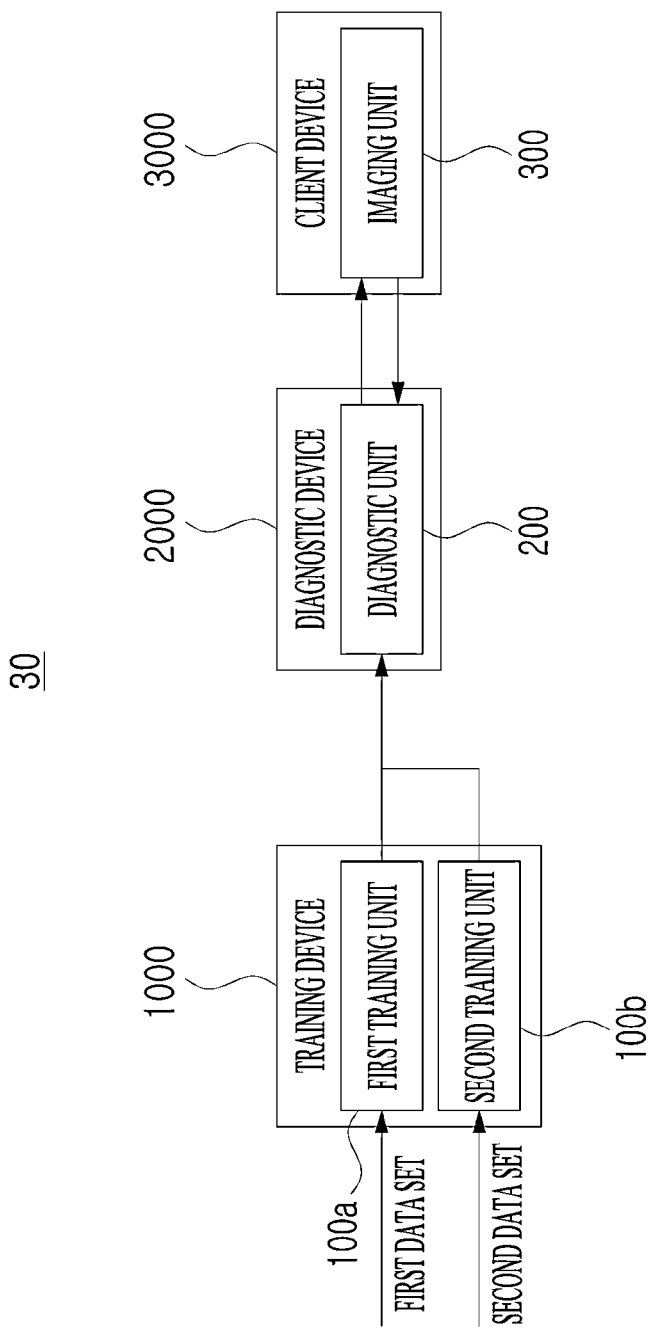
FIG. 21 is a view for describing a parallel diagnosis assistance system according to some embodiments of the present invention.
Figure 22:
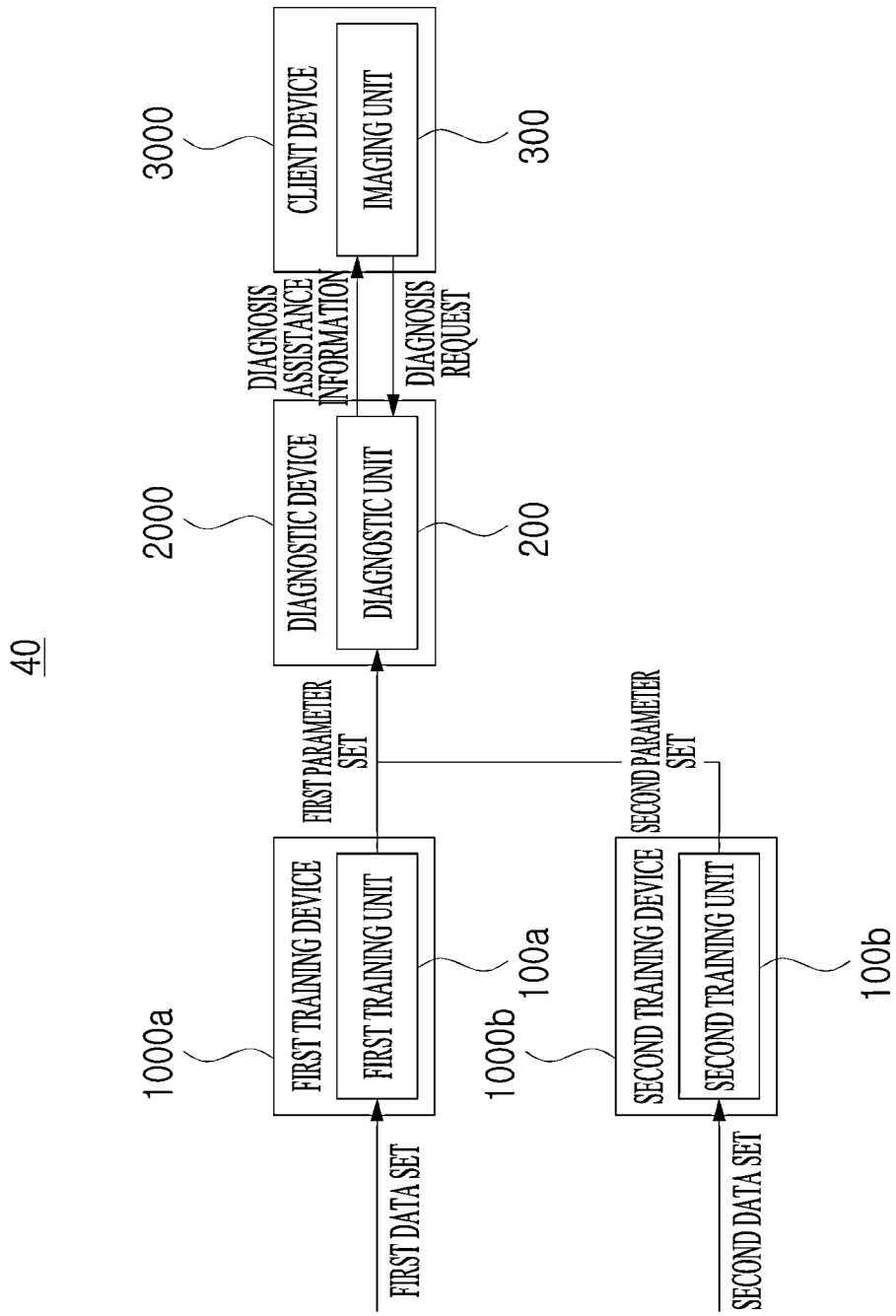
FIG. 22 is a view for describing a parallel diagnosis assistance system according to some embodiments of the present invention.

FIGS. 21 and 22 are views for describing a parallel diagnosis assistance system according to some embodiments of the present invention. Referring to FIGS. 21 and 22, the parallel diagnosis assistance system may include a plurality of training units.

Referring to FIG. 21, a parallel diagnosis assistance system 30 according to an embodiment of the present invention may include a training device 1000, a diagnostic device 2000, and a client device 3000. In this case, the training device 1000 may include a plurality of training units. For example, the training device 1000 may include a first training unit 100a and a second training unit 100b.

Referring to FIG. 22, a parallel diagnosis assistance system 40 according to an embodiment of the present invention may include a first training device 1000a, a second training device 1000b, a diagnostic device 2000, and a client device 3000. The first training device 1000a may include a first training unit 100a. The second training device 1000b may include a second training unit 100b.

Referring to FIGS. 21 and 22, the first training unit 100a may obtain a first data set and output a first parameter set of a first neural network model obtained as a result of training the first neural network model. The second training unit 100b may obtain a second data set and output a second parameter set of a second neural network model obtained as a result of training the second neural network model.

The diagnostic device 2000 may include a diagnostic unit 200. Description similar to that given above with reference to FIG. 1 may be applied to the diagnostic device 2000 and the diagnostic unit 200. The diagnostic unit 200 may obtain a first diagnosis assistance information and a second diagnosis assistance information using the trained first neural network model and second neural network model through the first training unit 100*a* and the second training unit 100*b*. The diagnostic unit 200 may store parameters of the trained first neural network model and parameters of the trained second neural network model obtained from the first training unit 100*a* and the second training unit 100*b*.

The client device 3000 may include a data obtaining unit, e.g., an imaging unit 300. However, the imaging unit 300 may be substituted with other data obtaining means used for obtaining diagnosis assistance information. The client device may transmit a diagnosis request and diagnosis target data (for example, a fundus image obtained by the imaging unit) to the diagnostic device. In response to the transmitting of the diagnosis request, the client device 3000 may obtain, from the diagnostic device, a plurality of diagnosis assistance information according to the transmitted diagnosis target data.

Meanwhile, although the case in which the diagnosis assistance system 40 includes the first training unit 100*a* and the second training unit 100*b* has been described above with reference to FIGS. 21 and 22, content of the invention is not limited thereto. According to another embodiment of the present invention, a training device may include a training unit configured to obtain three or more different diagnosis assistance information. Alternatively, a diagnosis assistance system may also include a plurality of training devices configured to obtain different diagnosis assistance information The operations of the training device, the diagnostic device, and the client device will be described in more detail below.

1.4.2 Parallel Training Process

According to an embodiment of the present invention, a plurality of neural network models may be trained. Training processes for training the respective neural network models may be performed in parallel.

1.4.2.1 Parallel Training Units

Training processes may be performed by a plurality of training units. The training processes may be performed independently of each other. The plurality of training units may be provided in a single training device or respectively provided in a plurality of training devices.

Figure 23:
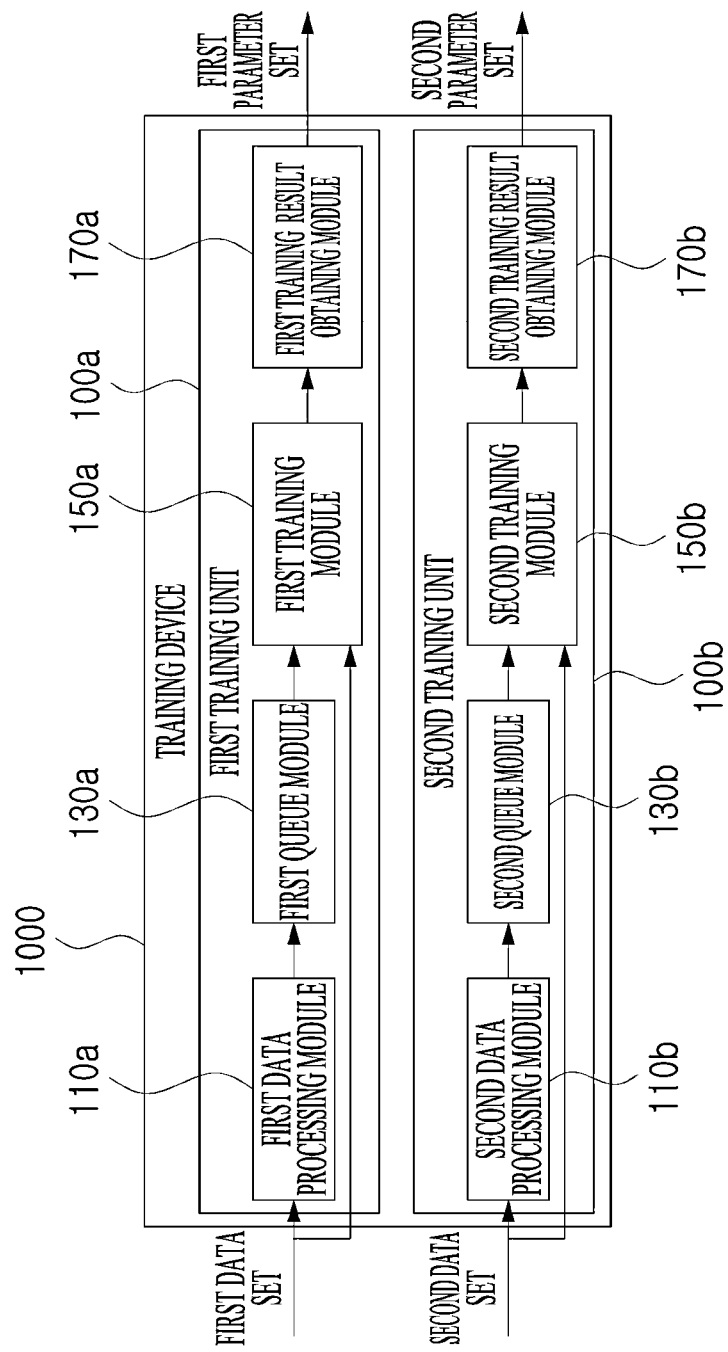
FIG. 23 is a view for describing a configuration of a training device including a plurality of training units according to an embodiment of the present invention.

FIG. 23 is a view for describing a configuration of a training device including a plurality of training units according to an embodiment of the present invention. The configuration and operation of each of the first training unit 100*a* and the second training unit 100*b* may be implemented similar to those described above with reference to FIG. 9.

Referring to FIG. 23, a process of a neural network model according to an embodiment of the present invention may be performed by a training device 1000 including a first training unit 100*a* which includes a first data processing module 110*a*, a first queue module 130*a*, a first training module 150*a*, and a first training result obtaining module 170*a* and a second training unit 100*b* which includes a second data processing module 110*b*, a second queue module 130*b*, a second training module 150*b*, and a second training result obtaining module 170*b*.

Referring to FIG. 23, a training process of a neural network model according to an embodiment of the present invention may be performed by each of the first training unit 100*a* and the second training unit 100*b*. The first training unit 100*a* and the second training unit 100*b* may independently perform training of the first neural network model and the second neural network model. Referring to FIG. 23, the first training unit 100*a* and the second training unit 100*b* may be provided in the above-described training device. Alternatively, the first training unit and the second training unit may also be provided in different training devices.

1.4.2.2 Obtaining Parallel Data

According to an embodiment of the present invention, a plurality of training units may obtain data. The plurality of training units may obtain different data sets. Alternatively, the plurality of training units may also obtain the same data set. According to circumstances, the plurality of training units may also obtain partially common data sets. The data sets may be fundus image data sets.

A first training unit may obtain a first data set, and a second training unit may obtain a second data set. The first data set and the second data set may be distinguished from each other. The first data set and the second data set may be partially common. The first data set and the second data set may be labeled fundus image data sets.

The first data set may include data labeled as normal in relation to a first feature and data labeled as abnormal in relation to the first feature. For example, the first data set may include a fundus image labeled as normal and a fundus image labeled as abnormal in relation to the opacity of crystalline lens.

The second data set may include data labeled as normal in relation to a second feature (distinguished from the first feature) and data labeled as abnormal in relation to the second feature. For example, the second data set may include a fundus image labeled as normal and a fundus image labeled as abnormal in relation to diabetic retinopathy.

The data labeled as normal in relation to the first feature and data labeled as normal in relation to the second feature respectively included in the first data set and the second data set may be common. For example, the first data set may include a fundus image labeled as normal and a fundus image labeled as abnormal in relation to the opacity of crystalline lens, and the second data set may include a fundus image labeled as normal and a fundus image labeled as abnormal in relation to diabetic retinopathy, wherein the fundus image labeled as normal in relation to the opacity of crystalline lens included in the first data set and the fundus image labeled as normal in relation to diabetic retinopathy included in the second data set may be common.

Alternatively, the data labeled as abnormal in relation to the first feature and the data labeled as abnormal in relation to the second feature respectively included in the first data set and the second data set may also be common. That is, data labeled in relation to a plurality of features may be used in training a neural network model in relation to the plurality of features.

Meanwhile, the first data set may be a fundus image data set captured using a first method, and the second data set may be a fundus image data set captured using a second method. The first method and the second method may be any one method selected from red-free imaging, panoramic imaging, autofluorescence imaging, infrared imaging, and the like.

A data set used in each training unit may be determined in consideration of diagnosis assistance information obtained by a trained neural network model. For example, when the first training unit trains a first neural network model which desires to obtain diagnosis assistance information related to abnormal findings of the retina (for example, microaneurysms, exudates, and the like), the first training unit may obtain a first fundus image data set captured by red-free imaging. Alternatively, when the second training unit trains a second neural network model which desires to obtain diagnosis assistance information related to macular degeneration, the second training unit may obtain a second fundus image data set captured by autofluorescence imaging.

1.4.3 Parallel Data Processing

The plurality of training units may process obtained data. As described above in Section "2.2 Data processing process," each training unit may process data by applying one or more of image resizing, a pre-processing filter, image augmentation, and image serialization to obtained data. The first data processing module of the first training unit may process a first data set, and the second data processing module of the second training unit may process a second data set.

The first training unit and second training unit included in the plurality of training units may differently process obtained data sets in consideration of diagnosis assistance information obtained from neural network models respectively trained by the first training unit and the second training unit. For example, to train a first neural network model for obtaining a first diagnosis assistance information related to hypertension, the first training unit may perform pre-processing that causes blood vessels to be emphasized in fundus images included in the first fundus image data set. Alternatively, to train a second neural network model for obtaining a second diagnosis assistance information related to abnormal findings on exudates, microaneurysms, and the like of the retina, the second training unit may perform pre-processing that causes fundus images included in the second fundus image data set to be converted to red-free images.

1.4.3.1 Parallel Queue

The plurality of training units may store data in a queue. As described above in Section "2.2.6 Queue," each training unit may store processed data in a queue and transmit the processed data to the training module. For example, the first training unit may store a first data set in a first queue module and provide the first data set to a first training module sequentially or randomly. The second training module may store a second data set in a second queue module and provide the second data set to a second training module sequentially or randomly.

1.4.3.2 Parallel Training Process

The plurality of training units may train a neural network model. The training modules may independently train diagnosis assistance neural network models that perform prediction on different labels using training data sets. A first training module of the first training unit may train the first neural network model, and a second training module of the second training unit may train the second neural network model.

The plurality of diagnosis assistance neural network models may be trained in parallel and/or independently. By training models to perform prediction on different labels through the plurality of neural network models in this way, accuracy of prediction on each label may be improved, and efficiency of the prediction operation may be enhanced.

Each diagnosis assistance neural network model may be provided similar to that described above in Section "2.3.2 Model design." Each sub-training process may be performed similar to that described above in Sections 2.3.1 to 2.3.5.

A parallel training process according to an embodiment of the present invention may include training diagnosis assistance neural network models that predict different labels. The first training unit may train a first diagnosis assistance neural network model that predicts a first label. The second training unit may train a second diagnosis assistance neural network model that predicts a second label.

The first training unit may obtain a first data set and train the first diagnosis assistance neural network model that predicts the first label. For example, the first training unit may train the first diagnosis assistance neural network model that predicts the presence of macular degeneration of a patient from a fundus image by using a fundus image training data set labeled in relation to the presence of macular degeneration.

The second training unit may obtain a second data set and train the second diagnosis assistance neural network model that predicts the second label. For example, the second training unit may train the second diagnosis assistance neural network model that predicts the presence of diabetic retinopathy of a patient from a fundus image by using a fundus image training data set labeled in relation to the presence of diabetic retinopathy.

The training process of a neural network model will be described in more detail below with reference to FIGS. 24 and 25.

Figure 24:
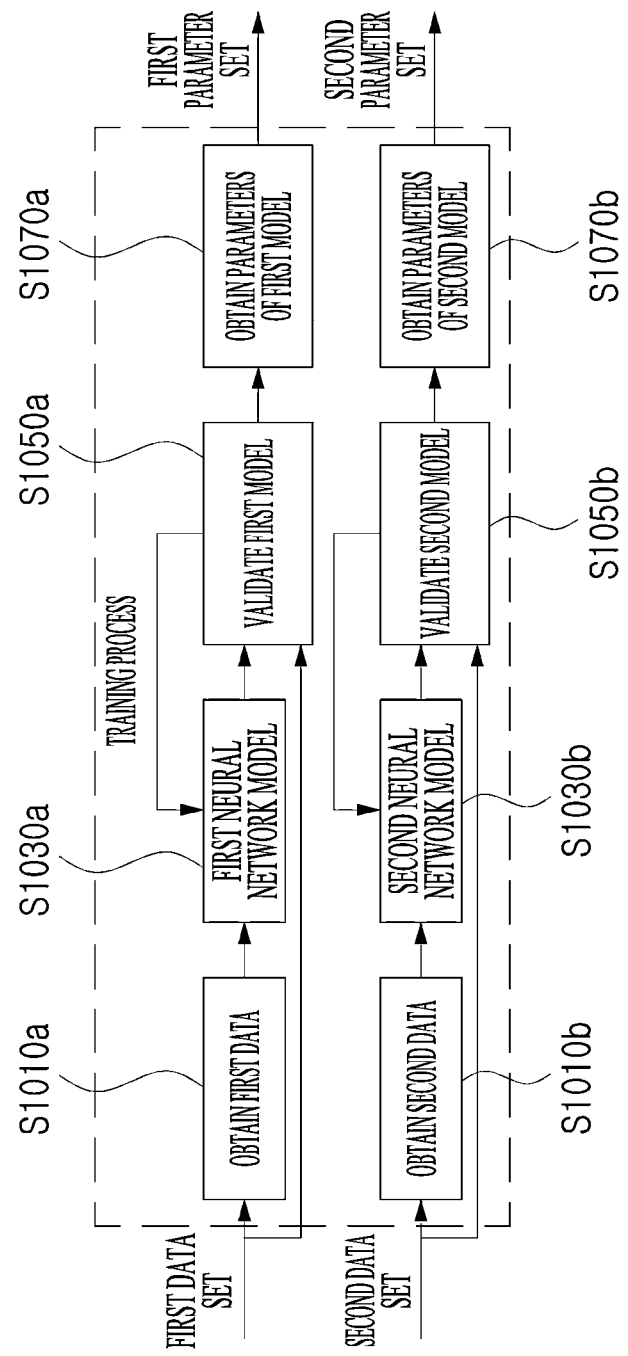
FIG. 24 is a view for describing a parallel training process according to an embodiment of the present invention.

FIG. 24 is a view for describing a parallel training process according to an embodiment of the present invention. The parallel training process may be applied to all of the cases in which the parallel diagnosis assistance system is implemented as shown in FIG. 21, implemented as shown in FIG. 22, and implemented in other forms. However, for convenience of description, description will be given below on the basis of the parallel diagnosis assistance system implemented as shown in FIG. 21.

Referring to FIG. 24, the parallel training process may include a plurality of sub-training processes that respectively train a plurality of diagnosis assistance neural network models that predict different labels. The parallel training process may include a first sub-training process that trains a first neural network model and a second sub-training process that trains a second neural network model.

For example, the first sub-training process may be performed by obtaining a first data (S1010a), using a first neural network model (S1030a), validating the first model (that is, first diagnosis assistance neural network model) (S1050a), and obtaining parameters of the first neural network model (S1070a). The second sub-training process may be performed by obtaining a second data (S1010b), using a second neural network model (S1030b), validating the second neural network model (that is, second diagnosis assistance neural network model) (S1050b), and obtaining parameters of the second neural network model (S1070b).

A sub-training process may include training a neural network model by inputting training data into a sub-neural network model, comparing a label value obtained by output with the input training data to validate the model, and reflecting a validation result back to the sub-neural network model.

Each sub-training process may include obtaining result values using a neural network model to which arbitrary weight values are assigned, comparing the obtained result values with label values of training data, and performing backpropagation according to errors therebetween to optimize the weight values.

In each sub-training process, a diagnosis assistance neural network model may be validated through a validation data set distinguished from a training data set. Validation data sets for validating a first neural network model and a second neural network model may be distinguished.

The plurality of training units may obtain training results. Each training result obtaining module may obtain information on neural network models trained from the training modules. Each training result obtaining module may obtain parameter values of neural network models trained from the training units. A first training result obtaining module of the first training unit may obtain a first parameter set of a first neural network model trained from a first training module. A second training result obtaining module of the second training unit may obtain a second parameter set of a second neural network model trained from a second training module.

By each sub-training process, optimized parameter values, that is, a parameter set, of a trained neural network model may be obtained. As training is performed using more training data sets, more suitable parameter values may be obtained.

A first parameter set of a first diagnosis assistance neural network model trained by a first sub-training process may be obtained. A second parameter set of a second diagnosis assistance neural network model trained by a second sub-training process may be obtained. As training is sufficiently performed, optimized values of weights and/or bias of the first diagnosis assistance neural network and the second diagnosis assistance neural network may be obtained.

The obtained parameter set of each neural network model may be stored in the training device and/or the diagnostic device (or server). The first parameter set of the first diagnosis assistance neural network and the second parameter set of the second diagnosis assistance neural network may be stored together or separately. A parameter set of each trained neural network model may also be updated by feedback obtained from the diagnostic device or client device.

1.4.3.3 Parallel Ensemble Training Process

Even when a plurality of neural network models are trained in parallel, The above-described ensemble form of model training may be used. Each sub-training process may include training a plurality of sub-neural network models. The plurality of sub-models may have different layer structures. Hereinafter, unless particularly mentioned otherwise, description similar to that given above in Section 2.3.7 may be applied.

When a plurality of diagnosis assistance neural network models are trained in parallel, some sub-training processes among the sub-training processes that train the diagnosis assistance neural network models may train a single model, and other sub-training processes may train a plurality of sub-models together.

Since models are trained using ensembles in each sub-training process, more optimized forms of neural network models may be obtained in each sub-training process, and error in prediction may be reduced.

Figure 25:
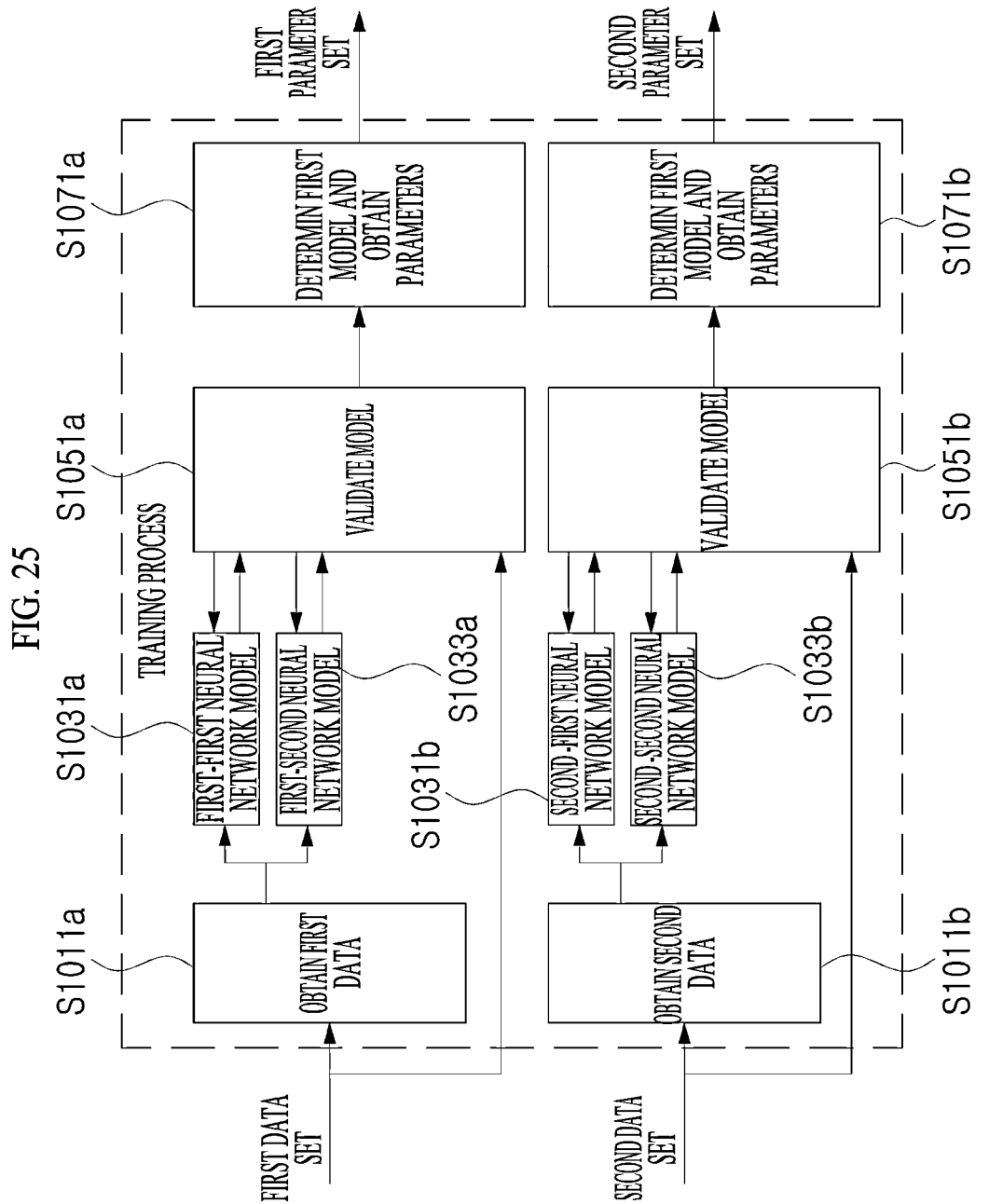
FIG. 25 is a view for describing the parallel training process according to another embodiment of the present invention.

FIG. 25 is a view for describing the parallel training process according to another embodiment of the present invention. Referring to FIG. 25, each training process may include training a plurality of sub-neural network models.

Referring to FIG. 25, a first sub-training process may be performed by obtaining a first data S1011$a$, using a first-first (1-1) neural network model and a first-second (1-2) neural network model (S1031$a$, S1033$a$), validating the first-first (1-1) neural network model and the first-second (1-2) neural network model (S1051$a$), and determining a final form of the first neural network model and parameters thereof (S1071$a$). A second sub-training process may be performed by obtaining a second data (S1011$b$), using a second-first (2-1) neural network model and a second-second (2-2) neural network model (S1031$b$, S1033$b$), validating the second-first (2-1) neural network model and the second-second (2-2) neural network model (S1051$b$), and determining a final form of the second model (that is, the second diagnosis assistance neural network model) and parameters thereof (S1071$b$).

The first neural network trained in the first sub-training process may include the first-first (1-1) neural network model and the first-second (1-2) neural network model. The first-first (1-1) neural network model and the first-second (1-2) neural network model may be provided in different layer structures. Each of the first-first (1-1) neural network model and the first-second (1-2) neural network model may obtain a first data set and output predicted labels. Alternatively, a label predicted by an ensemble of the first-first (1-1) neural network model and the first-second (1-2) neural network model may be determined as a final predicted label.

In this case, the first-first (1-1) neural network model and the first-second (1-2) neural network model may be validated using a validation data set, and a more accurate neural network model may be determined as a final neural network model. Alternatively, the first-first (1-1) neural network model, the first-second (1-2) neural network model, and the ensemble of the first-first (1-1) neural network model and the first-second (1-2) neural network model may be validated, and a neural network model form of the most accurate case may be determined as a final first neural network model.

For the second sub-training process, likewise, the most accurate form of neural network among the second-first (2-1) neural network model, the second-second (2-2) neural network model, and the ensemble of the second-first (2-1) neural network model and the second-second (2-2) neural network model may be determined as the final second model (that is, second diagnosis assistance neural network model).

Meanwhile, although, for convenience of description, the case in which each sub-training process includes two sub-models has been described above with reference to FIG. 25, this is merely an example, and the present invention is not limited thereto. A neural network model trained in each sub-training process may only include a single neural network model or include three or more sub-models.

1.4.4 Parallel Diagnostic Process

According to an embodiment of the present invention, a diagnostic process for obtaining a plurality of diagnosis assistance information may be provided. The diagnostic process for obtaining the plurality of diagnosis assistance information may be implemented in the form of a parallel diagnosis assistance process including a plurality of diagnostic processes which are independent from each other.

1.4.4.1 Parallel Diagnostic Unit

According to an embodiment of the present invention, a diagnosis assistance process may be performed by a plurality of diagnostic modules. Each diagnosis assistance process may be independently performed.

Figure 26:
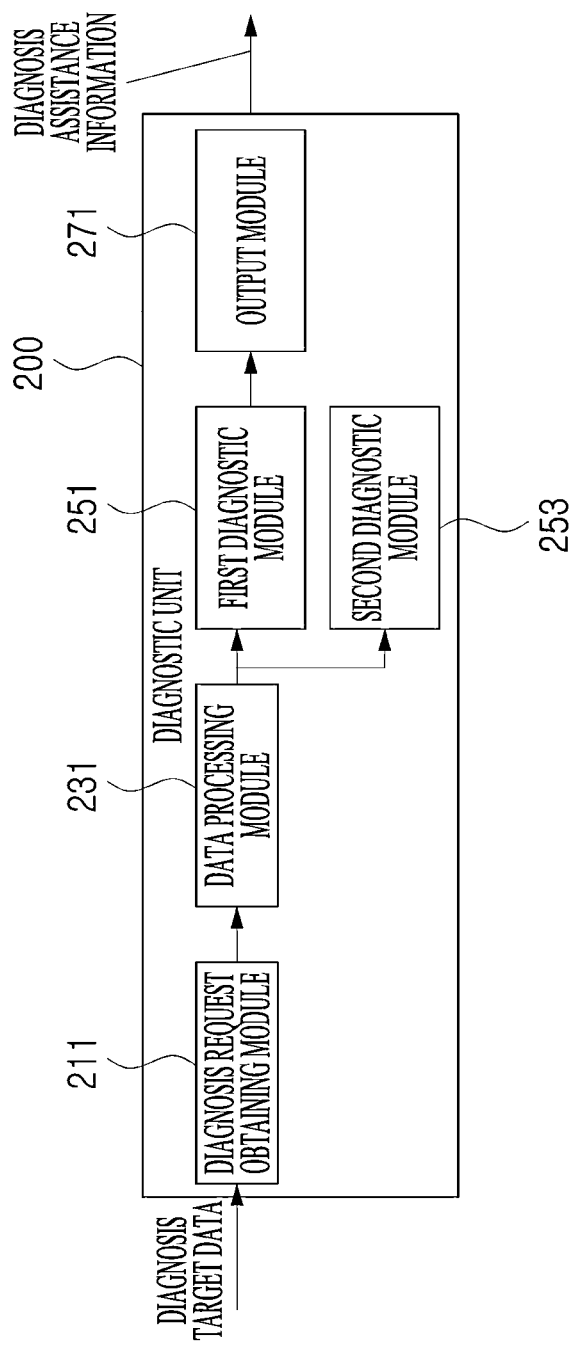
FIG. 26 is a block diagram for describing a diagnostic unit according to an embodiment of the present invention.

FIG. 26 is a block diagram for describing a diagnostic unit 200 according to an embodiment of the present invention.

Referring to FIG. 26, the diagnostic unit 200 according to an embodiment of the present invention may include a diagnosis request obtaining module 211, a data processing module 231, a first diagnostic module 251, a second diagnostic module 253, and an output module 271. Unless particularly mentioned otherwise, each module of the diagnostic unit 200 may operate similar to the diagnostic module of the diagnostic unit illustrated in FIG. 18.

In FIG. 26, the diagnosis request obtaining module 211, the data processing module 231, and the output module 271 have been illustrated as being common even when the diagnostic unit 200 includes a plurality of diagnostic modules, but the present invention is not limited to such a configuration. The diagnosis request obtaining module, the data processing module, and/or the output module may also be provided in plural. The plurality of diagnosis request obtaining modules, data processing modules, and/or output modules may also operate in parallel.

For example, the diagnostic unit 200 may include a first data processing module configured to perform first processing of an input diagnosis target image and a second data processing module configured to perform second processing of the diagnosis target image, the first diagnostic module may obtain a first diagnosis assistance information on the basis of the diagnosis target image on which the first processing has been performed, and the second diagnostic module may obtain a second diagnosis assistance information on the basis of the diagnosis target image on which the second processing has been performed. The first processing and/or second processing may be any one selected from image resizing, image color modulation, blur filter application, blood vessel emphasizing process, red-free conversion, partial region cropping, and extraction of some elements.

The plurality of diagnostic modules may obtain different diagnosis assistance information. The plurality of diagnostic modules may obtain diagnosis assistance information using different diagnosis assistance neural network models. For example, the first diagnostic module may obtain a first diagnosis assistance information related to the presence of an eye disease of a patient by using a first neural network model that predicts the presence of an eye disease of the patient, and the second diagnostic module may obtain a second diagnosis assistance information related to the presence of a systemic disease of a patient by using a second neural network model that predicts the presence of a systemic disease of the patient.

As a more specific example, the first diagnostic module may obtain a first diagnosis assistance information related to the presence of diabetic retinopathy of the patient using a first diagnosis assistance neural network model that predicts the presence of diabetic retinopathy of the patient, and the second diagnostic module may obtain a second diagnosis assistance information related to the presence of hypertension using a second diagnosis assistance neural network model that predicts the presence of hypertension of the patient.

1.4.4.2 Parallel Diagnostic Process

A diagnosis assistance process according to an embodiment of the present invention may include a plurality of sub-diagnostic processes. Each sub-diagnostic process may be performed using different diagnosis assistance neural network models. Each sub-diagnostic process may be performed in different diagnostic modules. For example, a first diagnostic module may perform a first sub-diagnostic process that obtains a first diagnosis assistance information through a first diagnosis assistance neural network model. Alternatively, a second diagnostic module may perform a second sub-diagnostic process that obtains a second diagnosis assistance information through a second diagnosis assistance neural network model.

The plurality of trained neural network models may output a predicted label or probability with diagnosis target data as input. Each neural network model may be provided in the form of a classifier and may classify input diagnosis target data as a predetermined label. In this case, the plurality of neural network models may be provided in forms of classifiers that are trained in relation to different characteristics. Each neural network model may classify diagnosis target data as described above in Section 3.4.2.

Meanwhile, a CAM may be obtained from each diagnosis assistance neural network model. The CAM may be obtained selectively. The CAM may be extracted when a predetermined condition is satisfied. For example, when a first diagnosis assistance information indicates that the patient is abnormal in relation to a first characteristic, a first CAM may be obtained from a first diagnosis assistance neural network model.

Figure 27:
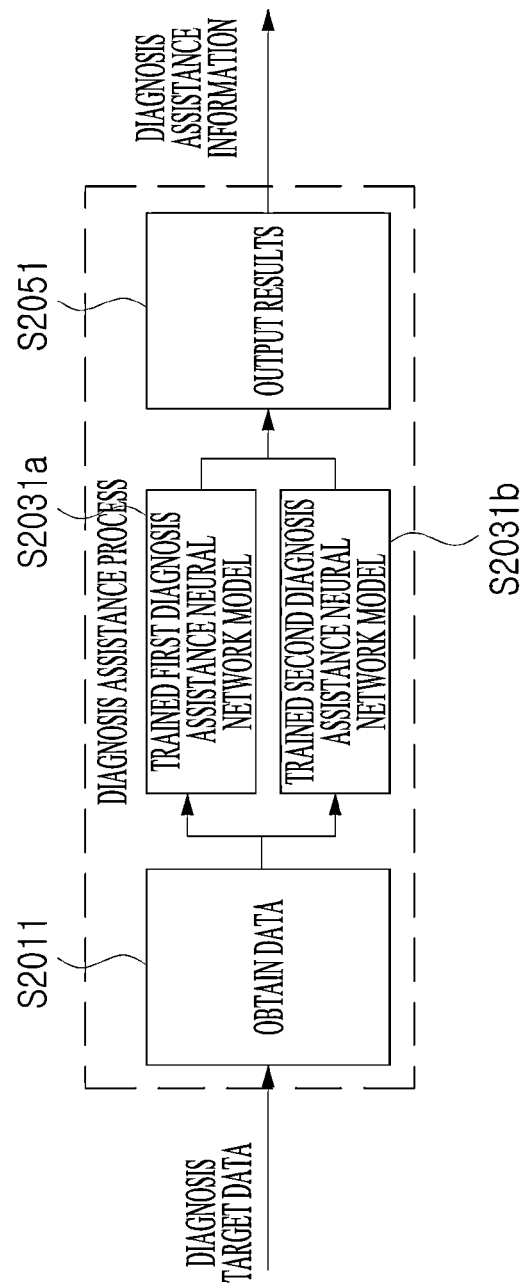
FIG. 27 is a view for describing a diagnosis assistance process according to an embodiment of the present invention.

FIG. 27 is a view for describing a diagnosis assistance process according to an embodiment of the present invention.

Referring to FIG. 27, a diagnosis assistance process according to an embodiment of the present invention may include obtaining diagnosis target data (S2011), using a first diagnosis assistance neural network model and a second diagnosis assistance neural network model (S2031a, S2031b), and obtaining diagnosis assistance information according to diagnosis target data (S2051). The diagnosis target data may be processed data.

The diagnosis assistance process according to an embodiment of the present invention may include obtaining a first diagnosis assistance information through the trained first diagnosis assistance neural network model and obtaining a second diagnosis assistance information through the trained second diagnosis assistance neural network model. The first diagnosis assistance neural network model and the second diagnosis assistance neural network model may obtain the first diagnosis assistance information and the second diagnosis assistance information respectively, on the basis of the same diagnosis target data.

For example, the first diagnosis assistance neural network model and the second diagnosis assistance neural network model may respectively obtain a first diagnosis assistance information related to the presence of macular degeneration of the patient and a second diagnosis assistance information related to the presence of diabetic retinopathy of the patient on the basis of a diagnosis target fundus image.

In addition, unless particularly described otherwise, the diagnosis assistance process described with reference to FIG. 27 may be implemented similar to the diagnosis assistance process described above with reference to FIG. 20.

1.4.4.3 Output of Diagnosis Assistance Information

According to an embodiment of the present invention, diagnosis assistance information may be obtained by a parallel diagnosis assistance process. The obtained diagnosis assistance information may be stored in the diagnostic device, server device, and/or client device. The obtained diagnosis assistance information may be transmitted to an external device.

A plurality of diagnosis assistance information may respectively indicate a plurality of labels predicted by a plurality of diagnosis assistance neural network models. The plurality of diagnosis assistance information may respectively correspond to the plurality of labels predicted by the plurality of diagnosis assistance neural network models. Alternatively, diagnosis assistance information may be information determined on the basis of a plurality of labels predicted by a plurality of diagnosis assistance neural network models. The diagnosis assistance information may correspond to the plurality of labels predicted by the plurality of diagnosis assistance neural network models.

In other words, a first diagnosis assistance information may be diagnosis assistance information corresponding to a first label predicted through a first diagnosis assistance neural network model. Alternatively, the first diagnosis assistance information may be diagnosis assistance information determined in consideration of a first label predicted through a first diagnosis assistance neural network model and a second label predicted through a second diagnosis assistance neural network model.

Meanwhile, CAM images obtained from a plurality of diagnosis assistance neural network models may be output. The CAM images may be output when a predetermined condition is satisfied. For example, in any one of the case in which a first diagnosis assistance information indicates that the patient is abnormal in relation to a first characteristic or the case in which a second diagnosis assistance information indicates that the patient is abnormal in relation to a second characteristic, a CAM image obtained from a diagnosis assistance neural network model, from which diagnosis assistance information indicating that the patient is abnormal has been output, may be output.

A plurality of diagnosis assistance information and/or CAM images may be provided to a user. The plurality of diagnosis assistance information or the like may be provided to the user through an output means of the diagnostic device or client device. The diagnosis assistance information may be visually output. This will be described in detail below in Section "5. User interface."

According to an embodiment of the present invention, diagnosis assistance information corresponding to a diagnosis target image may include level information. The level information may be selected from a plurality of levels. The level information may be determined on the basis of a plurality of diagnostic information and/or findings information obtained through neural network models. The level information may be determined in consideration of suitability information or quality information of a diagnosis target image. The level information may be determined in consideration of a class into which a diagnosis target image is classified by a plurality of neural network models. The level information may be determined in consideration of numerical values output from a plurality of neural network models.

For example, diagnosis assistance information obtained corresponding to a diagnosis target image may include any one level information selected from a first level information and a second level information. When at least one abnormal findings information or abnormal diagnostic information is obtained among of diagnostic information obtained through a plurality of neural network models, the first level information may be selected as the level information. When, of diagnostic information obtained through the neural network models does not include abnormal findings information or abnormal diagnostic information, the second level information may be selected as the level information.

A first level information may be selected as the level information when at least one numerical value among numerical values obtained through a neural network model exceeds a reference numerical value, and a second level information may be selected as the level information when all of the obtained numerical values are less than a reference numerical value. The first of level information may indicate that strong abnormal information is present in a diagnosis target image compared with the second of level information.

A third level information may be selected as the level information when it is determined using image analysis or a neural network model that the quality of a diagnosis target image is a reference quality or lower. Alternatively, diagnosis assistance information may include the third level information together with the first or second level information.

When diagnosis assistance information includes the first level information, a first user guide may be output through an output means. The first user guide may include matters corresponding to at least one of abnormal findings information or abnormal diagnostic information included in diagnosis assistance information. For example, the first user guide may indicate that a more precise test is required for a patient corresponding to abnormal information included in diagnosis assistance information. For example, the first user guide may indicate that secondary diagnosis (for example, diagnosis in a separate medical institution or a hospital transfer procedure) is required for the patient. Alternatively, the first user guide may indicate treatment required for the patient. As a specific example, when abnormal information on macular degeneration of the patient is obtained by diagnosis assistance information, the first user guide may include injection prescription and a guide on a hospital transfer procedure (for example, a list of hospitals to which transfer is possible) related to the patient.

When diagnosis assistance information includes the second level information, a second user guide may be output through an output means. The second user guide may include future care plans related to the patient corresponding to the diagnosis assistance information. For example, the second user guide may indicate the time of next visit and the next medical course.

When diagnosis target information includes the third level information, a third user guide may be output through an output means. The third user guide may indicate that a diagnosis target image has to be retaken. The third user guide may include information on the quality of the diagnosis target image. For example, the third user guide may include information on an artifact present in a diagnosis target image (for example, whether the artifact is a bright artifact or a dark artifact, or the degree thereof).

The first to third of level information may be output by an output unit of the client device or diagnostic device. Specifically, the first to third level information may be output through a user interface which will be described below.

1.4.5 Embodiment 2—Diagnosis Assistance System

A diagnosis assistance system according to an embodiment of the present invention may include a fundus image obtaining unit, a first processing unit, a second processing unit, a third processing unit, and a diagnostic information output unit.

According to an embodiment of the present invention, the diagnosis assistance system may include a diagnostic device. The diagnostic device may include a fundus image obtaining unit, a first processing unit, a second processing unit, a third processing unit, and/or a diagnostic information output unit. However, the present invention is not limited thereto, and each unit included in the diagnosis assistance system may be disposed at a proper position in a training device, a diagnostic device, a training diagnosis server, and/or a client device. Hereinafter, for convenience of description, the case in which a diagnostic device of a diagnosis assistance system includes a fundus image obtaining unit, a first processing unit, a second processing unit, a third processing unit, and a diagnostic information output unit will be described.

Figure 28:
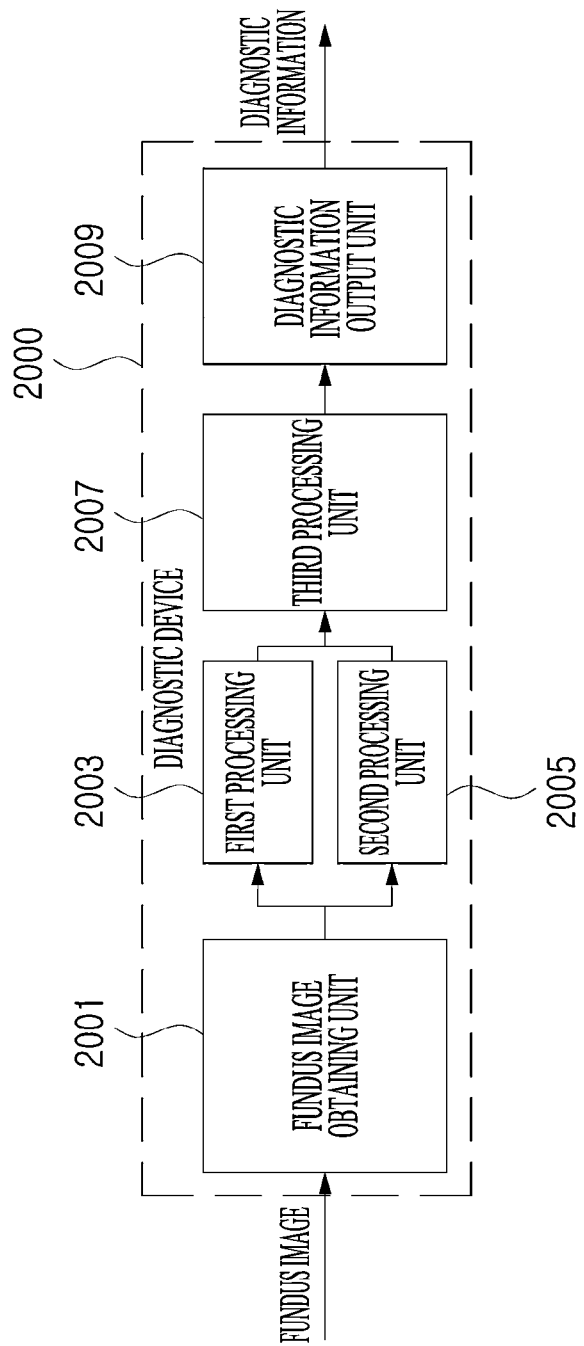
FIG. 28 is a view for describing a diagnosis assistance system according to an embodiment of the present invention.

FIG. 28 is a view for describing a diagnosis assistance system according to an embodiment of the present invention. Referring to FIG. 28, a diagnosis assistance system may include a diagnostic device, and the diagnostic device may include a fundus image obtaining unit, a first processing unit, a second processing unit, a third processing unit, and a diagnostic information output unit.

According to an embodiment of the present invention, a diagnosis assistance system that assists diagnosis of a plurality of diseases on the basis of a fundus image may include a fundus image obtaining unit configured to obtain a target fundus image which is a basis for acquiring diagnosis assistance information on a patient, a first processing unit configured to, for the target fundus image, obtain a first result related to a first finding of the patient using a first neural network model, wherein the first neural network model is trained on the basis of a first fundus image set, a second processing unit configured to, for the target fundus image, obtain a second result related to a second finding of the patient using a second neural network model, wherein the second neural network model is trained on the basis of a second fundus image set which is at least partially different from the first fundus image set, a third processing unit configured to determine, on the basis of the first result and the second result, diagnostic information on the patient, and a diagnostic information output unit configured to provide the determined diagnostic information to a user. Here, the first finding and the second finding may be used for diagnosing different diseases.

The first neural network model may be trained to classify an input fundus image as any one of a normal label and an abnormal label in relation to the first finding, and the first processing unit may obtain the first result by classifying the target fundus image as any one of the normal label and the abnormal label using the first neural network model.

The third processing unit may determine whether diagnostic information according to the target fundus image is normal information or abnormal information by taking the first result and the second result into consideration together.

The third processing unit may determine diagnostic information on the patient by assigning priority to the abnormal label so that accuracy of diagnosis is improved.

When the first label is a normal label related to the first finding, and the second label is a normal label related to the second finding, the third processing unit may determine the diagnostic information as normal. When the first label is not the normal label related to the first finding, or the second label is not the normal label related to the second finding, the third processing unit may determine the diagnostic information as abnormal.

The first finding may be related to an eye disease, and the first result may indicate whether the patient is normal in relation to the eye disease. The second finding may be related to a systemic disease, and the second result may indicate whether the patient is normal in relation to the systemic disease.

The first finding may be related to a first eye disease, and the first result may indicate whether the patient is normal in relation to the first eye disease. The second finding may be related to a second eye disease distinguished from the first eye disease, and the second result may indicate whether the patient is normal in relation to the second eye disease.

The first finding may be a finding for diagnosing a first eye disease, and the first result may indicate whether the patient is normal in relation to the first eye disease. The second finding may be a finding distinguished from the first finding for diagnosing the first eye disease, and the second result may indicate whether the patient is normal in relation to a second eye disease.

The first neural network model may include a first sub-neural network model and a second sub-neural network model, and the first result may be determined by taking a first predicted value predicted by the first sub-neural network model and a second predicted value predicted by the second sub-neural network model into consideration together.

The first processing unit may obtain a CAM related to the first label through the first neural network model, and the diagnostic information output unit may output an image of the CAM.

The diagnostic information output unit may output an image of the CAM when the diagnostic information obtained by the third processing unit is abnormal diagnostic information.

The diagnosis assistance system may further include a fourth processing unit configured to obtain quality information on the target fundus image, and the diagnostic information output unit may output the quality information on the target fundus image obtained by the fourth processing unit.

When it is determined in the fourth processing unit that the quality information on the target fundus image is at a predetermined quality level or lower, the diagnostic information output unit may provide information indicating that the quality information on the target fundus image is at the predetermined quality level or lower together with the determined diagnostic information to the user.

1.5 User Interface

According to an embodiment of the present invention, the above-described client device or diagnostic device may have a display unit for providing diagnosis assistance information to the user. In this case, the display unit may be provided to facilitate providing of diagnosis assistance information to the user and obtaining of feedback from the user.

As an example of the display unit, a display configured to provide visual information to the user may be provided. In this case, a graphical user interface for visually transferring diagnosis assistance information to the user may be used.

For example, in a fundus diagnosis assistance system that obtains diagnosis assistance information on the basis of a fundus image, a graphical user interface for effectively displaying obtained diagnosis assistance information and helping understanding of the user may be provided.

Figure 29:
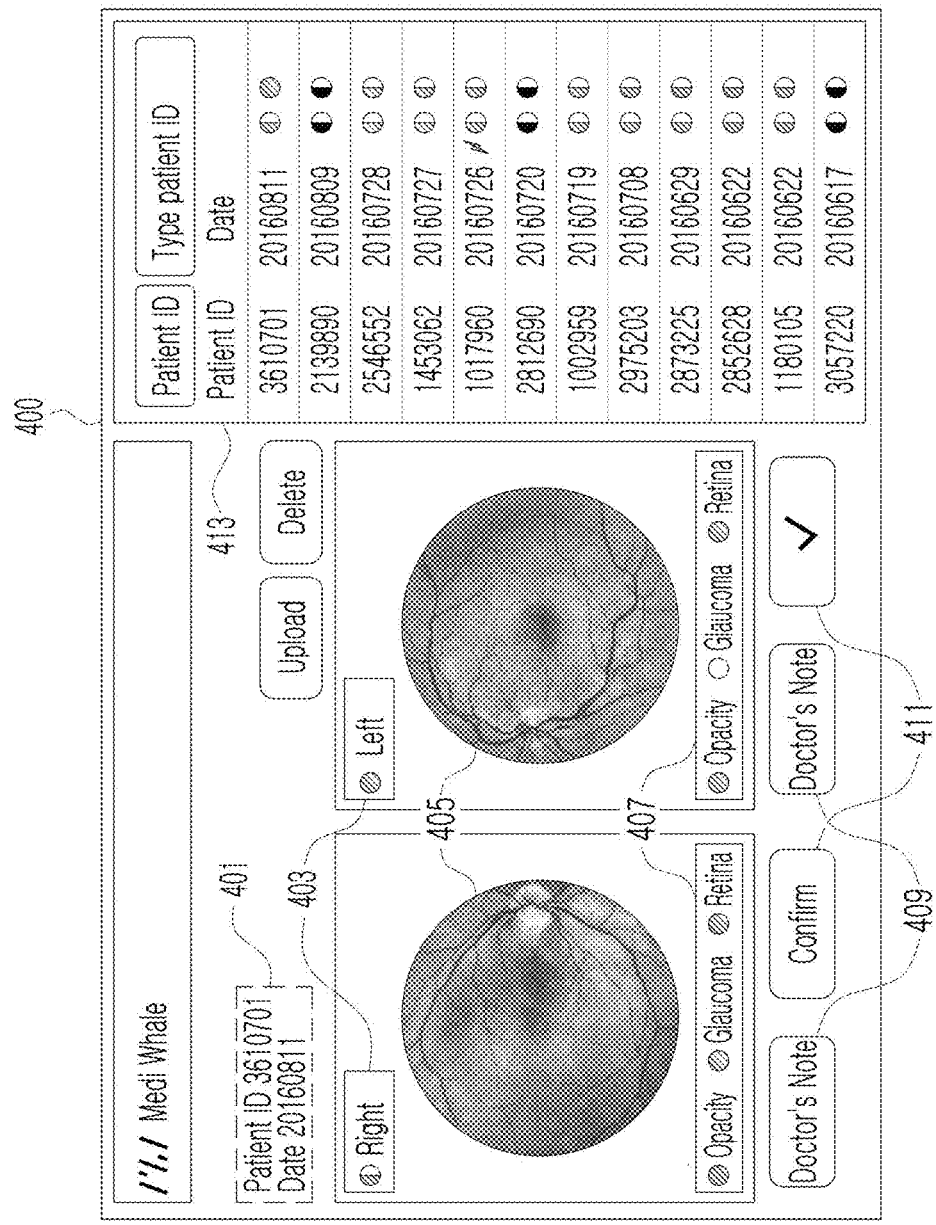
FIG. 29 is a view for describing a graphical user interface according to an embodiment of the present invention.
Figure 30:
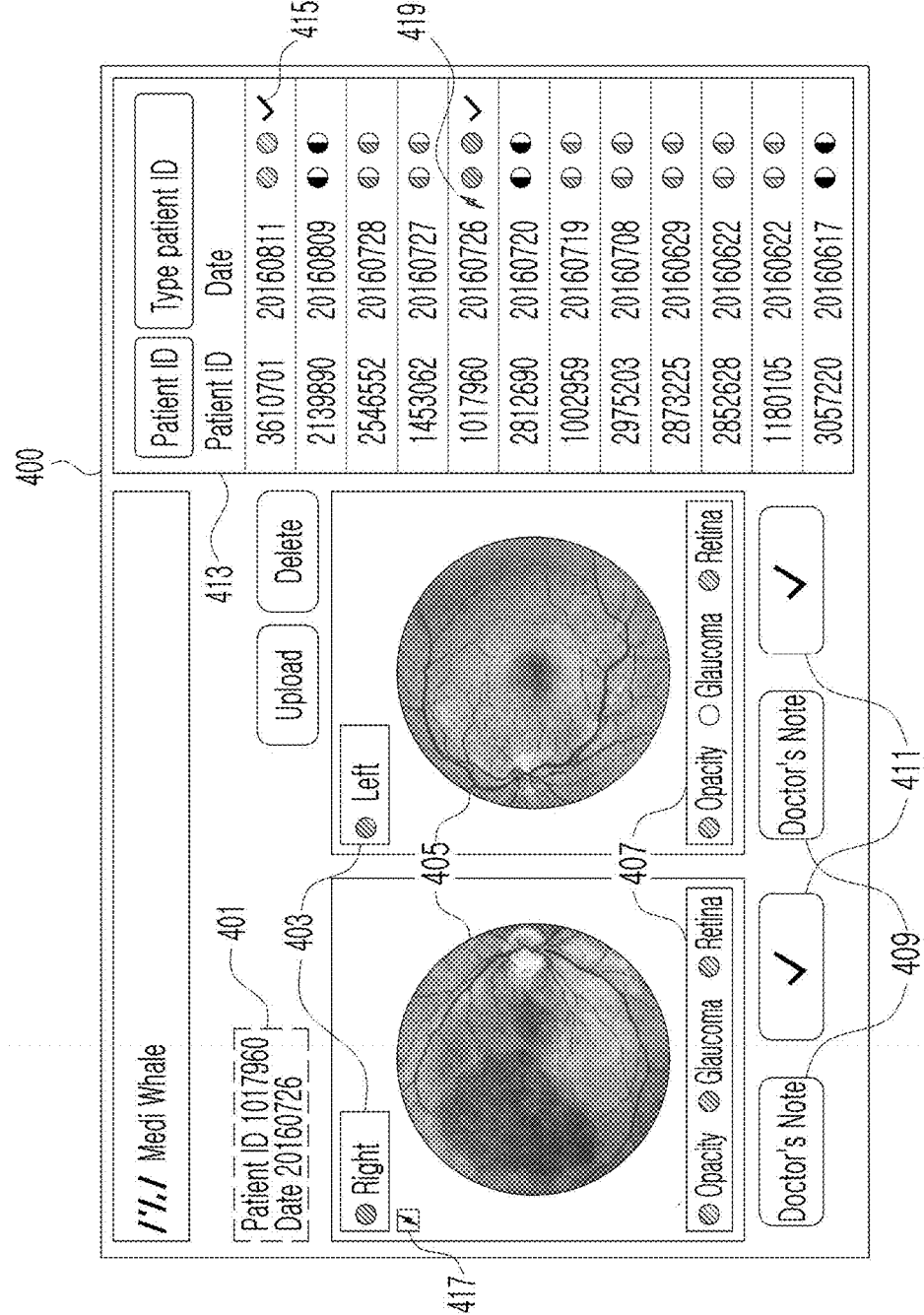
FIG. 30 is a view for describing a graphical user interface according to an embodiment of the present invention.

FIGS. 29 and 30 are views for describing a graphical user interface for providing diagnostic information to the user according to some embodiments of the present invention. Hereinafter, some embodiments of a user interface that may be used in a fundus diagnosis assistance system will be described with reference to FIGS. 29 and 30.

Referring to FIG. 29, a user interface according to an embodiment of the present invention may display identification information of a patient corresponding to a diagnosis target fundus image. The user interface may include a target image identification information display unit 401 configured to display identification information of a patient and/or imaging information (for example, the data and time of imaging) of a diagnosis target fundus image.

The user interface according to an embodiment of the present invention may include a fundus image display unit 405 configured to display a fundus image of the left eye and a fundus image of the right eye of the same patient. The fundus image display unit 405 may also display a CAM image.

The user interface according to an embodiment of the present invention may include a diagnostic information indicating unit 403 configured to indicate each of the fundus image of the left eye and the fundus image of the right eye as the image of the left eye or right eye and configured to display diagnostic information on each image and a diagnostic information indicator indicating whether the user has confirmed the diagnostic information.

Color of the diagnostic information indicator may be determined in consideration of diagnosis assistance information obtained on the basis of the target fundus image. The diagnostic information indicator may be displayed in a first color or a second color according to the diagnosis assistance information. For example, the diagnostic information indicator may be displayed in red when first to third diagnosis assistance information are obtained from a single target fundus image and when any one of the of diagnosis assistance information includes abnormal information (that is, indicates that there are abnormal findings), and the diagnostic information indicator may be displayed in green when all of the of diagnosis assistance information includes normal information (that is, indicates there are not abnormal findings).

The form of the diagnostic information indicator may be determined according to whether the user has confirmed the diagnostic information. The diagnostic information indicator may be displayed in a first form or a second form according to whether the user has confirmed the diagnostic information. For example, referring to FIG. 29, a diagnostic information indicator corresponding to a target fundus image that has been reviewed by the user may be displayed as a filled circle, and a diagnostic information indicator corresponding to a target fundus image that has not been reviewed by the user yet may be displayed as a half-circle.

The user interface according to an embodiment of the present invention may include a diagnostic information indicating unit 407 configured to indicate diagnosis assistance information. The diagnosis assistance information indicating may be disposed at each of the left eye image and the right eye image. The diagnosis assistance information indicating unit may indicate a plurality of findings information or diagnostic information.

The diagnosis assistance information indicating unit may include at least one diagnosis assistance information indicator. The diagnosis assistance information indicator may indicate corresponding diagnosis assistance information through a color change.

For example, when, in relation to a diagnosis target fundus image, a first diagnosis assistance information indicating the presence of the opacity of crystalline lens is obtained through a first diagnosis assistance neural network model, a second diagnosis assistance information indicating the presence of abnormal findings of diabetic retinopathy is obtained through a second diagnosis assistance neural network model, and a third diagnosis assistance information indicating the presence of abnormal findings of the retina is obtained through a third diagnosis assistance neural network model, the diagnostic information indicating unit may include first to third diagnosis assistance information indicators configured to respectively indicate the first diagnosis assistance information, the second diagnosis assistance information, and the third diagnosis assistance information.

As a more specific example, referring to FIG. 29, when, in relation to the left eye fundus image of the patient, a first diagnosis assistance information indicating that the obtained diagnosis assistance information is abnormal in terms of the opacity of crystalline lens is obtained, a second diagnosis assistance information indicating that the obtained diagnosis assistance information is normal (has no abnormal findings) in terms of diabetic retinopathy is obtained, and a third diagnosis assistance information indicating that the obtained diagnosis assistance information is abnormal (has abnormal findings) in terms of the retina is obtained, the diagnostic information indicating unit 407 may display a first diagnosis assistance information indicator with a first color, a second diagnosis assistance information indicator with a second color, and a third diagnosis assistance information indicator with the first color.

The user interface according to an embodiment of the present invention may obtain a user comment on a diagnosis target fundus image from the user. The user interface may include a user comment object 409 and may display a user input window in response to a user selection on the user comment object. A comment obtained from the user may also be used in updating a diagnosis assistance neural network model. For example, the user input window displayed in response to the user's selection on the user comment object may obtain a user's evaluation on diagnosis assistance information obtained through a neural network, and the obtained user's evaluation may be used in updating a neural network model.

The user interface according to an embodiment of the present invention may include a review indicating object 411 configured to display whether the user has reviewed each diagnosis target fundus image. The review indicating object may receive a user input indicating that the user's reviewing of each diagnosis target image has been completed, and display thereof may be changed from a first state to a second state. Referring to FIGS. 29 and 30, upon receiving a user input, the review indicating object may be changed from a first state in which a review request message is displayed to a second state indicating that the reviewing has been completed.

A diagnosis target fundus image list 413 may be displayed. In the list, identification information of the patient, the data on which the image has been captured, and the indicator 403 of whether the use has reviewed images of the both eyes may be displayed together.

In the diagnosis target fundus image list 413, a review completion indicator 415 indicating that the corresponding diagnosis target fundus image has been reviewed may be displayed. The review completion indicator 415 may be displayed when a user selection has been made for review indicating objects 411 of the both eyes of the corresponding images.

Referring to FIG. 30, the graphical user interface may include a poor quality warning object 417 indicating that there is an abnormality in the quality of a diagnosis target fundus image to the user when it is determined that there is an abnormality in the quality of the diagnosis target fundus image. The poor quality warning object 417 may be displayed when it is determined that the quality of the diagnosis target fundus image from the diagnostic unit is below a quality level at which appropriate diagnosis assistance information may be predicted from a diagnosis assistance neural network model (that is, a reference quality level).

In addition, referring to FIG. 30, the poor quality warning object 419 may also be displayed in the diagnosis target fundus image list 413.

2. Assistance of Heart Disease Diagnosis Using Fundus Image

2.1. Outline

According to the present specification, a system, a device, a method, and the like for assisting in heart disease (or cardiovascular disease or cerebrovascular disease; heart disease hereinafter) diagnosis using a fundus image may be provided. According to the present specification, a system, a device, a method, and the like for assisting in heart disease diagnosis that uses a neural network model and obtains diagnosis assistance information, which is helpful in heart disease diagnosis, on the basis of a fundus image may be provided.

Hereinafter, a system, a device, and a method for providing diagnosis assistance information related to a heart disease in order to assist in heart disease diagnosis using a fundus image will be described. The heart disease diagnosis assistance will be described below with reference to the foregoing description with reference to FIGS. 1 to 30.

For management of cardiovascular diseases, biomarkers which are used directly or indirectly for disease diagnosis may be used. For management of cardiovascular diseases, a method of managing an extent of risk of a disease in consideration of an index, a score, an indicator, or the like (hereinafter referred to as "score") related to the disease may be used. For diseases diagnosed in consideration of values such as scores, providing a score instead of the presence or absence of a disease may be more efficient because it allows a clinician to determine directly a patient's condition or treatment for the patient in consideration of the score.

The heart disease described herein may refer to cerebrovascular and cardiovascular diseases. The heart disease may refer to diseases related to the brain, heart, or blood vessels including a coronary artery disease such as a heart attack or angina, a coronary heart disease, an ischemic heart disease, a congestive heart failure, a peripheral vascular disease, cardiac arrest, a valvular heart disease, a cerebrovascular disease (for example, stroke, cerebral infarction, cerebral hemorrhage, or transient ischemic attack), and a renovascular disease.

The heart disease described herein may accompany complications. For example, the heart disease may accompany cardiac arrest, heart failure, stroke, aneurysm, peripheral arterial disease, renal failure, dementia, or skin ulcers as complications. The cardiovascular disease described herein may also refer to such complications.

According to a diagnosis assistance system, a diagnosis assistance device, a diagnosis assistance method, and the like described herein, diagnosis assistance information used in diagnosis of a disease may be provided. The diagnosis assistance information may include a parameter value related to a heart disease, a grade indicating an extent of risk of a heart disease, or information on the presence or absence of a heart disease.

A score which assists in diagnosis of a heart disease may be a score that may be measured from a testee or a score that is calculated by combining values measured from a testee and/or pieces of personal information of the testee. A score used in diagnosis of a heart disease may be a score proposed by a known cardiovascular/cerebrovascular disease prediction model. A score which assists in diagnosis of a heart disease may be an aortic valve calcification index indicating a degree of aortic valve calcification.

A score which assists in diagnosis of a heart disease may be a coronary artery calcium score. The score may be an arteriosclerosis risk score. A score which assists in diagnosis of a heart disease may be a carotid intima-media thickness (CIMT) value. The score may be Framingham risk score. A score which assists in diagnosis of a heart disease may be a value related to at least one factor included in the Framingham risk score. The score may be the QRISK score. A score which assists in diagnosis of a heart disease may be a value according to atherosclerotic cardiovascular disease (AS-CVD). The score may be a score according to the European Systematic Coronary Risk Evaluation (SCORE).

For example, the coronary artery calcium score may be used as an index for determining coronary artery calcification. When the plaque is deposited in the blood vessels and thus coronary artery calcification occurs, the artery narrows and the calcification causes various heart diseases such as coronary heart disease, cardiac arrest, angina, and ischemic heart disease. Accordingly, the coronary artery calcium index may be used as the basis for determining an extent of risk of various heart diseases. For example, when a value of the coronary artery calcium score is high, the extent of risk of the coronary artery disease may be determined to be high.

Particularly, as compared with factors indirectly related to heart diseases such as a smoking status, age, and gender, the coronary artery calcium score is directly related to a heart disease, the coronary artery disease (aortic valve calcification) in particular. Thus, the coronary artery calcium score may be used as an effective biomarker for heart health.

Also, diagnosis assistance information such as a score which assists in diagnosis of a heart disease may be used as criteria for selecting a specific medical treatment or prescription target. For example, the coronary artery calcium score may be used in selecting a subject of a close examination of coronary artery. In addition, for example, the coronary artery calcium score may be used in selecting a subject to be prescribed with an anti-hyperlipidemic drug. The coronary artery calcium score may be used as criteria for prescribing an anti-hyperlipidemic drug such as statin.

As another example, a Framingham risk score value or a value used for calculating the Framingham risk score may be obtained and provided as diagnosis assistance information for determining an extent of risk of a coronary artery disease. For example, the extent of risk of the coronary artery disease may be determined to be higher as the Framingham risk score is higher.

As still another example, the CIMT value may be obtained and provided as diagnosis assistance information for determining an extent of risk of cerebral infarction or acute myocardial infarction. For example, the extent of risk of cerebral infarction or acute myocardial infarction may be determined to be higher as the CIMT value is higher.

A grade which assists in diagnosis of a heart disease may be at least one grade indicating an extent of risk of a heart disease. For example, when a score or the like may be used in diagnosis of a disease, a grade may be used instead of or along with the score or the like.

The diagnosis assistance information may include a heart disease diagnosis assistance score and/or a heart disease diagnosis assistance grade. The grade may include a normal grade which indicates that a testee is normal in relation to a target heart disease and an abnormal grade which indicates that a testee is abnormal in relation to a target heart disease. Alternatively, the grade may include a plurality of grades which indicate an extent of risk of a target heart disease for a testee. This will be described in more detail below in "Method of assisting in heart disease diagnosis" section.

The score or the like described herein may be used in diagnosis of a disease. The score or the like may be used in diagnosis of a current status of a patient and/or prognosis of a disease. Generating and providing of diagnosis assistance information including the score or the like will be described in more detail below in "Diagnosis assistance information" section.

According to the diagnosis assistance system, diagnosis assistance device, diagnosis assistance method, and the like described herein, heart disease diagnosis assistance information may be obtained prior to diagnosis of various cardiovascular diseases (for example, a coronary artery disease). Also, according to an embodiment, the obtained heart disease diagnosis assistance information may be used in pre-diagnosis for selecting a subject of a close examination prior to a close examination for a heart disease. This will be described in more detail below in "Provision of diagnosis assistance information" section.

Hereinafter, although, for convenience, description will be given on the basis of the case of diagnosis of a cardiovascular disease, the scope of the invention disclosed herein is not limited thereto. The diagnosis assistance method, diagnosis assistance device, diagnosis assistance system, and the like which will be described below may similarly apply to all cases in which, for assisting in diagnosis of a specific disease that may be diagnosed in consideration of a numerical value or a grade, a numerical value or a grade is obtained as diagnosis assistance information related to the corresponding disease from a fundus image using a neural network model.

2.2 System and Device for Assisting in Diagnosis of Heart Disease

Hereinafter, a diagnosis assistance system, a diagnosis assistance device, and the like for obtaining information on the presence or absence of a heart disease or information that becomes a basis for determining the presence or absence of the heart disease on the basis of a fundus image will be described. Particularly, a system, a device, and the like for assisting in diagnosis of a heart disease by constructing a neural network model for predicting heart disease-related information using deep learning, training the constructed model, and predicting information using the trained model will be described.

2.2.1 System

According to the present specification, a heart disease diagnosis assistance system for obtaining heart disease diagnosis assistance information on the basis of a fundus image may be provided. The heart disease diagnosis assistance system or a device constituting the same may perform the diagnosis assistance and/or heart disease diagnosis assistance described throughout the present specification.

The heart disease diagnosis assistance system and/or heart disease diagnosis assistance device and the like disclosed herein may be implemented similarly as the diagnosis assistance system and/or diagnosis assistance device described above with reference to FIGS. 1 to 9. In other words, the diagnosis assistance system described above with reference to FIGS. 1 to 9 may also be implemented as the heart disease diagnosis assistance system which will be described below.

For example, the heart disease diagnosis assistance system may include a training device, a diagnostic device, and a client device, and each of the system and devices may operate similarly as the diagnosis assistance system described above with reference to FIG. 1. The training device may train a neural network model for assisting in heart disease diagnosis, the diagnostic device may perform assistance in heart disease diagnosis using the trained neural network model, and the client device may obtain a fundus image, obtain heart disease diagnosis assistance information generated on the basis of the fundus image, and provide the diagnosis assistance information to a user.

As another example, the heart disease diagnosis assistance system may include a diagnostic device and a client device. In this case, the diagnostic device may serve as a training device and/or a server device. The diagnostic device and/or the client device may perform the assistance in heart disease diagnosis described herein.

As still another example, the heart disease diagnosis assistance system may include a mobile device. The mobile device may perform all or some of operations of the above-described training device, diagnostic device, and/or client device. The mobile device may perform the assistance in heart disease diagnosis described herein.

The configuration and operation of each device will be described in more detail in "Device" section.

Some examples of an image management system have been described above, but it is apparent from the description related to the diagnosis assistance system given with reference to FIGS. 1 to 9 that, even in the case not described above, the heart disease diagnosis assistance system may be similarly configured.

2.2.2 Device

According to the present specification, a diagnosis assistance device may be provided. The diagnosis assistance device may include a heart disease diagnosis assistance unit. The heart disease diagnosis assistance unit may perform the assistance in heart disease diagnosis described herein.

The diagnosis assistance device may obtain heart disease diagnosis assistance information on the basis of a fundus image. The diagnosis assistance device may be one or more devices including a heart disease diagnosis assistance unit. The diagnosis assistance device may be the above-described training device, diagnostic device, or client device. The diagnosis assistance device may be a mobile device. The diagnosis assistance device may be a server device. The diagnosis assistance device may include a heart disease diagnosis assistance unit configured to perform the assistance in heart disease diagnosis described herein. The diagnosis assistance device may be included in a device or a unit described herein.

According to the present specification, the diagnosis assistance devices 10 and 20 described above with reference to FIGS. 1 to 9 and devices included therein may assist in heart disease diagnosis on the basis of a fundus image. The diagnosis assistance devices 10 and 20 described above with reference to FIGS. 1 to 9 and the devices included therein may perform an operation related to the heart disease diagnosis assistance in addition to performing the functions described above with reference to FIGS. 1 to 9. Hereinafter, some examples of a device for assisting in heart disease diagnosis will be described with reference to FIGS. 1 to 9.

For example, the training device 1000 may assist in heart disease diagnosis. The training device 1000 may include a heart disease diagnosis assistance unit configured to assist in heart disease diagnosis. The heart disease diagnosis assistance unit of the training device 1000 may train a neural network model which predicts heart disease diagnosis assistance information on the basis of a fundus image. The heart disease diagnosis assistance unit of the training device 1000 may assist in heart disease diagnosis by training the neural network model which predicts heart disease diagnosis assistance information on the basis of a fundus image.

The training unit 100 of the training device 1000 may serve as the heart disease diagnosis assistance unit configured to assist in heart disease diagnosis. The training unit 100 may include a heart disease diagnosis assistance unit. The processor 1050 or the training module 1053 of the training device 1000 may serve as the heart disease diagnosis assistance unit. The processor 1050 or the training module 1053 of the training device 1000 may include a heart disease diagnosis assistance unit.

The control unit 1200 of the training device 1000 may perform the assistance in heart disease diagnosis described herein. The control unit 1200 may include a heart disease diagnosis assistance unit. The memory unit 1100 (or the volatile memory 1030, the nonvolatile memory 1010, or the mass storage device 1070) of the training device 1000 may store a neural network model for assisting in heart disease diagnosis. The communication unit 1300 of the training device 1000 may transmit a trained model or information for driving the trained model to an external device. Alternatively, the training device 1000 may obtain information required for training a neural network model from an external device via the communication unit 1300.

As another example, the diagnostic device 2000 may assist in heart disease diagnosis. The diagnostic device 2000 may include a heart disease diagnosis assistance unit configured to assist in heart disease diagnosis. The heart disease diagnosis assistance unit of the diagnostic device 2000 may use a trained neural network model to obtain heart disease diagnosis assistance information related to a target fundus image. The heart disease diagnosis assistance unit of the diagnostic device 2000 may obtain heart disease diagnosis assistance information using a neural network model which outputs heart disease diagnosis assistance information on the basis of a fundus image.

The diagnostic unit 200 of the diagnostic device 2000 may serve as a heart disease diagnosis assistance unit configured to assist in heart disease diagnosis. The diagnostic unit 200 may include a heart disease diagnosis assistance unit. The processor 2050 or the diagnostic module 2053 may serve as a heart disease diagnosis assistance unit. The processor 2050 or the diagnostic module 2053 of the diagnostic device 2000 may include a heart disease diagnosis assistance unit.

The control unit 2200 of the diagnostic device 2000 may assist in heart disease diagnosis using a trained neural network model. The control unit 2200 of the diagnostic device 2000 may serve as a heart disease diagnosis assistance unit. The control unit 2200 of the diagnostic device 2000 may include a heart disease diagnosis assistance unit. The memory unit 2100 of the diagnostic device 2000 may store a trained neural network model for assistance in heart disease diagnosis. The memory unit 2100 of the diagnostic device 2000 may include a heart disease diagnosis assistance unit. The diagnostic device 2000 may communicate with an external device using the communication unit 2300. The diagnostic device 2000 may obtain a diagnosis target image from an external device or transmit diagnosis assistance information to an external device by using the communication unit 2300. The diagnostic device 2000 may obtain a trained neural network model or information required for using the trained neural network model from an external device (for example, a training device) by using the communication unit 2300.

As still another example, the client device 3000 may assist in heart disease diagnosis. The client device 3000 may include a heart disease diagnosis assistance unit configured to assist in heart disease diagnosis. The heart disease diagnosis assistance unit of the client device 3000 may train a neural network model, obtain diagnosis assistance information using a neural network model, or provide data (for example, fundus images) required for driving the neural network model. The client device 3000 may obtain information required for assisting in heart disease diagnosis from a user or provide heart disease diagnosis assistance information to the user.

The control unit 3200 of the client device 3000 may include a heart disease diagnosis assistance unit. The control unit 3200 of the client device 3000 may serve as a heart disease diagnosis assistance unit. The processor of the client device 3000 may include a heart disease diagnosis assistance unit or perform assistance in heart disease diagnosis. As yet another example, a server device 4000 may assist in heart disease diagnosis.

The server device 4000 may include a heart disease diagnosis assistance unit configured to assist in heart disease diagnosis. The heart disease diagnosis assistance unit of the server device 4000 may store, train, or drive a neural network model. The server device 4000 may store data (for example, fundus image data) required for storing, training, or driving a neural network model which assists in heart disease diagnosis. The server device 4000 may store user information used in assisting in heart disease diagnosis.

2.3 Method of Assisting in Heart Disease Diagnosis 2.3.1 Process of Assisting in Heart Disease Diagnosis Assisting in heart disease diagnosis may include training a heart disease diagnosis assistance neural network model using a training target fundus image and obtaining heart disease diagnosis assistance information on the basis of a diagnosis target fundus image by using the trained heart disease diagnosis assistance neural network model.

The heart disease diagnosis assistance neural network model may be a multi-layer neural network model which outputs a diagnosis assistance result related to a heart disease. The heart disease diagnosis assistance neural network model may be a convolutional neural network model which obtains diagnosis assistance information on the basis of a fundus image.

The heart disease diagnosis assistance neural network model may be provided in the above-described ensemble form. For example, the heart disease diagnosis assistance neural network model may include a first sub-neural network model which outputs a first result and a second sub-neural network model which outputs a second result, and obtained diagnosis assistance information may be determined in consideration of both the first result and the second result. Training of the heart disease diagnosis assistance neural network model provided in the ensemble form or assisting in diagnosis using such a neural network model may be performed similarly as the above description.

Assisting in heart disease diagnosis may be taken into consideration by being mainly classified into training a heart disease diagnosis assistance neural network model and assisting in diagnosis using the trained heart disease diagnosis assistance neural network model.

The training of the heart disease diagnosis assistance neural network model may include obtaining training data and training a heart disease diagnosis assistance neural network model on the basis of the obtained training data.

The obtaining of the training data may include obtaining fundus image training data. The obtained fundus image training data may be fundus image training data labeled with heart disease diagnosis information. This will be described in more detail below in "Obtaining fundus images" section.

In some cases, the training of the heart disease diagnosis assistance model may include converting (or pre-processing) the obtained fundus image. The heart disease diagnosis assistance neural network model may be trained using the converted fundus image. The fundus image may be converted or pre-processed into a form that is more suitable for obtaining heart disease diagnosis assistance information. This will be described in more detail below in "Fundus image pre-processing" section.

The training of the heart disease diagnosis assistance neural network model may include multiple repetitions of predicting a result for a unit training data, comparing the predicted result with a label, and updating a neural network model. This will be described in more detail below in "Training heart disease diagnosis assistance neural network model" section.

The assisting in the heart disease diagnosis using the neural network model may include obtaining a diagnosis target fundus image and obtaining heart disease diagnosis assistance information from the diagnosis target fundus image by using the trained neural network model.

The obtaining of the diagnosis target fundus image may be performed by an imaging unit or may include obtaining an image obtained by imaging by a separate imaging device.

The assisting in the heart disease diagnosis may also include pre-processing a diagnosis target fundus image. In this case, the obtained diagnosis target fundus image may be pre-processed. The obtaining of the heart disease diagnosis assistance information may include obtaining diagnosis assistance information related to the pre-processed fundus image by using the trained neural network model. This will be described in more detail below in "Fundus image pre-processing" section.

The pre-processing of the diagnosis target fundus image may include converting or pre-processing a diagnosis target fundus image into a form that is more suitable for obtaining heart disease diagnosis assistance information. This will be described in more detail below in "Fundus image pre-processing" section.

The obtaining of the heart disease diagnosis assistance information using the trained neural network model may include obtaining disease presence/absence information, numerical value information, grade information, and the like that may be used in heart disease diagnosis. This will be described in more detail below in "Assisting in heart disease diagnosis using neural network model" section.

Figure 31:
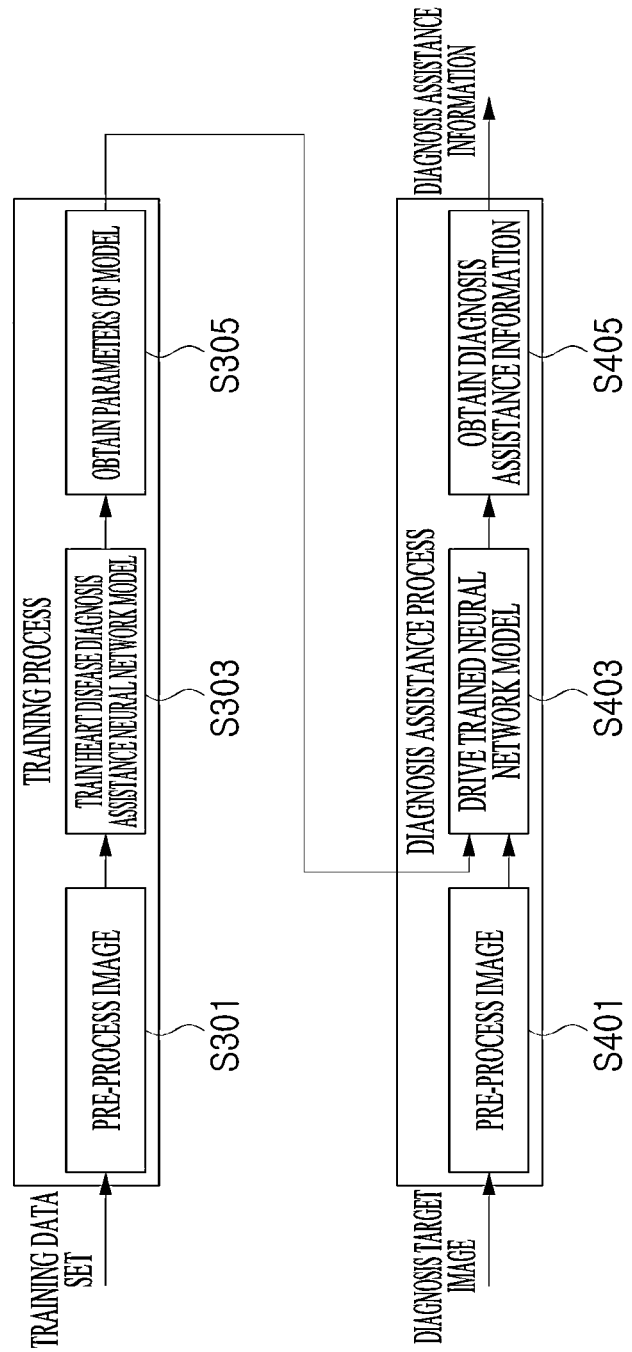
FIG. 31 is a view for describing fundus image area division according to an embodiment of the present invention.

FIG. 31 is a view for describing an example of a method of assisting in heart disease diagnosis. Referring to FIG. 31, a diagnosis assistance process according to an embodiment of the present invention may include a training process which includes pre-processing an image (S301), training a heart disease diagnosis assistance neural network model on the basis of the pre-processed image (S303), and obtaining parameters of the trained heart disease diagnosis assistance neural network model (S305) and a diagnosis assistance process which includes obtaining and pre-processing a diagnosis target image (S401), driving the trained heart disease diagnosis assistance neural network model (S403), and obtaining heart disease diagnosis assistance information (S405).

More specifically, the process of training the heart disease diagnosis assistance neural network model may include a pre-processing step in which a fundus image is pre-processed so that prediction accuracy of heart disease diagnosis information is improved and a training process in which the heart disease diagnosis assistance neural network model is trained using the pre-processed fundus image. The training process may be performed by the above-described training device.

The diagnosis assistance process using the heart disease diagnosis assistance neural network model may include a pre-processing process in which an input target fundus image is pre-processed and a diagnosis assistance process in which heart disease diagnosis is assisted using the pre-processed fundus image. The diagnosis assistance process may be performed by the above-described diagnostic device or server device.

Hereinafter, some examples of the training of the heart disease diagnosis assistance neural network model and diagnosis assistance using the heart disease diagnosis assistance neural network model will be described. First, image obtaining and conversion (or pre-processing) of the image which are common to the training and diagnosis assistance processes will be described, and then details unique to each process will be described.

2.3.2 Obtaining Fundus Images

A fundus image may be obtained for training of a heart disease diagnosis assistance neural network model or for assisting in heart disease diagnosis using the neural network model.

As described above in "Obtaining image data" section, a fundus image may be obtained using various devices including a non-mydriatic fundus camera. As described above, the fundus image may be obtained in various formats including JPG, PNG, and DCM.

Hereinafter, description will be given on the basis of the case in which a heart disease diagnosis assistance neural network model is trained to output heart disease diagnosis assistance information on the basis of a fundus image and heart disease diagnosis assistance information of a testee is obtained on the basis of a target fundus image.

In the present specification, fundus images used in training of a heart disease diagnosis assistance neural network model and obtaining of heart disease diagnosis assistance information through the heart disease diagnosis assistance neural network model may be understood as images in various forms that are obtained by imaging elements of a fundus. For example, fundus images may include an optical coherence tomography (OCT) image, an OCT angiography image, or a fundus angiography image. Also, various forms of fundus images described above in "Obtaining image data" section may be used as the fundus images described herein. For example, a panorama fundus image, a wide fundus image, a red-free fundus image, an infrared fundus image, an autofluorescence fundus image, or the like may be used as the fundus images described herein.

In other words, the heart disease diagnosis assistance neural network model which will be described below may be trained using an OCT image, an OCT angiography image, or a fundus angiography image. Alternatively, the heart disease diagnosis assistance neural network model which will be described below may be trained using a panorama fundus image, a wide fundus image, a red-free fundus image, an infrared fundus image, an autofluorescence fundus image, or the like.

Also, the heart disease diagnosis assistance neural network model which will be described below may output heart disease diagnosis assistance information on the basis of a target OCT image, a target OCT angiography image, or a target fundus angiography image obtained from a testee.

In other words, the heart disease diagnosis assistance neural network model which will be described below may be trained using a panorama fundus image, a wide fundus image, a red-free fundus image, an infrared fundus image, and an autofluorescence fundus image.

For example, a fundus image for training a heart disease diagnosis assistance neural network model may be obtained.

In a training step, a fundus image may be a fundus image obtained by imaging within a predetermined period from a point in time at which heart disease diagnosis information is obtained. For example, a fundus image may be a fundus image obtained by imaging about a year after a patient's heart computerized tomography (CT) is taken to obtain a coronary artery calcium score. The fundus image may be obtained together with heart disease diagnosis information.

The fundus image used in the training step may be a fundus image labeled with at least one piece of diagnosis assistance information.

The diagnosis assistance information which is labeled on the fundus image may be disease information which indicates the presence or absence of a disease. For example, a fundus image may be labeled with coronary artery disease information which indicates whether a patient corresponding to the image has a coronary artery disease.

Also, for example, a fundus image may be labeled with normality information which indicates whether a patient is normal in relation to a target disease (or whether a patient belongs to a risk group for the target disease). For example, a fundus image may be labeled with risk information which indicates whether a patient belongs to a risk group for a coronary artery disease.

Whether the patient belongs to the risk group may have been determined according to a coronary artery calcium score of the patient. For example, when the coronary artery calcium score is 10 or lower, the patient may be determined as belonging to a normal group. A fundus image obtained by imaging the patient may be labeled with a normal label. When the coronary artery calcium score is 11 or higher, the patient may be determined as belonging to a risk group or an abnormal group. A fundus image obtained by imaging the patient may be labeled with a risk label or an abnormal label.

The diagnosis assistance information with which the fundus image is labeled may be grade information which indicates a degree of a disease. For example, a fundus image may be labeled with a grade (for example, Grade A to Grade E) which indicates an extent of risk of a coronary artery disease for a patient corresponding to the image.

The grade indicating a degree of a disease may be provided with reference to a grade system which is generally used in order to indicate an extent of risk of a target disease. For grades indicating a degree of a disease, the numbers of the grades and/or a numerical value range indicated by each grade may be set according to a user's input.

According to an embodiment, a grade indicating a degree of a disease may be selected from grades generated using a neural network model or an algorithm provided in advance. The grade indicating a degree of a disease may be selected from grades set using a neural network model or an algorithm by taking at least one user input into consideration. In a specific example, a grade indicating a degree of a disease may be determined on the basis of diagnosis assistance information predicted from a fundus image by a neural network model and a prescription or grade classification selected by a user on the basis of the diagnosis assistance information.

The diagnosis assistance information with which the fundus image is labeled may be numerical value information which indicates a degree of a disease. A fundus image may be labeled with a score value used in diagnosis of a target disease. For example, a fundus image may be labeled with a coronary artery calcium score obtained by taking a heart CT of a patient corresponding to the image. For example, a fundus image may be labeled with a numerical value, such as 0, 5, 17, 134, or 587, as a coronary artery calcium score of the patient.

FIG. 32 is a view for describing heart disease diagnosis assistance information with which a fundus image is labeled. Referring to FIG. 32, as the heart disease diagnosis assistance information with which a fundus image is labeled, grade information which indicates an extent of risk of a target disease, score information which is used in diagnosis of the target disease, and/or disease presence/absence information (or risk information) which indicates whether a testee belongs to a risk group for the target disease may be matched with each other.

Referring to FIG. 32(a), disease presence/absence information, which includes risk information indicating that a testee belongs to a risk group for a target disease and normality information indicating that a testee belongs to a normal group, may be matched with numerical values, that is, score information, used in diagnosis of a target disease. As a specific example, referring to FIG. 32(a), normality information may be matched with score information corresponding to numerical values ranging from 0 to 10. Risk information (or abnormality information) may be matched with score information corresponding to numerical values higher than 10.

Referring to FIG. 32(b), heart disease diagnosis assistance information may be selected from Grade A which indicates that a patient is normal, Grade B which indicates that a patient has a mild risk of a target heart disease, Grade C which indicates that the patient has a moderate risk of the target heart disease, Grade D which indicates that the patient has a serious risk of the target heart disease, and Grade E which indicates that the patient has a severe risk of the target heart disease.

According to an embodiment, Grade A may indicate that a risk of a coronary artery disease is extremely low. Grade B may indicate that the risk of a coronary artery disease is low. Grade C may indicate that the risk of a coronary artery disease is slight. Alternatively, Grade C may indicate a slight possibility of coronary artery stenosis. Grade D may indicate that the risk of a coronary artery disease is high. Grade D may indicate a strong possibility of coronary artery stenosis. Grade E may indicate wide-range coronary artery calcification. Grade E may indicate the possibility of at least one coronary artery stenosis.

Referring to FIG. 32(b), as heart disease diagnosis assistance information, grade information including Grade A to Grade E which indicate an extent of risk of a target disease may be matched with score information used in diagnosis of the target disease.

For example, a grade label (or grade information) may be matched with a score range or a score label (or score information). For example, Grade A label may be matched with a score label corresponding to a score (numerical value range) of 0, Grade B label may be matched with a score label corresponding to a score ranging from 1 to 10, Grade C label may be matched with a score label corresponding to a score ranging from 10 to 100, Grade D label may be matched with a score label corresponding to a score ranging from 100 to 400, and Grade E label may be matched with a score label corresponding to a score of 400 or higher.

For example, a grade label may be determined on the basis of a coronary artery calcium score measured through a heart CT. Referring to FIG. 32(b), when the coronary artery calcium score of a patient is 0, the patient may be determined as being normal in relation to a coronary artery disease, and the Grade A label may be determined as a grade label to be assigned to a fundus image. When the coronary artery calcium score of a patient ranges from 1 to 10, the patient may be determined as having a mild risk of a coronary artery disease, and the Grade B label may be determined as a grade label to be assigned to a fundus image. When the coronary artery calcium score of a patient ranges from 10 to 100, the patient may be determined as having a moderate risk of a coronary artery disease, and the Grade C label may be determined as a grade label to be assigned to a fundus image. When the coronary artery calcium score of a patient ranges from 100 to 400, the patient may be determined as having a serious risk of a coronary artery disease, and the Grade D label may be determined as a grade label to be assigned to a fundus image. When the coronary artery calcium score of a patient is higher than 400, the patient may be determined as having a severe risk of a coronary artery disease, and the Grade E label may be determined as a grade label to be assigned to a fundus image.

Referring to FIGS. 32(a) and 32(b), the disease presence/absence information, grade information, and/or score information may be matched with each other. The matching relationship between the pieces of heart disease diagnosis assistance information described with reference to FIG. 32 may be used in training a neural network model, comparing or providing pieces of diagnosis assistance information, and the like.

Meanwhile, the grade or disease presence/absence information indicating an extent of risk may be determined differently according to additional factors such as gender and age of a testee. In other words, the matching relationship illustrated in FIG. 32 may be determined differently according to the gender, age, or the like of a testee.

As another example, a target fundus image for heart disease diagnosis using a neural network model may be obtained. The obtaining of the fundus image may be performed by a client device, an imaging unit, a mobile device, or the like. The above description may apply to the obtaining of the fundus image.

A fundus image used in a diagnosis assistance step may be a fundus image obtained within a predetermined period from a point in time at which heart disease diagnosis is performed. For example, a target fundus image which is the basis for diagnosis assistance may be an image obtained by imaging about a year after heart disease diagnosis is performed.

In the diagnosis assistance process, the obtained fundus image may be a diagnosis target fundus image. Together with the diagnosis target fundus image, identification information for identifying a testee or additional information that may be used in diagnosis of a target disease may be obtained. For example, relevant information such as gender, age, and smoking status of a patient may be obtained together with a target fundus image.

2.3.3 Fundus Image Reconstruction

A fundus image may be reconstructed for training of a heart disease diagnosis assistance neural network model or for assistance in heart disease diagnosis using the neural network model. The reconstruction of the fundus image may be performed by the above-described diagnosis assistance system, diagnostic device, client device, mobile device, or server device. The control unit or processor of each device may perform the reconstruction of the image.

The reconstruction of the fundus image may include modifying the fundus image to a form in which efficiency of the training of the heart disease diagnosis assistance neural network model or the assistance in the heart disease diagnosis using the neural network model may be improved. For example, the reconstruction of the image may include blurring the fundus image or changing chromaticity or saturation of the fundus image.

For example, when the size of a fundus image is reduced or a color channel thereof is simplified, since the amount of data that needs to be processed by a neural network model is reduced, accuracy of a result or a speed of obtaining a result may be improved.

Various forms of pre-processing or conversion may be applied to a fundus image. Pre-processing of a fundus image may refer to various forms of image processing tasks performed on a fundus image that has been obtained by imaging. The pre-processing of a fundus image may include at least some of the image resizing, image pre-processing, image augmentation, image serialization, and the like described above in "Data processing process" section.

According to an embodiment, a method of reconstructing a fundus image may include performing pre-processing which highlights a region of the fundus image in which blood vessels are distributed. Alternatively, the method of reconstructing a fundus image may include performing pre-processing which highlights a bleeding region of the fundus image.

The pre-processing which highlights blood vessels may include blurring the fundus image. The pre-processing which highlights blood vessels may include filtering the fundus image. For example, the pre-processing which highlights blood vessels may include applying the Gaussian filter to the fundus image.

The pre-processing which highlights blood vessels may include image noise filtering. The pre-processing which highlights blood vessels may include imprinting. The pre-processing which highlights blood vessels may include combining and/or optimizing a color space including RGV, La*b*, and HSV. The pre-processing which highlights blood vessels may include any one of histogram stretching, histogram equalization, and histogram normalization. The highlighting of the blood vessels may include equalizing the image. The equalizing may be performed using the Gaussian filter.

The highlighting of the blood vessels may include applying a separately-provided blood vessel highlighting filter. The blood vessel highlighting filter may be a filter including some of the various forms of pre-processing described herein.

The highlighting of the blood vessels may include converting a color space and highlighting a blood vessel region divided on the basis of a luminance component.

The highlighting of the blood vessels may include expanding and/or contracting an object. For example, the highlighting of the blood vessels may include adding a pixel to a boundary of a region in which blood vessels are distributed or removing a pixel from the boundary.

The highlighting of the blood vessels may include expanding the image and obtaining a luminance image of the expanded image. The highlighting of the blood vessels may include contracting the image and obtaining a luminance image of the contracted image.

According to an embodiment, reconstructing a fundus image to highlight blood vessels may include blurring the fundus image, applying the Gaussian filter to the blurred fundus image, and highlighting (or extracting) blood vessels included in the fundus image to which the Gaussian filter is applied. All or some of the above-described processes may be used in order to highlight or extract the blood vessels.

The reconstructing of the fundus image may include extracting blood vessels. For example, the reconstructing of the fundus image may include generating blood vessel segmentation.

The highlighting of blood vessels may include processing a region in which the blood vessels are distributed or processing an extracted blood vessel image. For example, the highlighting of blood vessels may include changing color, brightness, and histogram of a region of a fundus image in which blood vessels are distributed or a blood vessel image extracted from the fundus image.

The highlighting of blood vessels may include performing at least one of the above-described processes several times.

Meanwhile, the pre-processing which highlights blood vessels may be selectively performed. Whether to use the pre-processing which highlights blood vessels may be selected by a user. For example, a device which performs training of a heart disease diagnosis assistance neural network model or assistance in heart disease diagnosis using the neural network model may obtain a user input related to whether to use the pre-processing which highlights blood vessels and may perform or omit the pre-processing which highlights blood vessels according to the user input.

According to an embodiment, the method of reconstructing a fundus image may include performing pre-processing which highlights a region of the fundus image in which optic nerve fibers are distributed. The method of reconstructing a fundus image may include generating an optic nerve fiber extraction image by extracting a region in which optic nerve fibers are distributed. The highlighting of the region in which optic nerve fibers are distributed or extracting the optic nerve fibers may include performing pre-processing such as applying the Gaussian filter to the fundus image, blurring the fundus image, converting a histogram of the fundus image, and changing tone of the fundus image.

When a fundus image is used, there is an advantage in that the form of blood vessels may be observed non-invasively. Therefore, when a fundus image is used in heart disease diagnosis, assistance information that may be used in heart disease diagnosis may be obtained on the basis of the form of blood vessels obtained from the fundus image. Accordingly, when, as described herein, a fundus image which is reconstructed so that a blood vessel portion included in the fundus image is highlighted is used, more accurate heart disease diagnosis assistance information may be obtained.

2.3.4 Training Heart Disease Diagnosis Assistance Neural Network Model

2.3.4.1 Outline of Training Neural Network Model for Heart Disease Diagnosis The above-described diagnosis assistance system, training device, server device, or mobile device may train a heart disease diagnosis assistance neural network using a fundus image. The training unit, control unit, or processor of each device may perform training of a heart disease diagnosis assistance neural network model. The process of training a neural network model which has been described above with reference to FIGS. 8 and 13 to 17 may apply analogically to the training of the heart disease diagnosis assistance neural network model.

The heart disease diagnosis assistance neural network model may be trained using training data including a label. The heart disease diagnosis assistance neural network model may be trained using a labeled fundus image.

Hereinafter, on the basis of the description given above with reference to FIGS. 1 to 30, details unique to the case of training a neural network model for assisting in heart disease diagnosis will be mainly described.

Figure 33:
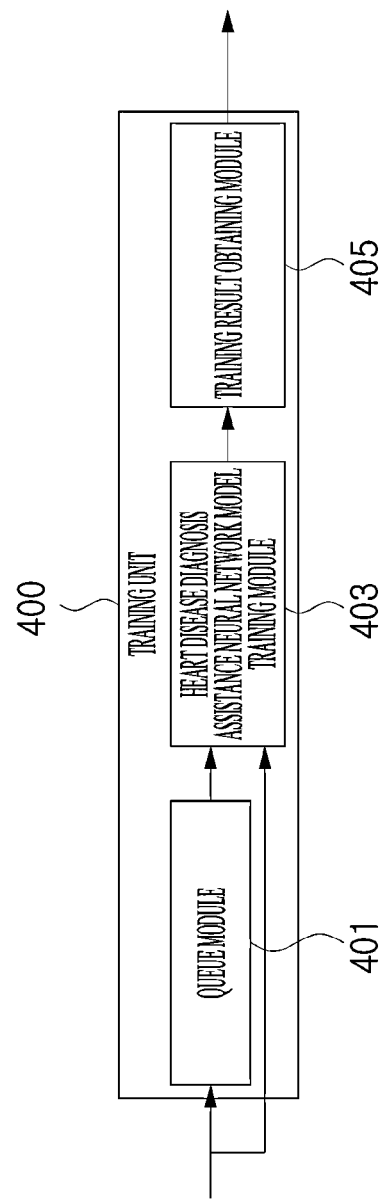
FIG. 33 is a view for describing a training unit 400 according to an embodiment of the present invention.

FIG. 33 is a view for describing a training unit 400 according to an embodiment of the present invention. Referring to FIG. 33, the training unit 400 according to an embodiment of the present invention may include a queue module 401, a heart disease diagnosis assistance neural network model training module 403, and a training result obtaining module 405.

The queue module 401 may temporarily store fundus image data and supply the fundus image data to a neural network model. The description given above in "Queue" section may similarly apply to the queue module 401.

The heart disease diagnosis assistance neural network model training module 403 may obtain a fundus image, obtain diagnosis assistance information using a heart disease diagnosis assistance neural network model, compare the obtained diagnosis assistance information with a label actually assigned to an input image, and update the heart disease diagnosis assistance neural network model according to a comparison result in order to train the heart disease diagnosis assistance neural network model.

The training result obtaining module 405 may obtain the trained heart disease diagnosis assistance neural network model or parameters of the trained heart disease diagnosis assistance neural network model. For example, the training result obtaining module 405 may obtain a weight value of a node included in the trained heart disease diagnosis assistance neural network model.

Figure 34:
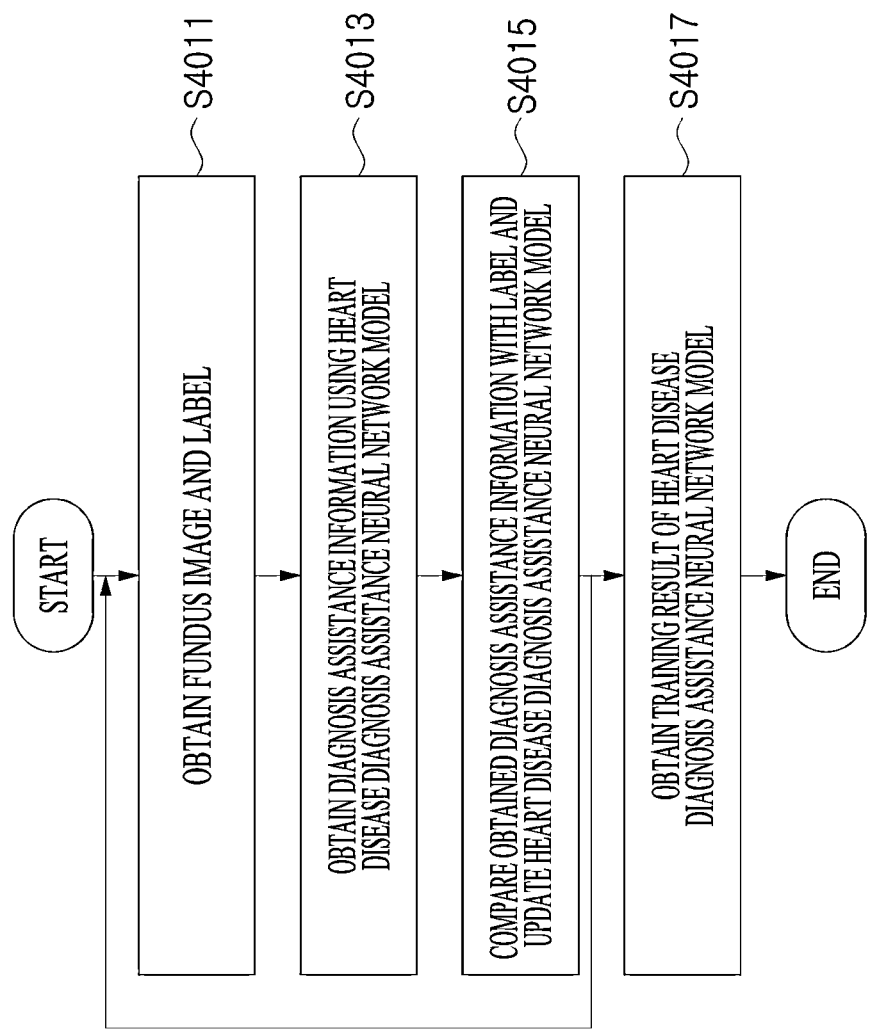
FIG. 34 is a view for describing a method of training a heart disease diagnosis assistance neural network model according to an embodiment of the present invention.

FIG. 34 is a view for describing a method of training a heart disease diagnosis assistance neural network model according to an embodiment of the present invention. Referring to FIG. 34, the method of training a heart disease diagnosis assistance neural network model according to an embodiment of the present invention may include obtaining a fundus image and a label (S4011), obtaining diagnosis assistance information using the heart disease diagnosis assistance neural network model (S4012), comparing the obtained information with the label and updating the heart disease diagnosis assistance neural network model (S4015), and obtaining a training result (S4017).

The obtaining of the fundus image and the label (S4011) may include obtaining fundus image training data. The obtaining of the fundus image training data may include obtaining a plurality of fundus images and labels respectively assigned to the fundus images. The obtained fundus images and labels may be separately managed. The obtained fundus images may be input to a neural network model and used as the basis for obtaining diagnosis assistance information, and the obtained labels may be compared with the obtained diagnosis assistance information for updating the neural network model.

The fundus image training data may include a first fundus image, a first label assigned to the first fundus image, a second fundus image, and a second label assigned to the second fundus image. The first label and the second label may be of the same type. For example, the first label and the second label may be numerical value labels or grade labels.

The obtaining of the diagnosis assistance information using the heart disease diagnosis assistance neural network model (S4013) may include obtaining heart disease diagnosis assistance information related to an input fundus image by using a neural network model provided to output heart disease diagnosis assistance information on the basis of the fundus image.

The obtained heart disease diagnosis assistance information may be the same type of information as a label assigned to a fundus image included in the fundus image training data. For example, when a grade label is assigned to a fundus image for training, a heart disease diagnosis assistance neural network model may obtain grade information on the basis of the fundus image.

Alternatively, the obtained heart disease diagnosis assistance information may be a different type of information from a label assigned to a fundus image included in the fundus image training data. For example, when a numerical value label is assigned to a fundus image for training, a heart disease diagnosis assistance neural network model may obtain grade information or disease presence/absence information.

The comparing of the obtained information with the label and updating of the heart disease diagnosis assistance neural network model (S4015) may include comparing the obtained information with a label assigned to an input image and updating the heart disease diagnosis assistance neural network model. The training of the heart disease diagnosis assistance neural network model may include comparing the obtained diagnosis assistance information with the label and updating the neural network model on the basis of an error between the obtained diagnosis assistance information and the label. The updating of the neural network model may include updating a weight value assigned to a node of the neural network model by using error back-propagation.

When the obtained information is of the same type as the label included in the input data, the updating of the heart disease diagnosis assistance neural network model may include comparing a label assigned to the input fundus image with diagnosis assistance information obtained on the basis of the corresponding fundus image and updating the neural network model on the basis of an error between the label and the diagnosis assistance information. For example, when a label assigned to an input fundus image is the Grade B label, and a label obtained by the heart disease diagnosis assistance neural network model on the basis of the input fundus image is the Grade C label, the neural network model may be updated on the basis of a difference in the labels.

When the obtained information is of a different type from the label included in the input data, the updating of the heart disease diagnosis assistance neural network model may include comparing a label assigned to the input fundus image with diagnosis assistance information obtained on the basis of the corresponding fundus image and updating the neural network model on the basis of an error between the label and the diagnosis assistance information. The label assigned to the input fundus image and the diagnosis assistance information obtained on the basis of the corresponding fundus image may be indirectly compared. The label assigned to the input fundus image and the diagnosis assistance information obtained on the basis of the corresponding fundus image may be compared on the basis of an inclusion relationship therebetween. The label assigned to the input fundus image and the diagnosis assistance information obtained on the basis of the corresponding fundus image may be compared on the basis of a matching table. For example, a matching table may be provided in the form described above with reference to FIG. 32.

For example, when a label assigned to an input fundus image is Grade A and diagnosis information obtained by a neural network model is normality information which indicates that a patient is healthy, the neural network model may be determined as having made a correct judgment, and such determination may be reflected in updating. Also, for example, when a score label assigned to an input fundus image is 0 and diagnosis information obtained by a neural network model is Grade B which indicates that a score ranges from 1 to 10, the diagnosis information obtained by the neural network model and the label may be determined as being different, and such determination may be reflected in updating.

The obtaining of the fundus image and the label (S4011), the obtaining of the diagnosis assistance information of the fundus image using a heart disease diagnosis assistance neural network model (S4013), and the comparing of the obtained information with the label and updating of the heart disease diagnosis assistance neural network model (S4015) may be repeatedly performed. The repetition of the updating of the neural network model may be performed a predetermined number of times. The updating of the neural network model may be stopped when accuracy of the neural network model has reached a reference value. The updating of the neural network model may be repeated until a user input is obtained. The updating of the neural network model may be performed until training data is used up.

The obtaining of the training result (S4017) may include obtaining a trained heart disease diagnosis assistance neural network model. The obtaining of the training result may include obtaining a value of a node included in the heart disease diagnosis assistance neural network model. The obtaining of the training result may include obtaining parameters (for example, weights or bias) of the neural network model. The obtained training result may be transmitted to an external device (for example, the diagnostic device, the server device, the client device, or the mobile device).

Accuracy of the heart disease diagnosis assistance neural network model may be obtained. The training of the heart disease diagnosis assistance neural network model may include obtaining accuracy of the heart disease diagnosis assistance neural network model. The accuracy of the heart disease diagnosis assistance neural network model may be obtained by performing verification or a test. Parameters of the neural network model may be changed according to a verification result. The verification of the neural network model may be performed using a verification data set which is differentiated from a training data set.

Meanwhile, the neural network model may also obtain diagnosis assistance information from an input of factors other than a fundus image. For example, age, gender, smoking status, the presence or absence of hyperlipidemia, the presence or absence of hypertension, the presence or absence of diabetes, and the like may be taken into consideration. Such additional factors may be input to the neural network model together with the fundus image or may be used as an input to a second neural network model together with a feature value obtained by a first neural network model from the fundus image.

According to an embodiment of the invention described herein, assisting in heart disease diagnosis may be performed using a plurality of neural network models. In addition to being performed using the plurality of neural network models in parallel as described below in the present specification, assisting in heart disease diagnosis may also be performed using the plurality of neural network models sequentially, i.e., in series.

According to an embodiment, heart disease diagnosis assistance neural network models may include a primary neural network model which obtains primary diagnosis assistance information and a secondary neural network model which obtains secondary diagnosis assistance information. For example, a heart disease diagnosis assistance system may include one or more diagnosis assistance neural network models connected in series.

For example, the one or more diagnosis assistance neural network models connected in series may include a primary neural network model which obtains primary diagnosis assistance information and a secondary neural network model which obtains secondary diagnosis assistance information with the primary diagnosis assistance information as an input.

The primary neural network model may be trained to obtain the primary diagnosis assistance information on the basis of a fundus image (and/or additional information). The secondary neural network model may be trained to obtain the secondary diagnosis assistance information on the basis of the primary diagnosis assistance information obtained by the primary neural network model.

As a specific example, the primary neural network model may be trained to obtain, on the basis of a fundus image of a testee, the probability that the testee has a predetermined heart disease (for example, coronary artery disease) (or the probability that the testee does not have the predetermined heart disease). The primary neural network model may be trained to obtain, on the basis of a fundus image, a probability that a coronary calcium score of the testee is larger than 0. In this case, the secondary neural network model may be trained to predict, on the basis of the probability obtained by the primary neural network model, a diagnosis factor (for example, numerical value information such as a coronary artery calcium score) related to the predetermined heart disease of the testee. The secondary neural network model may be trained to obtain a coronary calcium score based on the probability that the coronary calcium score is larger than 0 regarding the input fundus image The primary neural network model may be trained on the basis of primary training data in which primary diagnosis assistance information is assigned to a fundus image. The secondary neural network model may be trained on the basis of secondary training data in which secondary diagnosis assistance information is assigned to the primary diagnosis assistance information (or information of the same type and same level). The primary neural network model and the secondary neural network model may be trained together. For example, the primary neural network model and the secondary neural network model may be updated together on the basis of an error in the secondary diagnosis assistance information obtained through the secondary neural network model on the basis of the primary diagnosis assistance information obtained through the primary neural network model.

For another example, the secondary neural network model may obtain a secondary diagnosis assistance information using a primary diagnosis assistance information acquired via the primary neural network model and a numerical data originated from the testee which is distinguished from a fundus image of the testee. For example, the secondary neural network model may obtain a coronary calcium score of the testee, based on 1) a probability that the coronary calcium score of the testee is larger than 0 via the primary neural network model and 2) a numerical data of the testee. The numerical data may be a non-visual information obtained from the testee. For example, the numerical data may be any one of age data, gender data, smoking data and body weight data. The numerical data may be obtained from the testee's regular healthcare checkup.

Unless further described otherwise, similar to training of different neural network models described herein, training of the primary neural network model and training of the secondary neural network model may be performed separately or together.

As described herein, diagnosis assistance information having relatively higher accuracy may be obtained using the primary neural network model and the secondary neural network model as compared with when using a single neural network model. A more precise prediction may be possible by firstly obtaining primary diagnosis assistance information and then indirectly obtaining secondary diagnosis assistance information on the basis of the obtained primary diagnosis assistance information, rather than by directly obtaining diagnosis assistance information using a single neural network model.

The primary neural network model and/or secondary neural network model may be selected from various forms of diagnosis assistance neural network models described herein.

Hereinafter, a method of training a neural network model for obtaining the presence or absence of a heart disease on the basis of a fundus image (or a method of selecting a risk group), a method of training a neural network model for obtaining a grade which indicates an extent of risk of a heart disease, and a method of training a neural network model for obtaining a numerical value (or a score) used in heart disease diagnosis will be sequentially described in that order.

The following embodiments will be described on the basis of a training method in which any one of the presence/absence of a disease, a grade, and a numerical value is obtained and a neural network model is updated on the basis of the obtained information, but the present invention is not limited thereto. A method in which a neural network model which obtains two or more of the presence/absence of a disease, grade, and numerical value separately or together is used and at least one neural network model is updated on the basis of a result may also be used.

2.3.4.2 Training Risk Group Selection Model

According to an embodiment of the present invention, a heart disease diagnosis assistance neural network model which determines whether a patient has a certain heart disease on the basis of a fundus image may be trained. The heart disease diagnosis assistance neural network model may be trained to classify fundus images into two classes related to the presence/absence of a disease. The training of the heart disease diagnosis assistance neural network model which determines whether a patient has a certain heart disease may be performed by the above-described training unit.

The heart disease diagnosis assistance neural network model may be trained to classify a fundus image as normal or abnormal. The heart disease diagnosis assistance neural network model may be trained to output any one of abnormality information which indicates that a patient has a target heart disease and normality information which indicates that the patient does not have the target heart disease. The heart disease diagnosis assistance neural network model may be trained to output any one of risk information which indicates that a patient belongs to a risk group for a target heart disease and normality information which indicates that the patient does not belong to the risk group for the target heart disease. In addition, the heart disease diagnosis assistance neural network model may be trained as a binary classifier which outputs first information or second information obtained on the basis of an input fundus image as heart disease diagnosis assistance information.

As a specific example, a heart disease diagnosis assistance neural network model may be trained to classify a fundus image into a normal class which indicates that a testee does not have a target heart disease or an abnormal class which indicates that a risk of the target heart disease for the testee is at a level requiring certain medication (a level at which benefits from taking medications exceed losses).

For example, a heart disease diagnosis assistance neural network model may be trained to classify a fundus image into any one of a plurality of classes including a first class which indicates that a testee does not have a coronary artery disease and a second class which indicates that the testee has the coronary artery disease and thus taking statins is recommended.

The heart disease diagnosis assistance neural network model may be trained using a fundus image training data set which includes a plurality of fundus images to which an abnormal label or a normal label is assigned. Alternatively, the heart disease diagnosis assistance neural network model may be trained using a fundus image training data set which includes a plurality of fundus images to which score labels are assigned or using a fundus image training data set which includes a plurality of fundus images to which grade labels are assigned.

For example, the heart disease diagnosis assistance neural network model may be trained using a fundus image training data set which includes a plurality of fundus images to which a first label indicating that a testee does not have a coronary artery disease or a second label indicating that the testee has the coronary artery disease is assigned.

As another example, the heart disease diagnosis assistance neural network model may be trained using a fundus image training data set which includes a plurality of fundus images to which a first label indicating that taking statins (or aspirins) due to a coronary artery disease is not required for a testee or a second label indicating that taking statins (or aspirins) due to a coronary artery disease is required for the testee is assigned. Alternatively, the heart disease diagnosis assistance neural network model may also be trained using a fundus image training data set which includes a fundus image to which two or more types of labels are assigned. For example, the heart disease diagnosis assistance neural network model may be trained using a fundus image training data set which includes a fundus image to which a grade label and a disease presence/absence label are assigned together or a fundus image to which a grade label and a score label are assigned together.

Hereinafter, a method of training a heart disease diagnosis assistance neural network model for obtaining binarily-classified information as heart disease diagnosis assistance information will be described.

Figure 35:
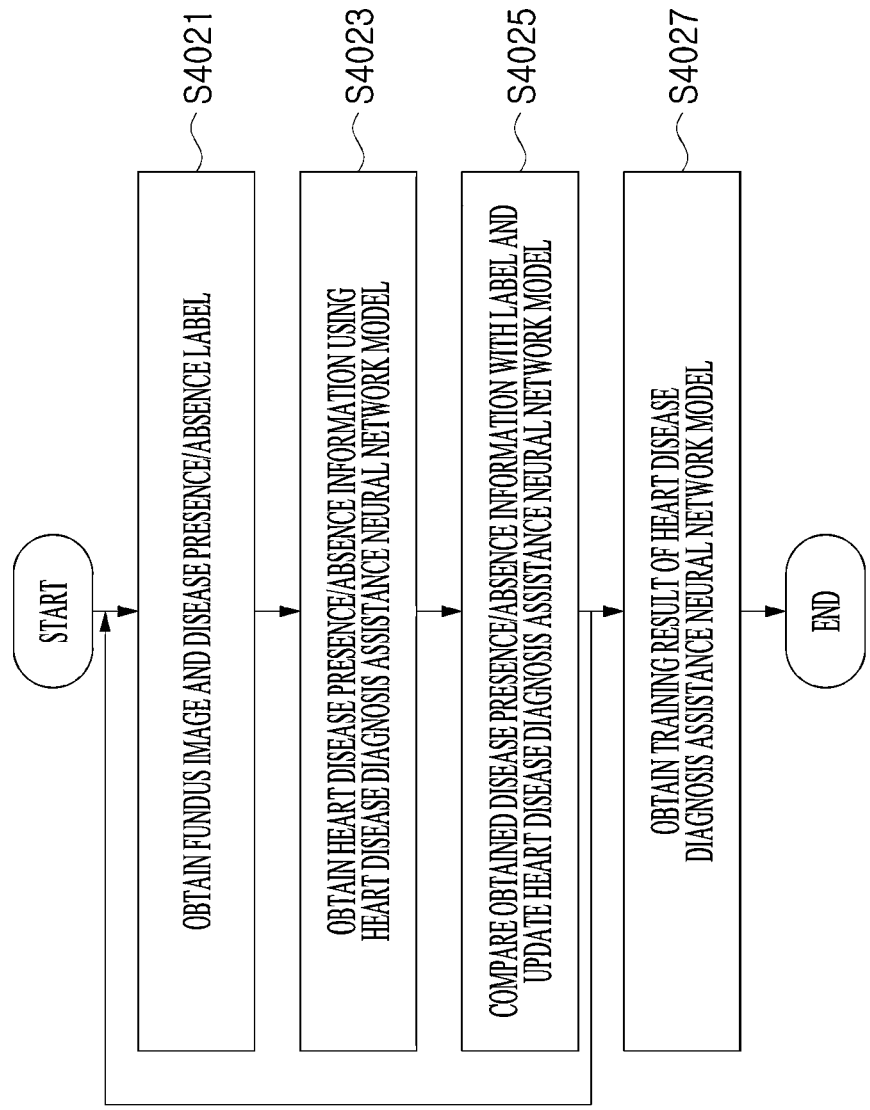
FIG. 35 is a view for describing a method of training a heart disease diagnosis assistance neural network model according to an embodiment of the present invention.

FIG. 35 is a view for describing a method of training a heart disease diagnosis assistance neural network model according to an embodiment of the present invention. Referring to FIG. 35, a method of training a neural network model for assisting in heart disease diagnosis may include obtaining a fundus image and a disease presence/absence label assigned to the fundus image (S4021), obtaining heart disease presence/absence information using the heart disease diagnosis assistance neural network model (S4023), comparing the obtained information with the label and updating the heart disease diagnosis assistance neural network model (S4025), and obtaining a training result of the heart disease diagnosis assistance neural network model (S4027).

The obtaining of the fundus image and the disease presence/absence label assigned to the fundus image (S4021) may include obtaining fundus image training data which includes the fundus image to which the disease presence/absence label is assigned. The fundus image and the disease presence/absence label included in the fundus image training data may be separately managed. For example, the obtained fundus image may be used as an input to the neural network model, and the obtained label may be used in updating the neural network model. The obtained fundus image training data may also include a fundus image to which a grade label or a score label is assigned in addition to the disease presence/absence label.

The fundus image training data may include a first fundus image to which a normal label, which indicates that a patient is normal in relation to a target heart disease, is assigned and a second fundus image to which an abnormal label which indicates that a patient is abnormal in relation to the target heart disease (or a risk label which indicates that a patient belongs to a risk group for the target heart disease) is assigned.

The obtaining of the fundus image and the disease presence/absence label assigned to the fundus image (S4021) may include obtaining fundus image training data which includes a fundus image to which a label other than the disease presence/absence label (for example, a grade label or a score label) is assigned.

The obtaining of the heart disease presence/absence information using the heart disease diagnosis assistance neural network model (S4023) may include obtaining heart disease presence/absence information related to an input fundus image by using a neural network model provided to output heart disease presence/absence information on the basis of a fundus image.

The comparing of the obtained information with the label and updating of the heart disease diagnosis assistance neural network model (S4025) may include comparing the obtained heart disease presence/absence information with the label assigned to the input fundus image and updating the heart disease diagnosis assistance neural network model. The training of the heart disease diagnosis assistance neural network model may include updating parameters of the neural network model using error back-propagation.

When a label included in training data used in training of the heart disease diagnosis assistance neural network model which obtains disease presence/absence information is a disease presence/absence label, the heart disease diagnosis assistance neural network model may be updated using a result of comparing the obtained disease presence/absence information and the disease presence/absence label. For example, when diagnosis assistance information obtained on the basis of an input fundus image from a heart disease diagnosis assistance neural network model is abnormality information and a label assigned to the input fundus image is an abnormality label, the neural network model may be updated on the basis of difference between the obtained information and the assigned label.

When the label included in the training data used in the training of the heart disease diagnosis assistance neural network model which obtains disease presence/absence information is not the disease presence/absence label, the heart disease diagnosis assistance neural network model may be updated using a result of comparing the obtained disease presence/absence information with the label. For example, when the label included in the training data is a grade label or a score label, the heart disease diagnosis assistance neural network model may be updated in consideration of whether the obtained disease presence/absence information matches the grade or score label included in the training data.

The comparison between the label and the obtained information may be performed in consideration of predetermined criteria. For example, a comparison between an input label and obtained information may be performed using the table illustrated in FIG. 32.

For example, when a label assigned to a fundus image included in training data is a grade label which indicates an extent-of-risk grade among a plurality of extent-of-risk grades to which a patient corresponds, the heart disease diagnosis assistance neural network model may be updated by determining whether the obtained disease presence/absence information matches the grade label assigned to the input fundus image. When the grade label assigned to the input fundus image is Grade A which indicates that a patient belongs to a normal group and the obtained diagnosis assistance information is abnormality information which indicates that the patient is abnormal, the neural network model may be updated on the basis of an error between the outputs.

The obtaining of the training result of the heart disease diagnosis assistance neural network model (S4027) may include obtaining the heart disease diagnosis assistance neural network model which is trained to binarily classify a fundus image as normal or abnormal. The obtaining of the training result may include obtaining parameters of the neural network model trained to binarily classify fundus image data.

According to an embodiment, risk group screening heart disease diagnosis assistance neural network models may include a primary neural network model which obtains primary diagnosis assistance information and a secondary neural network model which obtains secondary diagnosis assistance information connected in series with the primary neural network model.

For example, a primary neural network model which is trained to obtain, on the basis of a fundus image and/or additional information of a testee, the probability that the testee has a target heart disease and a second neural network model which is trained to obtain, on the basis of the probability that the testee has the target heart disease that has been obtained through the primary neural network model, the probability that the testee belongs to a risk group for the target heart disease may be used together.

For more specific example, a primary neural network model which is trained to obtain, on the basis of a fundus image and/or additional information of a testee, the probability that a coronary calcium score of the testee is larger than 0, and a second neural network model which is trained to obtain, on the basis of the probability that that the coronary calcium score of the testee is larger than 0 that has been obtained through the primary neural network model, the probability that the testee belongs to a risk group for a coronary calcium disease may be used together.

2.3.4.3 Training Grade Determination Model

According to an embodiment of the present invention, a heart disease diagnosis assistance neural network model which obtains grade information indicating an extent of risk of a certain heart disease for a patient on the basis of a fundus image may be trained. The heart disease diagnosis assistance neural network model may be trained to classify fundus images into a plurality of classes corresponding to a plurality of grades. The training of the heart disease diagnosis assistance neural network model obtaining the grade information may be performed by the above-described training unit.

The heart disease diagnosis assistance neural network model may be trained to classify fundus images into a plurality of grades. The heart disease diagnosis assistance neural network model may be trained to classify fundus images into a plurality of grades which indicate extents of risk of a target disease for a patient. The heart disease diagnosis assistance neural network model may be trained to classify fundus images into three classes corresponding to a first grade, a second grade, and a third grade which indicate extents of risk of a target disease for a patient. For example, the heart disease diagnosis assistance neural network model may be trained to classify fundus images into three classes corresponding to a first grade which indicates that a patient belongs to a normal group, a second grade which indicates that the patient belongs to a moderate risk group, and a third grade which indicates that the patient belongs to a severe risk group.

According to an embodiment of the present invention, a heart disease diagnosis assistance neural network model which assists in determining whether to prescribe medical practice related to a heart disease on the basis of a fundus image may be trained.

The heart disease diagnosis assistance neural network model according to an embodiment may be trained as a binary neural network model which classifies a plurality of fundus images into two classes distinguished according to the need of specific medical practice for a testee. For example, the heart disease diagnosis assistance neural network model may be trained to classify a fundus image into a first class which indicates that specific medical practice is required or a second class which indicates that the specific medical practice is not required.

Also, for example, the heart disease diagnosis assistance neural network model may be trained to classify a fundus image into a first class which indicates that specific medical practice is required soon (e.g., immediately), a second class which indicates that the specific medical practice is required within a predetermined period (e.g., within three years), or a third class which indicates that the specific medical practice is not required.

The specific medical practice may be medical treatment or prescription related to angina, coronary artery disease, heart attack, myocardial infarction, heart failure, arteriosclerosis, arrhythmia, cerebral hemorrhage, cerebral infarction, dyslipidemia, hyperlipidemia, hypertension, and the like.

The specific medical practice may include a drug therapy or a non-drug therapy recommended for improving a target disease of a testee.

The specific medical practice may be administration of a specific medicine or drug or prescription thereof. For example, the specific medical practice may be prescription of one or more of drugs based on statins (which include various drugs such as simvastatin, atorvastatin, rosuvastatin), which are HMG-CoA reductase inhibitors, aspirin, bile acid sequestrant, nicotinic acid, omega-3 fatty acid, ezetimibe, and fibrate.

The specific medical practice may be changed according to a condition of a testee and/or a target disease. For example, when the target disease is hypercholesterolemia, the specific medical practice may be prescription for taking a statin drug and another medicine (for example, ezetimibe, nicotinic acid, or bile acid sequestrant). When the target disease is hypertriglyceridemia, the specific medical practice may be prescription for taking a statin drug and nicotinic acid or fibrate. When a testee is diabetic and a target disease is hyperlipidemia, the specific medical practice may be prescription for taking a statin drug or taking a statin drug and nicotinic acid or fibrate.

For example, a heart disease diagnosis assistance neural network model may be trained to classify a plurality of fundus images into a first class indicating that taking statin or aspirin drugs is not required for a testee or a second class indicating that taking the statin or aspirin drugs is required for the testee. The first class may be treated similarly as the first grade described herein. The second class may be treated similarly as the second grade described herein.

For example, a heart disease diagnosis assistance neural network model may be trained to classify a plurality of fundus images into a first class indicating that a risk of a predetermined disease (for example, coronary artery disease) for a testee is insignificant and thus taking a statin (or aspirin) drug is not recommended for the testee or a second class indicating that a risk of the predetermined disease for the testee is significant and thus taking the statin (or aspirin) drug is recommended for the testee.

As a specific example, a heart disease diagnosis assistance neural network model may be trained to classify a plurality of fundus images into a first class indicating that a specific score value (for example, coronary artery calcification score value) is less than a reference value indicating that taking a statin drug is required or a second class indicating that the specific score value is greater than the reference value indicating that taking the statin drug is required.

Also, for example, a heart disease diagnosis assistance neural network model may be trained to classify a plurality of fundus images into a first class indicating that taking a statin (or aspirin) drug) is not required for a testee, a second class indicating that whether taking a statin drug is required for the testee is unclear (for example, a target group for which an additional diagnostic checkup is required), or a third class indicating that taking a statin drug is required for the testee (for example, a target group for which the need of an additional diagnostic checkup is low and certain benefits are expected when aspirin is taken). The first to third classes may be treated similarly as the first to third grades described herein.

As a specific example, a heart disease diagnosis assistance neural network model may classify a plurality of fundus images into a first class indicating that a specific score value related to taking a statin (or aspirin) drug is less than a first reference value, a second glass indicating that a specific score value related to taking statin is greater than the first reference value and less than a second reference value, or a third class indicating that a specific score value related to taking statin is greater than the second reference value. For example, a heart disease diagnosis assistance neural network model may classify a plurality of fundus images into a first class indicating that a coronary artery calcification score value is less than a first reference value (for example, 20), a second class indicating that the coronary artery calcification score value is greater than the first reference value (for example, 20) and less than a second reference value (for example, 100), or a third class indicating that the coronary artery calcification score value is greater than the second reference value (for example, 100). Also, for example, a heart disease diagnosis assistance neural network model may classify a plurality of fundus images into a first class indicating that prescription of a statin drug is not required, a second class indicating that primary prescription of statin is recommended, and a third class indicating that secondary prescription of the statin (for example, prescription of a larger amount of statin than the primary prescription of statin or prescription including an additional medicine) is recommended.

As a specific example, a heart disease diagnosis assistance neural network model may classify a plurality of fundus images into a first class indicating that a 10-year ASCVD risk is less than a first reference value (for example, 5%), a second glass indicating that the 10-year ASCVD risk is greater than the first reference value (for example, 5%) and less than a second reference value (for example, 7.5%), a third class indicating that the 10-year ASCVD risk is greater than the second reference value (for example, 7.5%) and less than a third reference value (for example, 20%), and a fourth class indicating that the 10-year ASCVD risk is greater than the third reference value (for example, 20%). The first to fourth classes may each correspond to different pieces of prescription information related to taking statin. For example, a heart disease diagnosis assistance neural network model may classify a plurality of fundus images into a first class indicating that taking a statin drug is not recommended, a second class indicating that whether taking the statin drug is recommended is required to be determined also in consideration of another factor (for example, a coronary artery calcification score), a third class indicating that prescription of a statin drug is required at a moderate level, and a fourth class indicating that prescription of a statin drug is required at a severe level.

The specific score values in the above embodiments may be values of various scores, indices, or factors for evaluating a risk of a heart disease that are described herein.

The heart disease diagnosis assistance neural network model may be trained using a fundus image training data set which includes a plurality of fundus images to which grade labels are assigned. For example, the heart disease diagnosis assistance neural network model may be trained using a training data set which includes a plurality of fundus images to which the first grade, the second grade, or the third grade is assigned. Alternatively, the heart disease diagnosis assistance neural network model may also be trained using a fundus image training data set which includes a plurality of fundus images to which a score label or a disease presence/absence label is assigned.

Alternatively, the heart disease diagnosis assistance neural network model may be trained using training data which includes a fundus image to which two or more types of labels are assigned together, such as a fundus image training data set which includes a fundus image to which a grade label and a disease presence/absence label are assigned together or a fundus image to which a grade label and a score label are assigned together.

Alternatively, a heart disease diagnosis assistance neural network model according to an embodiment may be trained using a fundus image training data set which includes a label related to specific prescription and a fundus image.

For example, a heart disease diagnosis assistance neural network model may be trained using a fundus image training data set which includes a prescription label related to whether taking a statin drug is required and a fundus image. As a specific example, the fundus image training data set may be a fundus image training data set which includes a plurality of pieces of fundus image data to which a first label indicating that taking the statin drug is not required or a second label indicating that taking the statin drug is required is assigned.

Also, for example, a heart disease diagnosis assistance neural network model may be trained to determine, on the basis of a fundus image of a testee, whether prescription of a statin drug is required, by using a training data set which includes a plurality of fundus images to which a first label indicating that prescription of a statin drug is required soon (e.g., immediately), a second label indicating that the prescription of the statin drug is highly expected to be required within a predetermined period (e.g., within three years), or a third label indicating that the prescription of the statin drug is not required.

A heart disease diagnosis assistance neural network model may be trained using a fundus image training data set which further includes pieces of information on factors related to target prescription. For example, the heart disease diagnosis assistance neural network model may be trained to obtain prescription information related to taking a statin drug, by using a fundus image training data set which includes fundus images to which prescription labels, which are related to taking the statin drug, and pieces of information on factors (for example, a family medical history, presence of diabetes, renal function, complications of diabetes, whether aspirin is taken, degree of obesity, weight, height, smoking status, gender, and the like), which are related to dyslipidemia whose symptoms may be alleviated by the statin drug, are assigned.

The heart disease diagnosis assistance neural network model trained to determine a grade on the basis of a fundus image may be provided in the form of a multiclass classifier which classifies a plurality of fundus images into a plurality of classes. Alternatively, the heart disease diagnosis assistance neural network model may also be provided in the form including at least one binary classifier which classifies a plurality of fundus images into two classes.

For example, the heart disease diagnosis assistance neural network model may include a first binary classification neural network model which classifies a plurality of fundus images into two classes corresponding to normality information and risk information and a second binary classification neural network model which classifies a plurality of fundus images into two classes corresponding to low risk information and high risk information. In this case, the heart disease diagnosis assistance neural network model may classify fundus images which are classified as normality information by the first binary classification neural network model as a first grade which indicates that a patient is normal, may classify fundus images which are classified as high risk information by the second binary classification neural network model as a third grade which indicates that the patient corresponds to a high risk group, and may classify images which are not classified as either the first grade or the third grade as a second grade which indicates that the patient corresponds to a moderate risk group.

Meanwhile, according to another embodiment, for predicting a grade related to a target disease for a testee, grade determination models including a primary neural network model and a secondary neural network model may be trained.

For example, a primary neural network model may be trained to obtain, on the basis of a fundus image of a testee and/or additional information, the probability that the testee has a target heart disease or a numerical value related to the target heart disease for the testee (for example, a coronary artery calcium score related to a coronary artery disease). Also, a secondary neural network model may be trained to classify testees into a plurality of classes or grades related a target heart disease, with output information of the primary neural network model as an input.

For example, for determining a grade of risk of a coronary artery disease for a testee, a first neural network model may be trained to obtain, on the basis of a fundus image of a testee, the probability that the testee has the coronary artery disease, and a second neural network model may be trained to determine, on the basis of the probability that the testee has the coronary artery disease, the grade of risk of the coronary artery disease for the testee.

Hereinafter, some embodiments of a method of training a heart disease diagnosis assistance neural network model for obtaining grade information as heart disease diagnosis assistance information will be described.

Figure 36:
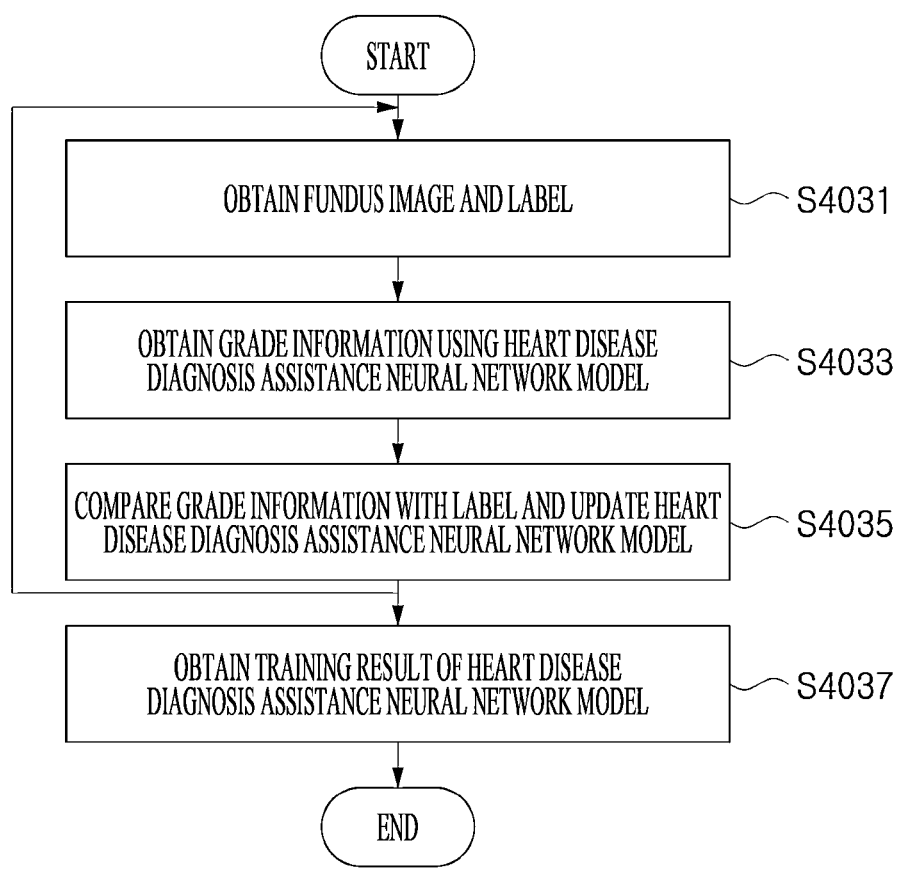
FIG. 36 is a view for describing a method of training a heart disease diagnosis assistance neural network model according to an embodiment of the present invention.

FIG. 36 is a view for describing a method of training a heart disease diagnosis assistance neural network model according to an embodiment of the present invention. Referring to FIG. 36, a method of training a neural network model for assisting in heart disease diagnosis may include obtaining a fundus image and a label assigned to the fundus image (S4031), obtaining grade information using the heart disease diagnosis assistance neural network model (S4033), comparing the grade information with the label and updating the heart disease diagnosis assistance neural network model (S4035), and obtaining a training result of the heart disease diagnosis assistance neural network model (S4037).

The obtaining of the fundus image and the label assigned to the fundus image (S4031) may include obtaining a fundus image training data set which includes a fundus image to which a grade label is assigned. The fundus image and the grade label included in the fundus image training data set may be separately managed. The fundus image may be used as an input to the neural network model, and the grade label may be used in updating the neural network model. The obtained fundus image training data set may also include a fundus image to which a disease presence/absence label or a score label is assigned in addition to the grade label.

The fundus image training data may include a first fundus image to which a first label, which indicates that a patient belongs to a normal group for a target heart disease, is assigned, a second fundus image to which a second label, which indicates that the patient belongs to a moderate risk group for the target heart disease, is assigned, and a third fundus image to which a third label, which indicates that the patient belongs to a severe risk group for the target heart disease, is assigned.

The obtaining of the fundus image and the label assigned to the fundus image may include obtaining a fundus image training data set which includes a fundus image to which a label other than the grade label (for example, a disease presence/absence label or a score label) is assigned.

The obtaining of the grade information using the heart disease diagnosis assistance neural network model (S4033) may include obtaining grade information related to an input fundus image by using a neural network model provided to classify fundus images into a plurality of classes corresponding to a plurality of grades related to a target heart disease.

The comparing of the grade information with the label and updating of the heart disease diagnosis assistance neural network model (S4035) may include comparing the obtained grade information with the label assigned to the input fundus image and updating the heart disease diagnosis assistance neural network model. The training of the heart disease diagnosis assistance neural network model may include updating parameters of the neural network model using error back-propagation.

When a label included in training data used in training of the heart disease diagnosis assistance neural network model which obtains grade information is a grade label, the heart disease diagnosis assistance neural network model may be updated using a result of comparing the obtained grade information and the input grade label. For example, when diagnosis assistance information obtained from the heart disease diagnosis assistance neural network model is first grade information and a label assigned to the input fundus image is a second grade label, the neural network model may be updated on the basis of discordance between the obtained information and the assigned label.

When the label included in the training data used in the training of the heart disease diagnosis assistance neural network model which obtains grade information is not the grade label, the heart disease diagnosis assistance neural network model may be updated using a result of comparing the obtained grade information with the assigned label. For example, when the label included in the training data is a disease presence/absence label or a score label, the heart disease diagnosis assistance neural network model may be updated in consideration of whether the obtained grade information matches the disease presence/absence label or score label included in the training data. For example, when the label included in the training data is a prescription label, the heart disease diagnosis assistance neural network model may be updated in consideration of whether prescription information obtained from the neural network model matches the prescription label included in the training data.

In this case, whether the obtained diagnosis assistance information matches the assigned label may be determined using a matching table exemplified herein (for example, the table illustrated in FIG. 32).

For example, when the label included in the training data is a coronary artery calcium score of a patient, the heart disease diagnosis assistance neural network model may be updated in consideration of whether the obtained grade information matches the coronary artery calcium score of the patient. For example, when the label assigned to the input fundus image is a coronary artery calcium score label which indicates a value of 17 and the grade information obtained on the basis of the input fundus image is the first grade information indicating that the patient is normal, it can be seen that the score and the grade do not match, and the neural network model may be updated on the basis of such discordance.

The obtaining of the training result of the heart disease diagnosis assistance neural network model (S4037) may include obtaining a heart disease diagnosis assistance neural network model which is trained to classify fundus images into a plurality of grades or parameters of such a neural network model.

2.3.4.4 Training Score Prediction Model

According to an embodiment of the present invention, a heart disease diagnosis assistance neural network model which obtains a patient's score related to a certain heart disease on the basis of a fundus image may be trained. The heart disease diagnosis assistance neural network model may be trained to predict a score used in heart disease diagnosis on the basis of a fundus image. The training of the heart disease diagnosis assistance neural network model which obtains a score may be performed by the above-described training unit.

The heart disease diagnosis assistance neural network model may be trained to predict a diagnosis assistance score corresponding to a fundus image. The heart disease diagnosis assistance neural network model may be trained to predict a value of a specific parameter related to a target heart disease of a patient. The heart disease diagnosis assistance neural network model may be trained to predict a score that may be used in diagnosing whether a patient has a target heart disease. For example, the heart disease diagnosis assistance neural network model may be trained to predict at least one of values of at least one factor for calculating any one of a coronary artery calcium score, an arteriosclerosis risk score, a CIMT value, an ankle-brachial index, a blood vessel stiffness test (pulse wave velocity analysis), 24-hour Holter monitoring, a Framingham risk score, a QRISK score, a value according to an extent of risk of an ASCVD within ten years, a score according to race- and sex-specific Pooled Cohort Equation (PCE), the Joint British Societies recommendations on the prevention of Cardiovascular Disease (JBS3) risk score value, a score according to the SCORE, and the above-listed scores.

The heart disease diagnosis assistance neural network model may be trained to predict a score on the basis of an input fundus image. The score may be predicted as a real number value. The score may also be predicted as an integer value. The score may also be predicted as a positive value.

The heart disease diagnosis assistance neural network model may be trained using a fundus image training data set which includes a fundus image to which a score label is assigned. For example, the heart disease diagnosis assistance neural network model may be trained using fundus image training data set which includes a fundus image to which a coronary artery calcium score label is assigned.

The heart disease diagnosis assistance neural network model may be trained using a fundus image training data set which includes a fundus image to which a label other than the score label (for example, a disease presence/absence label or a grade label) is assigned. The heart disease diagnosis assistance neural network model may be trained using fundus image training data set which includes a fundus image to which a score label and a label other than the score label is assigned together.

The neural network model which is trained to predict a score on the basis of a fundus image may be trained in the form of a linear regression model which outputs continuous values. Alternatively, the heart disease diagnosis assistance neural network model may simultaneously include a linear regression neural network model which predicts a score and a classifier model which outputs grade or disease presence/absence information.

Hereinafter, some embodiments of a method of training a heart disease diagnosis assistance neural network model which obtains score information as heart disease diagnosis assistance information will be described.

Figure 37:
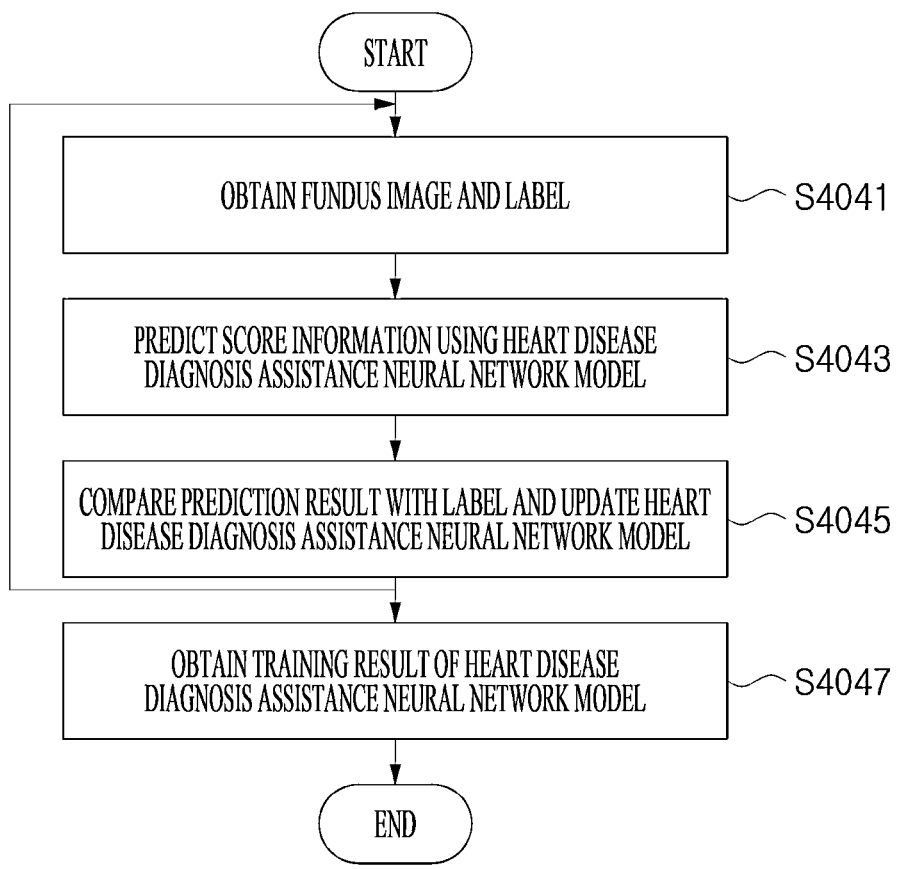
FIG. 37 is a view for describing a method of training a heart disease diagnosis assistance neural network model according to an embodiment of the present invention.

FIG. 37 is a view for describing a method of training a heart disease diagnosis assistance neural network model according to an embodiment of the present invention. Referring to FIG. 37, a method of training a neural network model for assisting in heart disease diagnosis may include obtaining a fundus image and a label assigned to the fundus image (S4041), predicting score information using the heart disease diagnosis assistance neural network model (S4043), comparing a prediction result with the label and updating the heart disease diagnosis assistance neural network model (S4045), and obtaining a training result of the heart disease diagnosis assistance neural network model (S4047).

The obtaining of the fundus image and the label assigned to the fundus image (S4041) may include obtaining fundus image training data which includes a fundus image to which a score label is assigned. The fundus image and the label may be separately managed. The fundus image training data may include a fundus image to which a score label and a label other than the score label, for example, a grade label or a disease presence/absence label, are assigned together.

The fundus image training data may include fundus image data to which a score label, which indicates a patient's coronary artery calcium score for heart disease diagnosis, is assigned. The fundus image training data may include a fundus image to which a score label, which indicates a patient's coronary artery calcium score, and a grade label, which indicates the patient's extent of risk of a coronary artery disease that is determined according to the patient's coronary artery calcium score, is assigned.

The fundus image training data may include fundus image data to which a label other than the score label is assigned. The fundus image training data may include fundus image data to which a grade label or a disease presence/absence label is assigned.

The predicting of the score information using the heart disease diagnosis assistance neural network model (S4043) may include obtaining score information related to an input fundus image by using a neural network model provided to obtain heart disease diagnosis assistance score information corresponding to a fundus image on the basis of the fundus image. The neural network model may also obtain score information and information other than the score information together. The neural network model may obtain grade information or disease presence/absence information together with the score information.

The comparing of the prediction result with the label and updating of the heart disease diagnosis assistance neural network model (S4045) may include comparing the obtained score information with the label assigned to the input fundus image and updating the heart disease diagnosis assistance neural network model.

When a label included in training data used in training of the heart disease diagnosis assistance neural network model is a score label, the training of the heart disease diagnosis assistance neural network model may include comparing a score label assigned to an input fundus image with score information according to the input fundus image that is predicted by a neural network model and updating the heart disease diagnosis assistance neural network model on the basis of a result of the comparison.

The training of the heart disease diagnosis assistance neural network model may include comparing the score label and the predicted score information in consideration of ranges thereof. The training of the heart disease diagnosis assistance neural network model may include comparing the score label and the predicted score by using a plurality of ranges, or grades which are provided in advance to classify scores according to values thereof. For example, the training of the heart disease diagnosis assistance neural network model may include updating the neural network model by determining that a prediction of the neural network model is correct when the obtained score belongs to the same range as the score that the label indicates and determining that a prediction of the neural network model is incorrect when the obtained score belongs to a different range from the score that the label indicates.

The training of the heart disease diagnosis assistance neural network model may be performed in consideration of an error range. For example, when a difference between a predicted score value and a score value of a label is within an error range, the prediction may be determined to be correct, and the neural network model may be updated accordingly.

When the label included in the training data used in the training of the heart disease diagnosis assistance neural network model is a grade label or a disease presence/absence label, the training of the heart disease diagnosis assistance neural network model may include comparing a label assigned to an input fundus image and score information according to the input fundus image that is predicted by a neural network model and updating the heart disease diagnosis assistance neural network model on the basis of a result of the comparison. In other words, the training of the heart disease diagnosis assistance neural network model may be performed by determining whether the score information and the non-score label match each other. For example, the training of the heart disease diagnosis assistance neural network model may be performed in consideration of whether the score information predicted by the neural network model matches grade information or disease presence/absence information assigned to the input fundus image.

The obtaining of the training result of the heart disease diagnosis assistance neural network model (S4047) may include obtaining the heart disease diagnosis assistance neural network model trained on the basis of the fundus image or parameters of such a neural network model.

According to an embodiment, score prediction models including a primary neural network model and a secondary neural network model, which are connected to each other in series, may be trained.

For example, score prediction models including a primary neural network model which obtains, on the basis of a fundus image of a testee, primary diagnosis assistance information related to a target heart disease for the testee and a secondary neural network model which obtains, on the basis of the primary diagnosis assistance information, score information related to the target heart disease as secondary diagnosis assistance information may be trained.

For example, when the target heart disease is a coronary artery disease, the primary diagnosis assistance information may be the probability that the testee has the coronary artery disease or the probability that the testee does not have the coronary artery disease. In this case, as the secondary diagnosis assistance information, the score information related to the target heart disease may be a coronary artery calcium score. That is, the lower the probability that a testee is normal (the higher the probability that the testee is abnormal) with regards to a heart disease, the higher the heart disease-related score (the risk of the heart disease). On the basis of this, a neural network model for predicting an extent of risk of a heart disease, a calcium score, or the like may be constructed and used.

For more specific example, when the target heart disease is a coronary artery disease, the primary diagnosis assistance information may be the probability that the coronary calcium score of the testee is larger than 0. In this case, the secondary neural network model may be trained to output coronary calcium score (or range thereof) based on the probability that the coronary calcium score of the testee is larger than 0.

The primary neural network model may be trained on the basis of primary training data. For example, the primary neural network model may be trained on the basis of primary training data which includes a plurality of fundus images to which a label indicating the probability related to whether a testee has a coronary artery disease is assigned. The secondary neural network model may be trained on the basis of secondary training data which includes a plurality of pieces of information on the probability that a coronary artery calcium score will correspond to a labeled coronary artery disease.

2.3.5 Assisting in Heart Disease Diagnosis Using Neural Network Model

2.3.5.1 Outline of Heart Disease Diagnosis

Heart disease diagnosis may be assisted using a trained heart disease diagnosis assistance neural network model. In other words, heart disease diagnosis may be assisted by obtaining diagnosis assistance information, which is useful in the heart disease diagnosis, by using a trained heart disease diagnosis assistance neural network model.

The above-described diagnostic device, client device, mobile device, or server device may obtain diagnosis assistance information on the basis of a fundus image of a patient. The diagnostic unit, control unit, or processor of each device may obtain diagnosis assistance information according to a target fundus image by using a heart disease diagnosis assistance neural network model.

Hereinafter, on the basis of the description given above with reference to FIGS. 1 to 30, details unique to a method of assisting in heart disease diagnosis using a trained neural network model will be described.

Figure 38:
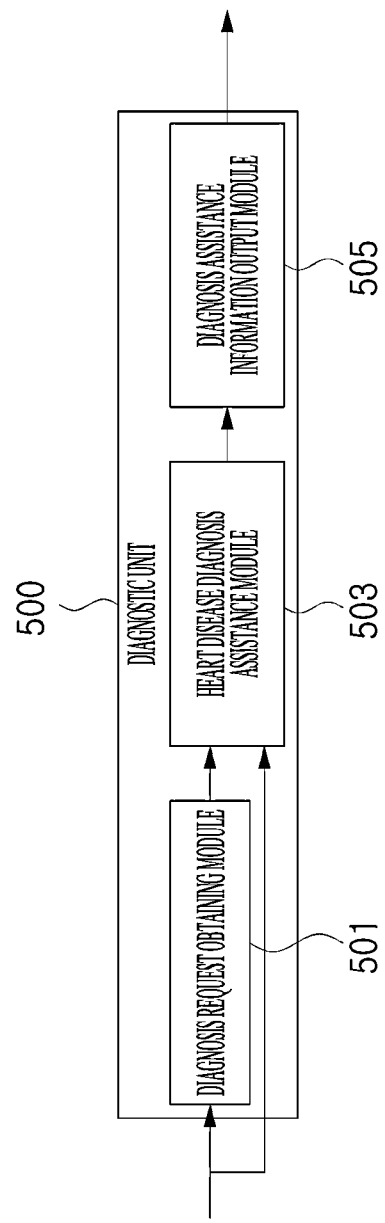
FIG. 38 is a view for describing a diagnostic unit 500 according to an embodiment of the present invention.

FIG. 38 is a view for describing a diagnostic unit 500 according to an embodiment of the present invention. Referring to FIG. 38, the diagnostic unit 500 according to an embodiment of the present invention may include a diagnosis request obtaining module 501, a heart disease diagnosis assistance module 503, and a diagnosis assistance information output module 505. The diagnostic unit 500 and each of the modules illustrated in FIG. 38 are merely illustrative on the basis of a logical configuration, and the diagnostic unit 500 and each of the modules may be included in at least one of the various devices described herein or other devices.

The diagnosis request obtaining module 501 may obtain a diagnosis request from an external device or a user. The diagnosis request obtaining module 501 may obtain a diagnosis request including a diagnosis target fundus image. The diagnosis request obtaining module 501 may obtain a diagnosis request including diagnosis assistance information identifying information for identifying requested diagnosis assistance information.

The diagnosis request obtaining module 501 may obtain a diagnosis request and start a diagnosis assistance information obtaining process. The diagnosis request obtaining module 501 may obtain a diagnosis request and then obtain a fundus image, may obtain a diagnosis request including a fundus image, or may obtain a fundus image and then obtain a diagnosis request.

The heart disease diagnosis assistance module 503 may obtain diagnosis assistance information using a trained heart disease diagnosis assistance neural network model. The heart disease diagnosis assistance module 503 may obtain diagnosis assistance information when a diagnosis assistance request is obtained. The heart disease diagnosis assistance module 503 may obtain a target fundus image and obtain heart disease diagnosis assistance information from a neural network model on the basis of the target fundus image. The heart disease diagnosis assistance module 503 may obtain a trained neural network model or parameters of the trained neural network model and use the obtained neural network model or parameters thereof to obtain diagnosis assistance information according to the target fundus image. The heart disease diagnosis assistance module 503 may obtain a target fundus image and obtain disease presence/absence information, grade information, or score information for heart disease diagnosis.

The heart disease diagnosis assistance module 503 may further obtain additional information (in other words, secondary diagnosis assistance information) other than primary heart disease diagnosis assistance information directly output from a neural network model. For example, the heart disease diagnosis assistance module 503 may obtain instruction information, prescription information or the like which will be described below. Also, for example, the heart disease diagnosis assistance module may obtain diagnosis assistance information related to a disease other than a target disease or a class activation map (CAM) image corresponding to the output diagnosis assistance information. The class activation map in this description can be construed as including similar or expanded concepts which refer to indicate relationship between locations in the image and the prediction result. For example, the class activation map may be a Saliency map, a heat map, a feature map or a probability map, which provide information in relationship between pixels in the image and the prediction result.

The diagnosis assistance information output module 505 may obtain diagnosis assistance information from the heart disease diagnosis assistance module. The diagnosis assistance information output module 505 may output diagnosis assistance information related to a heart disease. The diagnosis assistance information output module may transmit diagnosis assistance information to an external device or an external module. The diagnosis assistance information may be provided to a user via a user interface or the like.

Figure 39:
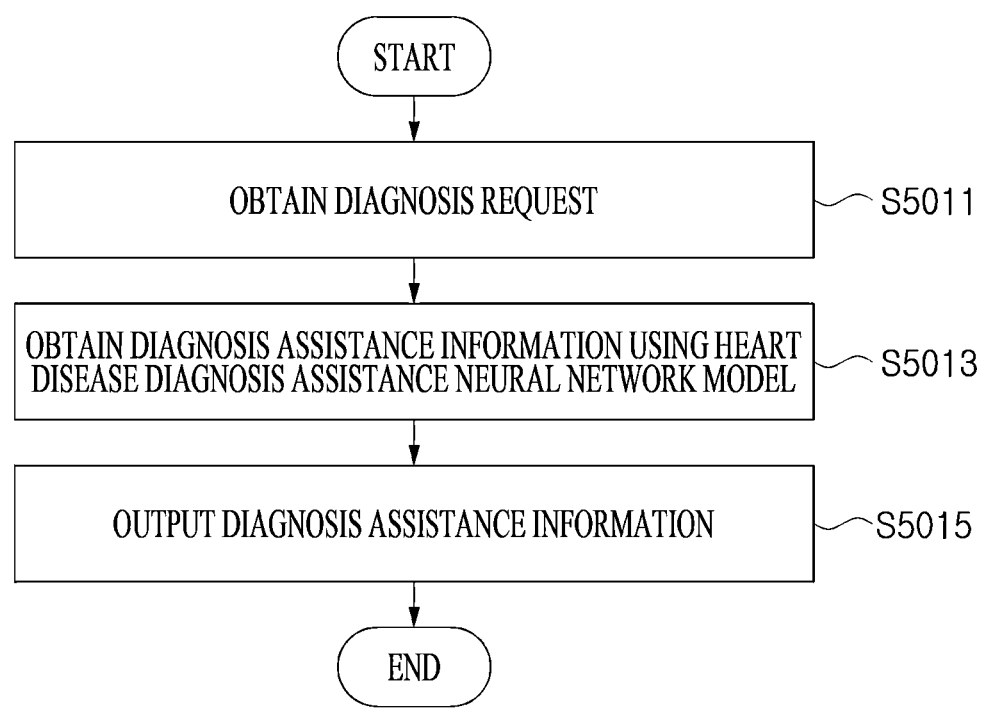
FIG. 39 is a view for describing a method of assisting in heart disease diagnosis according to an embodiment of the present invention.

FIG. 39 is a view for describing a method of assisting in heart disease diagnosis according to an embodiment of the present invention. Referring to FIG. 39, a method of assisting in heart disease diagnosis according to an embodiment of the present invention may include obtaining a diagnosis request (S5011), obtaining diagnosis assistance information using a heart disease diagnosis assistance neural network model (S5013), and outputting the diagnosis assistance information (S5015).

The obtaining of the diagnosis assistance information using the heart disease diagnosis assistance neural network model (S5013) may be configured differently according to the type of target diagnosis assistance information (that is, diagnosis assistance information to be obtained). For example, a heart disease diagnosis assistance neural network model used in obtaining diagnosis assistance information may be determined according to the type of target diagnosis assistance information.

The obtaining of the diagnosis assistance information using the heart disease diagnosis assistance neural network model (S5013) may include processing diagnosis assistance information obtained via the heart disease diagnosis assistance neural network model. In other words, the obtaining of the diagnosis assistance information may further include obtaining primary diagnosis assistance information directly obtained via the neural network model and/or secondary diagnosis assistance information obtained on the basis of the primary diagnosis assistance information.

The outputting of the diagnosis assistance information (S5015) may include outputting diagnosis assistance information in the form recognizable by a user. The outputting of the diagnosis assistance information may include outputting diagnosis assistance information in the form of visual or aural data. The outputting of the diagnosis assistance information may be configured differently according to the type of the output diagnosis assistance information. For example, the diagnosis assistance information may be output differently according to the type thereof.

Figure 40:
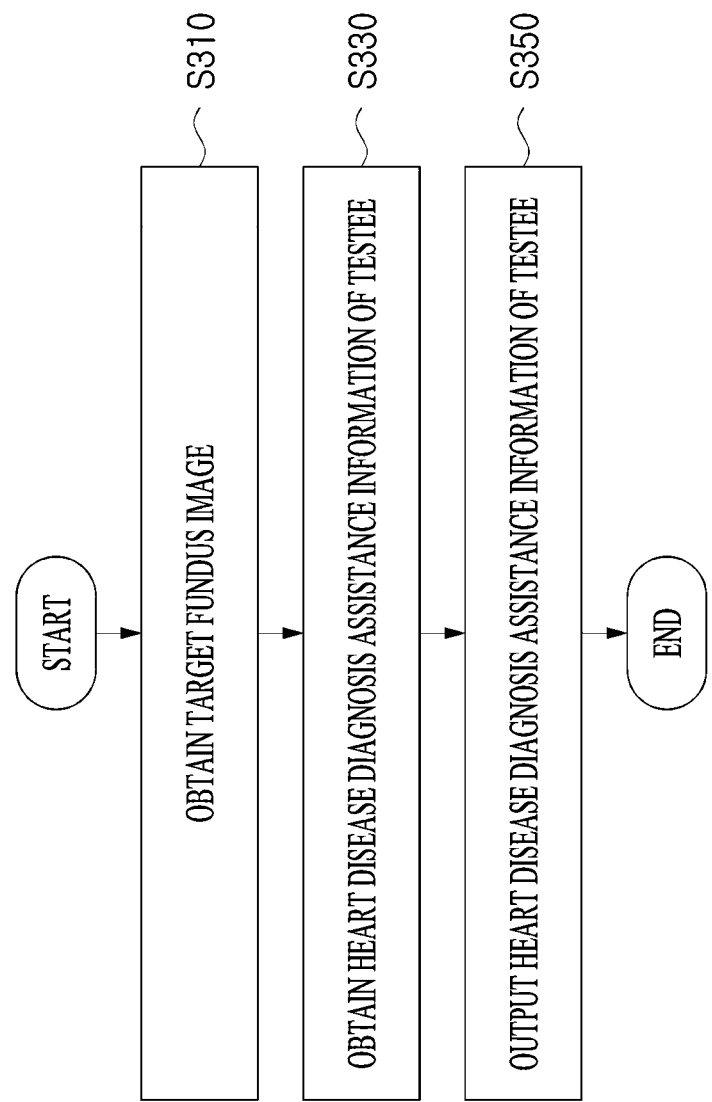
FIG. 40 is a view for describing a method of assisting in heart disease diagnosis according to an embodiment of the present invention.

FIG. 40 is a view for describing a method of assisting in heart disease diagnosis according to an embodiment of the present invention. Referring to FIG. 40, a method of assisting in heart disease diagnosis according to an embodiment of the present invention may include obtaining a target fundus image (S310), obtaining heart disease diagnosis assistance information of a testee (S330), and outputting the heart disease diagnosis assistance information of the testee (S350).

The obtaining of the target fundus image (S310) may include obtaining a target fundus image which is obtained by imaging a fundus of a testee.

The obtaining of the heart disease diagnosis assistance information of the testee (S330) may include, on the basis of the target fundus image, obtaining heart disease diagnosis assistance information of the testee according to the target fundus image, via a heart disease diagnosis assistance neural network model which obtains diagnosis assistance information used in diagnosis of a target heart disease according to a fundus image.

The heart disease diagnosis assistance information may include at least one of grade information which includes a grade selected from a plurality of grades indicating an extent of risk of a target heart disease, score information which is numerical value information for determining an extent of risk of a target heart disease, and risk information which indicates whether a testee belongs to a risk group for a target heart disease.

The obtaining of the heart disease diagnosis assistance information of the testee (S330) may further include obtaining a CAM related to the heart disease diagnosis assistance information according to the target fundus image.

The details described with reference to FIGS. 47 and 48 may apply analogically to an output of the CAM, feature map or other form of saliency map.

The outputting of the heart disease diagnosis assistance information of the testee (S350) may further include outputting a heart disease diagnosis assistance feature map which is generated on the basis of the CAM related to the heart disease diagnosis assistance information and is provided in the form corresponding to the target fundus image to indicate a feature region related to the heart disease diagnosis assistance information.

The outputting of the heart disease diagnosis assistance information of the testee (S350) may include outputting the target fundus image and the heart disease diagnosis assistance feature map to superimpose each other.

The outputting of the heart disease diagnosis assistance information of the testee (S350) may further include outputting instruction information determined on the basis of the heart disease diagnosis assistance information of the testee. In this case, the instruction information may be determined using a pre-stored heart disease diagnosis assistance information-instruction information relationship. For example, the instruction information may be determined using a matching table in which instruction information is matched according to heart disease diagnosis assistance information. The instruction information may be determined according to the heart disease diagnosis assistance information-instruction information relationship provided in advance, and the heart disease diagnosis assistance information-instruction information relationship may include a medical treatment method possible for a testee corresponding to the heart disease diagnosis assistance information.

According to an embodiment, the method of assisting in heart disease diagnosis may be performed by a device configured to assist in diagnosis of an eye disease. For example, the method of assisting in heart disease diagnosis may further include, on the basis of the target fundus image, obtaining eye disease diagnosis assistance information of the testee according to the target fundus image, via a heart disease diagnosis assistance neural network model which obtains eye disease diagnosis assistance information according to a fundus image.

Figure 41:
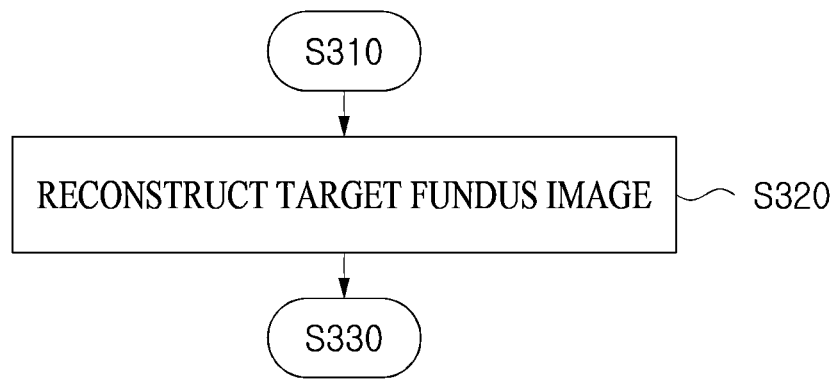
FIG. 41 is a view for describing a method of assisting in heart disease diagnosis according to an embodiment of the present invention.

FIG. 41 is a view for describing the method of assisting in heart disease diagnosis according to an embodiment of the present invention. Referring to FIG. 41, the method of assisting in heart disease diagnosis according to an embodiment of the present invention may further include reconstructing the target fundus image (S320).

The reconstructing of the target fundus image (S320) may include reconstructing the target fundus image so that a blood vessel element included in the target fundus image is highlighted in order to facilitate diagnosis of a target heart disease. In this case, the obtaining of the heart disease diagnosis assistance information of the testee (S330) may include obtaining heart disease diagnosis assistance information of the testee on the basis of the reconstructed target fundus image, and various pre-processing or reconstruction methods described herein may be applied to the reconstruction of the fundus image.

For example, the reconstructing of the target fundus image (S320) may include performing, on the target fundus image, pre-processing which highlights a region included in the target fundus image in which blood vessels are distributed. Alternatively, the reconstructing of the target fundus image (S320) may include extracting a region included in the target fundus image in which blood vessels are distributed.

The target heart disease may be a coronary artery disease.

The grade information may be coronary artery disease risk grade information which indicates an extent of risk of a coronary artery disease, the score information may be coronary artery calcium score information used in diagnosis of a coronary artery disease, and the risk information may be coronary artery disease risk information which indicates whether the testee belongs to a risk group for a coronary artery disease.

The heart disease diagnosis assistance neural network model may be trained to output heart disease diagnosis assistance information on the basis of a fundus image by using fundus image training data which includes a plurality of fundus images to which diagnosis assistance information labels are assigned.

According to an embodiment of the present invention, as a method for assisting in diagnosis of a target heart disease using a fundus image, a method of assisting in heart disease diagnosis which includes obtaining a target fundus image which is obtained by imaging a fundus of a testee, on the basis of a reconstructed target fundus image which is obtained by performing reconstruction to highlight blood vessel elements in the target fundus image, obtaining heart disease diagnosis assistance information of the testee via a heart disease diagnosis assistance neural network model which obtains heart disease diagnosis assistance information on the basis of a fundus image, and outputting the heart disease diagnosis assistance information of the testee may be provided.

The heart disease diagnosis assistance neural network model may be trained using fundus image training data which includes a plurality of fundus images in which blood vessel elements are highlighted and heart disease diagnosis assistance labels assigned to the plurality of fundus images.

The target heart disease may be a coronary artery disease, and the heart disease diagnosis assistance information may include at least one of grade information which includes a grade selected among a plurality of grades indicating an extent of risk of the target heart disease, score information which is numerical value information for determining an extent of risk of the target heart disease, and risk information which indicates whether a testee belongs to a risk group for the target heart disease.

The grade information may be coronary artery disease risk grade information which indicates an extent of risk of a coronary artery disease, the score information may be coronary artery calcium score information used in diagnosis of a coronary artery disease, and the risk information may be coronary artery disease risk information which indicates whether the testee belongs to a risk group for a coronary artery disease.

The outputting of the heart disease diagnosis assistance information of the testee may further include outputting instruction information obtained on the basis of the heart disease diagnosis assistance information. The instruction information may be determined according to the heart disease diagnosis assistance information-instruction information relationship provided in advance, and the heart disease diagnosis assistance information-instruction information relationship may include a medical treatment method possible for the testee corresponding to the heart disease diagnosis assistance information.

The method of assisting in heart disease diagnosis may further include, on the basis of the target fundus image, obtaining eye disease diagnosis assistance information of the testee according to the target fundus image via a heart disease diagnosis assistance neural network model which obtains eye disease diagnosis assistance information according to a fundus image.

The above-described method of assisting in heart disease diagnosis according to some embodiments may be provided in the form of a computer-readable recording medium in which a program for executing the method is recorded.

Figure 42:
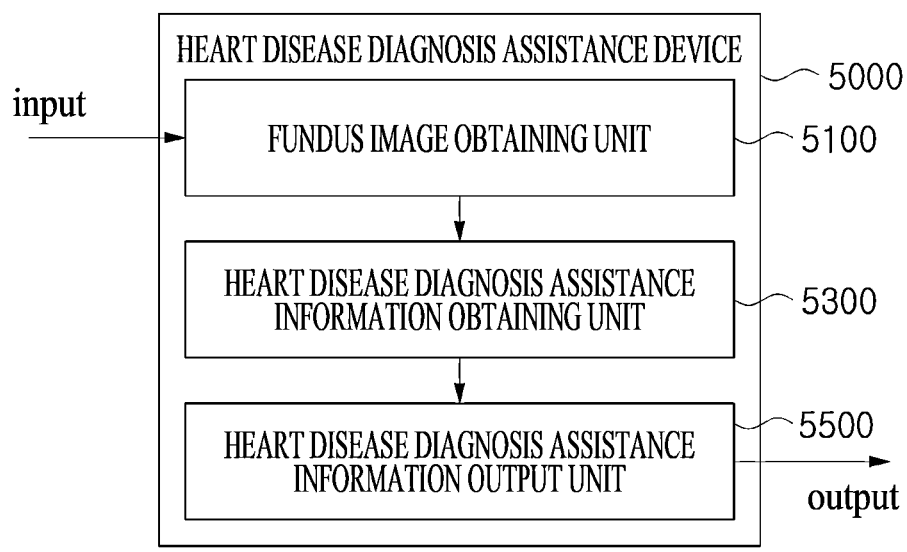
FIG. 42 is a view for describing a heart disease diagnosis assistance device 5000 according to an embodiment of the present invention.

FIG. 42 is a view for describing a heart disease diagnosis assistance device 5000 according to an embodiment of the present invention. Referring to FIG. 42, the heart disease diagnosis assistance device 5000 according to an embodiment of the present invention may include a fundus image obtaining unit 5100, a heart disease diagnosis assistance information obtaining unit 5300, and a heart disease diagnosis assistance information output unit 5500.

Referring to FIG. 42, the heart disease diagnosis assistance device 5000 for assisting in diagnosis of a target heart disease using a fundus image according to an embodiment of the present invention may include a fundus image obtaining unit configured to obtain a target fundus image by imaging a fundus of a testee, a heart disease diagnosis assistance information obtaining unit configured to, on the basis of the target fundus image, obtain heart disease diagnosis assistance information of a testee according to the target fundus image via a heart disease diagnosis assistance neural network model which obtains diagnosis assistance information used in diagnosis of the target heart disease according to a fundus image, and a heart disease diagnosis assistance information output unit configured to output the obtained heart disease diagnosis assistance information.

In this case, the heart disease diagnosis assistance information may include at least one of grade information which includes a grade selected among a plurality of grades indicating an extent of risk of a target heart disease, score information which is numerical value information for determining an extent of risk of a target heart disease, and risk information which indicates whether a testee belongs to a risk group for a target heart disease.

The target heart disease may be a coronary artery disease. In this case, the grade information may be coronary artery disease risk grade information which indicates an extent of risk of a coronary artery disease, the score information may be coronary artery calcium score information used in diagnosis of a coronary artery disease, and the risk information may be coronary artery disease risk information which indicates whether a testee belongs to a risk group for a coronary artery disease.

The heart disease diagnosis assistance information obtaining unit 5300 may obtain a CAM related to heart disease diagnosis assistance information.

The heart disease diagnosis assistance information output unit 5500 may output a heart disease diagnosis assistance feature map which is provided in the form corresponding to a target fundus image to indicate a feature region related to the heart disease diagnosis assistance information.

The heart disease diagnosis assistance information output unit 5500 may output instruction information which is based on the heart disease diagnosis assistance information of the testee and is determined using the pre-stored heart disease diagnosis assistance information-instruction information relationship.

The heart disease diagnosis assistance device 5000 may further include an eye disease diagnosis assistance information obtaining unit configured to, on the basis of the target fundus image, obtain eye disease diagnosis assistance information of the testee according to the target fundus image via a heart disease diagnosis assistance neural network model which obtains eye disease diagnosis assistance information according to a fundus image.

The heart disease diagnosis assistance information output unit 5500 may output eye disease diagnosis assistance information.

Figure 43:
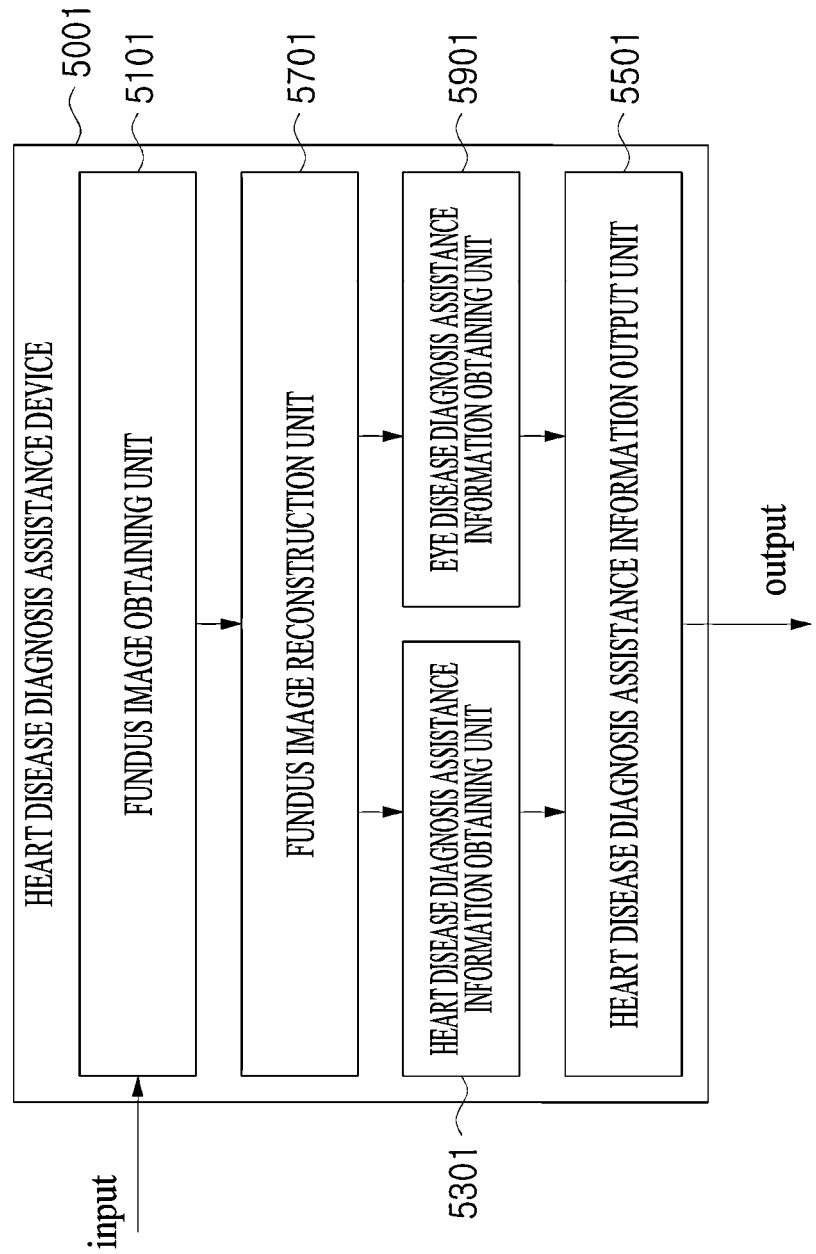
FIG. 43 is a view for describing a heart disease diagnosis assistance device 5001 according to another embodiment of the present invention.

FIG. 43 is a view for describing a heart disease diagnosis assistance device 5001 according to another embodiment of the present invention. Referring to FIG. 43, the heart disease diagnosis assistance device 5001 according to another embodiment of the present invention may include a fundus image obtaining unit 5101, a heart disease diagnosis assistance information obtaining unit 5301, and a heart disease diagnosis assistance information output unit 5501 and may further include a fundus image reconstruction unit 5701 or an eye disease diagnosis assistance information obtaining unit 5901.

For example, the heart disease diagnosis assistance device 5001 may further include the fundus image reconstruction unit 5701 configured to reconstruct the target fundus image so that a blood vessel element included in the target fundus image is highlighted in order to facilitate diagnosis of a target heart disease. In this case, the heart disease diagnosis assistance information obtaining unit may obtain heart disease diagnosis assistance information of the testee on the basis of the reconstructed target fundus image.

According to an embodiment, a heart disease diagnosis assistance device may obtain heart disease diagnosis assistance information using a heart disease neural network model including a primary neural network model which obtains a primary diagnosis assistance information and a secondary neural network model which is connected in series to the primary neural network model and obtains a secondary diagnosis assistance information at least partly based on the primary diagnosis assistance information. The heart disease diagnosis assistance device may obtain the primary diagnosis assistance information and/or the secondary diagnosis assistance information using the primary neural network model and the secondary neural network model.

Hereinafter, some embodiments of various cases in which diagnosis assistance information is obtained on the basis of a target fundus image will be described.

2.3.5.2 Risk Group Selection Using Neural Network Model

According to an embodiment of the present invention, a method of assisting in heart disease diagnosis using a heart disease diagnosis assistance neural network model which is trained to obtain disease presence/absence information related to a certain heart disease (or to select a risk group for the heart disease) on the basis of a fundus image may be provided. The method of assisting in heart disease diagnosis which will be described below may be performed by the diagnostic unit, control unit, or processor described herein.

Figure 44:
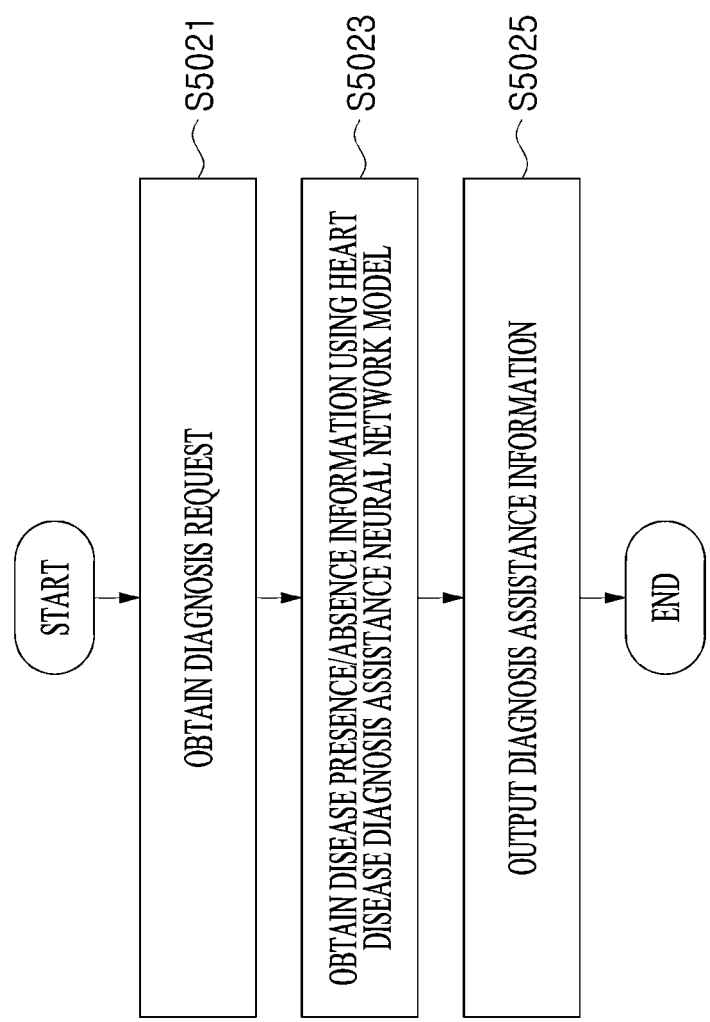
FIG. 44 is a view for describing a method of assisting in heart disease diagnosis according to an embodiment of the present invention.

FIG. 44 is a view for describing a method of assisting in heart disease diagnosis according to an embodiment of the present invention. Referring to FIG. 44, a method of assisting in heart disease diagnosis according to an embodiment of the present invention may include obtaining a diagnosis request (S5021), obtaining disease presence/absence information using a heart disease diagnosis assistance neural network model (S5023), and outputting diagnosis assistance information (S5025).

The obtaining of the diagnosis request (S5021) may include obtaining a diagnosis target fundus image (hereinafter referred to as "target fundus image"). The obtaining of the diagnosis request may include obtaining information on diagnosis assistance information to be obtained (obtainment target diagnosis assistance information).

The diagnosis request may be data that requests for a start of a diagnosis assistance process. The diagnosis request may be data which includes information on a target heart disease and requests for diagnosis assistance information related to the target heart disease. The diagnosis request may be data that requests for disease presence/absence information related to whether a patient belongs to a risk group for a target disease. For example, the diagnosis request may include a target fundus image and identification information of the target diagnosis assistance information.

For example, a diagnosis request obtaining module may obtain a target fundus image and a diagnosis request (or a diagnosis assistance request) that requests for diagnosis (or diagnosis assistance) related to a coronary artery disease on the basis of the target fundus image. Also, for example, a diagnostic unit may obtain a diagnosis request made by a user via a user input unit or obtain a diagnosis request from an external device via a communication unit.

For example, the diagnosis request obtaining module may obtain a diagnosis request that requests for diagnosis assistance information related to the presence of a target disease according to a target fundus image and/or the need for administration (or medication) related to the target disease.

The obtaining of the disease presence/absence information using the heart disease diagnosis assistance neural network model (S5023) may include obtaining disease presence/absence information on the basis of a diagnosis assistance request that requests for disease presence/absence information. The obtaining of the disease presence/absence information may include obtaining disease presence/absence information on the basis of a diagnosis assistance request that requests for diagnosis assistance related to a target heart disease.

For example, a heart disease diagnosis assistance module may, on the basis of the target fundus image, obtain disease presence/absence information or the disease presence/absence information and other information by using a neural network model which obtains disease presence/absence information indicating whether a patient has a coronary artery disease. Also, for example, a diagnostic unit may obtain information on the presence or absence of a target heart disease related to a fundus image from a neural network model via a control unit or a processor.

The heart disease diagnosis assistance module may further obtain information inferred on the basis of the information on the presence or absence of the target disease. For example, the heart disease diagnosis assistance module may further obtain, on the basis of a predetermined correlation or in consideration of an input value other than the fundus image as well as the fundus image, an extent of risk of a disease other than the target heart disease.

According to an embodiment, a heart disease diagnosis assistance device may obtain secondary diagnosis assistance information using a heart disease neural network model including a primary neural network model which obtains a primary diagnosis assistance information (for example, a probability that a testee has a target heart disease) and a secondary neural network model which is connected in series to the primary neural network model and obtains a secondary diagnosis assistance information (for example, a probability that a testee belongs to a risk group for a target heart disease) at least partly based on the primary diagnosis assistance information. The outputting of the diagnosis assistance information (S5025) may further include outputting disease presence/absence information related to the target heart disease. The outputting of the diagnosis assistance information may further include outputting the disease presence/absence information on the target heart disease and other information thereon together. For example, the outputting of the diagnosis assistance information may include outputting the disease presence/absence information and information inferred using the disease presence/absence information together.

For example, the diagnosis assistance information output module may output the disease presence/absence information on the target heart disease. The diagnosis assistance information output module may output the disease presence/absence information on the target heart disease and other information thereon. The diagnosis assistance information output module may transmit the disease presence/absence information to an external device or output the disease presence/absence information in the form recognizable by a user. Also, for example, the diagnostic unit may transmit diagnosis assistance information including disease presence/absence information to the display unit or the output unit so that the disease presence/absence information is provided to the user.

2.3.5.3 Grade Determination Using Neural Network Model

According to an embodiment of the present invention, a method of assisting in heart disease diagnosis using a heart disease diagnosis assistance neural network model which is trained to obtain grade information indicating an extent of risk of a certain heart disease on the basis of a fundus image may be provided. The method of assisting in heart disease diagnosis which will be described below may be performed by the diagnostic unit, control unit, or processor described herein.

Figure 45:
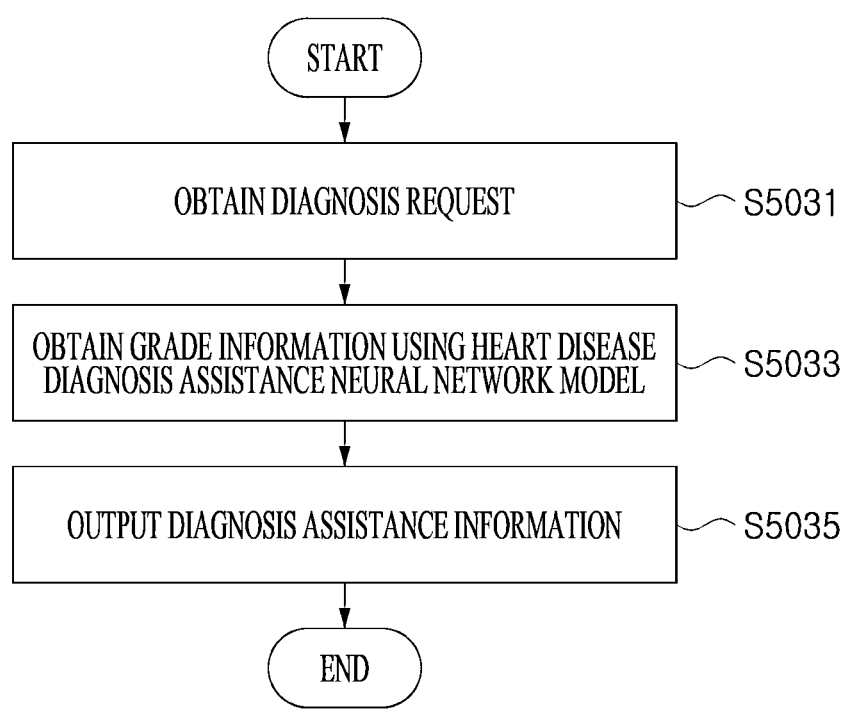
FIG. 45 is a view for describing a method of assisting in heart disease diagnosis according to an embodiment of the present invention.

FIG. 45 is a view for describing a method of assisting in heart disease diagnosis according to an embodiment of the present invention. Referring to FIG. 45, a method of assisting in heart disease diagnosis according to an embodiment of the present invention may include obtaining a diagnosis request (S5031), obtaining grade information using a heart disease diagnosis assistance neural network model (S5033), and outputting diagnosis assistance information (S5035).

The obtaining of the diagnosis request (S5031) may include obtaining a target fundus image. The details described above in relation to risk group selection may similarly apply to the obtaining of the diagnosis request.

The obtaining of the diagnosis request (S5031) may include obtaining a diagnosis request which includes a diagnosis target fundus image and information on a target heart disease. The obtaining of the diagnosis request (S5031) may include obtaining a diagnosis request that requests for grade information related to a target heart disease of a patient. The obtaining of the diagnosis request (S5031) may include obtaining a diagnosis request that requests for grade information and other information.

For example, the diagnosis request obtaining module may obtain a target fundus image and a diagnosis request that request for diagnosis assistance information of a coronary artery disease according to the target fundus image. The diagnosis request obtaining module may obtain a diagnosis request that requests for prescription information related to a cardiovascular disease according to a target fundus image. The diagnostic unit may obtain a diagnosis request related to the target fundus image via a user input unit, a user interface, or the like.

The obtaining of the grade information using the heart disease diagnosis assistance neural network model (S5033) may include, when a diagnosis request that requests for grade information is obtained, obtaining grade information on a target heart disease from the target fundus image by using the heart disease diagnosis assistance neural network model. The obtaining of the grade information may include identifying a grade information request included in the diagnosis request and obtaining grade information related to the target heart disease in response to the diagnosis request that requests for the grade information.

For example, the heart disease diagnosis assistance module may, on the basis of the target fundus image, obtain grade information or the grade information and other information by using a neural network model which obtains grade information indicating an extent of risk of a coronary artery disease for a patient. Also, for example, the diagnostic unit may obtain grade information of the target heart disease related to a fundus image from a neural network model via a control unit or a processor.

The heart disease diagnosis assistance module may further obtain information inferred on the basis of the grade information of the target disease. For example, the heart disease diagnosis assistance module may further obtain, on the basis of a predetermined correlation or in consideration of an input value other than the fundus image as well as the fundus image, an extent of risk of a disease other than the target heart disease. The heart disease diagnosis assistance module may obtain grade information and prescription information related to a target disease together with each other. The prescription information may be obtained on the basis of a matching table in which grades and prescriptions are matched and stored.

Also, for example, the heart disease diagnosis assistance module may obtain prescription information using a neural network model which obtains, on the basis of a target fundus image, prescription information related a heart disease condition of a patient. The heart disease diagnosis assistance module may obtain prescription information related to whether taking a statin drug is required for the patient, by using a neural network model which obtains, on the basis of a target fundus image (a fundus image received as an input), prescription information related to specific medical practice, e.g., the need of prescription for taking the statin drug.

According to an embodiment, a heart (cardiovascular) disease diagnosis assistance device may obtain heart disease diagnosis assistance information using a heart disease neural network model including a primary neural network model which obtains a primary diagnosis assistance information (for example, a probability that the testee has a target disease) and a secondary neural network model which is connected in series to the primary neural network model and obtains a secondary diagnosis assistance information (for example, a grade information related to the target disease for the testee or a prescription information indication whether taking statin is required for the testee) at least partly based on the primary diagnosis assistance information.

The outputting of the diagnosis assistance information (S5035) may further include outputting grade information related to the target heart disease. The outputting of the diagnosis assistance information (S5035) may further include outputting the grade information on the target heart disease and other information thereon together. For example, the outputting of the diagnosis assistance information may include outputting the grade information and information inferred using the grade information together.

For example, the diagnosis assistance information output module may output the grade information on the target heart disease. The diagnosis assistance information output module may output the grade information on the target heart disease and other information thereon. The diagnosis assistance information output module may transmit the grade information to an external device or output the grade information in the form recognizable by a user. Also, for example, the diagnostic unit may transmit diagnosis assistance information including grade information to the display unit or the output unit so that the grade information is provided to the user.

2.3.5.4 Score Prediction of Numerical Prediction Neural Network Model

According to an embodiment of the present invention, a method of assisting in heart disease diagnosis using a heart disease diagnosis assistance neural network model which is trained to obtain a score related to a certain heart disease on the basis of a fundus image may be provided. The method of assisting in heart disease diagnosis which will be described below may be performed by the diagnostic unit, control unit, or processor described herein.

Figure 46:
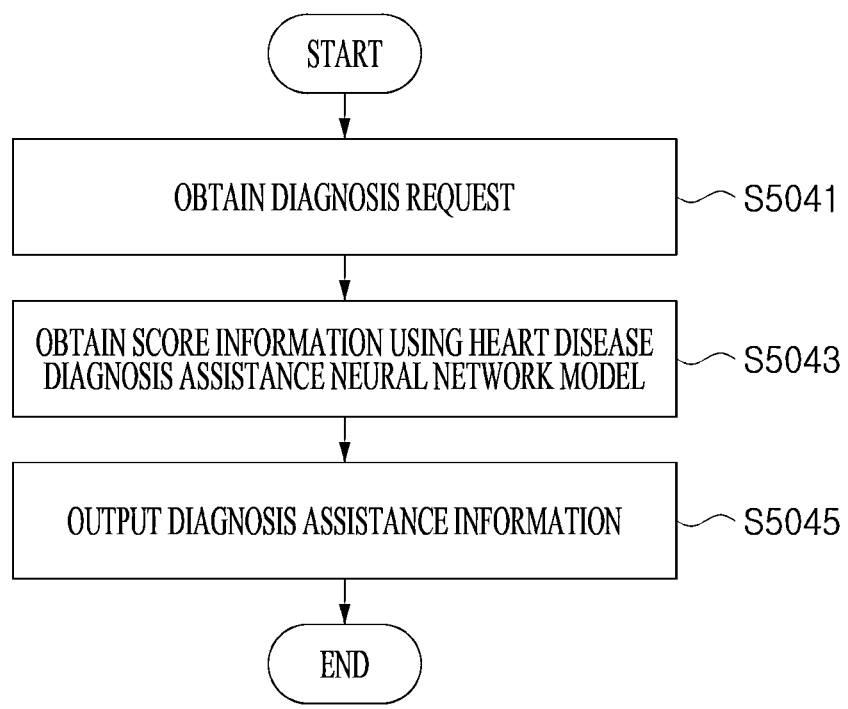
FIG. 46 is a view for describing a method of assisting in heart disease diagnosis according to an embodiment of the present invention.

FIG. 46 is a view for describing a method of assisting in heart disease diagnosis according to an embodiment of the present invention. Referring to FIG. 46, a method of assisting in heart disease diagnosis according to an embodiment of the present invention may include obtaining a diagnosis request (S5041), obtaining score information using a heart disease diagnosis assistance neural network model (S5043), and outputting diagnosis assistance information (S5045).

The obtaining of the diagnosis request (S5041) may include obtaining a target fundus image. The details described above in relation to risk group selection may similarly apply to the obtaining of the diagnosis request.

The obtaining of the diagnosis request (S5041) may include obtaining a diagnosis request which includes a diagnosis target fundus image and information on a target heart disease. The obtaining of the diagnosis request (S5041) may include obtaining a diagnosis request that requests for score information related to a target heart disease of a patient or obtaining a diagnosis request that requests for score information and other information.

For example, the diagnosis request obtaining module may obtain a diagnosis request that requests for a target fundus image and a coronary artery calcium score according to the target fundus image.

The obtaining of the score information using the heart disease diagnosis assistance neural network model (S5043) may include, when a diagnosis request that requests for score information is obtained, obtaining score information on a target heart disease from the target fundus image by using the heart disease diagnosis assistance neural network model. The obtaining of the score information may include obtaining a score information request included in the diagnosis request and obtaining the requested score information.

For example, the heart disease diagnosis assistance module may use the heart disease diagnosis assistance neural network model and, on the basis of the target fundus image, obtain a coronary artery calcium score for determining an extent of risk of a coronary artery disease for a patient. Also, for example, the diagnostic unit may obtain heart disease diagnosis assistance score information of the target heart disease related to a fundus image from a neural network model via a control unit or a processor.

The heart disease diagnosis assistance module may further obtain additional information related to the score information or additional diagnosis assistance information which is obtained in consideration of an input value other than the fundus image as well as the fundus image.

According to an embodiment, using the heart (or cardiovascular) disease diagnosis assistance neural network model, the heart disease diagnosis assistance module may obtain, as a score related to a heart disease according to a target fundus image, at least one of values of at least one factor for calculating any one of a coronary artery calcium score, an arteriosclerosis risk score, a CIMT (Carotid Intima-Media Thickness) value, a Framingham risk score, a QRISK score, a value according to an extent of risk of an ASCVD, a score according to the SCORE, a score according to a Score from Scottish Intercollegiate Guidelines Network (ASSIGN), and the above-listed scores. According to an embodiment, the heart disease diagnosis assistance module may obtain a score value for determining the need of predetermined medical practice for treating a target disease, by using a heart disease diagnosis assistance neural network model. For example, using the heart disease diagnosis assistance neural network model, the heart disease diagnosis assistance module may obtain a score value (for example, an ASCVD risk score value) for determining the need of prescription of a statin drug for a testee.

According to an embodiment, the heart disease diagnosis assistance module may obtain heart disease diagnosis assistance information with an additional data related to the testee other than the fundus image as an input value together with the fundus image. For example, the heart disease diagnosis assistance module may obtain heart disease diagnosis assistance information based on a testee's cholesterol level, triglyceride level, low-density lipoprotein (LDL) cholesterol level, high-density lipoprotein (HDL) cholesterol level, very-low-density liprotein (VDL) cholesterol level, gender, age and/or gender and the fundus image, as input data together with the fundus image.

According to an embodiment, a heart (cardiovascular) disease diagnosis assistance device may obtain heart disease diagnosis assistance information using a heart disease neural network model including a primary neural network model which obtains a primary diagnosis assistance information (for example, the probability that the testee has a coronary artery disease) and a secondary neural network model which is connected in series to the primary neural network model and obtains a secondary diagnosis assistance information (for example, a coronary artery calcium score of a testee) at least partly based on the primary diagnosis assistance information.

The outputting of the diagnosis assistance information (S5045) may include outputting score information related to the target heart disease and/or other information (for example, diagnosis assistance information on another disease or grade or disease presence/absence information on the target heart disease). The diagnosis assistance information output module or the diagnostic unit may output score information and/or other information related to the target heart disease.

2.3.6 Output of Diagnosis Assistance Information

Heart disease diagnosis assistance information obtained via a heart disease diagnosis assistance neural network model may be output. The heart disease diagnosis assistance information may be provided to a user. The client device, mobile device, diagnostic device, output unit, or the like described herein may output the heart disease diagnosis assistance information in the form recognizable by the user.

The heart disease diagnosis assistance information may be output in the form of visual and/or aural data. The heart disease diagnosis assistance information may be output via a user interface. For example, the heart disease diagnosis assistance information may be output via the user interface described above with reference to FIGS. 29 and 30.

The heart disease diagnosis assistance information may be output to an external device. For example, the diagnostic device, server device, diagnostic unit, or the like may transmit the obtained heart disease diagnosis assistance information to an external device via wired or wireless communication. Alternatively, the heart disease diagnosis assistance information may be stored in a memory or a server.

Secondary information obtained from diagnosis assistance information obtained via a neural network model may be output. The secondary information obtained from the diagnosis assistance information may be information for assisting in diagnosis of a heart disease or the like in more detail. For example, the secondary information obtained from the diagnosis assistance information may be implemented using prescription information, instruction information, prediction information, or the like which will be described below.

The diagnosis assistance information described herein may be understood as encompassing primary diagnosis assistance information obtained via a neural network model and/or secondary diagnosis assistance information obtained from the primary diagnosis assistance information.

Prescription information may be obtained on the basis of diagnosis assistance information. For example, the prescription information may include a type of drug to be administered to a user, a period in which the drug is administered to the user, a dosage of the drug, or the like. For example, the prescription information may include prescription information on an anti-hyperlipidemic drug. The prescription information may include information on drugs, with which a testee may be prescribed in relation to a target heart disease, such as an anti-hyperlipidemic drug, an antihypertensive drug, and an antithrombotic drug. For example, the prescription information may include administration information related to whether administration is required for a testee, an amount of administration, a period of administration, or the like for drugs based on statins (which include various drugs such as simvastatin, atorvastatin, rosuvastatin), which are HMG-CoA reductase inhibitors, bile acid sequestrant, nicotinic acid, and the like.

The prescription information may be pre-stored to match diagnosis assistance information. The prescription information may be determined using a database in which prescription behaviors of a user according to diagnosis assistance information are stored. For example, prescription information related to administration of statin may be obtained using a database in which risk grades related to hyperlipidemia, dyslipidemia, and the like are matched to the needs of administration of statin according to each grade.

According to an embodiment, when diagnosis assistance information is score information for determining an extent of risk of a cardiovascular disease, prescription information may be obtained as secondary information related to the score information. For example, when diagnosis assistance information is an ASCVD risk score or a score according to the SCORE for determining whether one has dyslipidemia, a first piece of prescription information indicating that the need of taking statin is low for a testee may be obtained when the obtained score is less than a reference value, and a second piece of prescription information indicating that the need of taking statin is high for the testee may be obtained when the obtained score is greater than the reference value.

According to an embodiment, when obtained diagnosis information is a coronary artery calcification score (CACs), prescription information that recommends that a testee take a statin drug may be obtained according to a predetermined guideline when the CACs exceeds a reference value (for example, 100), and prescription information that postpones taking the statin drug may be obtained when the CACs is less than the reference value.

The prescription information may be obtained via a neural network model which is trained using training data including prescription behavior information of a user according to diagnosis assistance information. As a specific example, a prescription assistance neural network model which is trained to obtain prescription data input from a user in response to an output of diagnosis assistance information, obtain prescription information training data in which a prescription data label is assigned to diagnosis assistance information, and output prescription information by using the obtained prescription information training data with the diagnosis assistance information as an input may be provided. The prescription information obtained using the prescription assistance neural network model may be provided to the user together with or separately from the diagnosis assistance information. For example, in response to obtaining diagnosis assistance information (for example, grade information or score information) through the diagnosis assistance information obtaining module, a diagnostic device may obtain prescription data related to a predetermined medicine (for example, statin) provided by a user and obtain training data including an input fundus image to which the prescription data is labeled.

Instruction information obtained on the basis of diagnosis assistance information may be output. The instruction information may include information on a medical treatment method. For example, instruction information for providing at least one candidate action that is expected to be suitable for a user or patient on the basis of the diagnosis assistance information may be obtained. The instruction information may instruct an action such as additionally-required checkups, the time of follow-up visit, suggestions of hospitals that a user may consider transferring to, recommended surgery or treatment, and the like. The instruction information may be pre-stored to match diagnosis assistance information. The instruction information may be determined using a database in which instruction behaviors of a user according to diagnosis assistance information are stored.

For example, the instruction information may include management guideline information related to a target heart disease such as recommended lifestyle and exercise prescription for a testee.

Also, for example, the instruction information may include additional checkup information indicating types of recommended in-depth medical checkups. For example, when obtained diagnosis information indicates that the need of taking statin is unclear for a testee (e.g., when score information is greater than a first reference value and less than a second reference value or when a target fundus image is classified into a second grade among first to third grades), the diagnostic device may obtain and/or output instruction information that recommends a coronary artery CT scan (or an ankle-brachial index), a blood vessel stiffness test (pulse wave velocity analysis), 24-hour Holter monitoring, and the like.

The instruction information may be obtained via a neural network model which is trained using training data including instruction behavior information according to diagnosis assistance information. As a specific example, an instruction assistance neural network model which is trained to obtain instruction data input from a user in response to diagnosis assistance information being provided to the user, obtain instruction information training data in which an instruction data label is assigned to diagnosis assistance information, and output instruction information by using the obtained instruction information training data with the diagnosis assistance information as an input may be provided. The instruction information obtained using the instruction assistance neural network model may be provided to the user together with or separately from the diagnosis assistance information.

Prediction information obtained on the basis of diagnosis assistance information may be output. The prediction information may include information on prognosis related to a target heart disease of a testee. For example, the prediction information may include death probability information which indicates the probability of death within the next five years or the probability of death within the next ten years in relation to the target heart disease of the testee.

According to an embodiment, the prediction information may be provided together with the instruction information or prescription information. For example, secondary information may include, in addition to specific instruction information and prescription information, prediction information related to when a subsequent procedure instructed in the corresponding information is performed.

For example, the secondary information may include first prediction information including the probability of death of a testee when the testee does not take a drug and second prediction information including the probability of death of the testee when the drug is administered at a recommended dose according to prescription information determined according to obtained heart disease diagnosis assistance information.

As another example, the secondary information may also include prediction information related to the probability of death or a decrease in the probability of death when the testee follows a guideline according to instruction information determined according to the obtained heart disease diagnosis assistance information.

Meanwhile, according to an embodiment of the present invention, diagnosis assistance information may include a CAM related to the output diagnosis assistance information. Together with the primary diagnosis assistance information or as the primary diagnosis assistance information, a CAM may be obtained from a neural network model. When the CAM is obtained, a visualized image of the CAM may be output. The CAM may be provided to a user via the above-described user interface. The CAM may be provided according to a user's selection. A CAM image may be provided together with a fundus image. The CAM image may be provided to superimpose the fundus image. The class activation map in this description is construed as including similar or expanded concepts which refer to indicate relationship between locations in the image and the prediction result. For example, the class activation map may be a Saliency map, a heat map, a feature map or a probability map, which provide information in relationship between pixels in the image and the prediction result. As a specific example, when a diagnosis assistance system for assisting in heart disease diagnosis on the basis of a fundus image includes a fundus image obtaining unit configured to obtain a target fundus image, a pre-processing unit configured to process the target fundus image so that blood vessels therein are highlighted, a diagnosis assistance unit configured to obtain heart disease diagnosis assistance information related to a patient on the basis of the pre-processed image, and an output unit configured to output the heart disease diagnosis assistance information, the diagnosis assistance unit may obtain a CAM related to a heart disease diagnosis assistance unit, and the output unit may output the obtained CAM to superimpose the target fundus image.

In other words, a method of providing diagnosis assistance information to a user may include obtaining a third image which is a CAM image obtained via a heart disease diagnosis assistance neural network model based on a first image corresponding to an image which is obtained by imaging (that is, original image) and a second image (for example, a blood vessel highlighting image or a blood vessel extraction image) obtained by reconstructing the first image so that target elements (for example, blood vessels) included in the first image are highlighted and displaying the first image and the third image to superimpose each other.

Figure 47:
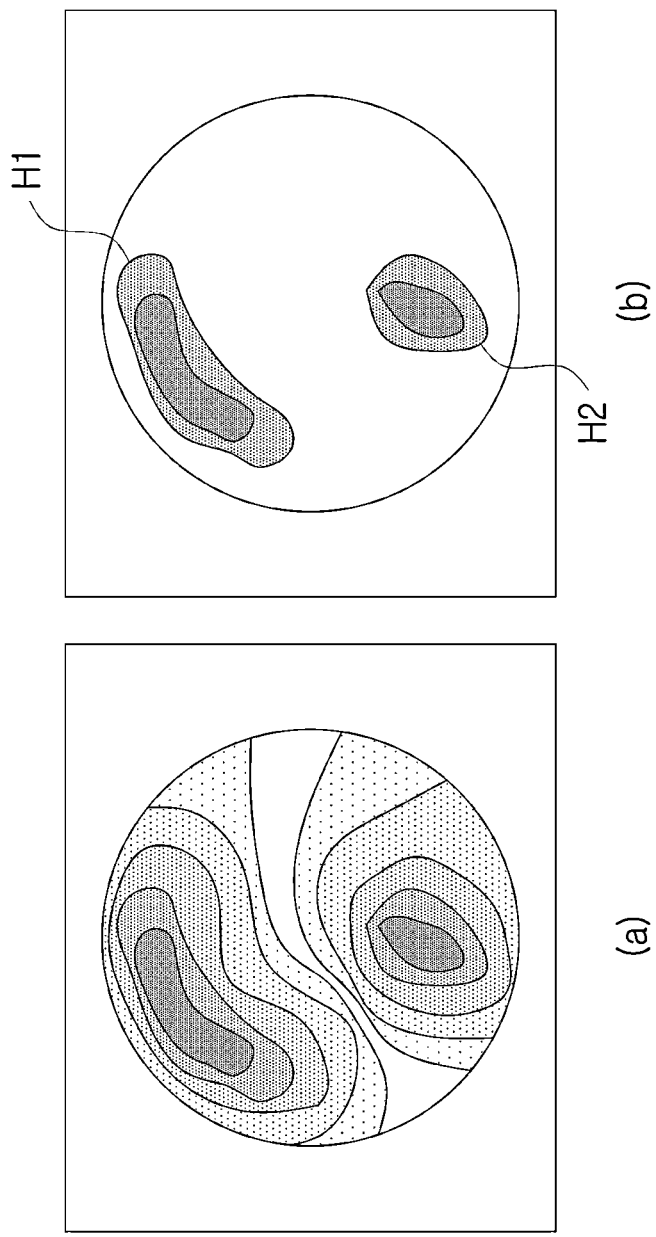
FIG. 47 is a view for describing a diagnosis assistance method according to an embodiment of the present invention.

FIG. 47 is a view for describing a diagnosis assistance method according to an embodiment of the present invention. Referring to FIG. 47, a diagnosis assistance method according to an embodiment of the present invention may include obtaining a CAM related to heart disease diagnosis assistance information or obtaining a feature map for displaying a region related to the obtained heart disease diagnosis assistance information in a fundus image from the CAM. The CAM or feature map may be provided in the form of visual information to a user.

FIG. 47(*a*) schematically illustrates a CAM obtained by the heart disease diagnosis assistance neural network model described herein. The CAM may refer to a feature map used in order to visualize the basis of inferred diagnosis assistance information that is output from the heart disease diagnosis assistance neural network model. The CAM may include pixels to which activity values indicating correlation with the output information are assigned. The pixels included in the CAM may have color values. The color values may be determined according to the activity values. For example, in FIG. 47(*a*), a dark region (or a region having a specific color) may be a region strongly related to heart disease diagnosis assistance information obtained by the heart disease diagnosis assistance neural network model.

FIG. 47(*b*) schematically illustrates a feature map obtained from the CAM illustrated in FIG. 47(*a*). The feature map may be generated by extracting, from the CAM, only the regions in which correlation with the heart disease diagnosis assistance information is a threshold value or higher. In other words, the feature map may be generated on the basis of pixels from the CAM whose activity values are the threshold value or higher.

The feature map may include a highlighting region which is visually highlighted. For example, referring to FIG. 47(*b*), the feature map according to an embodiment of the present invention may include a first highlighting region H1 and a second highlighting region H2 obtained on the basis of pixels from the CAM illustrated in FIG. 47(a) whose activity values are a reference value or higher.

Figure 48:
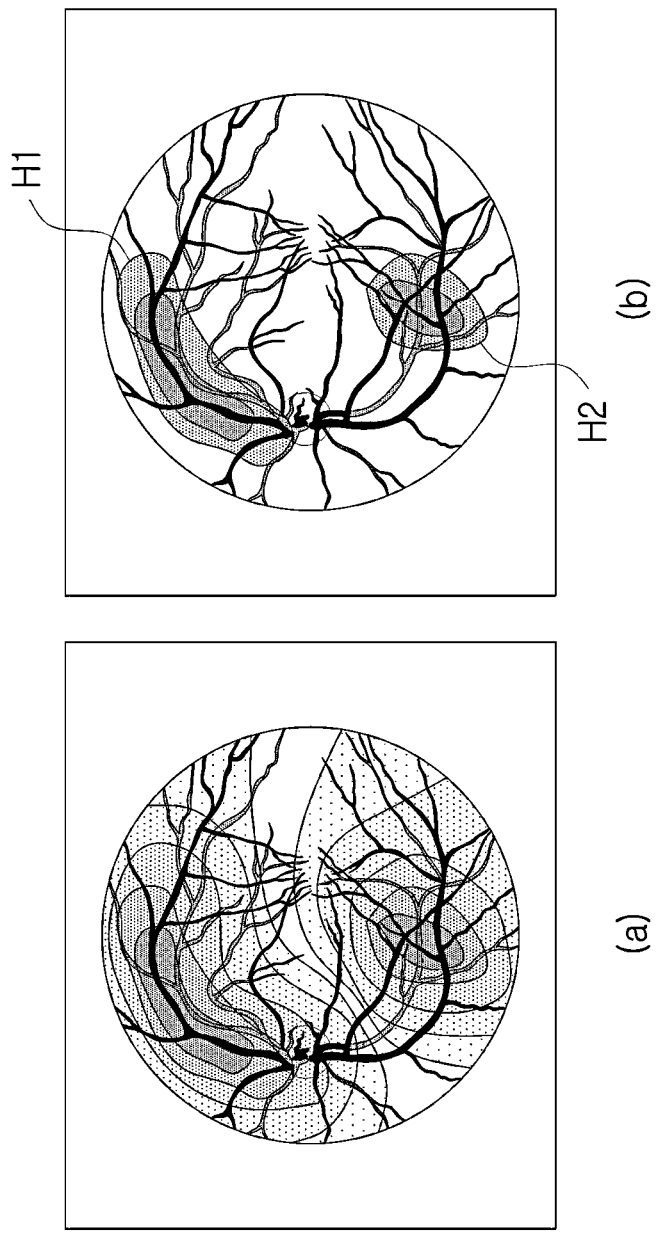
FIG. 48 is a view for describing a diagnosis assistance method according to an embodiment of the present invention.

FIG. 48 is a view for describing a diagnosis assistance method according to an embodiment of the present invention. Referring to FIG. 48, a diagnosis assistance method according to an embodiment of the present invention may include causing a CAM or a feature map to superimpose a fundus image. The fundus image and the CAM or feature map superimposing the fundus image may be provided in the form of visual information to a user.

FIG. 48(a) illustrates an example of a CAM superimposing on a fundus image. The CAM superimposing on the fundus image may visually show correlation between the output diagnosis assistance information and pixels included in the fundus image.

FIG. 48(b) illustrates an example of a feature map superimposing on a fundus image. Highlighting regions H1 and H2 included in the feature map may visually highlight predetermined regions in the fundus image. The highlighting regions H1 and H2 included in the feature map may visually highlight regions strongly related to the output diagnosis assistance information.

When visual information in which regions related to diagnosis assistance information are indicated as in FIG. 47, 48(a), or 48(b) is provided to the user, the user may more clearly recognize regions which are the basis of deriving the diagnosis assistance information that is output from the fundus image. For example, when risk information which indicates that a testee belongs to a risk group for a coronary artery disease is obtained via a heart disease diagnosis assistance neural network model, by providing a CAM or a feature map related to the risk information or a fundus image with the superimposed CAM or feature map to the user, the time required for the user to identify a blood vessel site related to a coronary artery disease may be shortened.

Although the description has been given above on the basis of the case in which a heart disease diagnosis assistance neural network model is used, the above description may be extensively applied to various diseases other than cardiovascular diseases.

According to an embodiment of the present invention, the output diagnosis assistance information may be changed. The output diagnosis assistance information may be changed according to accuracy of a neural network model or the number of pieces of training data used in training of the neural network model.

For example, as the accuracy of a heart disease diagnosis assistance neural network model used in obtaining diagnosis assistance information is improved, the output diagnosis assistance information may be changed from disease presence/absence information to grade information. Alternatively, as the accuracy of the heart disease diagnosis assistance neural network model is improved, the output diagnosis assistance information may be changed from grade information to score information.

Also, for example, as the number of pieces of training data used in training of the heart disease diagnosis assistance neural network model used in obtaining diagnosis assistance information is increased, the output diagnosis assistance information may be changed from disease presence/absence information to grade information. Alternatively, the output diagnosis assistance information may be changed from grade information to score information.

Diagnosis assistance information provided to a user may be determined differently for each range. A range which becomes the basis of determining a type of output diagnosis assistance information may be changed.

For example, when data included in training data used in a neural network model for outputting score information includes data that is not evenly distributed for each score label value, the output accuracy of a neural network model may be different according to a score value. In consideration of this aspect, outputting a score value for a score section whose accuracy is sufficiently secured while outputting a grade for a score section whose accuracy is not sufficiently secured may be useful for determination by a user.

As a specific example, when score information is obtained using a neural network model which outputs score information on the basis of a fundus image, the output diagnosis assistance information may be score information when the obtained score information belongs to a first score section, and the output diagnosis assistance information may be grade information when the obtained score information belongs to a second score section. In this case, the neural network model may be a neural network model which is trained such that accuracy of output information in the second score section is lower than accuracy of output information in the first score section.

Figure 74:
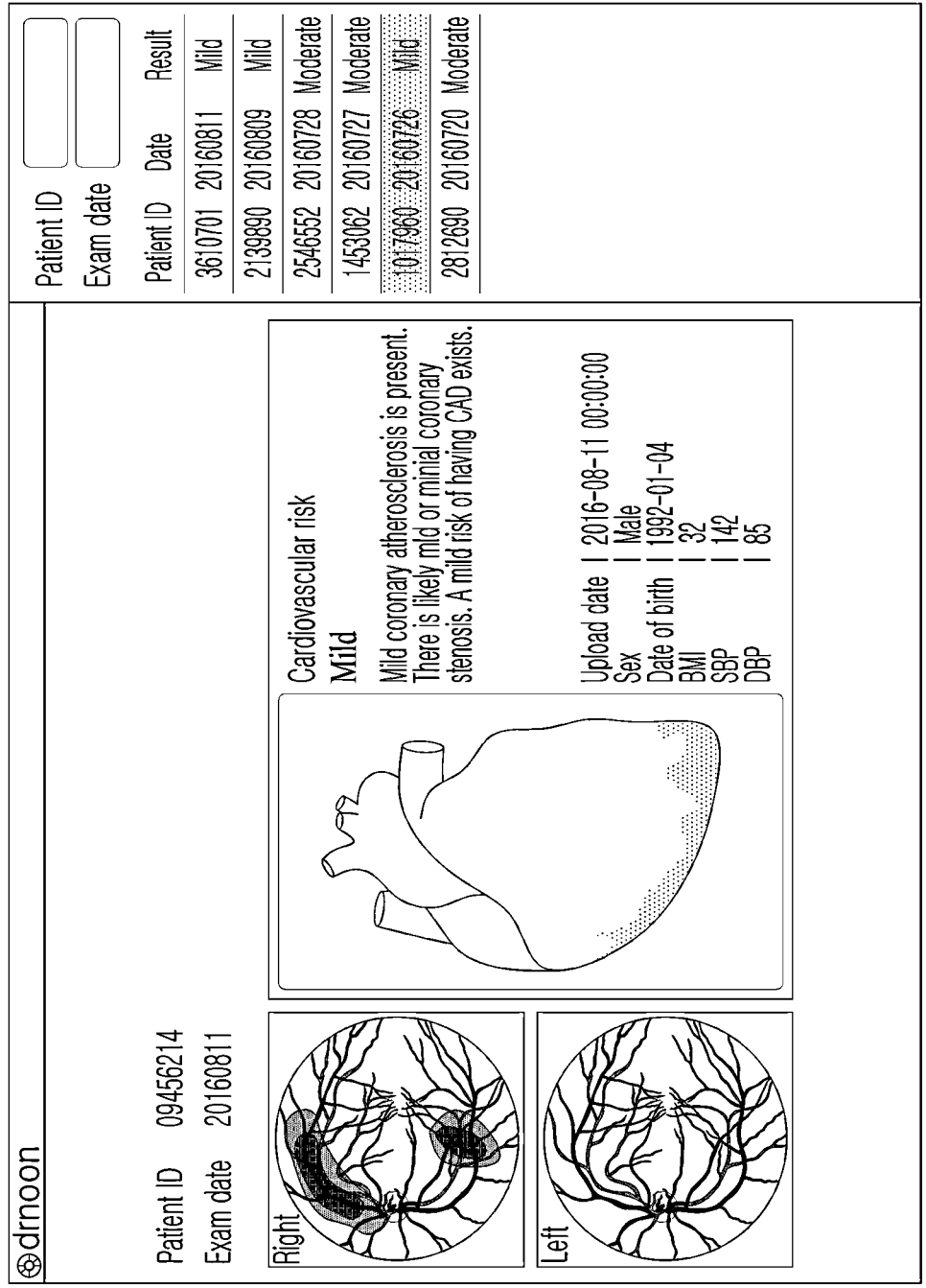
FIG. 74 is a view for describing a graphical interface for displaying diagnosis assistance information according to an embodiment of the invention described herein.
Figure 75:
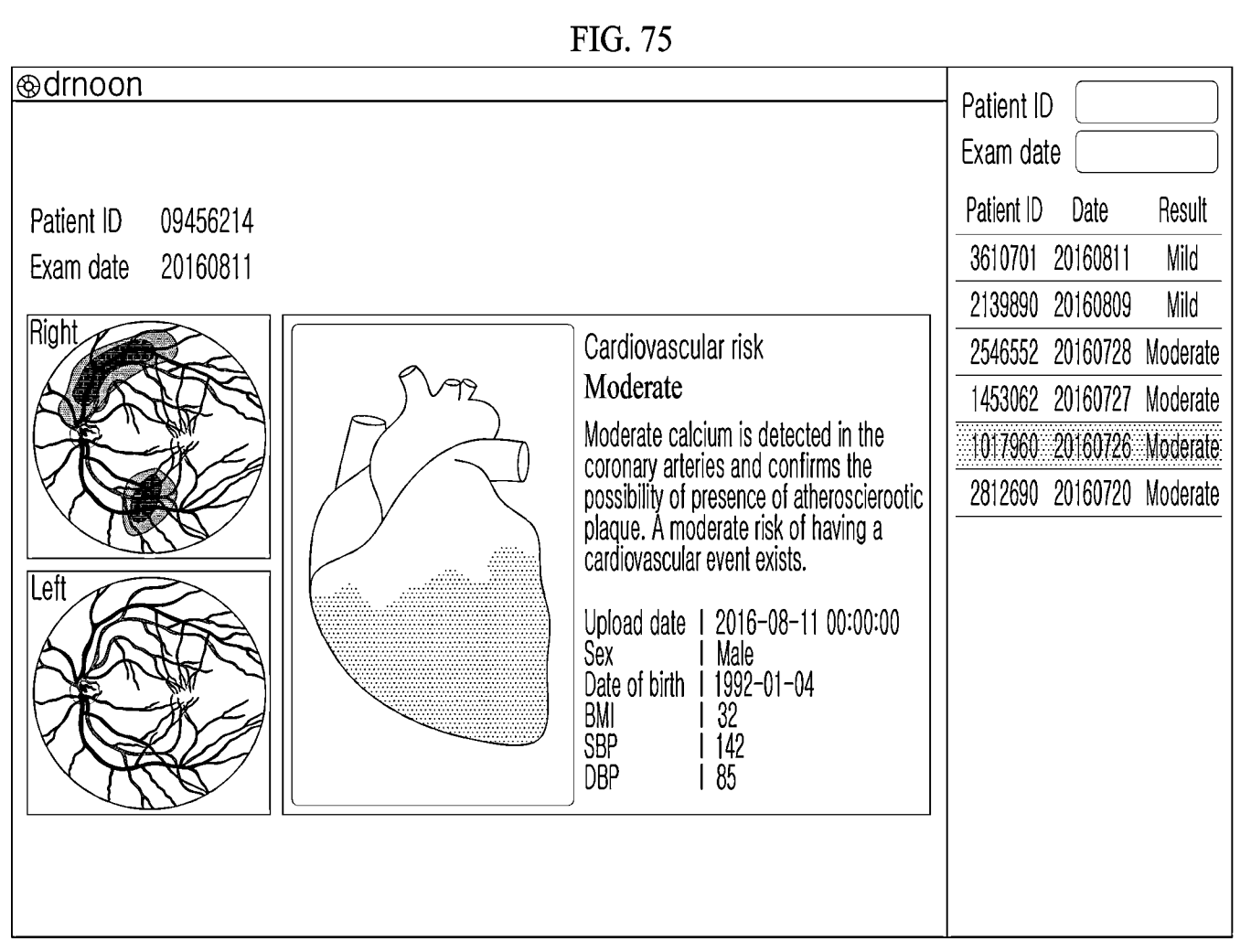

FIGS. 74 and 75 are views for describing a graphical interface for displaying diagnosis assistance information according to an embodiment of the invention described herein. The graphical interface may output diagnosis assistance information or the like described herein through a diagnostic device or a separate device having a display unit and communicating with the diagnostic device. Unless particularly described otherwise, the descriptions given above with reference to FIGS. 29, 30, and the like may be similarly applied to the graphical interface which will be described below with reference to FIGS. 74 and 75.

Referring to FIGS. 74 and 75, a graphical interface for displaying diagnosis assistance information obtained by the diagnosis assistance neural network model described herein may be provided.

Referring to FIGS. 74 and 75, the graphical interface according to an embodiment may display a target fundus image. The graphical interface may display the target fundus image and/or a CAM image obtained on the basis of the target fundus image. The CAM image obtained on the basis of the target fundus image may show a region related to determination of an extent of risk of a target disease, e.g., a coronary artery disease.

Referring to FIGS. 74 and 75, the graphical interface according to an embodiment may include an extent-of-risk display unit which visually shows an extent of risk related to a target heart disease. The extent-of-risk display unit may have a shape that changes according to an extent of risk of the target heart disease for a testee which is determined on the basis of a target fundus image. The extent-of-risk display unit may have a color that changes according to an extent of risk of the target heart disease. For example, the extent-of-risk display unit may be shown in a form related to a part related to the target disease.

As a specific example, as shown in FIGS. 74 and 75, the extent-of-risk display unit may include a schematic heart-shaped image in which a colored region changes according to an extent of risk. As shown in FIGS. 74 and 75, when an extent of risk of a target heart disease for a testee is mild, the extent-of-risk display unit may include a heart-shaped image which is only minimally colored, and, when the extent of risk of the target heart disease for the testee is moderate, the extent-of-risk display unit may include a heart-shaped image which is about half-colored.

The graphical interface according to an embodiment may include a score display unit which displays a numerical value or a score related to a target heart disease for a testee. For example, the graphical interface may include a score display unit which displays a CACs of the testee. The graphical interface may include a score display unit which displays the CACs of the testee for each ranges of the score.

For example, the graphical interface may include a score display unit which displays that the CACs of the testee is at Level 0 when the CACs of the testee is 0, displays that the CACs of the testee is at Level 1 when the CACs of the testee is in a range of 1 to 10, displays that the CACs of the testee is at Level 2 when the CACs of the testee is in a range of 10 to 100, displays that the CACs of the testee is at Level 3 when the CACs of the testee is in a range of 100 to 400, and displays that the CACs of the testee is at Level 4 when the CACs of the testee is in a range of 400 or higher.

For example, the graphical interface may include a score display unit which displays a numerical value or a score related to a target heart disease for a testee through a heart-shaped region as illustrated in FIGS. 74 and 75. The graphical interface may display the heart-shaped region by varying coloring thereof according to a numerical value related to a heart disease, e.g., a coronary artery calcium score, for the testee.

For example, the graphical interface may include a score display unit which displays a heart image which is colored 0% when the CACs of the testee is 0, displays a heart image which is colored 20% when the CACs of the testee is in the range of 1 to 10, displays a heart image which is colored 50% when the CACs of the testee is in the range of 10 to 100, displays a heart image which is colored 70% when the CACs of the testee is in the range of 100 to 400, and displays a heart image which is colored 90% when the CACs of the testee is in the range of 400 or higher.

The graphical interface according to an embodiment may display a prescription information related to an extent of risk of a target heart disease for a testee as well. For example, the graphical interface may display a prescription information related to a score related to a target heart disease for a testee. The graphical interface may display prescription information on a statin drug related to a a CAC score. The graphical interface may display prescription information on a statin drug related to a CACs, according to a pre-stored matching table. The graphical interface may display, on the basis of a pre-stored matching table, a prescription information on a statin drug that is calculated according to a CAC score and/or other pieces of information on the testee (for example, the HDL cholesterol level, the LDL cholesterol level, the triglyceride level, age, gender, smoking status, and the like).

2.4 Assisting in Heart Disease Diagnosis Using Parallel Neural Network Model According to an embodiment of the present invention, in assistance in heart disease diagnosis using a neural network model, the above-described parallel training process or parallel diagnostic process may be used. Unless particularly mentioned otherwise, the details related to the above-described diagnosis assistance system for a plurality of labels may apply analogically to the following details.

2.4.1 Parallel Diagnosis Assistance System for Heart Disease

According to an embodiment of the present invention, a parallel diagnosis assistance system for a heart disease may be provided. The parallel diagnosis assistance system for a heart disease may train a plurality of neural network models which output heart disease diagnosis assistance information or use the plurality of trained neural network models to obtain a plurality of pieces of heart disease diagnosis assistance information.

For example, the parallel diagnosis assistance system may train, on the basis of an input fundus image, a first neural network model which obtains a first piece of diagnosis assistance information used in heart disease diagnosis of a patient and a second neural network model which obtains a second piece of diagnosis assistance information used in non-heart disease diagnosis of the patient and may obtain heart disease diagnosis assistance information of the patient using the trained first neural network model and second neural network model.

Figure 49:
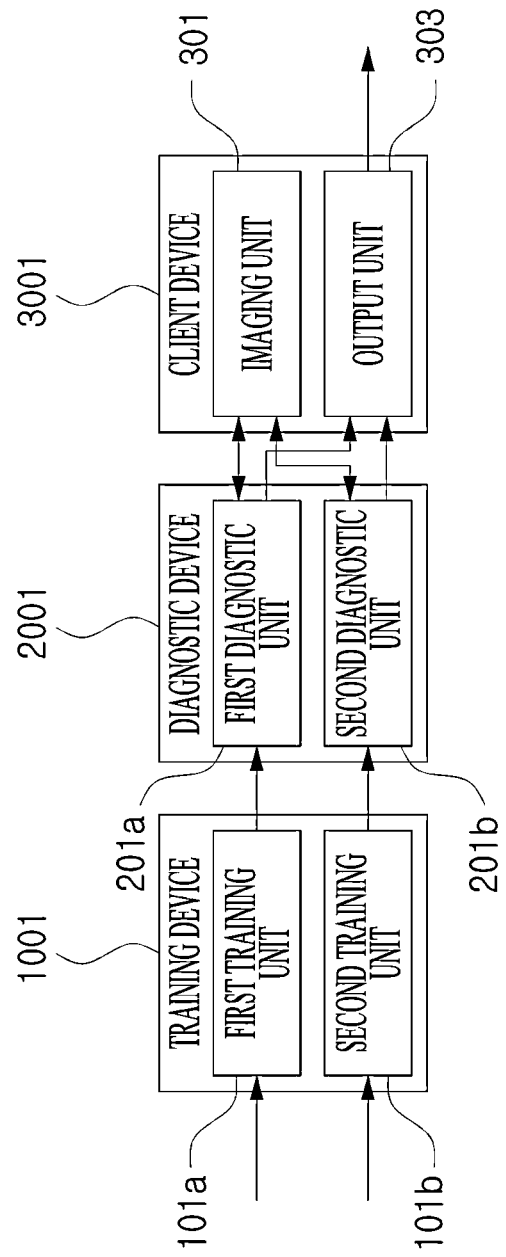
FIG. 49 is a view for describing a parallel diagnosis assistance system according to an embodiment of the present invention.

FIG. 49 is a view for describing a parallel diagnosis assistance system according to an embodiment of the present invention. Referring to FIG. 49, a parallel diagnosis assistance system according to an embodiment of the present invention may include a training device 1001, a diagnostic device 2001, and a client device 3001.

Referring to FIG. 49, the training device 1001 may include a first training unit 101*a* configured to train a first neural network model and a second training unit 101*b* configured to train a second neural network model. Referring to FIG. 49, the diagnostic device 2001 may include a first diagnostic unit 201*a* and a second diagnostic unit 201*b*. Referring to FIG. 49, the client device 3001 may include an imaging unit 301 and an output unit 303.

The first training unit 101*a* and the second training unit 1011*b* may be physically divided elements or may be elements that are logically divided but driven by one processor or stored in one memory. The training device 1001 may also include more than two training units.

Figure 50:
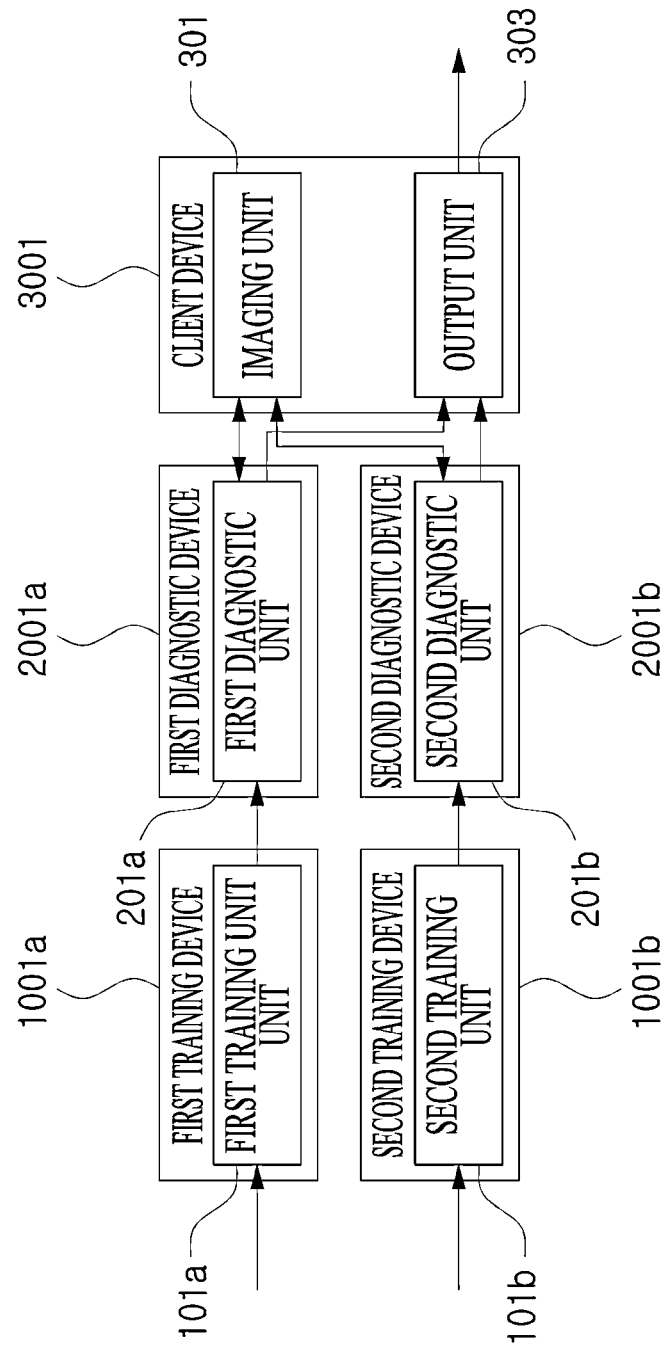
FIG. 50 is a view for describing a parallel diagnosis assistance system according to an embodiment of the present invention.

FIG. 50 is a view for describing a parallel diagnosis assistance system according to an embodiment of the present invention. Referring to FIG. 50, a parallel diagnosis assistance system may include a first training device 1001*a*, a second training device 1001*b*, a first diagnostic device 2001*a*, a second diagnostic device 2001*b*, and a client device 3001. A first training unit 101*a* and a second training unit 101*b* may be physically divided elements or may be elements that are logically divided but driven by one processor or stored in one memory. The training device 1001 may also include more than two training units.

Referring to FIG. 50, the first training device 1001*a* may include the first training unit 101*a*, and the second training device 1001*b* may include the second training unit 101*b*. Referring to FIG. 50, the first diagnostic device 2001*a* may include a first diagnostic unit 201*a*, and the second diagnostic device 2001*b* may include a second diagnostic unit 201*b*. The client device 3001 may include an imaging unit 301 and an output unit 303.

The first training unit 101*a* may obtain first training data, and the second training unit 101*b* may obtain second training data. The first training unit 101*a* may train a first neural network model which obtains a first piece of diagnosis assistance information, and the second training unit 101*b* may train a second neural network model which obtains a second piece of diagnosis assistance information.

For example, the first training unit 101*a* may train a first neural network model which obtains a first piece of diagnosis assistance information including a first type of information for assisting in diagnosis of a first heart disease, and the second training unit 101*b* may train a second neural network model which obtains a second piece of diagnosis assistance information including a second type of information for assisting in diagnosis of the first heart disease.

As a specific example, the first training unit 101*a* may train a first neural network model which obtains a first piece of diagnosis assistance information which is calcium score information for determining a degree of aortic valve calcification that affects a coronary artery disease, and the second training unit 101*b* may train a second neural network model which obtains a second piece of diagnosis assistance information which is grade information indicating an extent of risk of a coronary artery disease.

As another example, the first training unit 101*a* may train a first neural network model which obtains a first piece of diagnosis assistance information which is diagnosis assistance information related to a first heart disease, and the second training unit 101*b* may train a second neural network model which obtains a second piece of diagnosis assistance information which is diagnosis assistance information related to a second heart disease.

As a specific example, the first training unit 101*a* may train a first neural network model which obtains a first piece of diagnosis assistance information which is calcium score information for determining a degree of aortic valve calcification that affects a coronary artery disease, and the second training unit 101*b* may train a second neural network model which obtains a second piece of diagnosis assistance information which is grade information indicating a risk of diabetes.

As still another example, the first training unit 101*a* may train a first neural network model which obtains a first piece of diagnosis assistance information which is diagnosis assistance information related to a heart disease, and the second training unit 101*b* may train a second neural network model which obtains a second piece of diagnosis assistance information which is diagnosis assistance information related to a disease other than a heart disease (for example, an eye disease).

As a specific example, the first training unit 101*a* may train a first neural network model which obtains a first piece of diagnosis assistance information which is grade information related to a degree of aortic valve calcification that affects a coronary artery disease, and the second training unit 101*b* may train a second neural network model which obtains a second piece of diagnosis assistance information which is grade information indicating an extent of risk of glaucoma.

The first diagnostic unit 201*a* may obtain a first neural network model, and the second diagnostic unit 201*b* may obtain a second neural network model. The first diagnostic unit 201*a* may obtain a first piece of diagnostic assistance information using the first neural network model, and the second diagnostic unit 201*b* may obtain a second piece of diagnostic assistance information using the second neural network model.

For example, the first diagnostic unit 201*a* may obtain a first piece of diagnostic assistance information including a first type of information related to a first heart disease by using the first neural network model, and the second diagnostic unit 201*b* may obtain a second piece of diagnostic assistance information including a second type of information related to the first heart disease by using the second neural network model.

As a specific example, the first diagnostic unit 201*a* may obtain calcium score information for determining a degree of heart calcification that affects a coronary artery disease by using the first neural network model, and the second diagnostic unit 201*b* may obtain grade information indicating an extent of risk of a coronary artery disease by using the second neural network model.

As another example, the first diagnostic unit 201*a* may obtain a first piece of diagnostic assistance information which is diagnostic assistance information related to a first heart disease by using the first neural network model, and the second diagnostic unit 201*b* may obtain a second piece of diagnostic assistance information which is diagnostic assistance information related to a second heart disease by using the second neural network model.

As a specific example, the first diagnostic unit 201*a* may obtain calcium score information for determining a degree of aortic valve calcification that affects a coronary artery disease by using the first neural network model, and the second diagnostic unit 201*b* may obtain grade information indicating an extent of risk of diabetes by using the second neural network model.

As still another example, the first diagnostic unit 201*a* may obtain a first piece of diagnostic assistance information which is diagnostic assistance information related to a heart disease by using the first neural network model, and the second diagnostic unit 201*b* may obtain a second piece of diagnostic assistance information which is diagnostic assistance information related to a disease other than a heart disease (for example, an eye disease) by using the second neural network model.

As a specific example, the first diagnostic unit 201*a* may obtain calcium score information for determining a degree of aortic valve calcification that affects a coronary artery disease by using the first neural network model, and the second diagnostic unit 201*b* may obtain grade information indicating an extent of risk of glaucoma by using the second neural network model.

The first diagnostic unit 201*a* and the second diagnostic unit 201*b* may be physically divided elements or may be elements that are logically divided but driven by one processor or stored in one memory. The diagnostic device may also include more than two diagnostic units.

The diagnostic device may also include a diagnostic unit including a plurality of diagnostic modules. This will be described in more detail below in "Parallel diagnosis assistance for heart disease" section.

The client device may include the imaging unit 301 configured to obtain a fundus image. The client device may transmit the obtained target fundus image to the diagnostic device and obtain heart disease diagnosis assistance information according to the target fundus image from the diagnostic device.

The client device may provide the obtained heart disease diagnosis assistance information to a user via the output unit 303. The client device may provide the obtained heart disease diagnosis assistance information in the form of visual and/or aural data via the output unit 303.

Although the case in which a plurality of heart disease diagnosis assistance neural network models are trained by a diagnosis assistance system including a training device, a diagnostic device, and a client device has been described above with reference to FIGS. 49 and 50, the present invention is not limited thereto. The training of the plurality of heart disease diagnosis assistance neural network models may be performed by various other forms of systems including one or more devices.

Figure 51:
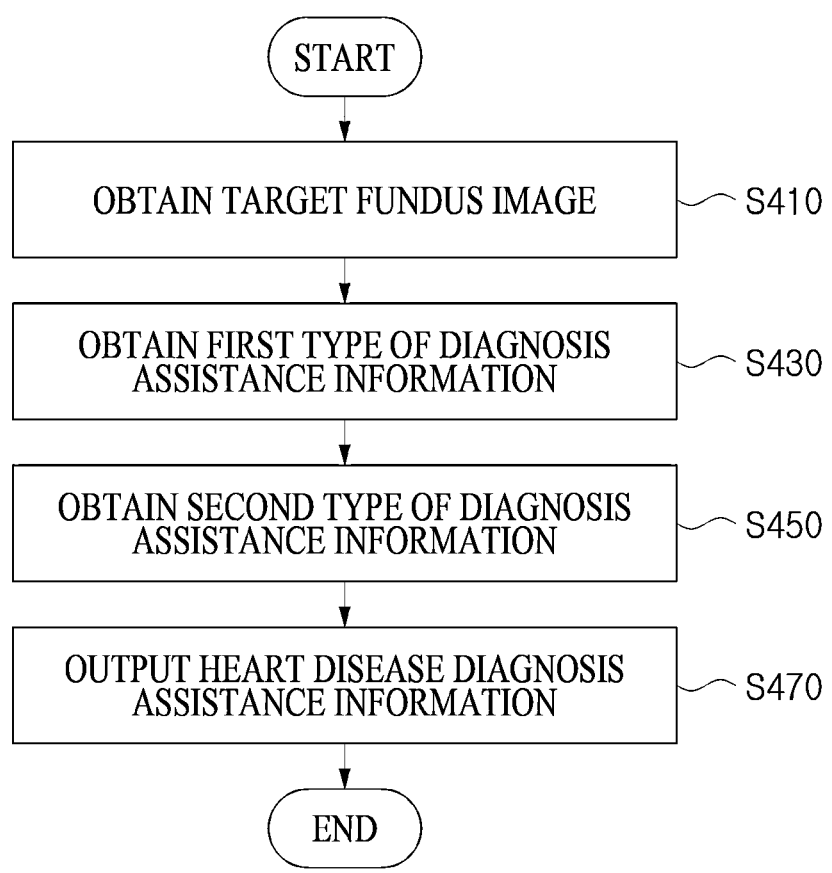
FIG. 51 is a view for describing a method of assisting in heart disease diagnosis according to an embodiment of the present invention.

FIG. 51 is a view for describing a method of assisting in heart disease diagnosis according to an embodiment of the present invention. Referring to FIG. 51, a method for assisting in diagnosis of a target heart disease using a fundus image may include obtaining a target fundus image (S410), obtaining a first type of diagnosis assistance information (S430), obtaining a second type of diagnosis assistance information (S450), and outputting heart disease diagnosis assistance information (S470).

The obtaining of the target fundus image (S410) may include obtaining a target fundus image which is obtained by imaging a fundus of a testee.

The obtaining of the first type of diagnosis assistance information (S430) may include, on the basis of the target fundus image, obtaining a first type of diagnosis assistance information according to the target fundus image via a first neural network model which is trained to obtain a first type of diagnosis assistance information used in diagnosis of a target heart disease on the basis of a fundus image.

The obtaining of the second type of diagnosis assistance information (S450) may include, on the basis of the target fundus image, obtaining a second type of diagnosis assistance information according to the target fundus image via a second neural network model which is trained to obtain a second type of diagnosis assistance information used in diagnosis of a target heart disease on the basis of a fundus image.

The outputting of the heart disease diagnosis assistance information (S470) may include, on the basis of the first type of diagnosis assistance information and the second type of diagnosis assistance information, outputting the heart disease diagnosis assistance information for assisting in diagnosis of a target heart disease of a testee.

The second type of diagnosis assistance information may be obtained as information having a different dimension from the first type of diagnosis assistance information, via a second neural network model which is at least partially different from a first neural network model.

The first neural network model may be a neural network model which is trained to classify fundus images into a plurality of pieces of grade information indicating an extent of risk of a target heart disease. In this case, the first type of diagnosis assistance information may be a selected piece of grade information among the plurality of pieces of grade information.

The second neural network model may be a neural network model which is trained to predict score information which is a numerical value used in diagnosis of a target heart disease according to a fundus image. In this case, the second type of diagnosis assistance information may be score information.

The first neural network model may be trained to classify a fundus image as normality information which indicates that a testee belongs to a normal group for a target heart disease or abnormality information which indicates that the testee belongs to a risk group for the target heart disease.

The first type of diagnosis assistance information may be risk information which indicates whether a testee belongs to a risk group for a target heart disease.

The first neural network model may be provided to perform multiclass classification of fundus images into a plurality of pieces of diagnosis assistance information, and the second neural network model may be provided to perform binary classification of fundus images into a first piece of diagnosis assistance information and a second piece of diagnosis assistance information.

The first type of diagnosis assistance information may be any one of grade information which indicates an extent of risk of a target heart disease, score information which is a numerical value used in diagnosis of a target heart disease, and abnormality information which indicates that a testee belongs to a risk group for a target heart disease.

The second type of diagnosis assistance information may be any one, which is different from the first type of diagnosis assistance information, of grade information which indicates an extent of risk of a target heart disease, score information which is a numerical value used in diagnosis of a target heart disease, and abnormality information which indicates that a testee belongs to a risk group for a target heart disease.

The target heart disease may be a coronary artery disease.

The first type of diagnosis assistance information may be coronary artery disease grade information selected among a plurality of pieces of grade information for indicating an extent of risk of a coronary artery disease. In this case, the second type of diagnosis assistance information may be coronary artery calcium score information used in determining an extent of risk of the coronary artery disease.

Figure 52:
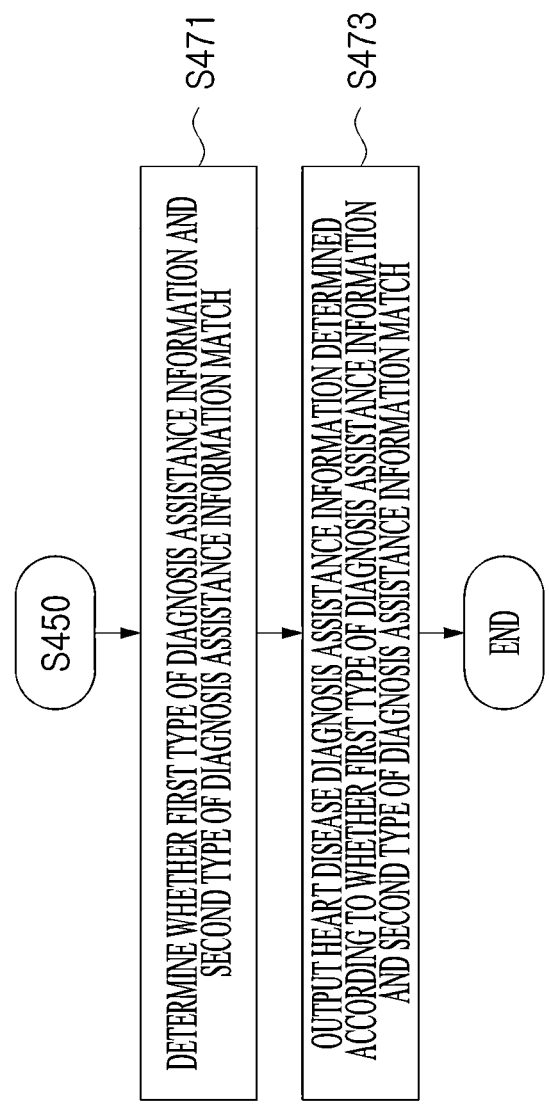
FIG. 52 is a view for describing a method of assisting in heart disease diagnosis according to an embodiment of the present invention.

FIG. 52 is a view for describing a method of assisting in heart disease diagnosis according to an embodiment of the present invention. Referring to FIG. 52, the outputting of the heart disease diagnosis assistance information (S470) may include determining whether the first type of diagnosis assistance information and the second type of diagnosis assistance information match each other (S471) and outputting heart disease diagnosis assistance information determined according to whether the first type of diagnosis assistance information and the second type of diagnosis assistance information match each other (S473).

The determining of whether the first type of diagnosis assistance information and the second type of diagnosis assistance information match each other (S471) may include comparing the first type of information and the second type of information based on a matching table.

The outputting of the heart disease diagnosis assistance information determined according to whether the first type of diagnosis assistance information and the second type of diagnosis assistance information match each other (S473) may further include, when the first type of diagnosis assistance information and the second type of diagnosis assistance information match each other, outputting heart disease diagnosis assistance information including at least one of the first type of diagnosis assistance information and the second type of diagnosis assistance information.

The outputting of the determined heart disease diagnosis assistance information (S473) may further include, when the first type of diagnosis assistance information and the second type of diagnosis assistance information do not match each other, outputting heart disease diagnosis assistance information including any one piece of diagnosis assistance information selected from the first type of diagnosis assistance information and the second type of diagnosis assistance information.

The outputting of the determined heart disease diagnosis assistance information (S473) may further include, when the first type of diagnosis assistance information and the second type of diagnosis assistance information do not match each other, outputting reference diagnosis assistance information, which is any one piece of diagnosis assistance information selected from the first type of diagnosis assistance information and the second type of diagnosis assistance information, and heart disease diagnosis assistance information including the other piece of diagnosis assistance information which is corrected to match the reference diagnosis assistance information.

The determining of whether the first type of diagnosis assistance information and the second type of diagnosis assistance information match each other may include determining whether the first type of diagnosis assistance information and the second type of diagnosis assistance information match each other by using a first type information-second type information matching table which is provided in advance.

The above-described method of assisting in heart disease diagnosis may be provided in the form of a computer-readable recording medium in which a program for executing the method is recorded.

Figure 53:
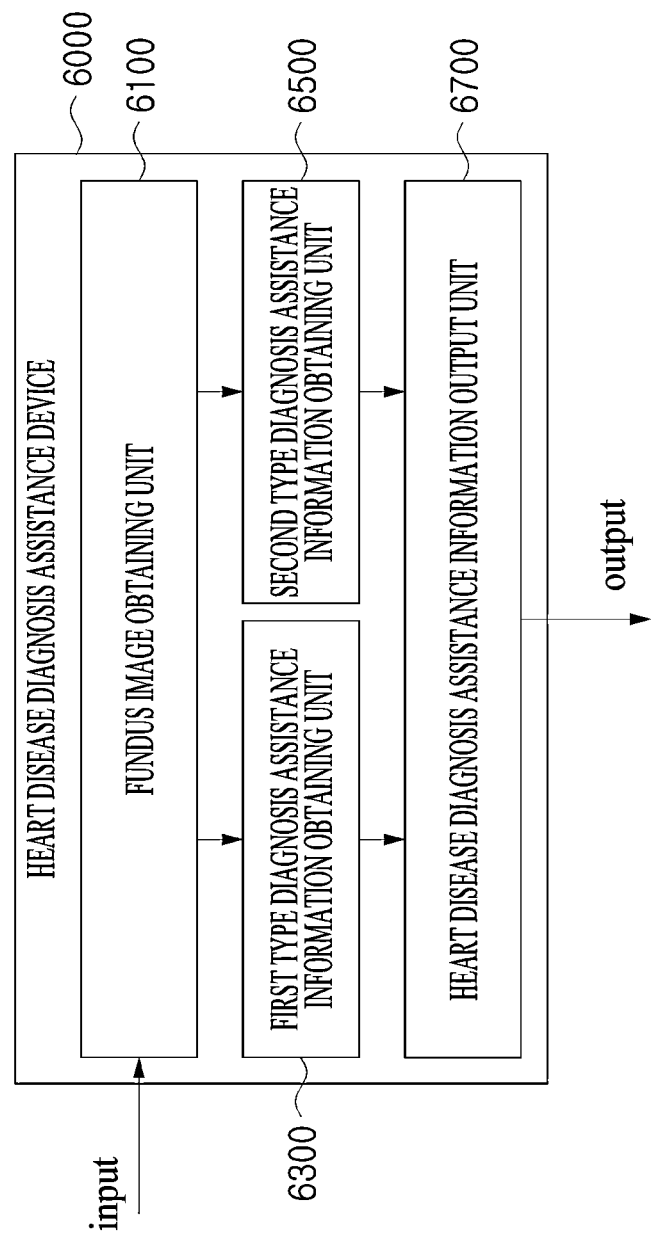
FIG. 53 is a view for describing a heart disease diagnosis assistance device according to an embodiment of the present invention.

FIG. 53 is a view for describing a heart disease diagnosis assistance device according to an embodiment of the present invention. Referring to FIG. 53, a heart disease diagnosis assistance device 6000 for assisting in diagnosis of a target heart disease using a fundus image according to an embodiment of the present invention may include a fundus image obtaining unit 6100, a first type diagnosis assistance information obtaining unit 6300, a second type diagnosis assistance information obtaining unit 6500, and a heart disease diagnosis assistance information output unit 6700.

The fundus image obtaining unit 6100 may obtain a target fundus image which is obtained by imaging a fundus of a testee.

The first type diagnosis assistance information obtaining unit 6300 may, on the basis of the target fundus image, obtain first type of diagnosis assistance information according to the target fundus image via a first neural network model which is trained to obtain a first type of diagnosis assistance information used in diagnosis of a target heart disease on the basis of a fundus image.

The second type diagnosis assistance information obtaining unit 6500 may, on the basis of the target fundus image, obtain second type of diagnosis assistance information according to the target fundus image via a second neural network model which is trained to obtain a second type of diagnosis assistance information used in diagnosis of a target heart disease on the basis of a fundus image.

The heart disease diagnosis assistance information output unit 6700 may, on the basis of the first type of diagnosis assistance information and the second type of diagnosis assistance information, output heart disease diagnosis assistance information for assisting in diagnosis of a target heart disease of a testee.

The second type of diagnosis assistance information may be obtained as information having a different dimension from the first type of diagnosis assistance information, via a second neural network model which is at least partially different from a first neural network model.

The first neural network model may be provided to perform multiclass classification of fundus images into a plurality of pieces of diagnosis assistance information, and the second neural network model may be provided to perform binary classification of fundus images into a first piece of diagnosis assistance information and a second piece of diagnosis assistance information.

The first type of diagnosis assistance information may be any one of grade information which indicates an extent of risk of a target heart disease, score information which is a numerical value used in diagnosis of a target heart disease, and abnormality information which indicates that a testee belongs to a risk group for a target heart disease.

The second type of diagnosis assistance information may be any one, which is different from the first type of diagnosis assistance information, of grade information which indicates an extent of risk of a target heart disease, score information which is a numerical value used in diagnosis of a target heart disease, and abnormality information which indicates that a testee belongs to a risk group for a target heart disease.

The first neural network model may be a neural network model which is trained to classify fundus images into a plurality of pieces of grade information indicating an extent of risk of a target heart disease. In this case, the first type of diagnosis assistance information may be grade information selected from a plurality of pieces of grade information.

The second neural network model may be a neural network model which is trained to predict score information which is a numerical value used in diagnosis of a target heart disease according to a fundus image. In this case, the second type of diagnosis assistance information may be score information.

The first neural network model may be trained to classify a fundus image as normality information which indicates that a testee belongs to a normal group for a target heart disease or abnormality information which indicates that the testee belongs to a risk group for the target heart disease. The first type of diagnosis assistance information may be risk information which indicates whether a testee belongs to a risk group for a target heart disease.

The target heart disease may be a coronary artery disease. The first type of diagnosis assistance information may be coronary artery disease grade information selected among a plurality of pieces of grade information for indicating an extent of risk of a coronary artery disease. The second type of diagnosis assistance information may be coronary artery calcium score information used in determining an extent of risk of the coronary artery disease.

Figure 54:
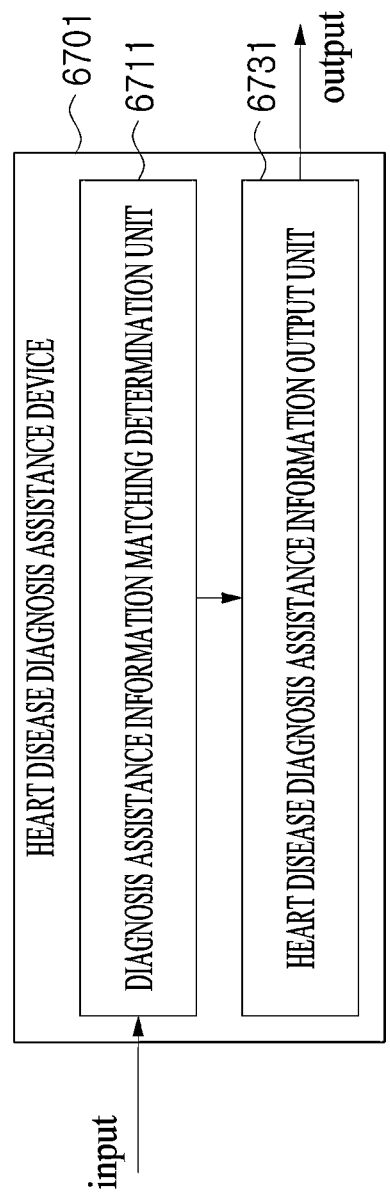
FIG. 54 is a view for describing a heart disease diagnosis assistance device according to an embodiment of the present invention.

FIG. 54 is a view for describing a heart disease diagnosis assistance device according to an embodiment of the present invention. Referring to FIG. 54, a heart disease diagnosis assistance device 6701 may include a diagnosis assistance information matching determination unit 6711 and a heart disease diagnosis assistance information output unit 6731.

The diagnosis assistance information matching determination unit 6711 may determine whether a first type of diagnosis assistance information and a second type of diagnosis assistance information match each other.

The heart disease diagnosis assistance information output unit 6731 may output heart disease diagnosis assistance information determined according to whether the first type of diagnosis assistance information and the second type of diagnosis assistance information match each other.

The heart disease diagnosis assistance information output unit 6731 may output heart disease diagnosis assistance information including at least one of the first type of diagnosis assistance information and the second type of diagnosis assistance information when the first type of diagnosis assistance information and the second type of diagnosis assistance information match each other.

The heart disease diagnosis assistance information output unit 6731 may output heart disease diagnosis assistance information including any one piece of diagnosis assistance information selected from the first type of diagnosis assistance information and the second type of diagnosis assistance information when the first type of diagnosis assistance information and the second type of diagnosis assistance information do not match each other.

The heart disease diagnosis assistance information output unit 6731 may further include, when the first type of diagnosis assistance information and the second type of diagnosis assistance information do not match each other, outputting reference diagnosis assistance information, which is any one piece of diagnosis assistance information selected from the first type of diagnosis assistance information and the second type of diagnosis assistance information, and heart disease diagnosis assistance information including the other piece of diagnosis assistance information which is corrected to match the reference diagnosis assistance information.

2.4.2 Parallel Training of Heart Disease Diagnosis Assistance Neural Network Models According to the present specification, a method and/or a device for training two or more neural network models in parallel to assist in heart disease diagnosis may be provided. According to the present specification, a method and/or a device for training a plurality of diagnosis assistance neural network models, which include a neural network model for obtaining diagnosis assistance information related to a heart disease, in parallel may be provided.

The parallel training of heart disease diagnosis assistance neural network models may be performed by a training device.

Figure 55:
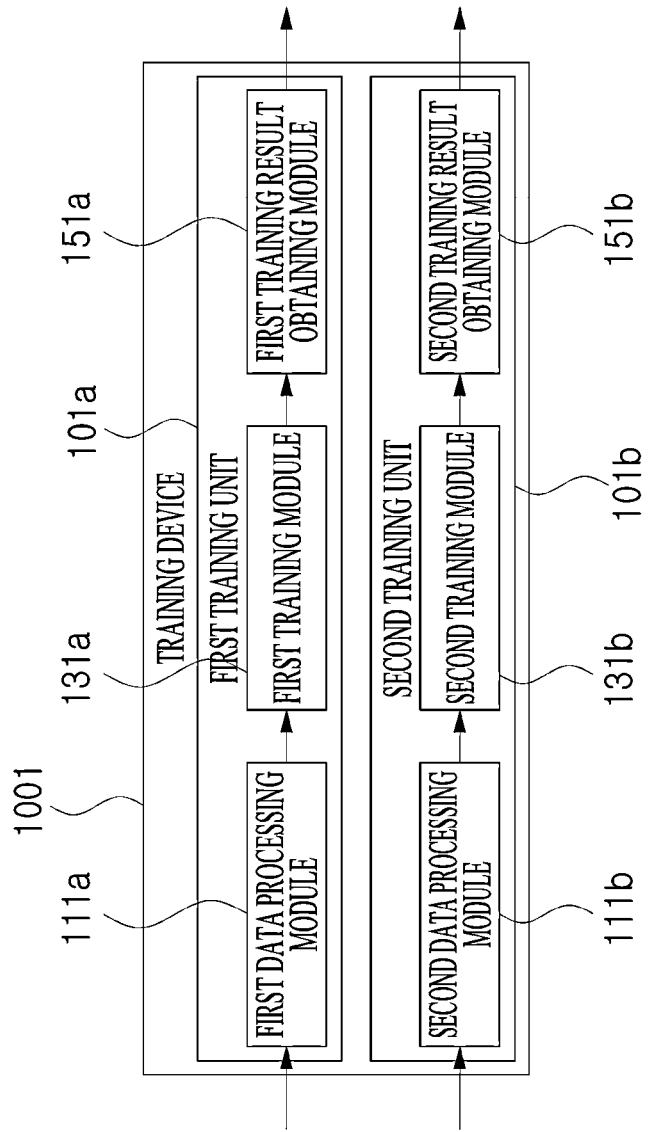
FIG. 55 illustrates a training device 1001 according to an embodiment of the present invention.

FIG. 55 illustrates a training device 1001 according to an embodiment of the present invention. Referring to FIG. 55, the training device 1001 according to an embodiment of the present invention may include a first training unit 101a and a second training unit 101b.

The first training unit 101a may include a first data processing module 111a, a first training module 131a, and a first training result obtaining module 151a. The second training unit 101b may include a second data processing module 111b, a second training module 131b, and a second training result obtaining module 151b.

The first training unit 101a may obtain first fundus image training data. The first data processing module 111a may reconstruct a fundus image included in the first fundus image training data. The first data processing module 111a may suitably reconstruct the fundus image in consideration of a type of diagnosis assistance information to be obtained by the first training module. The first data processing module 111a may reconstruct the fundus image so that blood vessels in the fundus image are highlighted. The first data processing module 111a may obtain a fundus image in which blood vessels are highlighted.

The second training unit 101b may obtain second fundus image training data. The second data processing module 111b may reconstruct a fundus image included in the second fundus image training data. The second data processing module 111b may suitably reconstruct the fundus image in consideration of a type of diagnosis assistance information to be obtained by the second training module. The second data processing module 111b may process the fundus image so that blood vessels are highlighted.

The first training unit 101a may train a first neural network model, and the second training unit 101b may train a second neural network model. Alternatively, the first training module may train the first neural network model, and the second training module may train the second neural network model.

For example, the first training unit 101a may train a first neural network model which obtains diagnosis assistance information related to a first heart disease on the basis of a fundus image, and the second training unit 101b may train a second neural network model which obtains diagnosis assistance information related to a second heart disease on the basis of a fundus image.

As a specific example, the first training unit 101a may train a first neural network model which obtains score information for diagnosis of a coronary artery disease on the basis of a fundus image, and the second training unit 101b may train a second neural network model which obtains score information related to hypertension on the basis of a fundus image.

As another example, the first training unit 101a may train a first neural network model which obtains a first piece of diagnosis assistance information related to a first heart disease on the basis of a fundus image, and the second training unit 101b may train a second neural network model which obtains a second piece of diagnosis assistance information related to the first heart disease on the basis of a fundus image.

As a specific example, the first training unit 101a may train a first neural network model which obtains score information for diagnosis of a coronary artery disease on the basis of a fundus image, and the second training unit 101b may train a second neural network model which obtains grade information for diagnosis of a coronary artery disease on the basis of a fundus image.

As still another example, the first training unit 101a may train a first neural network model which obtains a first piece of diagnosis assistance information related to a heart disease on the basis of a fundus image, and the second training unit 101b may train a second neural network model which obtains a second piece of diagnosis assistance information related to another disease.

As a specific example, the first training unit 101a may train a first neural network model which obtains grade information for diagnosis of a coronary artery disease on the basis of a fundus image, and the second training unit 101b may train a second neural network model which obtains grade information which indicates an extent of risk of glaucoma for a patient.

Although the case in which the first training unit 101a and the second training unit 101b are included in a single training device has been above described with reference to FIG. 55, this is merely an example, and the first training unit 101a and the second training unit 101b may also be included in a first training device and a second training device, respectively.

Figure 56:
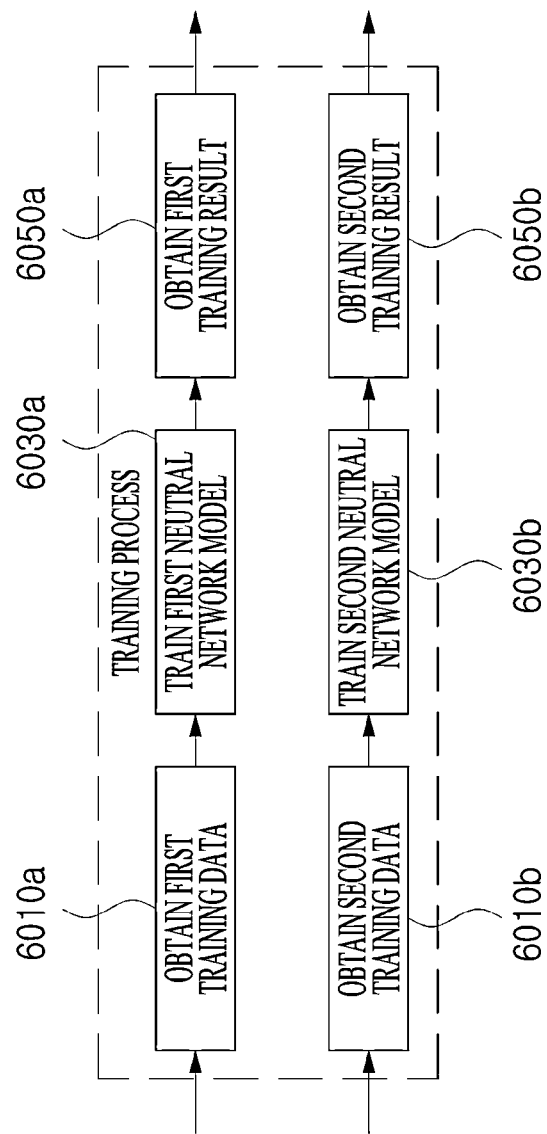
FIG. 56 is a view for describing a method of training a heart disease diagnosis assistance neural network model according to an embodiment of the present invention.

FIG. 56 is a view for describing a method of training a heart disease diagnosis assistance neural network model according to an embodiment of the present invention. Referring to FIG. 56, a first neural network model and a second neural network model may be trained in parallel with each other (or independently of each other).

A process for training a first neural network model and a process for training a second neural network model which are described with reference to FIG. 56 may be performed sequentially or performed concurrently during at least a certain time interval.

Referring to FIG. 56, a method of training a heart disease diagnosis assistance neural network model according to an embodiment of the present invention may include obtaining first training data (6010a), training a first neural network model (6030a), obtaining a first training result (6050a), obtaining second data (6010b), training a second neural network model (6030b), and obtaining a second training result (6050b).

The first neural network model and the second neural network model may be provided to have different layer structures from each other. The first neural network model and the second neural network model may output pieces of diagnosis assistance information different from each other. The first neural network model and the second neural network model may output diagnosis assistance information using pieces of input data different from each other.

The first neural network model and the second neural network model may be provided to have at least some of common layers which are common to each other. The first neural network model and the second neural network model may output pieces of diagnosis assistance information different from each other, using pieces of input data at least partly common to each other.

The first neural network model may be trained to obtain diagnosis assistance information related to a first heart disease on the basis of a fundus image, and the second neural network model may be trained to obtain diagnosis assistance information related to a second heart disease on the basis of a fundus image.

The first neural network model may be trained to obtain a first piece of diagnosis assistance information related to a first heart disease on the basis of a fundus image, and the second neural network model may be trained to obtain a second piece of diagnosis assistance information related to the first heart disease on the basis of a fundus image.

The first neural network model may be trained to obtain a first piece of diagnosis assistance information related to a heart disease on the basis of a fundus image, and the second neural network model may be trained to obtain a second piece of diagnosis assistance information related to a disease other than the heart disease.

The obtaining of the first training data (6010a), the training of the first neural network model (6030a), and the obtaining of the first training result (6050a) may be sequentially performed.

The obtaining of the first training data (6010a) may include obtaining fundus image training data. The obtaining of the first data may include obtaining fundus image training data which includes a label for assisting in heart disease diagnosis.

The obtaining of the first training data may include obtaining training data which includes labeled fundus images that satisfy predetermined criteria selected from a database provided in advance. For example, the obtaining of the first training data may include obtaining training data which includes fundus image data selected in consideration of a target disease or target diagnosis assistance information.

The first training data may include a disease presence/absence label related to a target heart disease, a grade label related to the target heart disease, and/or a score label related to the target heart disease. At least one of the disease presence/absence label, the grade label, and the score label may be assigned to a fundus image included in the first training data.

A label included in the training data may be of the same type as diagnosis assistance information output by a neural network model. For example, when the first neural network model is a neural network model which outputs score information on the basis of a fundus image, the first training data may include a score label. As another example, when the first neural network model outputs grade information on the basis of a fundus image, the first training data may include a grade label. As still another example, when the first neural network model outputs disease presence/absence information on the basis of a fundus image, the first training data may include a disease presence/absence label. However, when a matching relationship between different types of information is provided in advance, training data which includes a label of a different type from diagnosis assistance information output by a neural network model may also be used in training.

The method of training a heart disease diagnosis assistance neural network model may further include reconstructing a fundus image included in the obtained first training data. The fundus image reconstruction may be selectively performed.

The reconstructing of the fundus image included in the first training data may include performing pre-processing which causes blood vessel elements included in the fundus image to be highlighted. The above description may apply analogically to the reconstruction or pre-processing of the fundus image.

In other words, the first neural network model may be trained using fundus image training data which includes at least one of an original fundus image which is obtained by imaging and an image reconstructed so that blood vessels are highlighted.

The training of the first neural network model (6030a) may include comparing diagnosis assistance information, which is obtained with a fundus image included in the first training data as an input fundus image, with a label assigned to the input fundus image and updating the first neural network model. For example, the training of the first neural network model (6030a) may include obtaining grade information related to a coronary artery disease on the basis of an input fundus image, comparing the obtained grade information with a label assigned to the input fundus image, and updating the first neural network model. When the label assigned to the fundus image is of a different type from the grade information, the comparison thereof may be performed using a matching table provided in advance or a matching relationship designated by a user. The above description may apply analogically to details related to the training of the neural network model.

The obtaining of the first training result (6050a) may include obtaining parameters of the first neural network model which are generated as a result of repeatedly performing the training using the fundus image included in the first training data. When the first neural network model is a neural network model in the ensemble form which includes two or more sub-neural network models, the first training result may include weights related to each sub-neural network model or a finally selected sub-neural network model.

The obtaining of the second training data (6010b), the training of the second neural network model (6030b), and the obtaining of the second training result (6050b) may be sequentially performed.

The second training data may include a fundus image and other input data. The second training data may include data that is partially in common with or totally differentiated from the first training data.

For example, when the first neural network model obtains a first piece of diagnosis assistance information related to a heart disease on the basis of a fundus image, and the second neural network model obtains a second piece of diagnosis assistance information related to the heart disease, the first training data and the second training data may be partially in common with each other.

For example, the first neural network model and the second neural network model may be trained using different types of labels included in the same training data. The first neural network model may be trained to output score information using a score label included in the training data, and the second neural network model may be trained to output grade information using a grade label included in the training data.

Also, for example, the first neural network model and the second neural network model may be trained using the same type of label included in the same training data. The first neural network model may be trained to output score information using a score label included in the training data, and the second neural network model may be trained to output grade information using the score label included in the training data and a matching table in which scores and grades are matched.

As another example, when the first neural network model obtains a first piece of diagnosis assistance information related to a first heart disease on the basis of a fundus image, and the second neural network model obtains a second piece of diagnosis assistance information related to a second heart disease (or a disease other than the heart disease), the first training data and the second training data may be partially in common with each other or differentiated from each other.

For example, the first neural network model and the second neural network model may be trained using different types of labels included in the same training data. The first neural network model may be trained to output diagnosis assistance information for diagnosis of a coronary artery disease using a diagnosis assistance label related to the coronary artery disease included in the training data, and the second neural network model may be trained to output diagnosis assistance information for diagnosing hypertension using a diagnosis assistance label for diagnosing hypertension or glaucoma that is included in the training data.

Also, for example, the first neural network model and the second neural network model may be trained using different pieces of training data which include different types of labels. The first neural network model may be trained to output diagnosis assistance information for diagnosis of a coronary artery disease using first training data including a diagnosis assistance label related to the coronary artery disease, and the second neural network model may be trained to output diagnosis assistance information for diagnosing hypertension using second training data including diagnosis assistance information for diagnosing hypertension or glaucoma.

The first training data and the second training data may be pieces of training data which are at least partially in common with each other and may be obtained together or separately. As a specific example, first data and second data may be pieces of training data which are selected from pieces of data provided in advance and determined to be at least partially different from each other.

The method of training a heart disease diagnosis assistance neural network model may further include reconstructing a fundus image included in the obtained second training data. The second neural network model may be trained on the basis of a reconstructed fundus image or an original fundus image. The image reconstruction may be performed similarly as that described above.

The fundus image included in the second training data may be reconstructed in a form suitable for training of the second neural network model. The fundus image included in the second training data may be reconstructed so that accuracy of diagnosis assistance information output from the second neural network model is improved.

The fundus image included in the first training data and the fundus image included in the second training data may be reconstructed differently from each other. For example, the fundus image included in the first training data may be processed so that blood vessels are highlighted in order to facilitate obtaining of heart disease diagnosis assistance information, and the fundus image included in the second training data may be processed in order to facilitate obtaining of eye disease diagnosis assistance information.

The training of the second neural network model may include comparing diagnosis assistance information, which is obtained with the fundus image included in the second training data as an input fundus image, with a label assigned to the input fundus image and updating the second neural network model.

For example, the training of the second neural network model may include obtaining grade information related to a coronary artery disease on the basis of the input fundus image, comparing the obtained grade information with a label assigned to the input fundus image, and updating the first neural network model. When the label assigned to the fundus image is of a different type from the grade information, the comparison thereof may be performed using a matching table provided in advance or a matching relationship designated by a user.

The first neural network model and the second neural network model may be trained independently of each other. Alternatively, the first neural network model and the second neural network model may also be trained dependently.

For example, when the first training data and the second training data are at least partially in common with each other, and a first piece of diagnosis assistance information obtained by the first neural network model and a second piece of diagnosis assistance information obtained by the second neural network model are of different types, the first neural network model and the second neural network model may be trained together in consideration of correlation between the first piece of diagnosis assistance information and the second piece of diagnosis assistance information.

As a specific example, the first neural network model may classify input fundus images, to which score labels are assigned, into a first to third piece of grade information, and the second neural network model may classify the input fundus images into a first to fifth piece of grade information. In this case, the training of the first neural network model and the second neural network model may be performed in consideration of both the correlation between the first to third grades and the first to fifth grades and the correlation between each grade and score values.

2.4.3 Parallel Diagnosis Assistance for Heart Disease

According to the present specification, a device and/or a method for performing diagnosis assistance processes in parallel using a plurality of neural network models may be provided. A device and/or a method for obtaining a plurality of pieces of diagnosis assistance information which include diagnosis assistance information related to a heart disease by using a plurality of diagnosis assistance neural network models may be provided. The parallel diagnosis assistance process which will be described below may be performed by the above-described diagnostic device, diagnostic unit, control unit, or processor.

Figure 57:
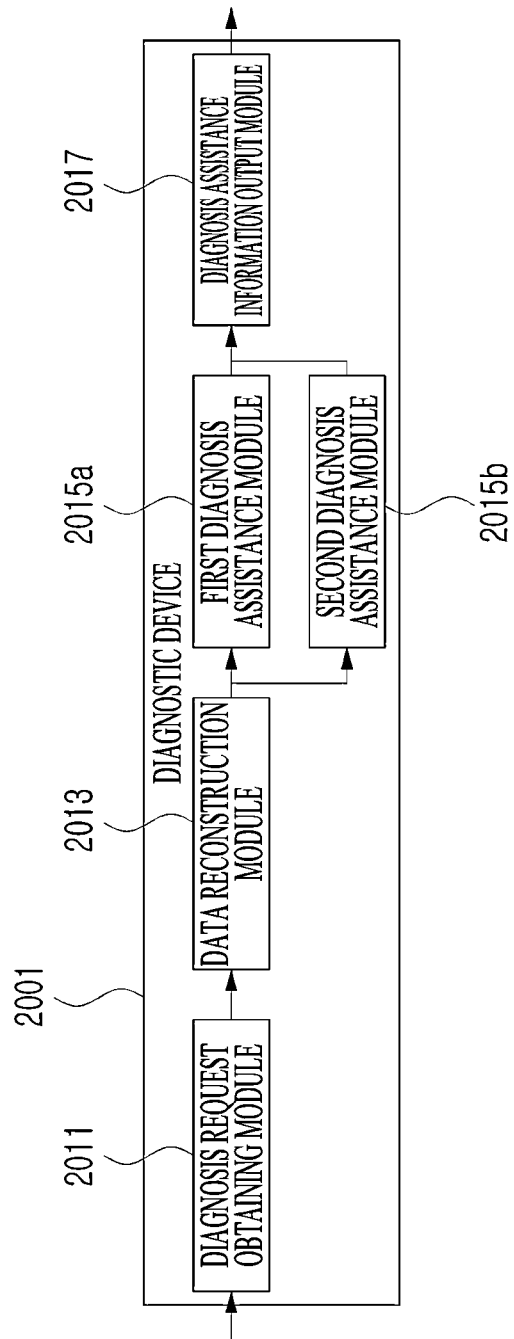
FIG. 57 is a view for describing a diagnostic device 2001 according to an embodiment of the present invention.

FIG. 57 is a view for describing a diagnostic device 2001 according to an embodiment of the present invention. Referring to FIG. 57, the diagnostic device 2001 may include a diagnosis request obtaining module 2011, a data reconstruction module 2013, diagnosis assistance modules 2015a and 2015b, and a diagnosis assistance information output module 2017.

The diagnosis request obtaining module 2011 may obtain a request for diagnosis assistance information. The diagnosis request obtaining module may obtain a request for diagnosis assistance information as well as a diagnosis target fundus image. The diagnosis request obtaining module 2011 may obtain a diagnosis request that requests for a first piece of diagnosis assistance information and a second piece of diagnosis assistance information. The diagnosis request may include an information type (for example, disease presence/absence information or grade information) of the requested first piece of diagnosis assistance information and/or second piece of diagnosis assistance information.

The diagnosis request obtaining module 2011 may obtain a diagnosis request via a user interface. Alternatively, the diagnosis request obtaining module may receive a diagnosis request obtained from a user via an external device.

The data reconstruction module 2013 may process the obtained data. For example, the data reconstruction module may reconstruct image data. Alternatively, the data reconstruction module may perform various processes for optimizing the training data described herein, such as image pre-processing or data serialization.

The diagnosis assistance module 2015 may include a first diagnosis assistance module 2015a and a second diagnosis assistance module 2015b. The first diagnosis assistance module 2015a may obtain a first piece of diagnosis assistance information using a first neural network model. The second diagnosis assistance module 2015b may obtain a second piece of diagnosis assistance information using a second neural network model. Although the case in which a single diagnostic device includes a plurality of diagnosis assistance modules has been described above with reference to FIG. 57, the invention described herein is not limited thereto, and a plurality of diagnostic devices may have their own diagnostic units (or diagnosis assistance modules) and obtain diagnosis assistance information using different neural network models.

For example, the first diagnosis assistance module (or first diagnostic unit) 2015a may obtain diagnosis assistance information related to a first heart disease using a first neural network model, and the second diagnosis assistance module (or second diagnostic unit) 2015b may obtain diagnosis assistance information related to a second heart disease using a second neural network model.

As a specific example, the first diagnosis assistance module (or first diagnostic unit) 2015a may obtain score information for diagnosis of a coronary artery disease using a first neural network model, and the second diagnosis assistance module (or second diagnostic unit) 2015b may obtain score information related to hypertension using a second neural network model.

As another example, the first diagnosis assistance module (or first diagnostic unit) 2015a may obtain a first piece of diagnosis assistance information related to a first heart disease using a first neural network model, and the second diagnosis assistance module (or second diagnostic unit) 2015b may obtain a second piece of diagnosis assistance information related to the first heart disease.

As a specific example, the first diagnosis assistance module (or first diagnostic unit) 2015a may obtain score information for diagnosis of a coronary artery disease using a first neural network model, and the second diagnosis assistance module (or second diagnostic unit) 2015b may obtain grade information for diagnosis of a coronary artery disease.

As still another example, the first diagnosis assistance module (or first diagnostic unit) 2015a may obtain a first piece of diagnosis assistance information related to diagnosis of a heart disease using a first neural network model, and the second diagnosis assistance module (or second diagnostic unit) 2015b may obtain a second piece of diagnosis assistance information related to diagnosis of another disease using a second neural network model.

As a specific example, the first diagnosis assistance module (or first diagnostic unit) 2015a may obtain grade information for diagnosis of a coronary artery disease using a first neural network model, and the second diagnosis assistance module (or second diagnostic unit) 2015b may obtain grade information for diagnosis of glaucoma.

A diagnosis assistance information output module may output diagnosis assistance information. The diagnosis assistance information output module may output final diagnosis assistance information obtained on the basis of a first piece of diagnosis assistance information and a second piece of diagnosis assistance information and/or secondary diagnosis assistance information obtained from the first piece of diagnosis assistance information, second piece of diagnosis assistance information, or final diagnosis assistance information. The diagnosis assistance information output module may provide diagnosis assistance information to a user or transmit diagnosis assistance information to an external device.

Figure 58:
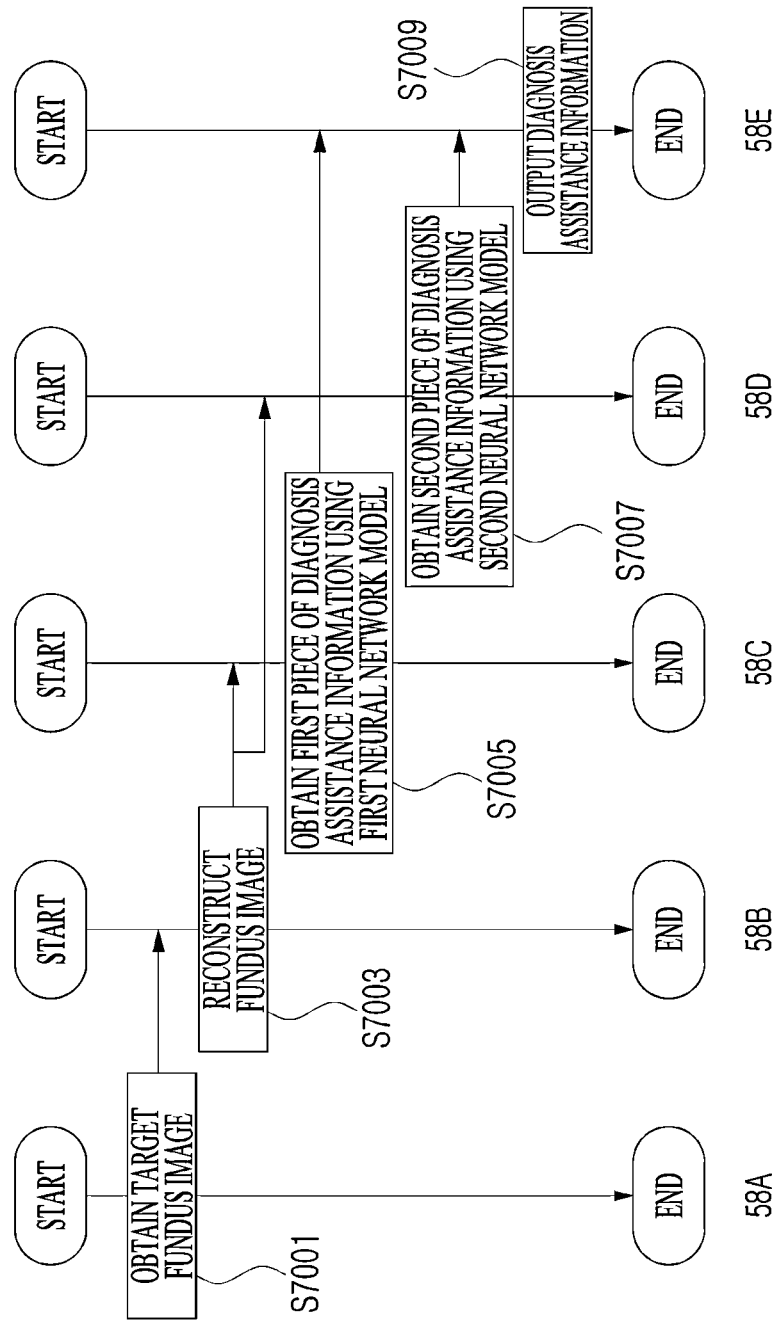
FIG. 58 is a view for describing a method of assisting in heart disease diagnosis according to an embodiment of the present invention.

FIG. 58 is a view for describing a method of assisting in heart disease diagnosis according to an embodiment of the present invention.

Referring to FIG. 58, 58A is a flowchart for describing an operation of a data obtaining module (or diagnosis request obtaining module). Referring to FIG. 58, 58B is a flowchart for describing an operation of a data reconstruction module. 58C is a flowchart for describing an operation of a first diagnosis assistance module. 58D is a flowchart for describing an operation of a second diagnosis assistance module. 58E is a flowchart for describing an operation of a diagnosis assistance information output module. However, the operations illustrated in 58A to 58E are not necessarily performed by the modules described above. For example, the operations described with reference to 58A to 58E may also be performed by a single module, for example, a binocular diagnosis assistance module, or a processor or a control unit of a diagnostic device.

Referring to FIG. 58, a method of assisting in heart disease diagnosis according to an embodiment of the present invention may include obtaining a target fundus image (S7001), reconstructing the target fundus image (S7003), obtaining a first piece of diagnosis assistance information via a first neural network model on the basis of the reconstructed image (S7005), obtaining a second piece of diagnosis assistance information via a second neural network model on the basis of the reconstructed image (S7007), and outputting diagnosis assistance information on the basis of the first piece of diagnosis assistance information and the second piece of diagnosis assistance information (S7009).

The obtaining of the target fundus image (S7001) may be performed by a diagnosis request obtaining module or an imaging unit. For example, the obtaining of the target fundus image (S7001) may include obtaining a target fundus image and a diagnosis request that requests for diagnosis assistance information related to the target fundus image. Also, for example, the obtaining of the target fundus image (S7001) may include obtaining a target fundus image via an imaging unit. Alternatively, the obtaining of the target fundus image may include obtaining a target fundus image in response to obtaining a diagnosis request.

The reconstructing of the target fundus image (S7003) may be performed by a data reconstruction module, a control unit, or a processor. The above description may similarly apply to the reconstruction or pre-processing of the target fundus image.

The target fundus image may be reconstructed differently according to diagnosis assistance information to be obtained. In other words, a plurality of diagnostic units (or diagnostic modules) that operate in parallel may obtain diagnosis assistance information using a plurality of reconstructed images which are provided by reconstructing the same target fundus image differently. As a specific example, when a diagnosis assistance method includes, on the basis of a target fundus image, obtaining a first piece of diagnosis assistance information related to a coronary artery disease using a first neural network model and obtaining a second piece of diagnosis assistance information related to an eye disease using a second neural network model, the reconstructing of the target fundus image may include obtaining a first reconstructed fundus image obtained by reconstructing the target fundus image so that blood vessels are highlighted and a second reconstructed fundus image obtained by reconstructing the target fundus image so that optic discs are highlighted.

Although the case in which a target fundus image is reconstructed and then a first piece of diagnosis assistance information and/or a second piece of diagnosis assistance information are obtained on the basis of the reconstructed image has been described above with reference to FIG. 58, this is merely an example, and the reconstructing may be omitted.

The obtaining of the first piece of diagnosis assistance information via the first neural network model (S7005) may be performed by a control unit or a processor. The obtaining of the second piece of diagnosis assistance information via the second neural network model (S7007) may be performed by a control unit or a processor. The obtaining of the first piece of diagnosis assistance information (S7005) and the obtaining of the second piece of diagnosis assistance information (S7007) may be performed by the same processor or performed by differentiated processors. The obtaining of the first piece of diagnosis assistance information and the obtaining of the second piece of diagnosis assistance information may be performed concurrently or sequentially.

For example, the obtaining of the first piece of diagnosis assistance information via the first neural network model may include obtaining a first piece of diagnosis assistance information including a first type of information related to a first heart disease, and the obtaining of the second piece of diagnosis assistance information via the second neural network model may include obtaining a second piece of diagnosis assistance information including a second type of information related to the first heart disease.

As a specific example, the obtaining of the first piece of diagnosis assistance information via the first neural network model may include obtaining score information which indicates a calcium score used in diagnosis of a coronary artery disease, and the obtaining of the second piece of diagnosis assistance information via the second neural network model may include obtaining grade information which indicates an extent of risk of a coronary artery disease.

As another example, the obtaining of the first piece of diagnosis assistance information via the first neural network model may include obtaining a first piece of diagnosis assistance information related to a first heart disease, and the obtaining of the second piece of diagnosis assistance information via the second neural network model may include obtaining a second piece of diagnosis assistance information related to a second heart disease (or a non-heart disease).

Each of the obtaining of the diagnosis assistance information using the neural network model may be performed similarly as that described above in "Assisting in heart disease diagnosis using neural network model" section.

The outputting of the diagnosis assistance information (S7009) may be performed by a control unit or a processor. The above description in "Output of diagnosis assistance information" section may similarly apply to the outputting of the diagnosis assistance information unless particularly mentioned otherwise.

The outputting of the diagnosis assistance information (S7009) may include outputting the first piece of diagnosis assistance information and/or the second piece of diagnosis assistance information. The outputting of the diagnosis assistance information may include outputting final diagnosis assistance information generated on the basis of the first piece of diagnosis assistance information and the second piece of diagnosis assistance information. Alternatively, the outputting of the diagnosis assistance information (S7009) may include outputting information selected from the first piece of diagnosis assistance information and the second piece of diagnosis assistance information.

The outputting of the diagnosis assistance information will be described in more detail below.

2.4.4 Output of Plurality of Pieces of Diagnosis Assistance Information

According to an embodiment of the present invention, a plurality of pieces of diagnosis assistance information obtained via a plurality of neural network models which are driven in parallel may be output. Hereinafter, output of diagnosis assistance information will be described on the basis of the above-described case in which a first piece of diagnosis assistance information is obtained using a first neural network model and a second piece of diagnosis assistance information is obtained using a second neural network model.

According to an embodiment of the present invention, output information may be determined on the basis of a first piece of diagnosis assistance information and/or a second piece of diagnosis assistance information. The output information may be provided to a user or transmitted to an external device. The output information may be provided to a user via a client device, a diagnostic device, or a mobile device. The output information may be provided to a user via a user interface. The output information may be provided to a user via visual and/or aural data. The output information may be transmitted to an external device via a communication unit or a communication interface configured to perform wired or wireless communication. The output information may be transmitted to a server device, a client device, or a mobile device.

The output diagnosis assistance information may include a first piece of diagnosis assistance information obtained by a first neural network model and a second piece of diagnosis assistance information obtained by a second neural network model.

For example, the output diagnosis assistance information may be score information related to a coronary artery disease that is obtained by a first neural network model and risk grade information related to a coronary artery disease that is obtained by a second neural network model. Also, for example, the output diagnosis assistance information may be score information related to a coronary artery disease that is obtained by a first neural network model and risk grade information related to stroke (or an eye disease such as glaucoma) that is obtained by a second neural network model. Also, for example, the output diagnosis assistance information may be prescription information (for example, prescription information on HMG-CoA reductase inhibitors) according to score information (for example, an ASCVD score) obtained by a first neural network model and grade information (for example, coronary artery disease risk grade information) obtained by a second neural network model.

The output diagnosis assistance information may be information selected from a first piece of diagnosis assistance information obtained by a first neural network model and a second piece of diagnosis assistance information obtained by a second neural network model.

According to an embodiment of the present invention, diagnosis assistance information selected from a plurality of pieces of diagnosis assistance information obtained by a plurality of neural network models may be output. For example, the output diagnosis assistance information may be diagnosis assistance information selected from a first piece of diagnosis assistance information and a second piece of diagnosis assistance information. The output diagnosis assistance information may be diagnosis assistance information selected, on the basis of accuracy or an extent of risk, from a plurality of pieces of diagnosis assistance information.

In some cases, a first neural network model and/or a second neural network model may be continuously trained and updated. As the first neural network model and/or the second neural network model are trained, the output information may be changed. In other words, as the first neural network model and/or the second neural network model are updated, the number of pieces of training data input to each neural network model or the accuracy of each neural network model may be changed, and accordingly, the form of the output information may also be changed.

For example, output information that is output on the basis of a first piece of diagnosis assistance information and a second piece of diagnosis assistance information which are obtained on the basis of a first target fundus image may be a first type of information (for example, grade information) included in the first piece of diagnosis assistance information, and output information that is output on the basis of a first piece of diagnosis assistance information and a second piece of diagnosis assistance information which are obtained on the basis of a second target fundus image after the first type of information is obtained may be a second type of information (for example, score information) included in the second piece of diagnosis assistance information.

In some cases, pieces of information indicated by the first piece of diagnosis assistance information and the second piece of diagnosis assistance information may be logically inconsistent. In this case, the output diagnosis assistance information may be information selected from the first piece of diagnosis assistance information and the second piece of diagnosis assistance information.

For example, when the first piece of diagnosis assistance information is a first type of information related to a first heart disease and the second piece of diagnosis assistance information is a second type of information related to the first heart disease, extents of risk that the first type of information and the second type of information indicate may be different from each other. In this case, the output diagnosis assistance information may be a type of information according to a predetermined order of priority or may be a type of information determined according to predetermined criteria.

The output diagnosis assistance information may be set according to an order of priority. The order of priority may be set in relation to types of information. For example, the order of priority may be set such that disease presence/absence information has a higher priority than grade information and the grade information has a higher priority than score information. The order of priority may be designated by a user. The order of priority may be predetermined according to the form or accuracy of a neural network model.

According to an embodiment, when the first piece of diagnosis assistance information and the second piece of diagnosis assistance information match each other, the output diagnosis assistance information may include the first piece of diagnosis assistance information and the second piece of diagnosis assistance information, and when the first piece of diagnosis assistance information and the second piece of diagnosis assistance information do not match each other, the output diagnosis assistance information may include information having a higher priority between the first piece of diagnosis assistance information and the second piece of diagnosis assistance information.

The output diagnosis assistance information may be information with higher accuracy between the first type of information and the second type of information. In other words, a higher output priority may be assigned to information obtained from a neural network model with relatively higher accuracy.

The output diagnosis assistance information may be information which indicates a higher extent of risk between the first type of information and the second type of information. In other words, a higher output priority may be assigned to information indicating a relatively higher extent of risk.

For example, when the first type of information is grade information indicating an extent of risk of a coronary artery disease and the second type of information is score information indicating a calcium score for diagnosis of a coronary artery disease, in the case in which the score information has a value indicating that a patient has a mild risk of a coronary artery disease, e.g., a value of 8, and the grade information is Grade C information indicating that the patient has a moderate risk of the coronary artery disease, the Grade C information may be determined as the output diagnosis assistance information.

A first piece of diagnosis assistance information having a higher priority and a second piece of diagnosis assistance information having a lower priority may also be provided together. In this case, a notice that informs a user of the order of priority may be provided together.

When pieces of information that the first piece of diagnosis assistance information and the second piece of diagnosis assistance information indicate are logically inconsistent, the first piece of diagnosis assistance information and/or the second piece of diagnosis assistance information may be corrected so that the meanings thereof become logically consistent. In other words, the output diagnosis assistance information may include a first piece of diagnosis assistance information and a second piece of diagnosis assistance information which is corrected.

In this case, according to reference information determined according to a predetermined order of priority, another piece of information may be corrected. For example, when grade information has a higher priority than score information, and grade information according to the obtained first piece of diagnosis assistance information and score information according to the second piece of diagnosis assistance information do not match each other, the score information may be corrected with the grade information as the reference information.

In other words, when the first piece of diagnosis assistance information and the second piece of diagnosis assistance information match each other, the output diagnosis assistance information may include the first piece of diagnosis assistance information and the second piece of diagnosis assistance information, and when the first piece of diagnosis assistance information and the second piece of diagnosis assistance information do not match each other, the output diagnosis assistance information may include a first piece of diagnosis assistance information, which is determined as the reference information, and a second piece of diagnosis assistance information which is corrected corresponding to the first piece of diagnosis assistance information.

The corrected information may be corrected to match the reference information. For example, when the reference information is Grade B information as grade information, score information may be corrected to have a numerical value ranging from 1 to 10 to match the grade information. The output diagnosis assistance information may include the Grade B information and the score information having a value corrected to 10 to match the Grade B.

The corrected information may be corrected to have a meaning closer to that of the reference information. For example, when the reference information is Grade B information as grade information and the obtained score information is 14, the output diagnosis assistance information may include the Grade B information and score information having a value corrected to 11 to be closer to the Grade B.

When the corrected information is output together with the reference information, display information for informing the user of the reference information and the corrected information may also be output together.

The output diagnosis assistance information may be determined on the basis of the first piece of diagnosis assistance information obtained by the first neural network model and the second piece of diagnosis assistance information obtained by the second neural network model. The output diagnosis assistance information may include secondary information determined in consideration of the first piece of diagnosis assistance information and/or the second piece of diagnosis assistance information.

For example, when the first piece of diagnosis assistance information is score information which indicates a value of a first parameter used in diagnosis of a first heart disease, and the second piece of diagnosis assistance information is grade information which indicates a second parameter related to the first heart disease, the output diagnosis assistance information may include information on an extent of risk of the first heart disease for a patient that is determined on the basis of the first piece of diagnosis assistance information and the second piece of diagnosis assistance information.

Also, for example, when the first piece of diagnosis assistance information is a first piece of score information used in diagnosis of a first heart disease, and the second piece of diagnosis assistance information is a second piece of score information related to the first heart disease, the output diagnosis assistance information may be a third piece of score information obtained in consideration of both the first piece of score information and the second piece of score information. For example, the first piece of score information and/or the second piece of score information may be factors used in Framingham score calculation, and the third piece of score information may indicate a Framingham score value.

Meanwhile, although the case in which a plurality of neural network models driven in parallel include a first neural network model and a second neural network model has been described above, the present invention is not limited thereto, and a larger number of neural network models may be trained in parallel, a plurality of pieces of diagnosis assistance information may be obtained using the trained neural network models, and the obtained pieces of diagnosis assistance information may be output.

For example, a diagnosis assistance method may include obtaining a first piece of diagnosis assistance information via a first neural network model, obtaining a second piece of diagnosis assistance information via a second neural network model, and obtaining a third piece of diagnosis assistance information via a third neural network model.

In this case, the output diagnosis assistance information may be output information which includes the first to third pieces of diagnosis assistance information, includes at least one piece of diagnosis assistance information selected from the first to third pieces of diagnosis assistance information, or is determined on the basis of the first to third pieces of diagnosis assistance information.

For example, when the first piece of diagnosis assistance information is a first type of information related to a first heart disease, the second piece of diagnosis assistance information is a second type of information related to the first heart disease, and the third piece of diagnosis assistance information is diagnosis assistance information related to a second heart disease, the output diagnosis assistance information may include the third piece of diagnosis assistance information and any one selected from the first piece of diagnosis assistance information and the second piece of diagnosis assistance information.

2.5 Use of Binocular Images

2.5.1 Background

According to an embodiment of the present invention, binocular images may be used in assisting in diagnosis. In the case of assisting in diagnosis of a heart disease, accurate and stable diagnosis assistance may be possible by obtaining a left-eye image and a right-eye image of a patient and obtaining diagnosis assistance information based on each image.

In other words, when it is attempted to detect an abnormality in a cardiovascular system on the basis of a fundus image, there may be a case in which an abnormal symptom is discovered only in one of a left-eye fundus image and a right-eye fundus image or a case in which abnormal symptoms indicated by the left-eye fundus image and the right-eye fundus image are different. In such cases, when diagnosis assistance information is only obtained in consideration of a fundus image from which an abnormal symptom is not discovered or diagnosis assistance information is only obtained in consideration of a fundus image indicating a relatively low extent of risk, a suitable action may not be taken for a patient.

The above problem may occur in a similar manner in various cases in which it is attempted to assist in disease diagnosis using a fundus image. Hereinafter, description will be given on the basis of the case in which a neural network model is used in order to assist in heart disease diagnosis, but details of the invention described herein are not limited thereto, and the above problem may similarly apply to various other cases in which diagnosis assistance is performed using a fundus image.

Hereinafter, some embodiments of a method in which a neural network model is trained in consideration of binocular fundus images and diagnosis assistance information is obtained in consideration of the binocular fundus images in order to address the above problem will be described.

2.5.2 Binocular Diagnosis Assistance System

According to an embodiment of the present invention, a heart disease diagnosis assistance system that assists in heart disease diagnosis by using binocular images together (hereinafter referred to as "binocular diagnosis assistance system") may be provided. The binocular diagnosis assistance system may train a neural network model using a left eye image and a right eye image or may obtain diagnosis assistance information using the left eye image and the right eye image.

Unless particularly described otherwise, the binocular diagnosis assistance system that assists in heart disease diagnosis using binocular images may be implemented similarly as the diagnosis assistance system described above with reference to FIGS. 1 to 9, 42, and 43.

Figure 59:
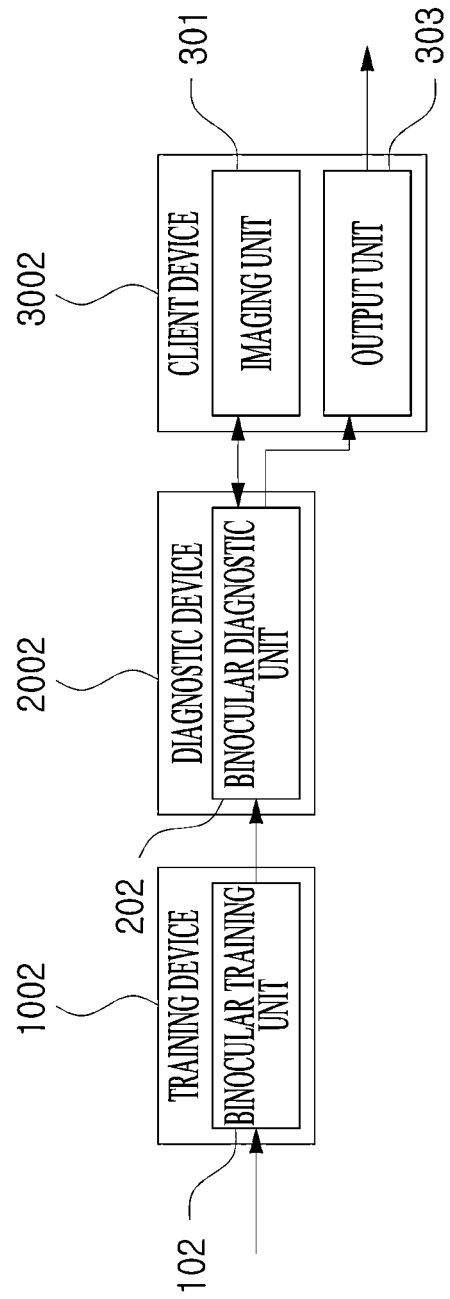
FIG. 59 is a view for describing a diagnosis assistance system according to an embodiment of the present invention.

FIG. 59 is a view for describing a diagnosis assistance system according to an embodiment of the present invention. Referring to FIG. 59, a diagnosis assistance system according to an embodiment of the present invention may include a training device 1002, a diagnostic device 2002, and a client device 3002.

The training device 1002 may include a binocular training unit 102. The binocular training unit 102 may obtain binocular images and train a neural network model for assisting in heart disease diagnosis. The binocular training unit 102 may be provided in a control unit, a processor, or a memory of the training device 1002.

The binocular training unit 102 may include fundus image training data including a left-eye fundus image and a right-eye fundus image and may train a neural network model which outputs heart disease diagnosis assistance information on the basis of a fundus image. The binocular training unit 102 may train a neural network model which outputs heart disease diagnosis assistance information of a patient on the basis of fundus image training data including a fundus image labeled as left eye or right eye. The binocular training unit 102 may train a neural network model which outputs heart disease diagnosis assistance information of a patient on the basis of fundus image training data including a left-eye fundus image and a right-eye fundus image which are labeled as left eye or right eye and are matched with each other.

The diagnostic device 2002 may include a binocular diagnostic unit 202. The binocular diagnostic unit 201c may obtain diagnosis assistance information for heart disease diagnosis of a patient by using a heart disease diagnosis assistance neural network model. The diagnostic unit 202 may be provided in a control unit or a processor of the diagnostic device 2002.

The binocular diagnostic unit 202 may obtain binocular fundus images of a patient and obtain heart disease diagnosis assistance information of the patient. The binocular diagnostic unit 202 may obtain a left-eye fundus image and a right-eye fundus image of a patient and obtain heart disease diagnosis assistance information of the patient. The binocular diagnostic unit 202 may also obtain binocular diagnosis assistance information which is obtained in consideration of both left-eye and right-eye fundus images of the patient. The binocular diagnostic unit 202 may obtain left-eye diagnosis assistance information corresponding to the left-eye fundus image of the patient and right-eye diagnosis assistance information corresponding to the right-eye fundus image of the patient.

The binocular diagnostic unit 202 may obtain left-eye diagnosis assistance information and right-eye diagnosis assistance information using a single model. The binocular diagnostic unit 202 may obtain left-eye diagnosis assistance information using a left-eye diagnosis assistance neural network model and may obtain right-eye diagnosis assistance information using a right-eye diagnosis assistance neural network model.

The client device 3002 may include an imaging unit 301 and an output unit 303. The client device 3002 may operate similarly as that described above. The client device 3002 may obtain a target fundus image, transmit the obtained target fundus image to a diagnostic device, and obtain diagnosis assistance information according to the target fundus image from the diagnostic device.

Figure 60:
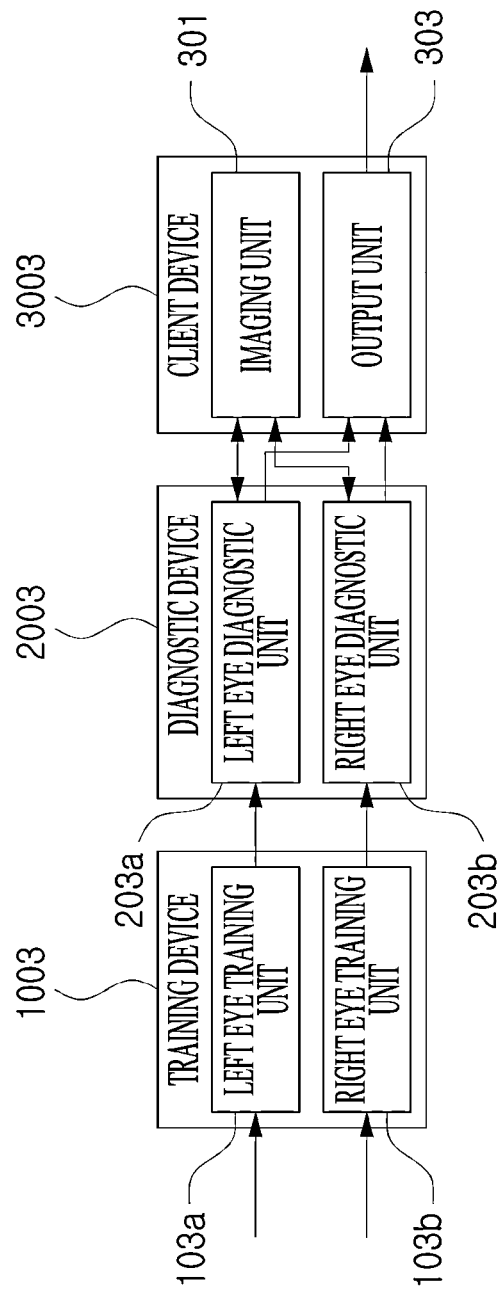
FIG. 60 is a view for describing a diagnosis assistance system according to an embodiment of the present invention.

FIG. 60 is a view for describing a diagnosis assistance system according to an embodiment of the present invention. Referring to FIG. 60, a diagnosis assistance system according to an embodiment of the present invention may include a training device 1003, a diagnostic device 2003, and a client device 3003.

Referring to FIG. 60, the training device 1003 may include a left eye training unit 103a and a right eye training unit 103b. Each of the left eye training unit 103a and the right eye training unit 103b may obtain fundus image training data including a left-eye or right-eye fundus image and train a neural network model which outputs diagnosis assistance information. The left eye training unit 103a and the right eye training unit 103b may also be included in the above-described binocular training unit. The left eye training unit 103a and the right eye training unit 103b may also be provided in a control unit, a processor, or a memory of the training device 1003.

The left eye training unit 103a may use the fundus image training data including the left eye image to train a left-eye diagnosis assistance neural network model which obtains diagnosis assistance information according to a target left-eye fundus image. The right eye training unit 103b may use the fundus image training data including a right eye image to train a right-eye diagnosis assistance neural network model which obtains diagnosis assistance information according to a target right-eye fundus image.

Initial forms of the left-eye diagnosis assistance neural network model and the right-eye diagnosis assistance neural network model may be provided in different layer structures. Alternatively, the initial forms of the left-eye diagnosis assistance neural network model and the right-eye diagnosis assistance neural network model may be provided in similar structures. For example, the right-eye diagnosis assistance neural network model and the left-eye diagnosis assistance neural network model include at least some common layers which are common in both models. In this case, parameters constituting each neural network model may be changed as training is progressed.

Referring to FIG. 60, the diagnostic device 2003 may include a left-eye diagnostic unit 203a and a right-eye diagnostic unit 203b. Each of the left-eye diagnostic unit 203a and the right-eye diagnostic unit 203b may obtain diagnosis assistance information according to a left-eye fundus image and a right-eye fundus image by using a neural network model. The left-eye diagnostic unit 203a and the right-eye diagnostic unit 203b may also be provided in a controller, a processor, or a memory of the diagnostic device 2003.

The left-eye diagnostic unit 203a may obtain left eye diagnosis assistance information corresponding to a left-eye fundus image of a patient. The left-eye diagnostic unit 203a may obtain left eye diagnosis assistance information using a left-eye diagnosis assistance neural network model.

The right-eye diagnostic unit 203b may obtain right eye diagnosis assistance information corresponding to a right-eye fundus image of the patient. The right-eye diagnostic unit 203b may obtain right eye diagnosis assistance information using a right-eye diagnosis assistance neural network model.

The client device 3003 may operate similarly as that described above. The imaging unit 301 may obtain a left-eye fundus image and provide the obtained left-eye fundus image to the left-eye diagnostic unit 203a. The imaging unit 301 may obtain a right-eye fundus image and provide the obtained right-eye fundus image to the right-eye diagnostic unit 203b. The output unit 303 may obtain left eye diagnosis assistance information from the left-eye diagnostic unit 203a and output the obtained left eye diagnosis assistance information. The output unit 303 may obtain right eye diagnosis assistance information from the right-eye diagnostic unit 203b and output the obtained right eye diagnosis assistance information.

Figure 61:
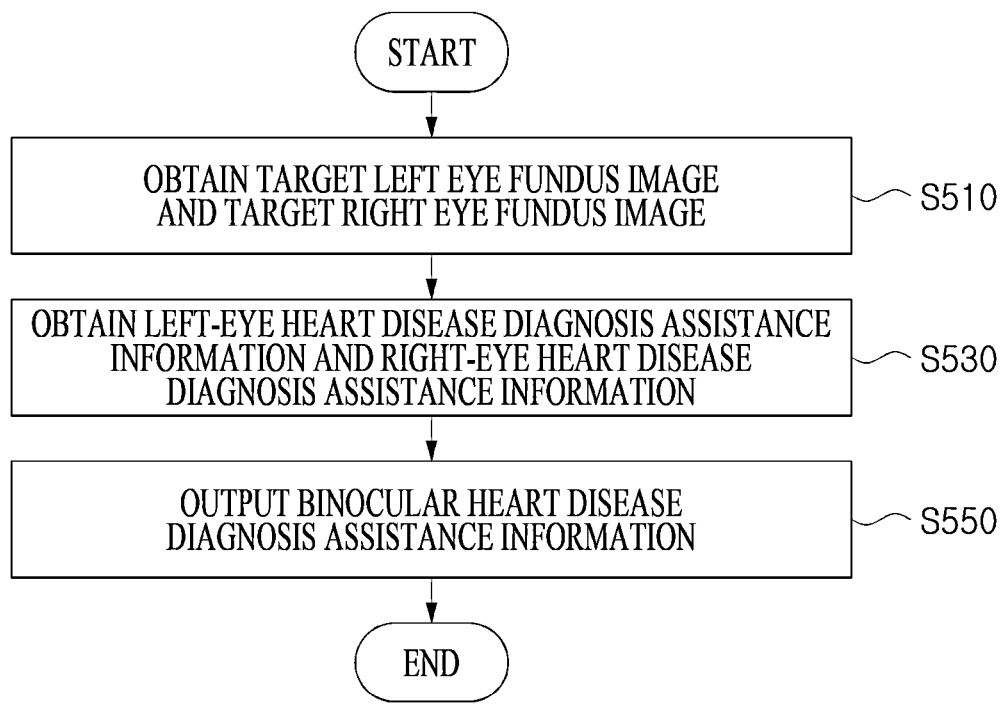
FIG. 61 is a view for describing a method of assisting in heart disease diagnosis according to an embodiment of the present invention.

FIG. 61 is a view for describing a method of assisting in heart disease diagnosis according to an embodiment of the present invention. Referring to FIG. 61, the method of assisting in heart disease diagnosis according to an embodiment of the present invention may include obtaining a target left-eye fundus image and a target right-eye fundus image (S510), obtaining left-eye heart disease diagnosis assistance information and right-eye heart disease diagnosis assistance information (S530), and outputting binocular heart disease diagnosis assistance information (S550).

The obtaining of the target left-eye fundus image and the target right-eye fundus image (S510) may include obtaining a target left-eye fundus image and a target right-eye fundus image of a testee.

The obtaining of the left-eye heart disease diagnosis assistance information and right-eye heart disease diagnosis assistance information (S530) may include, by using a heart disease diagnosis assistance neural network model which obtains heart disease diagnosis assistance information on the basis of a fundus image, obtaining left-eye heart disease diagnosis assistance information according to the target left-eye fundus image and right-eye heart disease diagnosis assistance information according to the target right-eye fundus image.

The outputting of the binocular heart disease diagnosis assistance information (S550) may include outputting binocular heart disease diagnosis assistance information generated in consideration of the left-eye heart disease diagnosis assistance information and the right-eye heart disease diagnosis assistance information.

The left-eye heart disease diagnosis assistance information and the right-eye heart disease diagnosis assistance information may include at least one of score information used in diagnosis of a target heart disease, grade information which includes a grade selected from a plurality of grades indicating an extent of risk of a target heart disease, and risk information indicating whether a test belongs to a risk group for a target heart disease.

The obtaining of the left-eye heart disease diagnosis assistance information and right-eye heart disease diagnosis assistance information (S530) may include obtaining left-eye heart disease diagnosis assistance information using a left-eye heart disease diagnosis assistance neural network model which obtains heart disease diagnosis assistance information on the basis of the left-eye fundus image and obtaining right-eye heart disease diagnosis assistance information using a right-eye heart disease diagnosis assistance neural network model which obtains heart disease diagnosis assistance information on the basis of the right-eye fundus image.

Meanwhile, in addition to the above-described method, the method of assisting in heart disease diagnosis according to an embodiment of the present invention may further include, on the basis of the target left-eye fundus image and the target right-eye fundus image, obtaining left-eye eye disease diagnosis assistance information according to the target left-eye fundus image and right-eye eye disease diagnosis assistance information according to the target right-eye fundus image by using an eye disease diagnosis assistance neural network model which obtains eye disease diagnosis assistance information and/or outputting the left-eye eye disease diagnosis assistance information and the right-eye eye disease diagnosis assistance information.

Figure 62:
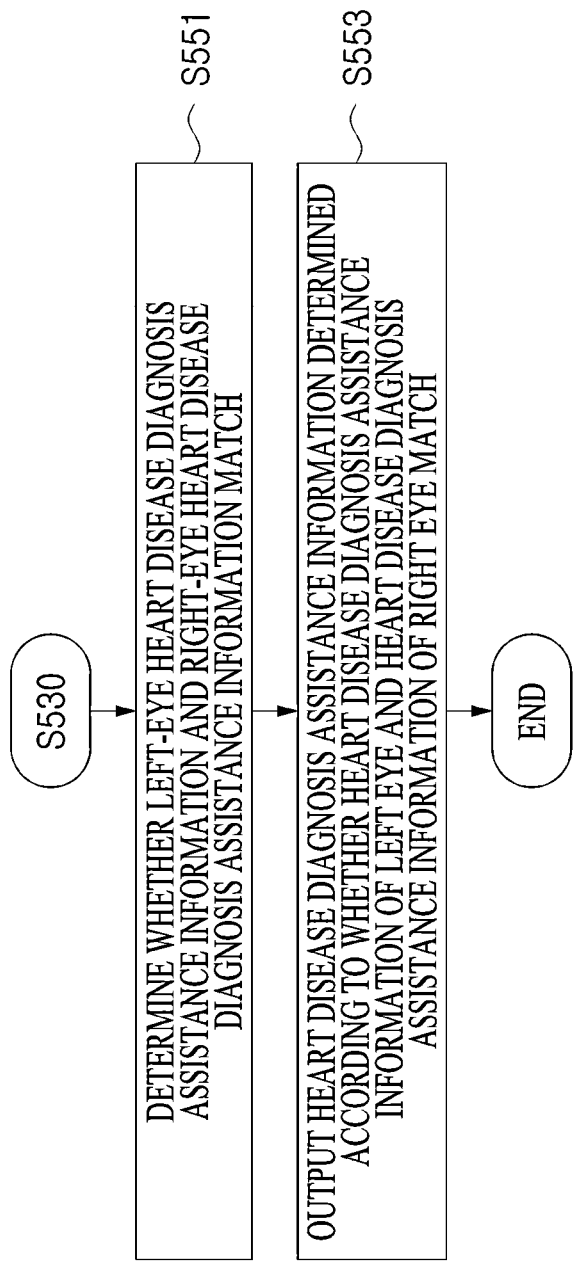
FIG. 62 is a view for describing a method of assisting in heart disease diagnosis according to an embodiment of the present invention.

FIG. 62 is a view for describing a method of assisting in heart disease diagnosis according to an embodiment of the present invention. Referring to FIG. 62, the outputting of the binocular heart disease diagnosis assistance information (S550) according to an embodiment of the present invention may include determining whether the left-eye heart disease diagnosis assistance information and the right-eye heart disease diagnosis assistance information match each other (S551) and outputting heart disease diagnosis assistance information determined according to whether the left-eye heart disease diagnosis assistance information and the right-eye heart disease diagnosis assistance information match each other (S553).

The outputting of the binocular heart disease diagnosis assistance information (S553) may include, when the left-eye heart disease diagnosis assistance information and the right-eye heart disease diagnosis assistance information match each other, outputting binocular heart disease diagnosis assistance information, which is determined as the left-eye heart disease diagnosis assistance information, the right-eye heart disease diagnosis assistance information, or intermediate information between the left-eye heart disease diagnosis assistance information and the right-eye heart disease diagnosis assistance information.

The outputting of the binocular heart disease diagnosis assistance information (S553) may further include, when the left-eye heart disease diagnosis assistance information and the right-eye heart disease diagnosis assistance information do not match each other, determining one of the left-eye heart disease diagnosis assistance information and the right-eye heart disease diagnosis assistance information that indicates a relatively higher risk of a target heart disease as the binocular heart disease diagnosis assistance information.

The left-eye heart disease diagnosis assistance information may include a left-eye coronary artery calcium score used in determining a degree of aortic valve calcification that is obtained from the left-eye fundus image, and the right-eye heart disease diagnosis assistance information may include a right-eye coronary artery calcium score used in determining a degree of aortic valve calcification that is obtained from the right-eye fundus image.

In this case, the determining of whether the left-eye heart disease diagnosis assistance information and the right-eye heart disease diagnosis assistance information match each other (S551) may include determining whether a difference between the left-eye coronary artery calcium score and the right-eye coronary artery calcium score is a threshold value or less.

The outputting of the binocular heart disease diagnosis assistance information (S553) may include, when the difference between the left-eye coronary artery calcium score and the right-eye coronary artery calcium score is higher than the threshold value, determining a higher value of the left-eye coronary artery calcium score and the right-eye coronary artery calcium score as the binocular heart disease diagnosis assistance information.

The outputting of the binocular heart disease diagnosis assistance information (S553) may include, when the difference between the left-eye coronary artery calcium score and the right-eye coronary artery calcium score is higher than the threshold value, determining information including a higher value of the left-eye coronary artery calcium score and the right-eye coronary artery calcium score as the binocular heart disease diagnosis assistance information, and outputting a notice, which notifies of the fact that a difference has occurred between the left-eye coronary artery calcium score and the right-eye coronary artery calcium score, together with the determined binocular heart disease diagnosis assistance information.

The outputting of the binocular heart disease diagnosis assistance information (S553) may include, when the difference between the left-eye coronary artery calcium score and the right-eye coronary artery calcium score is higher than the threshold value, determining a relatively higher value of the left-eye coronary artery calcium score and the right-eye coronary artery calcium score as the binocular heart disease diagnosis assistance information, and outputting an abnormal fundus image notice, which notifies a user of a target fundus image from which information including a relatively higher value of the left-eye coronary artery calcium score and the right-eye coronary artery calcium score is obtained, together with the determined binocular heart disease diagnosis assistance information.

Figure 63:
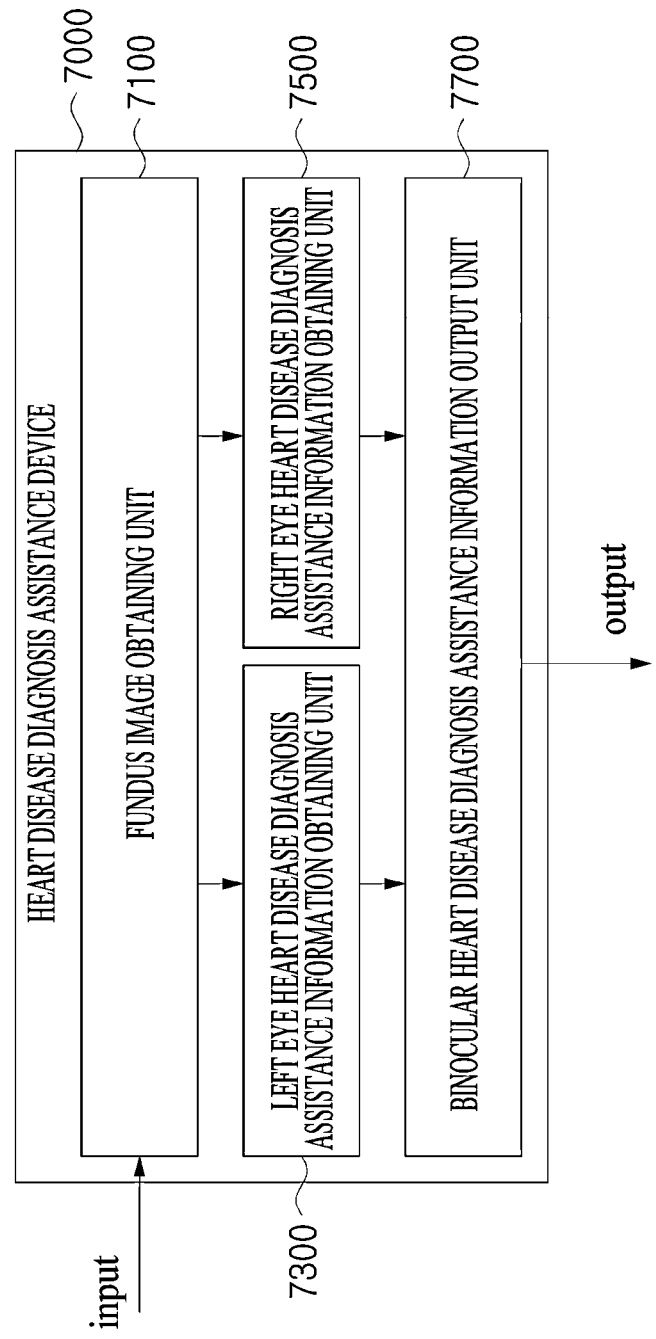
FIG. 63 is a view for describing a heart disease diagnosis assistance device 7000 according to an embodiment of the present invention.

FIG. 63 is a view for describing a heart disease diagnosis assistance device 7000 according to an embodiment of the present invention. Referring to FIG. 63, the heart disease diagnosis assistance device 7000 that assists in diagnosis of a target heart disease using a fundus image according to an embodiment of the present invention may include a fundus image obtaining unit 7100, a left-eye heart disease diagnosis assistance information obtaining unit 7300, a right-eye heart disease diagnosis assistance information obtaining unit 7500, and a binocular heart disease diagnosis assistance information output unit 7700.

The fundus image obtaining unit 7100 may obtain a target left-eye fundus image and a target right-eye fundus image of a testee.

The left-eye heart disease diagnosis assistance information obtaining unit 7300 may obtain left-eye heart disease diagnosis assistance information according to the target left-eye fundus image by using a heart disease diagnosis assistance neural network model which obtains heart disease diagnosis assistance information on the basis of a fundus image.

The right-eye heart disease diagnosis assistance information obtaining unit 7500 may obtain right-eye heart disease diagnosis assistance information according to the target right-eye fundus image by using the heart disease diagnosis assistance neural network model.

The binocular heart disease diagnosis assistance information output unit 7700 may output binocular heart disease diagnosis assistance information generated in consideration of the left-eye heart disease diagnosis assistance information and the right-eye heart disease diagnosis assistance information.

The left-eye heart disease diagnosis assistance information and the right-eye heart disease diagnosis assistance information may include at least one of score information used in diagnosis of a target heart disease, grade information including a grade selected from a plurality of grades indicating an extent of risk of a target heart disease, and risk information indicating whether a testee belongs to a risk group for a target heart disease.

The left-eye heart disease diagnosis assistance information obtaining unit 7300 may obtain the left-eye heart disease diagnosis assistance information using the left-eye heart disease diagnosis assistance neural network model which obtains heart disease diagnosis assistance information on the basis of the left-eye fundus image.

The right-eye heart disease diagnosis assistance information obtaining unit 7500 may obtain the right-eye heart disease diagnosis assistance information using the right-eye heart disease diagnosis assistance neural network model which obtains heart disease diagnosis assistance information on the basis of the right-eye fundus image.

The left-eye heart disease diagnosis assistance neural network model may be provided to output the left-eye heart disease diagnosis assistance information on the basis of the left-eye fundus image obtained by imaging the left eye. The right-eye heart disease diagnosis assistance neural network model may be provided to output the right-eye heart disease diagnosis assistance information on the basis of the right-eye fundus image obtained by imaging the right eye. Parameters constituting each of the left-eye heart disease diagnosis assistance neural network model and the right-eye heart disease diagnosis assistance neural network model may be at least partially different.

The heart disease diagnosis assistance device 7000 may further include an eye disease diagnosis assistance information obtaining unit configured to obtain left-eye eye disease diagnosis assistance information according to the target left-eye fundus image and right-eye eye disease diagnosis assistance information according to the target right-eye fundus image by using an eye disease diagnosis assistance neural network model which obtains eye disease diagnosis assistance information on the basis of the target left-eye fundus image and the target right-eye fundus image.

Figure 64:
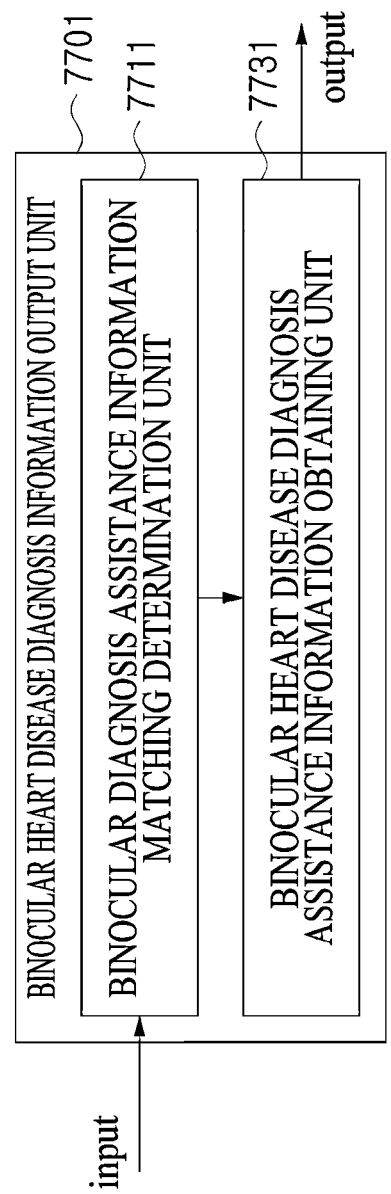
FIG. 64 is a view for describing the heart disease diagnosis assistance device 7000 according to an embodiment of the present invention.

FIG. 64 is a view for describing the heart disease diagnosis assistance device 7000 according to an embodiment of the present invention. Referring to FIG. 64, a binocular heart disease diagnosis information output unit 7701 of the heart disease diagnosis assistance device 7000 according to an embodiment of the present invention may include a binocular diagnosis assistance information matching determination unit 7711 and a binocular heart disease diagnosis assistance information obtaining unit 7731.

The binocular diagnosis assistance information matching determination unit 7711 may determine whether the left-eye heart disease diagnosis assistance information and the right-eye heart disease diagnosis assistance information match each other.

The binocular heart disease diagnosis assistance information output unit 7731 may obtain and output binocular heart disease diagnosis assistance information determined according to whether the left-eye heart disease diagnosis assistance information and the right-eye heart disease diagnosis assistance information match each other.

The binocular heart disease diagnosis assistance information output unit 7731 may, when the left-eye heart disease diagnosis assistance information and the right-eye heart disease diagnosis assistance information match each other, obtain and output binocular heart disease diagnosis assistance information, which is determined as the left-eye heart disease diagnosis assistance information, the right-eye heart disease diagnosis assistance information, or intermediate information between the left-eye heart disease diagnosis assistance information and the right-eye heart disease diagnosis assistance information.

The binocular heart disease diagnosis assistance information output unit 7731 may, when the left-eye heart disease diagnosis assistance information and the right-eye heart disease diagnosis assistance information do not match each other, determine one of the left-eye heart disease diagnosis assistance information and the right-eye heart disease diagnosis assistance information that indicates a relatively higher risk of a target heart disease as the binocular heart disease diagnosis assistance information. In other words, the binocular heart disease diagnosis assistance information output unit 7731 may output binocular heart disease diagnosis assistance information, which is determined as one of the left-eye heart disease diagnosis assistance information and the right-eye heart disease diagnosis assistance information that indicates a relatively higher risk of the target heart disease.

The left-eye heart disease diagnosis assistance information may include a left-eye coronary artery calcium score used in determining a degree of aortic valve calcification that is obtained from the left-eye fundus image, and the right-eye heart disease diagnosis assistance information may include a right-eye coronary artery calcium score used in determining a degree of aortic valve calcification that is obtained from the right-eye fundus image.

The binocular diagnosis assistance information matching determination unit 7711 may determine whether a difference between the left-eye coronary artery calcium score and the right-eye coronary artery calcium score is a threshold value or less.

The binocular heart disease diagnosis assistance information output unit 7731 may, when the difference between the left-eye coronary artery calcium score and the right-eye coronary artery calcium score is higher than the threshold value, output binocular heart disease diagnosis assistance information, which is determined as a higher score of the left-eye coronary artery calcium score and the right-eye coronary artery calcium score.

The binocular heart disease diagnosis assistance information output unit 7731 may, when the difference between the left-eye coronary artery calcium score and the right-eye coronary artery calcium score is higher than the threshold value, determine information including a higher value of the left-eye coronary artery calcium score and the right-eye coronary artery calcium score as binocular heart disease diagnosis assistance information.

The binocular heart disease diagnosis assistance information output unit 7731 may output a notice, which notifies of the fact that a difference has occurred between the left-eye coronary artery calcium score and the right-eye coronary artery calcium score, together with the determined binocular heart disease diagnosis assistance information.

2.5.3 Obtaining Binocular Fundus Images

According to an embodiment of the present invention, binocular fundus image training data for training a neural network model may be obtained.

The binocular fundus image data may include a left-eye fundus image and a right-eye fundus image. The binocular fundus image data may include left-eye fundus image data including a left-eye fundus image and right-eye fundus image data including a right-eye fundus image. The binocular fundus image data may include a left-eye fundus image and a right-eye fundus image which are matched with each other. In other words, the binocular fundus image data may include a plurality of binocular image sets each including a left-eye fundus image and a right-eye fundus image which are matched with each other.

For example, the binocular fundus image data may include a left-eye fundus image to which a left-eye label is assigned and a right-eye image to which a right-eye label is assigned. Alternatively, the binocular fundus image data may also include a left eye image and a right eye image to which specific information indicating binocular information is not assigned.

For example, the binocular fundus image data may include a first image obtained by imaging the left eye of a testee and a second image obtained by imaging the right eye of the testee. Also, for example, the binocular fundus image data may include a first fundus image obtained by imaging the left eye of a first testee and labeled as left eye and a second fundus image obtained by imaging the right eye of a second testee and labeled as right eye. Also, for example, the binocular fundus image data may include a first binocular image set which includes a first image obtained by imaging the left eye of a first testee and labeled as the left eye of the first testee and a second image obtained by imaging the right eye of the first testee and labeled as the right eye of the first testee.

The left-eye fundus image data and the right-eye fundus image data may be separately stored and/or managed. Alternatively, the left-eye fundus image data and the right-eye fundus image data may be stored and/or managed together and differentiated by labels assigned thereto.

According to an embodiment of the present invention, binocular target fundus images for obtaining diagnosis assistance information may be obtained. For obtaining of diagnosis assistance information, a left-eye target fundus image and a right-eye target fundus image may be obtained.

The left-eye target fundus image (or left-eye fundus image) and the right-eye target fundus image (or right-eye fundus image) may be obtained via a user input. For example, the obtaining of the left-eye target fundus image may include obtaining a fundus image which is obtained by imaging after a user input, which indicates a start of imaging the left eye, is obtained. The fundus image obtained by imaging after the user input indicating the start of imaging the left eye is obtained may be determined as the left-eye target fundus image. The left-eye label may be assigned to the image determined as the left-eye target fundus image.

Alternatively, the left-eye fundus image and the right-eye fundus image may be differentiated via an algorithm provided in advance or a neural network model. The left-eye label or right-eye label may also be assigned via the algorithm provided in advance or the neural network model.

2.5.4 Training Neural Network Model Using Binocular Fundus Image Data

The above-described diagnosis assistance system, training device, server device, or mobile device may train a neural network model which assists in heart disease diagnosis using binocular fundus image training data. The training unit, control unit, or processor of each device may perform training of a heart disease diagnosis assistance neural network model.

The heart disease diagnosis assistance neural network model may be trained using training data including a left-eye fundus image and a right-eye fundus image. The heart disease diagnosis assistance neural network model may be trained using training data including a fundus image labeled as left eye or right eye.

Hereinafter, on the basis of the above description, details unique to the case in which a neural network model for assisting in heart disease diagnosis is trained using binocular fundus images will be described.

Figure 65:
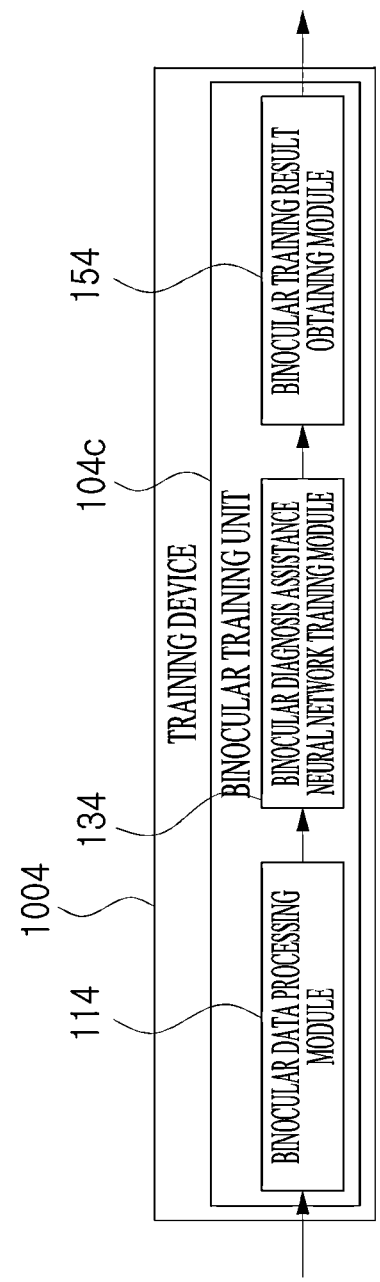
FIG. 65 is a view for describing a training device according to an embodiment of the present invention.

FIG. 65 is a view for describing a training device according to an embodiment of the present invention. Referring to FIG. 65, a training device 1004 according to an embodiment of the present invention may include a binocular training unit 104c including a binocular data processing module 114, a binocular diagnosis assistance neural network training module 134, and a binocular training result obtaining module 154.

The binocular data processing module 114 may obtain fundus image training data and process a fundus image included in the obtained fundus image training data. For example, the binocular data processing module 114 may reconstruct a fundus image into a form that facilitates assisting in heart disease diagnosis. The binocular data processing module 114 may pre-process the fundus image so that blood vessel elements included therein are highlighted or extract blood vessel elements included in the fundus image. In addition, the binocular data processing module 114 may perform various other image pre-processing, processing, or reconstructing operations described throughout the present specification. In some cases, the binocular data processing module 114 may be omitted.

The binocular diagnosis assistance neural network training module 134 may train a binocular diagnosis assistance neural network model using the processed binocular fundus images. The binocular diagnosis assistance neural network training module 134 may output heart disease diagnosis assistance information on the basis of input binocular fundus images, compare the output heart disease diagnosis assistance information with labels assigned to the input binocular fundus images, and train the binocular diagnosis assistance neural network model.

For example, the binocular diagnosis assistance neural network training module 134 may output binocular diagnosis assistance information (or left-eye diagnosis assistance information and right-eye diagnosis assistance information) by using binocular fundus image training data including a left-eye fundus image and a right-eye fundus image to which diagnosis assistance labels are assigned and may train the binocular diagnosis assistance neural network model on the basis of a comparison between the output information and the labels.

As another example, the binocular diagnosis assistance neural network training module 134 may output diagnosis assistance information by using binocular fundus image training data including a left-eye fundus image to which a diagnosis assistance label and a left-eye label are assigned and a right-eye fundus image to which a diagnosis assistance label and a right-eye label are assigned and may train the binocular diagnosis assistance neural network model on the basis of a comparison between the output information and the labels.

In this case, according to an embodiment of the present invention, a pair of a left-eye fundus image and a right-eye fundus image may constitute a piece of unit training data. More specifically, the binocular diagnosis assistance neural network training module 134 may compare a first piece of diagnosis assistance information, which is output via a binocular diagnosis assistance neural network model on the basis of a first piece of unit training data including a first left-eye fundus image and a first right-eye fundus image, and a first diagnosis assistance label assigned to the first left-eye fundus image and the first right-eye fundus image and may update the binocular diagnosis assistance neural network model on the basis of a result of the comparison.

For example, the training of the binocular diagnosis assistance neural network model on the basis of the first piece of unit training data including the first left-eye fundus image and the first right-eye fundus image may include comparing the first diagnosis assistance label with the first piece of diagnosis assistance information obtained on the basis of the first left-eye fundus image and the second piece of diagnosis assistance information obtained on the basis of the first right-eye fundus image and updating the binocular diagnosis assistance neural network model on the basis of a result of the comparison.

As a specific example, the binocular diagnosis assistance neural network model may be trained to obtain calcium information for assisting in diagnosis of a coronary artery disease on the basis of binocular fundus images. In this case, the training of the binocular diagnosis assistance neural network model may include updating the binocular diagnosis assistance neural network model by comparing left-eye calcium information according to an input left-eye fundus image with a calcium score label assigned to the input left-eye fundus image or comparing right-eye calcium information according to an input right-eye fundus image with a calcium score label assigned to the input right-eye fundus image.

As another specific example, when a left-eye fundus image and a right-eye fundus image constitute a piece of unit training data, the binocular diagnosis assistance neural network model may compare binocular calcium score information, which is obtained in consideration of both the input left-eye fundus image and the input right-eye fundus image, with calcium score labels assigned to the input left-eye and right-eye images and then update the binocular diagnosis assistance neural network model on the basis of a result of the comparison.

The binocular calcium information may be an average value, a maximum value, or a minimum value of a left-eye calcium score obtained on the basis of the left-eye fundus image and a right-eye calcium score obtained on the basis of the right-eye fundus image. The binocular calcium information may be calcium score information obtained with a binocular combination image, in which the left-eye fundus image and the right-eye fundus image are combined, as an input fundus image.

Meanwhile, according to an embodiment of the present invention, the binocular diagnosis assistance neural network model may output binocular diagnosis assistance information on the basis of left-eye diagnosis assistance information obtained from the left-eye fundus image and right-eye diagnosis assistance information obtained from the right-eye fundus image, but the form of the binocular diagnosis assistance neural network model may be different according to a method in which binocular diagnosis assistance information is determined.

For example, the binocular diagnosis assistance neural network model may be any one of a first binocular diagnosis assistance neural network model which is trained so that a maximum value (or diagnosis assistance information indicating that an extent of risk is relatively high) of left-eye diagnosis assistance information and right-eye diagnosis assistance information is determined as output binocular diagnosis assistance information, a second binocular diagnosis assistance neural network model which is trained so that a minimum value (or diagnosis assistance information indicating that an extent of risk is relatively low) of left-eye diagnosis assistance information and right-eye diagnosis assistance information is determined as output binocular diagnosis assistance information, and a third binocular diagnosis assistance neural network model which is trained so that an average value (or diagnosis assistance information indicating that an extent of risk is moderate) of left-eye diagnosis assistance information and right-eye diagnosis assistance information is determined as output binocular diagnosis assistance information. In this case, layers or training aspects of the first to third binocular diagnosis assistance neural network models may be different from each other.

The binocular training result obtaining module 154 may obtain a result of training the binocular diagnosis assistance neural network model using the binocular fundus image training data. The binocular training result obtaining module 154 may obtain parameters of the trained binocular diagnosis assistance neural network model.

Figure 66:
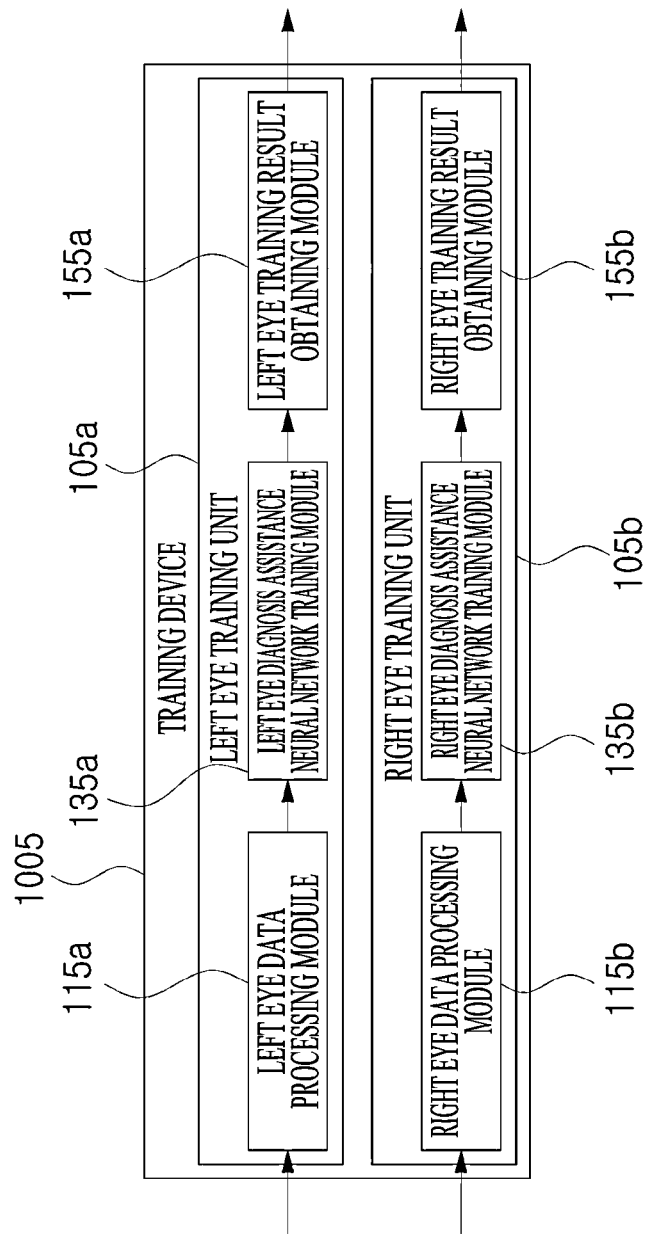
FIG. 66 is a view for describing a training device according to an embodiment of the present invention.

FIG. 66 is a view for describing a training device according to an embodiment of the present invention. Referring to FIG. 66, a training device 1005 may include a left-eye training unit 105a, which includes a left-eye data processing module 115a, a left-eye diagnosis assistance neural network training module 135a, and a left-eye training result obtaining module 155a, and a right-eye training unit 105b, which includes a right-eye data processing module 115b, a right-eye diagnosis assistance neural network training module 135b, and a right-eye training result obtaining module 155b.

The above description related to parallel training of neural network models may apply to training of a left-eye diagnosis assistance neural network model and a right-eye diagnosis assistance neural network model which will be described below with reference to FIG. 66.

The left-eye data processing module 115a may obtain left-eye fundus image training data including a left-eye fundus image and process the left-eye fundus image. The left-eye data processing module 115a may align directions of left-eye fundus images. The left-eye data processing module 115a may align directions of left-eye fundus images included in training data. The left-eye data processing module 115a may reconstruct or pre-process (for example, to highlight blood vessels) the left-eye fundus images included in the training data. The left-eye data processing module 115a may obtain an arbitrary fundus image and reconstruct the obtained arbitrary fundus image into a form of the left-eye fundus image. For example, the left-eye data processing module 115a may obtain a right-eye fundus image and invert the fundus image 180° in a vertical direction to modify the fundus image into the form of the left-eye fundus image. The left-eye data processing module 115a may be omitted.

The left-eye diagnosis assistance neural network training module 135a may train a left-eye diagnosis assistance neural network model which obtains left-eye diagnosis assistance information on the basis of a left-eye fundus image by using left-eye fundus image training data including processed left-eye fundus images. The left-eye diagnosis assistance neural network training module 135a may obtain heart disease diagnosis assistance information from an input left-eye fundus image via the left-eye diagnosis assistance neural network, compare the obtained information with a label assigned to the input fundus image, and update the left-eye diagnosis assistance neural network model.

The left-eye training result obtaining module 155a may obtain a result of training the left-eye diagnosis assistance neural network model using left-eye fundus image training data or parameters of the trained left-eye diagnosis assistance neural network model.

The right-eye data processing module 115b may obtain right-eye fundus image training data including a right-eye fundus image and process the right-eye fundus image. The right-eye data processing module 115b may reconstruct or process the right-eye fundus image. The right-eye data processing module 115b may operate similarly as the above-described left-eye data processing module 115a.

The right-eye diagnosis assistance neural network training module 135b may train a right-eye diagnosis assistance neural network model which obtains right-eye diagnosis assistance information on the basis of a right-eye fundus image by using right-eye fundus image training data including processed right-eye fundus images. The right-eye diagnosis assistance neural network training module 135b may obtain heart disease diagnosis assistance information from an input right-eye fundus image via the right-eye diagnosis assistance neural network, compare the obtained information with a label assigned to the input fundus image, and update the right-eye diagnosis assistance neural network model.

The right-eye training result obtaining module 155b may obtain a result of training the right-eye diagnosis assistance neural network model using right-eye fundus image training data or parameters of the trained right-eye diagnosis assistance neural network model.

Figure 67:
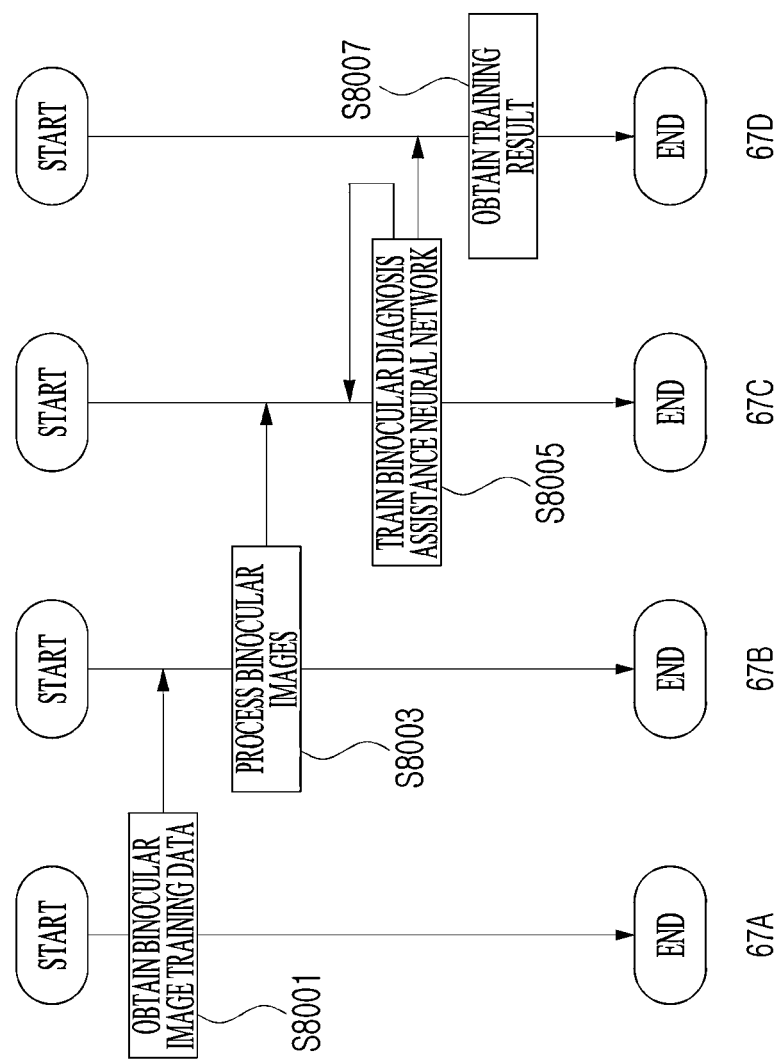
FIG. 67 is a view for describing a method of training a diagnosis assistance neural network model according to an embodiment of the present invention.

FIG. 67 is a view for describing a method of training a diagnosis assistance neural network model according to an embodiment of the present invention.

Referring to FIG. 67, 67A is a flowchart for describing an operation of a data obtaining module. 67B is a flowchart for describing an operation of a binocular data processing module. 67C is a flowchart for describing an operation of a binocular diagnosis assistance neural network training module. 67D is a flowchart for describing an operation of a binocular training result obtaining module. However, the operations illustrated in 67A to 67D are not necessarily performed by the modules described above. For example, the operations described with reference to 67A to 67D may also be performed by a single module, for example, a binocular diagnosis assistance neural network training module.

Referring to FIG. 67, a method of training a diagnosis assistance neural network model may include obtaining binocular image training data (S8001), processing the obtained binocular images (S8003), training a binocular diagnosis assistance neural network on the basis of the processed binocular image (S8005), and obtaining a training result. The method of training a diagnosis assistance neural network model which will be described below may be performed by the above-described training device, training unit, control unit, or processor.

The obtaining of the binocular image training data (S8001) may include obtaining binocular fundus image training data from an external device or loading binocular fundus image training data from a memory. The binocular image training data may include a plurality of fundus images which are not labeled as left eye or right eye. The binocular image training data may include a plurality of fundus images to which a left-eye label or a right-eye label is assigned. The binocular image training data may include a plurality of pieces of unit binocular training data each including a left-eye fundus image and a right-eye fundus image which are matched with each other. Diagnosis information related to a heart disease may be labeled to the left-eye fundus image, the right-eye fundus image, or the unit binocular training data included in the binocular image training data. For example, one or more labels of a score label, a grade label, and a disease presence/absence label related to a heart disease may be assigned to the left-eye fundus image, the right-eye fundus image, or the unit binocular training data included in the binocular image training data.

The processing of the obtained binocular images (S8003) may include reconstructing the left-eye fundus image and/or the right-eye fundus image included in the binocular fundus image training data. The processing of the obtained binocular images may include reconstructing the left-eye fundus image or the right-eye fundus image so that blood vessel elements included therein are highlighted. The processing of the obtained binocular images (S8003) may be performed by the above-described binocular data processing module.

The training of the binocular diagnosis assistance neural network on the basis of the processed binocular images (S8005) may include training a binocular diagnosis assistance neural network model, which outputs heart disease diagnosis assistance information (for example, coronary artery score information or coronary artery disease risk grade information) according to a left-eye fundus image or a right-eye fundus image, by using training data including the left-eye fundus image or the right-eye fundus image. The training of the binocular diagnosis assistance neural network on the basis of the processed binocular images (S8005) may include training a diagnosis assistance neural network model, which outputs heart disease diagnosis assistance information according to a pair of fundus images, by using training data which includes a plurality of pieces of unit training data each including a pair of a left-eye fundus image and a right-eye fundus image of the same person (that is, originated from the same testee). The training of the binocular diagnosis assistance neural network (S8005) may be performed using the above-described binocular diagnosis assistance neural network training module 131c.

The obtaining of the training result (S8007) may include obtaining the trained binocular diagnosis assistance neural network or parameters constituting the trained binocular diagnosis assistance neural network. The obtaining of the training result (S8007) may be performed by the above-described binocular training result obtaining module 151c.

Figure 68:
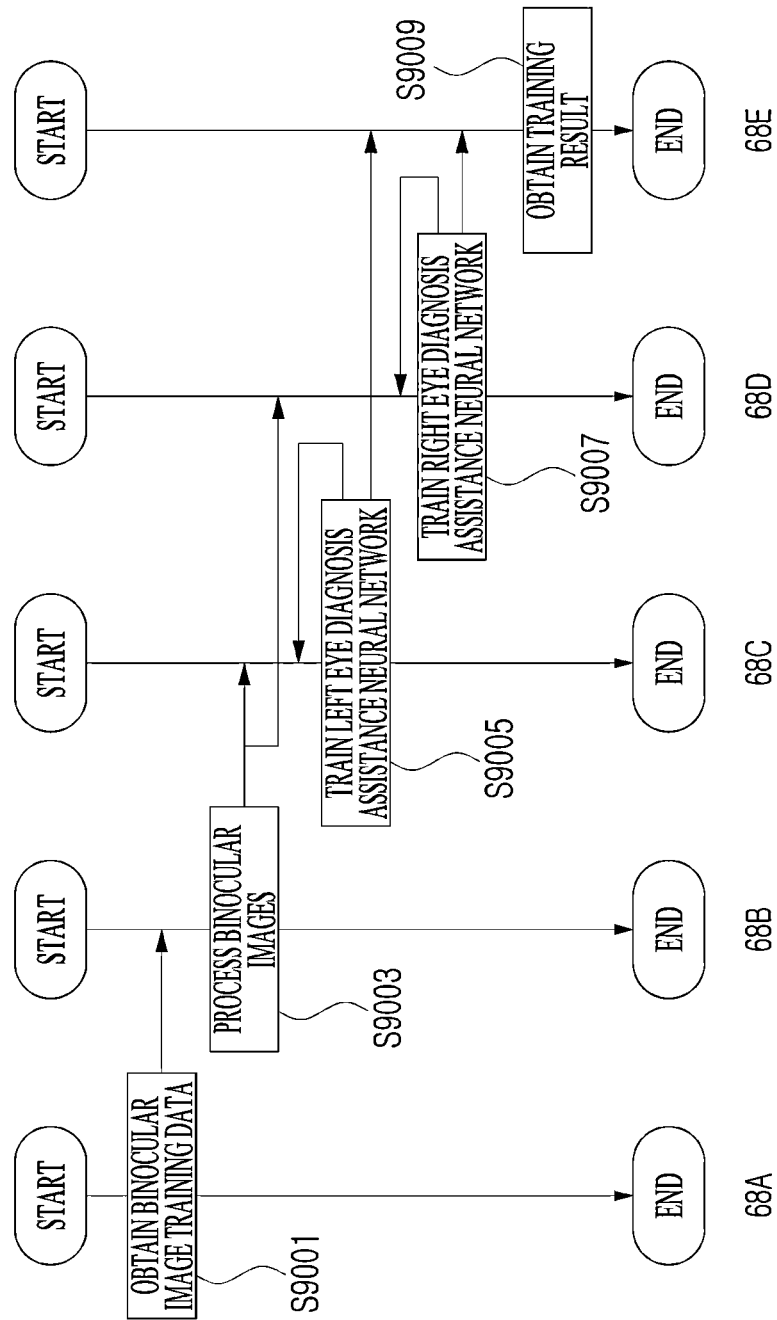
FIG. 68 is a view for describing a method of training a diagnosis assistance neural network model according to an embodiment of the present invention.

FIG. 68 is a view for describing a method of training a diagnosis assistance neural network model according to an embodiment of the present invention.

Referring to FIG. 68, 68A is a flowchart for describing an operation of a data obtaining module. 68B is a flowchart for describing an operation of a binocular data processing module (or a left-eye data processing module and a right-eye data processing module). 68C is a flowchart for describing an operation of a left-eye diagnosis assistance neural network training module. 68D is a flowchart for describing an operation of a right-eye diagnosis assistance neural network training module. 68E may be a flowchart for describing an operation of a training result obtaining module (or a left-eye training result obtaining module and a right-eye training result obtaining module).

However, the operations illustrated in 68A to 68E are not necessarily performed by the modules described above. For example, the operations described with reference to 68A to 68E may also be performed by a single module, for example, a binocular diagnosis assistance neural network training module.

Referring to FIG. 68, a method of training a diagnosis assistance neural network model may include obtaining binocular image training data (S9001), processing the obtained binocular images (S9003), training a left-eye diagnosis assistance neural network (S9005), training a right-eye diagnosis assistance neural network (S9007), and obtaining a training result (S9009). The method of training a diagnosis assistance neural network model which will be described below may be performed by the above-described training device, training unit, control unit, or processor.

The obtaining of the binocular image training data (S9001) may include obtaining binocular fundus images including a left-eye fundus image and a right-eye fundus image. The binocular image training data may include left-eye fundus image training data and right-eye fundus image training data. In other words, the binocular image training data may include the left-eye fundus image training data and the right-eye fundus image training data which are differentiated from each other. The binocular image training data may include a left-eye fundus image to which a left-eye label is assigned and a right-eye fundus image to which a right-eye label is assigned.

The obtaining of the binocular image training data (S9001) may be performed by the data obtaining module and the binocular data processing module. The obtaining of the binocular image training data (S9001) may be performed by each of the left-eye data processing module 111d or the right-eye data processing module 115b.

The processing of the binocular images (S9003) may include processing the binocular images included in the binocular fundus image training data. The processing of the binocular images included in the binocular fundus image training data may include converting a left-eye fundus image or a right-eye fundus image included in the binocular fundus image training data into a form that facilitates training of a neural network model. The above description may analogically apply to the reconstructing, converting, or processing of the fundus image. The processing of the binocular images (S9003) may be performed by the binocular data processing module 111c.

The processing of the binocular images (S9003) may include separately processing a left-eye fundus image and a right-eye fundus image. In other words, the processing of the binocular images (S9003) may include performing left-eye fundus image pre-processing on the left-eye fundus image and performing right-eye fundus image pre-processing on the right-eye fundus image. In this case, the pre-processing applied to the left-eye fundus image may be different from the pre-processing applied to the right-eye fundus image. For example, a pre-processing filter applied to the left-eye fundus image and a pre-processing filter applied to the right-eye fundus image may be provided in forms which are inverted 180° in the vertical direction from each other.

According to an embodiment, the processing of the binocular images (S9003) may include obtaining an arbitrary fundus image and converting the obtained arbitrary fundus image into the left-eye fundus image and/or obtaining an arbitrary fundus image and converting the obtained arbitrary fundus image into the right-eye fundus image.

The processing of the binocular images (S9003) may be performed by the left-eye data processing module 111d and the right-eye data processing module 115b. The processing of the binocular images (S9003) may be omitted.

The training of the left-eye diagnosis assistance neural network (S9005) may include training a left-eye diagnosis assistance neural network model, which outputs left-eye diagnosis assistance information on the basis of the left-eye fundus image, by using the processed left-eye fundus image data. The training of the left-eye diagnosis assistance neural network (S9005) may include obtaining left-eye diagnosis assistance information according to an input left-eye fundus image via a left-eye diagnosis assistance neural network model, comparing the obtained left-eye diagnosis assistance information with a label assigned to the input left-eye fundus image, and updating the left-eye diagnosis assistance neural network model on the basis of a result of the comparison. The training of the left-eye diagnosis assistance neural network (S9005) may be performed by the left-eye diagnosis assistance neural network training module.

The training of the right-eye diagnosis assistance neural network (S9007) may include training a right-eye diagnosis assistance neural network model, which outputs right-eye diagnosis assistance information on the basis of the right-eye fundus image, by using the processed right-eye fundus image data. The training of the right-eye diagnosis assistance neural network (S9007) may include obtaining right-eye diagnosis assistance information according to an input right-eye fundus image via a right-eye diagnosis assistance neural network model, comparing the obtained right-eye diagnosis assistance information with a label assigned to the input right-eye fundus image, and updating the right-eye diagnosis assistance neural network model on the basis of a result of the comparison. The training of the right-eye diagnosis assistance neural network (S9007) may be performed by the right-eye diagnosis assistance neural network training module.

The training of the left-eye diagnosis assistance neural network (S9005) and the training of the right-eye diagnosis assistance neural network (S9007) may be performed in parallel. The above description on the parallel training of neural network models may apply thereto.

The obtaining of the training result (S9009) may include obtaining the trained left-eye diagnosis assistance neural network model and the trained right-eye diagnosis assistance neural network model. Alternatively, the obtaining of the training result (S9009) may include obtaining parameters constituting the trained left-eye diagnosis assistance neural network model and parameters constituting the trained right-eye diagnosis assistance neural network model.

2.5.5 Assisting in Diagnosis Using Binocular Fundus Images

According to the present specification, a system, a device, or a method for obtaining heart disease diagnosis assistance information related to a testee by using binocular fundus images may be provided. By obtaining heart disease diagnosis assistance information using binocular images and providing the obtained heart disease diagnosis assistance information to a user, reliability of a diagnosis result may be improved.

The above-described diagnosis assistance system, diagnostic device, server device, client device, or mobile device may use a trained heart disease diagnosis assistance neural network model. The diagnostic unit, control unit, or processor of each device may perform diagnosis assistance using a heart disease diagnosis assistance neural network model.

Hereinafter, on the basis of the above description, details unique to the case in which heart disease diagnosis is assisted using binocular fundus images will be described.

Figure 69:
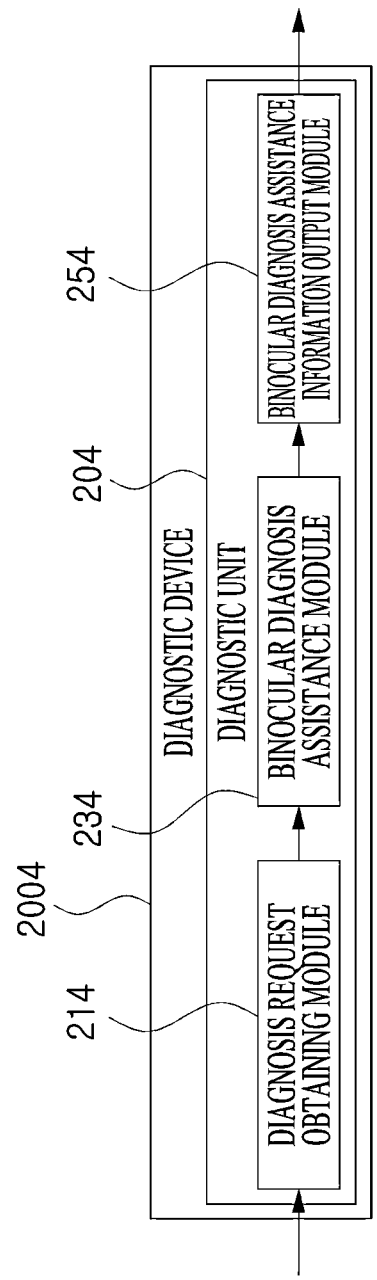
FIG. 69 is a view for describing a diagnostic device 2004 according to an embodiment of the present invention.

FIG. 69 is a view for describing diagnostic device 2004 according to an embodiment of the present invention. Referring to FIG. 69, the diagnostic device 2004 according to an embodiment of the present invention may include a diagnostic unit 204 including a diagnosis request obtaining module 214, a binocular diagnosis assistance module 234, and a binocular diagnosis assistance information output module 254.

The binocular diagnosis request obtaining module 214 may obtain a diagnosis request. The binocular diagnosis request obtaining module 214 may obtain a diagnosis request that includes binocular fundus images (a left-eye fundus image and a right-eye fundus image) and requests for diagnosis assistance information related to the binocular fundus images. The binocular diagnosis request obtaining module 214 may sequentially obtain a target left-eye fundus image and a target right-eye fundus image. The binocular diagnosis request obtaining module 214 may sequentially obtain a diagnosis request related to a target left-eye fundus image and a diagnosis request related to a target right-eye fundus image. The binocular diagnosis request obtaining module 214 may obtain a diagnosis request that includes target binocular fundus image data, which includes a target left-eye fundus image and a target right-eye fundus image, and requests for diagnosis assistance information.

The binocular diagnosis assistance module 234 may obtain target binocular fundus images (or a target left-eye fundus image and a target right-eye fundus image) and obtain heart disease diagnosis assistance information according to the obtained target binocular fundus images.

The binocular diagnosis assistance module 234 may use a binocular diagnosis assistance neural network model which is trained to obtain diagnosis assistance information for both target left-eye and right-eye fundus images. The binocular diagnosis assistance module 234 may obtain a target left-eye fundus image and obtain left-eye diagnosis assistance information related to the target left-eye fundus image via the binocular diagnosis assistance neural network model. The binocular diagnosis assistance module 234 may obtain a target right-eye fundus image and obtain right-eye diagnosis assistance information related to the target right-eye fundus image via the binocular diagnosis assistance neural network model.

The binocular diagnosis assistance module 234 may use a binocular diagnosis assistance neural network model which is trained to obtain diagnosis assistance information on the basis of a unit target fundus image including a left-eye fundus image and a right-eye fundus image. The binocular diagnosis assistance module 234 may obtain a unit target fundus image including a left-eye fundus image and a right-eye fundus image obtained by imaging a testee on the same date (or imaging the testee within a reference period) and may obtain right-eye diagnosis assistance information related to the unit target fundus image via the binocular diagnosis assistance neural network model. The unit target fundus image may have a form in which a left-eye fundus image and a right-eye fundus image are combined or have a form in which features of a left-eye fundus image and a right-eye fundus image are combined.

The binocular diagnosis assistance information output module 254 may output the obtained binocular diagnosis assistance information. The binocular diagnosis assistance information output module 254 may output left-eye diagnosis assistance information obtained on the basis of a left-eye fundus image or right-eye diagnosis assistance information obtained on the basis of a right-eye fundus image. The binocular diagnosis assistance information output module 254 may output the left-eye diagnosis assistance information and the right-eye diagnosis assistance information concurrently or sequentially.

The binocular diagnosis assistance information output module 254 may transmit binocular diagnosis assistance information to an external device or may store binocular diagnosis assistance information, left-eye diagnosis assistance information, or right-eye diagnosis assistance information in a separate memory. The binocular diagnosis assistance information output module 254 may output binocular diagnosis assistance information, left-eye diagnosis assistance information, or right-eye diagnosis assistance information via a user interface. The binocular diagnosis assistance information output module 254 may output diagnosis assistance information in the form of visual or aural data.

Information output by the binocular diagnosis assistance information output module 254 may be left-eye diagnosis assistance information, right-eye diagnosis assistance information, or binocular diagnosis assistance information. The output information may be secondary information determined on the basis of the left-eye diagnosis assistance information, right-eye diagnosis assistance information, and/or binocular diagnosis assistance information. This will be described in more detail below in "Output of binocular diagnosis assistance information" section.

According to an embodiment of the present invention, the diagnostic device 2004 may operate in a left-eye diagnosis mode. The left-eye diagnosis mode may be started as the diagnostic device 2004 obtains a left-eye diagnosis request or a binocular diagnosis request from a user.

In the left-eye diagnosis mode, the binocular diagnosis request obtaining module 214 may obtain a left-eye diagnosis request from a user. In the left-eye diagnosis mode, the binocular diagnosis request obtaining module 214 may obtain a left-eye diagnosis request that requests for a target left-eye fundus image and left-eye diagnosis assistance information.

In the left-eye diagnosis mode, the binocular diagnosis assistance module 234 may obtain a target left-eye fundus image and obtain heart disease diagnosis assistance information according to the target left-eye fundus image via the binocular diagnosis assistance neural network model.

In the left-eye diagnosis mode, the binocular diagnosis assistance information output module 254 may output heart disease diagnosis assistance information related to the target left-eye fundus image. For example, the binocular diagnosis assistance information output module 254 may output heart disease diagnosis assistance information related to the target left-eye fundus image together with the target left-eye fundus image via a left-eye diagnosis information display unit of a user interface.

When the left-eye diagnosis mode is obtained by a left-eye diagnosis request of a user, the binocular diagnosis assistance information output module 254 may output left-eye diagnosis assistance information. When the left-eye diagnosis mode is obtained by a binocular diagnosis request of the user, the binocular diagnosis assistance information output module 254 may output left-eye diagnosis assistance information together with right-eye diagnosis assistance information.

According to an embodiment of the present invention, the diagnostic device 2004 may operate in a right-eye diagnosis mode. The right-eye diagnosis mode may be started as the diagnostic device 2004 obtains a right-eye diagnosis request or a binocular diagnosis request from a user.

In the right-eye diagnosis mode, the binocular diagnosis request obtaining module 214 may obtain a right-eye diagnosis request, for example, a right-eye diagnosis request that requests for a target right-eye fundus image and right-eye diagnosis assistance information.

In the right-eye diagnosis mode, the binocular diagnosis assistance information output module 254 may output heart disease diagnosis assistance information related to the target right-eye fundus image. For example, the binocular diagnosis assistance information output module 254 may output heart disease diagnosis assistance information related to the target right-eye fundus image together with the target right-eye fundus image via a right-eye diagnosis information display unit of a user interface.

When the right-eye diagnosis mode is obtained by a right-eye diagnosis request of a user, the binocular diagnosis assistance information output module 254 may output right-eye diagnosis assistance information, and when the right-eye diagnosis mode is obtained by a binocular diagnosis request of the user, the binocular diagnosis assistance information output module 254 may output right-eye diagnosis assistance information together with left-eye diagnosis assistance information According to an embodiment of the present invention, the diagnostic device 2004 may operate in a binocular diagnosis mode. The binocular diagnosis mode may be started as the diagnostic device 2004 obtains a binocular diagnosis request from a user.

In the binocular diagnosis mode, the binocular diagnosis request obtaining module 214 may obtain a binocular diagnosis request from a user. In the binocular diagnosis mode, the binocular diagnosis assistance information output module 254 may output heart disease diagnosis assistance information related to target binocular fundus images (for example, target data including a left-eye fundus image and a right-eye fundus image which are matched with each other or a composite image generated on the basis of a left-eye fundus image and a right-eye fundus image which are matched with each other). For example, the binocular diagnosis assistance information output module 254 may output binocular heart disease diagnosis assistance information obtained via neural network models together with the target binocular fundus images via a diagnosis information display unit of a user interface.

Figure 70:
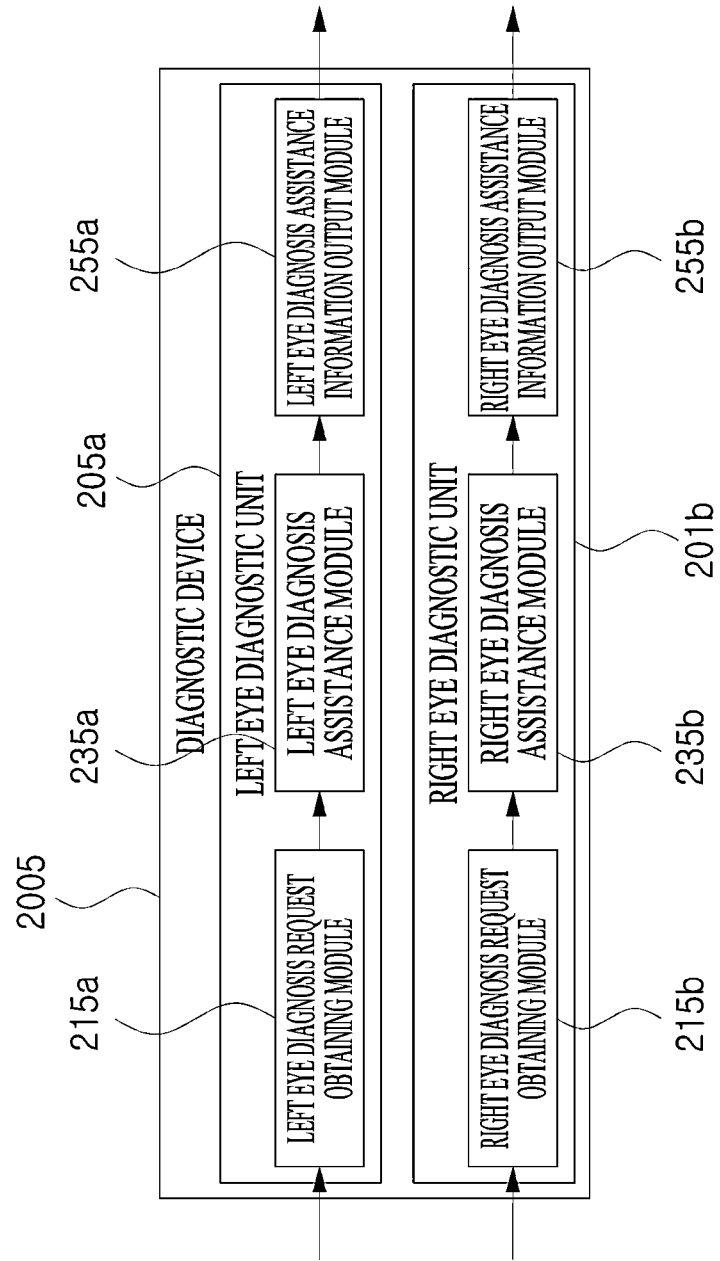
FIG. 70 is a view for describing a diagnostic device 2005 according to an embodiment of the present invention.

FIG. 70 is a view for describing a diagnostic device 2005 according to an embodiment of the present invention. Referring to FIG. 70, the diagnostic device 2005 according to an embodiment of the present invention may include a left-eye diagnostic unit 205*a* which includes a left-eye diagnosis request obtaining module 215*a*, a left-eye diagnosis assistance module 235*a*, and a left-eye diagnosis assistance information output module 255*a* and a right-eye diagnostic unit 201*b* which includes a right-eye diagnosis request obtaining module 215*b*, a right-eye diagnosis assistance module 235*b*, and a right-eye diagnosis assistance information output module 255*b*.

The above description related to the parallel use of neural network models may similarly apply to diagnosis assistance using a left-eye diagnosis assistance neural network model and a right-eye diagnosis assistance neural network model which will be described below with reference to FIG. 70.

The left-eye diagnosis request obtaining module 215*a* may obtain a left-eye diagnosis request that requests for diagnosis assistance information corresponding to a left-eye fundus image. The left-eye diagnosis request obtaining module 215*a* may obtain a left-eye fundus image and a left-eye diagnosis request.

The left-eye diagnosis assistance module 235*a* may obtain a target left-eye fundus image and obtain left-eye diagnosis assistance information, which is heart disease diagnosis assistance information related to the target left-eye fundus image, by using a left-eye diagnosis assistance neural network model.

The left-eye diagnosis assistance information output module 255*a* may output the left-eye diagnosis assistance information.

The right-eye diagnosis request obtaining module 215*b* may obtain a right-eye diagnosis request that requests for diagnosis assistance information corresponding to a right-eye fundus image. The right-eye diagnosis request obtaining module 215b may obtain a right-eye fundus image and a right-eye diagnosis request.

The right-eye diagnosis assistance module 235b may obtain a target right-eye fundus image and obtain right-eye diagnosis assistance information, which is heart disease diagnosis assistance information related to the target right-eye fundus image, by using a right-eye diagnosis assistance neural network model.

The right-eye diagnosis assistance information output module 255b may output the right-eye diagnosis assistance information. The right-eye diagnosis assistance information output module 255b and the left-eye diagnosis assistance information output module 255b may output diagnosis assistance information together. The right-eye diagnosis assistance information output module 255b and the left-eye diagnosis assistance information output module 255b may output diagnosis assistance information via a single user interface.

According to an embodiment of the present invention, the diagnostic device 2005 may operate in a left-eye diagnosis mode. The left-eye diagnosis mode may be started as the diagnostic device 2005 obtains a left-eye diagnosis request or a binocular diagnosis request from a user.

In the left-eye diagnosis mode, the left-eye diagnosis request obtaining module 215a may obtain a left-eye fundus image, the left-eye diagnosis assistance module 235a may obtain left-eye diagnosis assistance information on the basis of the left-eye fundus image, and the left-eye diagnosis assistance information output module 255b may output left-eye diagnosis assistance information.

According to an embodiment of the present invention, the diagnostic device 2005 may operate in a right-eye diagnosis mode. The right-eye diagnosis mode may be started as the diagnostic device 2005 obtains a right-eye diagnosis request or a binocular diagnosis request from a user.

In the right-eye diagnosis mode, the right-eye diagnosis request obtaining module 215a may obtain a right-eye fundus image, the right-eye diagnosis assistance module 235a may obtain right-eye diagnosis assistance information on the basis of the right-eye fundus image, and the right-eye diagnosis assistance information output module 255a may output right-eye diagnosis assistance information.

According to an embodiment of the present invention, the diagnostic device 2005 may operate in a binocular diagnosis mode. The binocular diagnosis mode may be started as the diagnostic device 2005 obtains a binocular diagnosis request from a user.

In the binocular diagnosis mode, the left-eye diagnosis request obtaining module 215a may obtain a left-eye fundus image, the right-eye diagnosis request obtaining module 215b may obtain a right-eye fundus image, the left-eye diagnosis assistance module 235b may obtain left-eye diagnosis assistance information on the basis of the left-eye fundus image, the right-eye diagnosis assistance module 235b may obtain right-eye diagnosis assistance information on the basis of the right-eye fundus image, the left-eye diagnosis assistance information output module 255b may output left-eye diagnosis assistance information, and the right-eye diagnosis assistance information output module 255b may output right-eye diagnosis assistance information.

Figure 71:
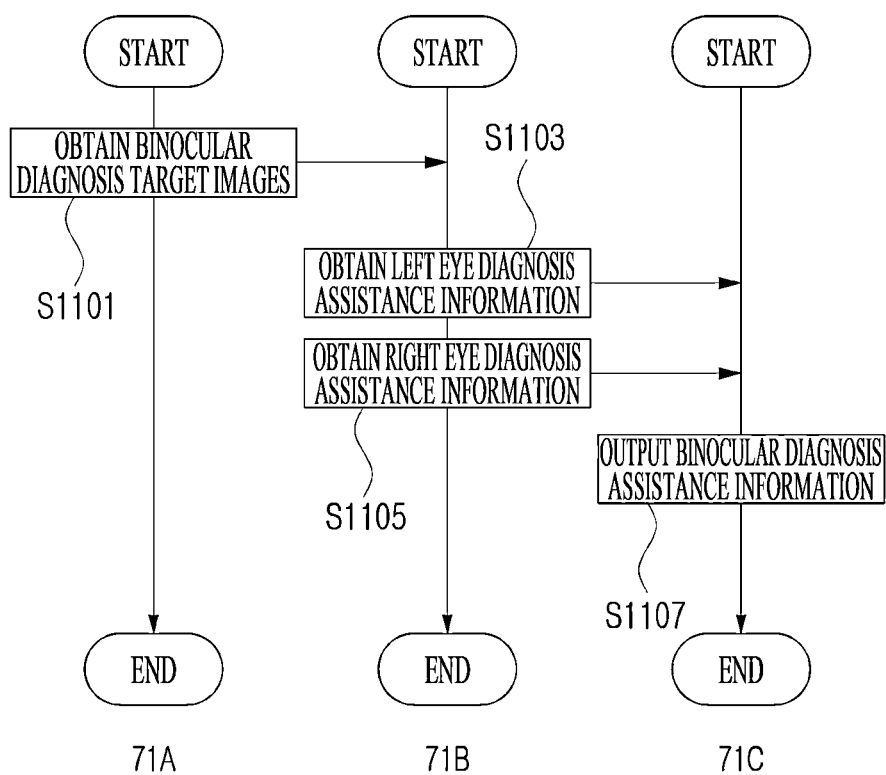
FIG. 71 is a view for describing a method of assisting in heart disease diagnosis according to an embodiment of the present invention.

FIG. 71 is a view for describing a method of assisting in heart disease diagnosis according to an embodiment of the present invention.

Referring to FIG. 71, 71A is a flowchart for describing an operation of a data obtaining module (or a diagnosis request obtaining module). 71B is a flowchart for describing an operation of a diagnosis assistance module. 71C is a flowchart for describing an operation of binocular diagnosis assistance information output module. However, the operations illustrated in 71A to 71C are not necessarily performed by the modules described above. For example, the operations described with reference to 71A to 71C may also be performed by a single module, for example, a binocular diagnosis assistance module, or a processor or a control unit of a diagnostic device.

Referring to FIG. 71, a method of assisting in heart disease diagnosis according to an embodiment of the present invention may include obtaining binocular diagnosis target images (S1101), obtaining left-eye diagnosis assistance information (S1103), obtaining right-eye diagnosis assistance information (S1105), and outputting diagnosis assistance information (S1107). The method of assisting in heart disease diagnosis described with reference to FIG. 71 may be entirely or partially performed when a diagnostic device is in a left-eye diagnosis mode, a right-eye diagnosis mode, or a binocular diagnosis mode.

The obtaining of the binocular diagnosis target images (S1101) may include obtaining a left-eye target fundus image and a right-eye target fundus image. The obtaining of the binocular diagnosis target images (S1101) may include obtaining binocular diagnosis target images and a diagnosis request.

The obtaining of the left-eye diagnosis assistance information (S1103) may include obtaining heart disease diagnosis assistance information related to the obtained left-eye target fundus image by using a binocular diagnosis assistance neural network model which is trained to output heart disease diagnosis assistance information according to a fundus image. For example, the obtaining of the left-eye diagnosis assistance information (S1103) may include obtaining calcium score information related to the obtained left-eye target fundus image by using the binocular diagnosis assistance neural network model.

The obtaining of the right-eye diagnosis assistance information (S1105) may include obtaining heart disease diagnosis assistance information related to the obtained right-eye target fundus image by using the binocular diagnosis assistance neural network model which is trained to output heart disease diagnosis assistance information according to a fundus image. For example, the obtaining of the right-eye diagnosis assistance information (S1105) may include obtaining calcium score information related to the obtained right-eye target fundus image by using the binocular diagnosis assistance neural network model.

The obtaining of the left-eye diagnosis assistance information (S1103) and the obtaining of the right-eye diagnosis assistance information (S1105) may be performed sequentially or partially concurrently, or the order of performing the obtaining of the left-eye diagnosis assistance information (S1103) and the obtaining of the right-eye diagnosis assistance information (S1105) may be changed. The order of performing the obtaining of the left-eye diagnosis assistance information (S1103) and the obtaining of the right-eye diagnosis assistance information (S1105) may be determined according to a user input.

The outputting of the diagnosis assistance information (S1107) may include outputting the obtained left-eye diagnosis assistance information and right-eye diagnosis assistance information. The outputting of the diagnosis assistance information (S1107) may include outputting the obtained left-eye diagnosis assistance information and right-eye diagnosis assistance information sequentially or concurrently.

The outputting of the diagnosis assistance information (S1107) may include outputting the obtained left-eye diagnosis assistance information and right-eye diagnosis assistance information via a user interface.

The outputting of the diagnosis assistance information (S1107) may include determining output diagnosis assistance information in consideration of the left-eye diagnosis assistance information and the right-eye diagnosis assistance information.

The output diagnosis assistance information may be diagnosis assistance information selected from the left-eye diagnosis assistance information and the right-eye diagnosis assistance information. The output diagnosis assistance information may be diagnosis assistance information selected according to a predetermined order of priority. The output diagnosis assistance information may be reference diagnosis assistance information, which is selected from the left-eye diagnosis assistance information and the right-eye diagnosis assistance information, and the remaining diagnosis assistance information, which is corrected corresponding to the reference diagnosis assistance information.

The output diagnosis assistance information may be secondary diagnosis assistance information which is generated on the basis of the left-eye diagnosis assistance information and the right-eye diagnosis assistance information. The output diagnosis assistance information may be prescription information, instruction information, or the like generated on the basis of the left-eye diagnosis assistance information and the right-eye diagnosis assistance information.

Meanwhile, the left-eye diagnosis assistance information and the right-eye diagnosis assistance information may be logically inconsistent in some cases.

For example, when the left-eye or right-eye diagnosis assistance information is disease presence/absence information, the left-eye diagnosis assistance information may be abnormality information indicating that a testee has a target disease, and the right-eye diagnosis assistance information may be normality information indicating that the testee does not have the target disease. Also, for example, when the left-eye or right-eye diagnosis assistance information is grade information, the left-eye diagnosis assistance information may be Grade B information indicating that a testee belongs to a mild risk group, and the right-eye diagnosis assistance information may be Grade C information indicating that the testee belongs to a moderate risk group. Also, for example, when the left-eye or right-eye diagnosis assistance information is score information, the left-eye diagnosis assistance information may be score information indicating that a score for assisting in heart disease diagnosis of a testee is 5, and the right-eye diagnosis assistance information may be score information indicating that a score for assisting in heart disease diagnosis of the testee is 12.

Hereinafter, some embodiments will be described in relation to the outputting of the diagnosis assistance information (S1107) which includes determining output diagnosis assistance information in consideration of the left-eye diagnosis assistance information and the right-eye diagnosis assistance information, when the case in which the left-eye diagnosis assistance information and the right-eye diagnosis assistance information are logically inconsistent as in the above cases are taken in to consideration.

For example, the outputting of the diagnosis assistance information (S1107) may include comparing the left-eye diagnosis assistance information and the right-eye diagnosis assistance information and determining the output diagnosis assistance information in consideration of a result of comparing the left-eye diagnosis assistance information and the right-eye diagnosis assistance information.

The determining of the output diagnosis assistance information in consideration of the result of the comparison may include, when the left-eye diagnosis assistance information and the right-eye diagnosis assistance information are logically consistent, determining the left-eye diagnosis assistance information, the right-eye diagnosis assistance information, or intermediate information (a median) between the left-eye diagnosis assistance information and the right-eye diagnosis assistance information as the output diagnosis assistance information.

The determining of the output diagnosis assistance information in consideration of the result of the comparison may include, when the left-eye diagnosis assistance information and the right-eye diagnosis assistance information are logically inconsistent, determining any one selected from the left-eye diagnosis assistance information and the right-eye diagnosis assistance information as the output diagnosis assistance information. Alternatively, the determining of the output diagnosis assistance information in consideration of the result of the comparison may include, when the left-eye diagnosis assistance information and the right-eye diagnosis assistance information are logically inconsistent, determining any one selected from the left-eye diagnosis assistance information and the right-eye diagnosis assistance information according to a predetermined order of priority as the output diagnosis assistance information.

For example, when the left-eye diagnosis assistance information and the right-eye diagnosis assistance information are logically inconsistent, information indicating a higher extent of risk of the left-eye diagnosis assistance information and the right-eye diagnosis assistance information may be determined as the output diagnosis assistance information.

As a specific example, when left-eye heart disease risk grade information obtained on the basis of the left-eye fundus image and right-eye heart disease risk grade information obtained on the basis of the right-eye fundus image are logically consistent, the heart disease risk grade information may be determined as the output diagnosis assistance information, and when the left-eye heart disease risk grade information and the right-eye heart disease risk grade information are logically inconsistent, grade information among the two pieces of information that indicates that a testee has a higher risk may be determined as the output diagnosis assistance information.

For example, when the left-eye heart disease risk grade information is Grade A information indicating that a testee belongs to a normal group, and the right-eye heart disease risk grade information is Grade B information indicating that the testee belongs to a mild risk group, the Grade B information may be determined as the output diagnosis assistance information.

As another specific example, when left-eye heart disease presence/absence information obtained on the basis of a left-eye fundus image and right-eye heart disease presence/absence information obtained on the basis of a right-eye fundus image are logically consistent, the heart disease presence/absence information may be determined as the output diagnosis assistance information, and when the left-eye heart disease presence/absence information and the right-eye heart disease presence/absence information are logically inconsistent, the disease presence/absence information indicating that a testee belongs to a risk group may be determined as the output diagnosis assistance information.

For example, when the left-eye heart disease presence/absence information is normality information indicating that the testee belongs to a normal group, and the right-eye heart disease presence/absence information is abnormality information indicating that the testee belongs to an abnormal group, the abnormality diagnosis assistance information may be determined as the output diagnosis assistance information.

The determining of the output diagnosis assistance information in consideration of the result of the comparison may include determining whether a difference between the left-eye diagnosis assistance information and the right-eye diagnosis assistance information exceeds a threshold value.

The determining of the output diagnosis assistance information in consideration of the result of the comparison may include, when the difference between the left-eye diagnosis assistance information and the right-eye diagnosis assistance information exceeds a threshold value, determining the output diagnosis assistance information in the same manner as when the left-eye diagnosis assistance information and the right-eye diagnosis assistance information are logically inconsistent. The determining of the output diagnosis assistance information in consideration of the result of the comparison may include, when the difference between the left-eye diagnosis assistance information and the right-eye diagnosis assistance information exceeds a threshold value, determining any one selected from the left-eye diagnosis assistance information and the right-eye diagnosis assistance information as the output diagnosis assistance information.

The determining of the output diagnosis assistance information in consideration of the result of the comparison may include, when the difference between the left-eye diagnosis assistance information and the right-eye diagnosis assistance information does not exceed a threshold value, determining the output diagnosis assistance information in the same manner as when the left-eye diagnosis assistance information and the right-eye diagnosis assistance information are logically consistent. The determining of the output diagnosis assistance information in consideration of the result of the comparison may include, when the difference between the left-eye diagnosis assistance information and the right-eye diagnosis assistance information does not exceed a threshold value, determining the left-eye diagnosis assistance information, the right-eye diagnosis assistance information, or intermediate information (median) between the left-eye diagnosis assistance information and the right-eye diagnosis assistance information as the output diagnosis assistance information.

As another example, the outputting of the diagnosis assistance information (S1107) may include determining whether the left-eye diagnosis assistance information and the right-eye diagnosis assistance information match each other and determining output diagnosis assistance information on the basis of a result of the determination.

The determining of the output diagnosis assistance information on the basis of the result of the determination may include, when the left-eye diagnosis assistance information and the right-eye diagnosis assistance information match each other, determining the diagnosis assistance information as the output diagnosis assistance information. Alternatively, the determining of the output diagnosis assistance information on the basis of the result of the determination may include, when the left-eye diagnosis assistance information and the right-eye diagnosis assistance information match each other, determining the left-eye diagnosis assistance information, the right-eye diagnosis assistance information, or intermediate information (median) between the left-eye diagnosis assistance information and the right-eye diagnosis assistance information as the output diagnosis assistance information. Alternatively, the determining of the output diagnosis assistance information on the basis of the result of the determination may include, when the left-eye diagnosis assistance information and the right-eye diagnosis assistance information match each other, determining information having a maximum value or information having a minimum value among the left-eye diagnosis assistance information and the right-eye diagnosis assistance information as the output diagnosis assistance information.

The determining of the output diagnosis assistance information on the basis of the result of the determination may include, when the left-eye diagnosis assistance information and the right-eye diagnosis assistance information do not match each other, determining the left-eye diagnosis assistance information, the right-eye diagnosis assistance information, or intermediate information (median or average) between the left-eye diagnosis assistance information and the right-eye diagnosis assistance information as the output diagnosis assistance information. The determining of the output diagnosis assistance information on the basis of the result of the determination may include, when the left-eye diagnosis assistance information and the right-eye diagnosis assistance information do not match each other, determining information having a maximum value or information having a minimum value among the left-eye diagnosis assistance information and the right-eye diagnosis assistance information as the output diagnosis assistance information.

The determining of the output diagnosis assistance information on the basis of the result of the determination may include, when the left-eye diagnosis assistance information and the right-eye diagnosis assistance information do not match each other, determining any one selected from the left-eye diagnosis assistance information and the right-eye diagnosis assistance information as the output diagnosis assistance information. For example, when the left-eye diagnosis assistance information and the right-eye diagnosis assistance information do not match each other, information indicating a higher extent of risk among the left-eye diagnosis assistance information and the right-eye diagnosis assistance information may be determined as the output diagnosis assistance information.

As a specific example, when left-eye score information, which is left-eye diagnosis assistance information, indicating a heart disease diagnosis assistance score obtained on the basis of a left-eye image of a testee and right-eye score information, which is right-eye diagnosis assistance information, indicating a heart disease diagnosis assistance score obtained on the basis of a right-eye image of the testee match each other, the right-eye score information, the left-eye score information, or an average value between the right-eye score information and the left-eye score information may be determined as the output score information. When the right-eye score information and the left-eye score information do not match each other, score information indicating a higher extent of risk may be determined as the output score information.

Whether the right-eye score information and the left-eye score information match each other may be determined on the basis of predetermined criteria. For example, the determining of whether the right-eye score information and the left-eye score information match each other may include, by using the grade-score relationship table illustrated in FIG. 32, determining that the left-eye score information and the right-eye score information match each other when the left-eye score information and the right-eye score information match the same grade and determining that the left-eye score information and the right-eye score information do not match each other when the left-eye score information and the right-eye score information match different grades.

The above embodiments have been described on the basis of the cases in which, in order to provide a more stable diagnosis assistance result to a testee, information indicating a higher extent of risk is selected and output when information that the left eye indicates and information that the right eye indicates are logically inconsistent, but the invention disclosed herein is not limited thereto. For example, when an extent of risk tends to be determined to be higher than reality when a close examination is complex or when the determination performed via a neural network model, diagnosis assistance information indicating a lower risk may also be determined as the output diagnosis assistance information and be output.

Figure 72:
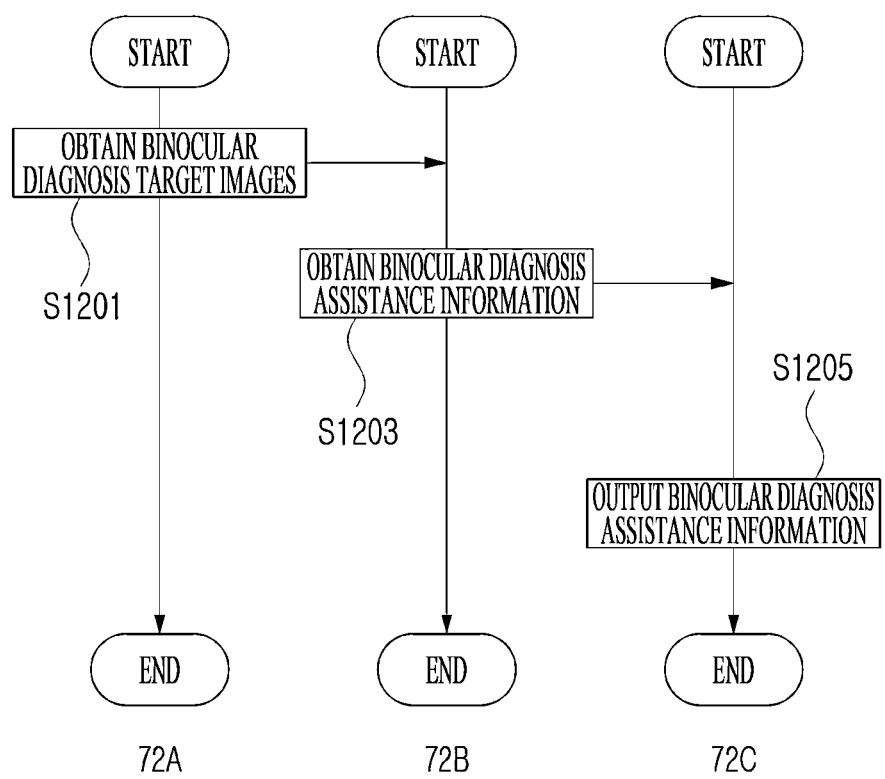
FIG. 72 is a view for describing a method of assisting in heart disease diagnosis according to an embodiment of the present invention.

FIG. 72 is a view for describing a method of assisting in heart disease diagnosis according to an embodiment of the present invention.

Referring to FIG. 72, 72A is a flowchart for describing an operation of a data obtaining module (or a diagnosis request obtaining module). 72B is a flowchart for describing an operation of a binocular diagnosis assistance module. 72C is a flowchart for describing an operation of a binocular diagnosis assistance information output module. However, the operations illustrated in 72A to 72C are not necessarily performed by the modules described above. For example, the operations described with reference to 72A to 72C may also be performed by a single module, for example, a binocular diagnosis assistance module, or a processor or a control unit of a diagnostic device.

Referring to FIG. 72, a method of assisting in heart disease diagnosis according to an embodiment of the present invention may include obtaining binocular diagnosis target images (S1201), obtaining binocular diagnosis assistance information (S1203), and outputting diagnosis assistance information (S1205). The method of assisting in heart disease diagnosis described with reference to FIG. 72 may be entirely or partially performed when a diagnostic device is in a left-eye diagnosis mode, a right-eye diagnosis mode, or a binocular diagnosis mode.

The obtaining of the binocular diagnosis target images (S1201) may include obtaining a binocular diagnosis request including a left-eye fundus image and a right-eye fundus image of a testee.

The obtaining of the binocular diagnosis assistance information (S1203) may include obtaining heart disease diagnosis assistance information related to the testee from target binocular fundus images by using a binocular diagnosis assistance neural network model which is trained to output heart disease diagnosis assistance information with binocular fundus images as inputs. The binocular diagnosis assistance neural network model may be a neural network model which is trained to output heart disease diagnosis assistance information of the testee with binocular target fundus images, which include a left-eye fundus image and a right-eye fundus image which are matched with each other (in other words, which are obtained by imaging the same person in the same period), as inputs. The obtaining of the binocular diagnosis assistance information (S1203) may include obtaining binocular heart disease diagnosis assistance information, e.g., binocular calcium information, binocular grade information, or binocular disease presence/absence information, according to the target binocular fundus images by using the trained binocular diagnosis assistance neural network model.

The outputting of the diagnosis assistance information (S1205) may include outputting the obtained binocular diagnosis assistance information or secondary information obtained on the basis of the binocular diagnosis assistance information. The outputting of the diagnosis assistance information may be performed similarly as that described above.

Figure 73:
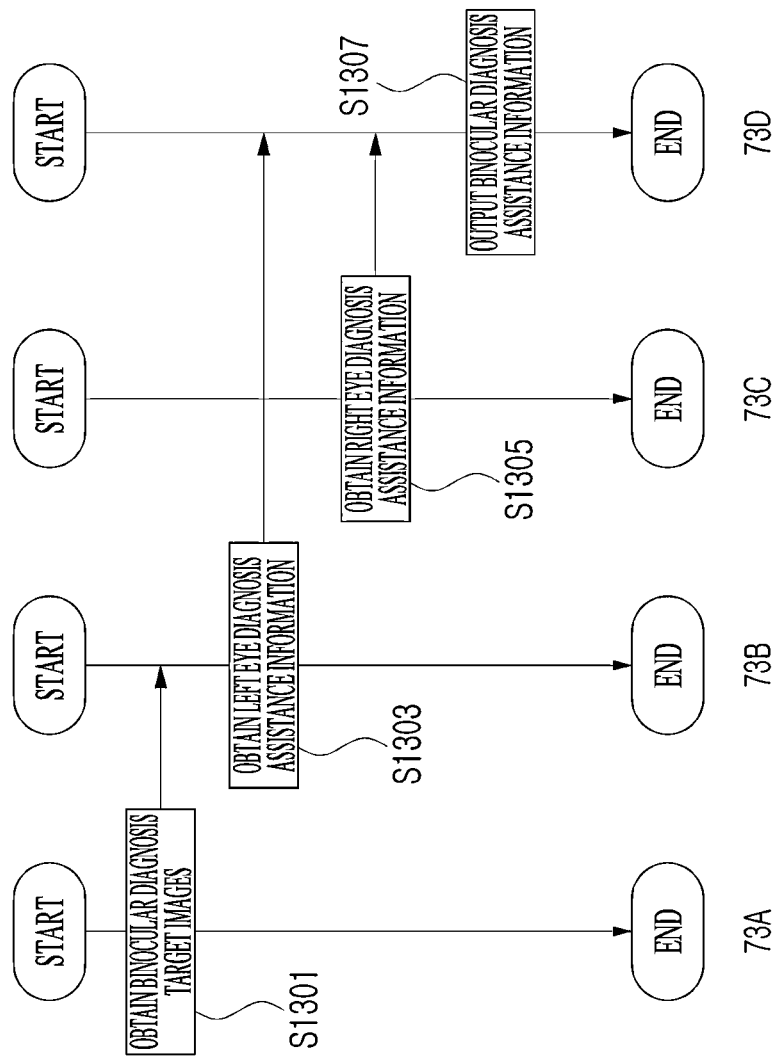
FIG. 73 is a view for describing a method of assisting in heart disease diagnosis according to an embodiment of the present invention.

FIG. 73 is a view for describing a method of assisting in heart disease diagnosis according to an embodiment of the present invention. 73A of FIG. 73 is a flowchart for describing an example of an operation of a data obtaining module (or a diagnosis request obtaining module). 73B is a flowchart for describing an example of an operation of a left-eye diagnosis assistance module. 73C is a flowchart for describing an example of an operation of a right-eye diagnosis assistance module. 73D is a flowchart for describing an example of an operation of a binocular diagnosis assistance information output module. However, the operations illustrated in 73A to 73D are not necessarily performed by the modules described above. For example, the operations illustrated in 73A to 73D may also be performed by a single module, for example, a binocular diagnosis assistance module, or a processor or a control unit of a diagnostic device.

Referring to FIG. 73, a method of assisting in heart disease diagnosis according to an embodiment of the present invention may include obtaining binocular diagnosis target images (S1301), obtaining left-eye diagnosis assistance information (S1303), obtaining right-eye diagnosis assistance information (S1305), and outputting diagnosis assistance information (S1307). The method of assisting in heart disease diagnosis described with reference to FIG. 73 may be entirely or partially performed when a diagnostic device is in a left-eye diagnosis mode, a right-eye diagnosis mode, or a binocular diagnosis mode.

The obtaining of the binocular diagnosis target images (S1301) may include obtaining a left-eye fundus image and a right-eye fundus image. The obtaining of the binocular diagnosis target images (S1301) may include obtaining a diagnosis request related to the left-eye fundus image and/or a diagnosis request related to the right-eye fundus image.

The obtaining of the left-eye diagnosis assistance information (S1303) may include obtaining heart disease diagnosis assistance information related to the left-eye target fundus image, e.g., left-eye calcium information, left-eye grade information, or left-eye disease presence/absence information, by using a left-eye diagnosis assistance neural network model which is trained to output heart disease diagnosis assistance information according to the left-eye fundus image. For example, the obtaining of the left-eye diagnosis assistance information (S1303) may include obtaining calcium score information related to the left-eye target fundus image by using the left-eye diagnosis assistance neural network model.

The obtaining of the right-eye diagnosis assistance information (S1305) may include obtaining heart disease diagnosis assistance information related to the obtained right-eye target fundus image, e.g., right-eye calcium information, right-eye grade information, or right-eye disease presence/absence information, by using a right-eye diagnosis assistance neural network model which is trained to output heart disease diagnosis assistance information according to the right-eye fundus image. For example, the obtaining of the right-eye diagnosis assistance information (S1305) may include obtaining calcium score information related to the right-eye target fundus image by using the right-eye diagnosis assistance neural network model.

The obtaining of the left-eye diagnosis assistance information (S1303) and the obtaining of the right-eye diagnosis assistance information (S1305) may be performed in parallel. The left-eye diagnosis assistance neural network model and the right-eye diagnosis assistance neural network model may be provided and used in parallel. The above-described details related to the parallel diagnosis assistance system may apply to the parallel heart disease diagnosis assistance using the left-eye diagnosis assistance neural network model and the right-eye diagnosis assistance neural network model.

The outputting of the diagnosis assistance information (S1307) may include outputting the left-eye diagnosis assistance information and the right-eye diagnosis assistance information or outputting secondary information generated on the basis of the left-eye diagnosis assistance information and the right-eye diagnosis assistance information.

The left-eye diagnosis assistance information and the right-eye diagnosis assistance information may be logically inconsistent in some cases. The outputting of the diagnosis assistance information (S1307) when the left-eye diagnosis assistance information and the right-eye diagnosis assistance information are logically inconsistent may be implemented similarly as the outputting of the diagnosis assistance information (S1107) described above with reference to FIG. 71.

2.5.6 Providing Binocular Diagnosis Assistance Information

Diagnosis assistance information obtained on the basis of binocular images may be provided to a user. The client device, mobile device, or diagnostic device may provide diagnosis assistance information to the user. The diagnosis assistance information may be provided to the user via a user interface.

When the diagnosis assistance information includes left-eye diagnosis assistance information and right-eye diagnosis assistance information, each piece of diagnosis assistance information may be provided to the user. For example, the user interface may include a left-eye information display unit and a right-eye information display unit, and the client device may output left-eye diagnosis assistance information via the left-eye information display unit and output right-eye diagnosis assistance information via the right-eye information display unit.

According to an embodiment of the present invention, binocular diagnosis assistance information obtained via a neural network model, output diagnosis assistance information obtained on the basis of the binocular diagnosis assistance information, or secondary information obtained on the basis of the binocular diagnosis assistance information or the output diagnosis assistance information may be provided to the user.

The binocular diagnosis assistance information provided to the user may be left-eye diagnosis assistance information obtained on the basis of a left-eye fundus image, right-eye diagnosis assistance information obtained on the basis of a right-eye fundus image, or binocular diagnosis assistance information obtained on the basis of binocular fundus images (or a binocular composite image or binocular composite data). For example, the binocular diagnosis assistance information may include left-eye disease presence/absence information, left-eye grade information, or left-eye score information which is obtained on the basis of the left-eye fundus image and indicates an extent of risk of a heart disease. Also, for example, the binocular diagnosis assistance information may be right-eye disease presence/absence information, right-eye grade information, or right-eye score information which is obtained on the basis of the right-eye fundus image and indicates an extent of risk of a heart disease.

The output diagnosis assistance information provided to the user may be output diagnosis assistance information which is obtained on the basis of the left-eye diagnosis assistance information and the right-eye diagnosis assistance information. The output diagnosis assistance information may be the left-eye diagnosis assistance information, the right-eye diagnosis assistance information, or intermediate information (or median) between the left-eye diagnosis assistance information and the right-eye diagnosis assistance information. The output diagnosis assistance information may be information selected from the left-eye diagnosis assistance information and the right-eye diagnosis assistance information. The output diagnosis assistance information may include reference information, which is selected from the left-eye diagnosis assistance information and the right-eye diagnosis assistance information, and the remaining information which is corrected.

The secondary information provided to the user may be secondary information obtained on the basis of the left-eye diagnosis assistance information, the right-eye diagnosis assistance information, and/or the binocular diagnosis assistance information. The secondary information (or additional information) may include prescription information, instruction information, or a CAM. The above description may apply to the secondary information.

Additional information may be provided for each of both eyes. For example, left-eye additional information which is obtained from the left-eye diagnosis assistance information obtained on the basis of the left eye and right-eye additional information which is obtained from the right-eye diagnosis assistance information obtained on the basis of the right eye may be provided. The additional information may be provided via a user interface. For example, the client device may output the left-eye additional information via the left-eye information display unit of a user interface and output the right-eye additional information via the right-eye information display unit.

According to an embodiment, when a difference between the left-eye diagnosis assistance information and the right-eye diagnosis assistance information exceeds a threshold value, a notice that notifies the user of the fact that an abnormal difference has occurred may be output together with the left-eye diagnosis assistance information and the right-eye diagnosis assistance information.

For example, when a difference between left-eye score information indicating a calcium score obtained on the basis of the left eye and right-eye score information indicating a calcium score obtained on the basis of the right eye exceeds a reference difference, the client device may output a notice that notifies the user of the fact that a difference between the pieces of score information obtained from both eyes is abnormally large, together with the left-eye score information and the right-eye score information. For example, when the left-eye score information is larger than the right-eye score information, the client device may output a visual effect which highlights the left-eye score information, together with the left-eye score information and the right-eye score information.

Also, for example, when heart disease diagnosis assistance information obtained from the left eye (for example, left-eye calcium information) is significantly larger than heart disease diagnosis assistance information obtained from the right eye, the client device may output a notice that informs of the fact that an abnormal state has occurred in the circulatory system related to the left eye. For example, the client device may output a notice indicating that an abnormal symptom such as sclerosis, stenosis, or thrombus may be found in blood vessels connected to the left eye.

2.6 Embodiments of Cardiovascular Disease Diagnosis Assistance Information

Hereinafter, various embodiments in which a cardiovascular disease can be diagnosed using the above-mentioned cardiovascular disease diagnosis assistance information will be described.

Here, the cardiovascular disease diagnosis assistance information may include any piece of information relating to a cardiovascular disease such as score information, grade information, or prescription information relating to the cardiovascular disease. Here, the cardiovascular disease diagnosis assistance information may be obtained using the above-mentioned cardiovascular disease diagnosis assistance neural network.

Figure 76:
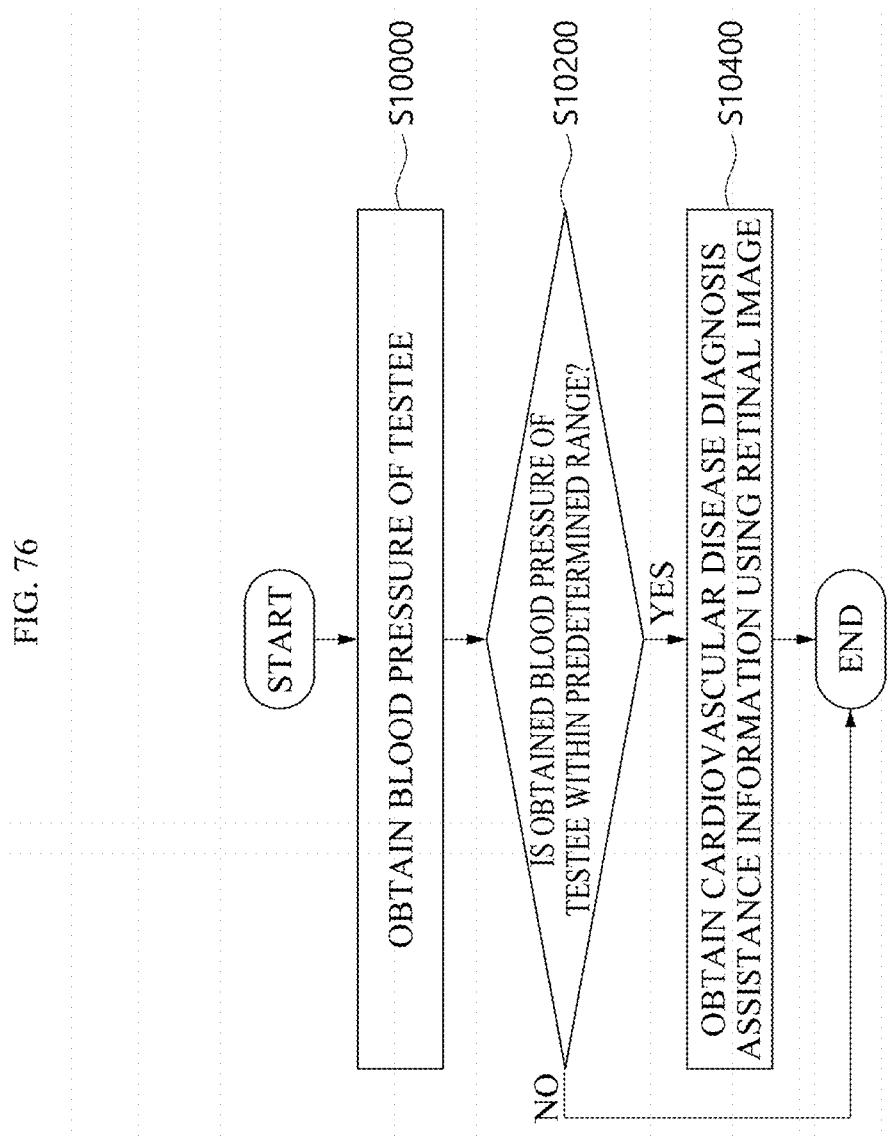
FIG. 76 is a flowchart for describing the obtaining of diagnosis assistance information relating to blood pressure among cardiovascular diseases according to an embodiment of the present invention.

FIG. 76 is a flowchart for describing the obtaining of diagnosis assistance information relating to blood pressure among cardiovascular diseases according to an embodiment of the present invention.

Referring to FIG. 76, the obtaining of the diagnosis assistance information relating to blood pressure among cardiovascular diseases may include obtaining a blood pressure of a testee (S10000), determining whether the obtained blood pressure of the testee is within a predetermined range (S10200), and obtaining cardiovascular disease diagnosis assistance information using a retinal image (S10400).

Here, the obtaining of the blood pressure of the testee (S10000) may include obtaining the blood pressure of the testee using a blood pressure monitor that can measure systolic and diastolic blood pressure on the arm, such as a mercury sphygmomanometer, a home sphygmomanometer, or a medical sphygmomanometer. However, the obtaining of the blood pressure of the testee (S10000) is not limited thereto and may also include obtaining an inferred blood pressure of the testee through photoplethysmography (PPG) measurement, an electrocardiogram (ECG), or heart rate measurement.

According to the obtaining of the blood pressure of the testee (S10000), a systolic blood pressure and a diastolic blood pressure of the testee may be obtained.

Also, the determining of whether the obtained blood pressure of the testee is within a predetermined range (S10200) may include determining whether the systolic blood pressure and diastolic blood pressure of the testee, which are obtained in the previous step, are within a specific range.

The unit of blood pressure values which will be described below may be mmHg, but the unit is not limited thereto, and any other unit that can express pressure may be the unit of blood pressure values.

For example, the predetermined range may refer to a range in which a systolic blood pressure range of the testee is between 130 and 139 and a diastolic blood pressure range of the testee is between 80 and 89. However, the predetermined range in the corresponding step is not limited to the above-mentioned range, and in a case in which a result of measuring the blood pressure of the testee corresponds to a hypertension risk group, the result may be included in the predetermined range in this step.

As a specific example, in a case in which the blood pressure range that can be measured can be divided into a normal blood pressure range, an elevated blood pressure range, a stage 1 hypertension range, and a stage 2 hypertension range, the predetermined range may include the stage 1 hypertension range. That is, the predetermined range may indicate a blood pressure range in which, in the case of hypertension, it is unclear as to whether a blood pressure lowering drug should be used. Here, for example, the normal blood pressure range may indicate a range in which a systolic blood pressure is 120 or lower and a diastolic blood pressure is 80 or lower, the elevated blood pressure range may indicate a range in which a systolic blood pressure is between 120 and 129 and a diastolic blood pressure is 80 or lower, the stage 1 hypertension range may indicate a range in which a systolic blood pressure is between 130 and 139 and a diastolic blood pressure is between 80 and 89, and the stage 2 hypertension range may indicate a range in which a systolic blood pressure is 140 or higher and a diastolic blood pressure is 90 or higher.

Here, in a case in which the obtained blood pressure of the testee is within the predetermined range, a subsequent step may be performed, and in a case in which the obtained blood pressure of the testee is not within the predetermined range, the process may be ended.

Also, the obtaining of the cardiovascular disease diagnosis assistance information using a retinal image (S10400) may include a method of assisting in diagnosis of a cardiovascular disease using the above-described retinal image.

According to an embodiment, in a case in which the blood pressure of the testee that is obtained in the previous step corresponds to the stage 1 hypertension range which is a predetermined range, a retinal image of the testee may be obtained and the atherosclerotic cardiovascular disease (ASCVD) score may be derived using the retinal image. Here, the ASCVD score may refer to a risk of having a cardiovascular disease within a 10-year but is not limited thereto and may also refer to a risk of having a cardiovascular disease within a predetermined period.

For example, in a case in which the obtained blood pressure of the testee is within the predetermined range, the ASCVD score may be derived using a retinal image of the testee, and here, in a case in which the risk of having a cardiovascular disease within a 10-year that is derived through the ASCVD score is 10% or more, additional diagnosis assistance information may be obtained.

Also, although not illustrated in the drawings, the process may further include, after the obtaining of the cardiovascular disease diagnosis assistance information using a retinal image (S10400), providing drug prescription information.

For example, in the case in which the risk of having a cardiovascular disease within a 10-year that is derived in the previous step is 10% or more, prescription information for prescribing a drug for lowering the blood pressure of the testee may be provided. Here, examples of drugs that may be prescribed may include angiotensin-converting enzyme inhibitors such as captopril, enalapril, or ramipril, angiotensin receptor blockers such as candesartan, fimasartan, losartan, olmesartan, telmisartan, or valsartan, calcium channel blockers such as diltiazem, verapamil, nifedipine, felodipine, amlodipine, or lercanidipine, beta blockers such as carteolol, nadolol, propranolol, atenolol, bisoprolol, celiprolol, metoprolol, amosulalol, carvedilol, or bevantolol, alpha blockers such as doxazosin or terazosin, diuretics such as hydrochlorothiazide, indapamide, furosemide, torasemide, spironolactone, or amiloride, and direct vasodilators such as hydralazine, minoxidil, or nitroprusside.

Figure 77:
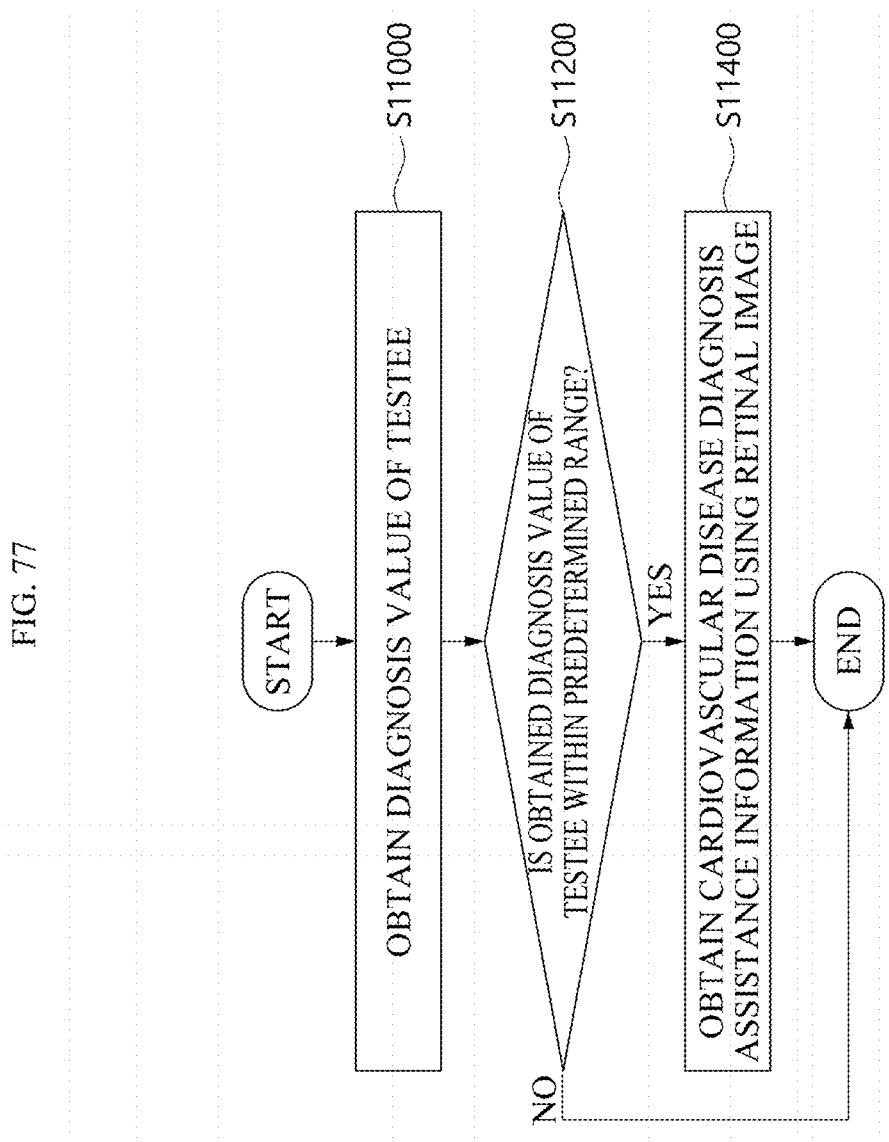
FIG. 77 is a flowchart for describing the obtaining of diagnosis assistance information relating to dyslipidemia among cardiovascular diseases according to an embodiment of the present invention.

FIG. 77 is a flowchart for describing the obtaining of diagnosis assistance information relating to dyslipidemia among cardiovascular diseases according to an embodiment of the present invention.

Referring to FIG. 77, the obtaining of the diagnosis assistance information relating to dyslipidemia among cardiovascular diseases may include obtaining a diagnosis value of a testee (S11000), determining whether the obtained diagnosis value of the testee is within a predetermined range (S11200), and obtaining cardiovascular disease diagnosis assistance information using a retinal image (S11400). Here, dyslipidemia refers to a case in which blood lipid levels are abnormal and may refer to any disease in which blood lipid levels are abnormal, such as hyperlipidemia or hypertriglyceridemia.

Here, the obtaining of the diagnosis value of the testee (S11000) may include obtaining a diagnosis value through a blood test performed on the testee.

For example, the diagnosis value may refer to a concentration of low-density lipoprotein (LDL-C) that is obtained through the blood test performed on the testee. However, the obtained diagnosis value is not limited thereto and may also include any other value that indicates blood lipid levels such as total serum cholesterol concentration, LDL cholesterol concentration, triglyceride concentration, or HDL cholesterol concentration.

Also, for example, the diagnosis value may include a risk of having a cardiovascular disease within a predetermined period that is obtained through the blood test performed on the testee. More specifically, the diagnosis value may include a risk of having a cardiovascular disease within a 10-year that is obtained using values obtained through the blood test performed on the testee. Here, the risk of having a cardiovascular disease within a predetermined period may be obtained using a plurality of values, including blood lipid levels, which may be obtained during a blood test.

Also, the determining of whether the obtained diagnosis value of the testee is within a predetermined range (S11200) may include determining whether the diagnosis value of the testee that is obtained in the previous step is within a specific range.

According to an embodiment, in a case in which, among the obtained diagnosis values of the testee, a value indicating a blood lipid level is within a predetermined range and the risk of having a cardiovascular disease within a predetermined period is also within a predetermined range, a subsequent step may be performed.

For example, in a case in which, among the obtained diagnosis values of the testee, the concentration of low-density lipoprotein is between 70 mg/dl and 190 mg/dl and the risk of having a cardiovascular disease within a predetermined period is between 5% and 20%, a subsequent step may be performed.

Here, in a case in which the concentration of low-density lipoprotein among the obtained diagnosis values of the testee is lower than 70 mg/dl, an additional step may not be performed, and in a case in which the concentration of low-density lipoprotein is between 70 mg/dl and 190 mg/dl and the risk of having a cardiovascular disease within 10-year is 20% or higher or in a case in which the concentration of low-density lipoprotein is higher than 190 mg/dl, prescription information among pieces of diagnosis assistance information may be output without performing a subsequent step.

Also, the obtaining of the cardiovascular disease diagnosis assistance information using a retinal image (S11400) may include a method of assisting in diagnosis of a cardiovascular disease using the above-described retinal image.

As a specific example, the obtaining of the cardiovascular disease diagnosis assistance information using a retinal image (S11400) may include obtaining a coronary artery calcification score (CAC score) using a retinal image. For example, the obtaining of the cardiovascular disease diagnosis assistance information using a retinal image (S11400) may include predicting the CAC score and obtaining the predicted CAC score.

Also, in a case in which, in the previous step, the diagnosis value of the testee is within a predetermined range, the CAC score of the testee may be obtained.

According to an embodiment, in a case in which the obtained CAC score of the testee is a predetermined value or more, additional diagnosis assistance information may be obtained.

Although not illustrated in the drawings, in a case in which the obtained CAC score of the testee is a predetermined value or more, the process may further include, after the obtaining of the cardiovascular disease diagnosis assistance information using a retinal image (S11400), providing drug prescription information.

For example, in a case in which the CAC score of the testee that is obtained in the previous step is greater than 0, prescription information for prescribing a drug for treating dyslipidemia may be provided. Here, examples of drugs that may be prescribed may include statins such as rosuvastatin, atorvastatin, simvastatin, pravastatin, lovastatin, fluvastatin, or pitavastatin, ezetimibes, cholestyramines, fibrates such as bezafibrate, fenofibric acid, ciprofibrate, clofibrate, fenofibrate, or gemfibrozil, niacins, or omega-3 acid ethyl esters.

Figure 78:
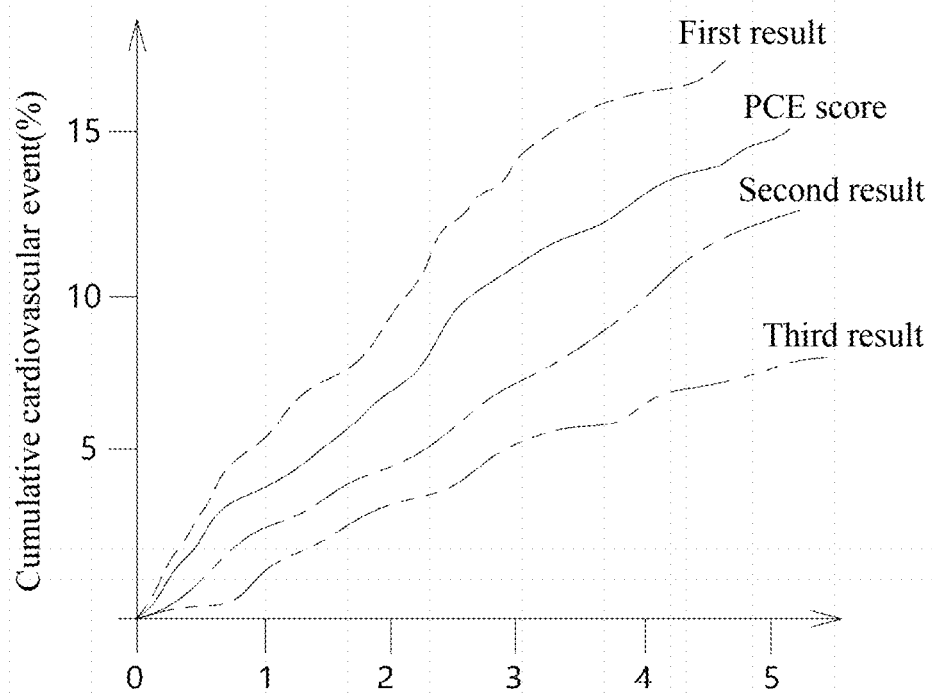
FIG. 78 is a graph showing the stratification of a degree of cardiovascular disease occurrence in a group of patients having the same score according to an embodiment of the present invention.

FIG. 78 is a graph showing the stratification of a degree of cardiovascular disease occurrence in a group of patients having the same score according to an embodiment of the present invention.

In FIG. 78, the horizontal axis indicates time shown in years, and the vertical axis indicates cumulative cardiovascular events. That is, the graph of FIG. 78 may show the risk of cardiovascular disease occurrence over time.

Referring to FIG. 78, even among a group of patients having the same pooled cohort equations (PCE) score, stratification may occur through the above-described cardiovascular disease diagnosis assistance information using a retinal image. Here, stratification may refer to different risks of having a cardiovascular disease being exhibited among the group of patients that correspond to the same PCE score.

As a specific example, in a case in which diagnosis assistance information is obtained using retinal images of a group of patients having the same PCE score, a first result, a second result, and a third result may be obtained according to a diagnosis assistance information result. Here, the first result may indicate a higher risk of having a cardiovascular disease over time than the risk derived using the PCE score, but the second result and the third result may indicate a lower risk of having a cardiovascular disease than the risk derived using the PCE score.

As another example, when a group of patients that correspond to a second PCE score, in which a risk of having a cardiovascular disease is lower than the first PCE score, is present, and a first group of patients and a second group of patients that correspond to the first PCE score and the second PCE score, respectively, are present, a first-third result, in which a risk of having a cardiovascular disease is the lowest among the diagnosis assistance results obtained using retinal images of the first group of patients, may be lower than a second-first result, in which a risk of having a cardiovascular disease is the highest among the diagnosis assistance results obtained using the retinal images of retinal images of the second group of patients. In other words, according to the PCE score, a subject whose risk of having a cardiovascular disease is high may be determined as having a low risk of having a cardiovascular disease according to the diagnosis assistance information using a retinal image.

Accordingly, in a case in which the cardiovascular disease diagnosis assistance information using a retinal image is used, prescription information relating to prescribing a drug may be different as compared to when using the PCE score.

The cases in which a method of determining quality or suitability of a fundus image is applied to database construction, training of neural network models, and driving of neural network models has been mainly described above, but details of the invention disclosed herein are not limited thereto. Even in the case of images other than fundus images, a defect may occur in a predetermined region of the image, and when predetermined information is obtained on the basis of the image, details of the invention disclosed herein may analogically apply.

While the embodiments have been described above with a few embodiments and the accompanying drawings, one of ordinary skill in the art may make various modifications and changes to the description above. For example, appropriate results can be achieved even if the above-described techniques are performed in a different order from that in the above-described method, and/or the above-described elements such as systems, structures, devices, and circuits are coupled or combined in different forms from those in the above-described method or are replaced or substituted with other elements or their equivalents.

Therefore, other implementations, other embodiments, and equivalents to the claims are also within the scope of the following claims.

What is claimed is:

1. A cardiovascular disease diagnosis assistant device which assists a diagnosis of a cardiovascular disease using a retinal image, comprising:
   a memory; and
   at least one processor operably connected to the memory and configured to:
   obtain clinical information of a testee, wherein the clinical information includes blood pressure information or blood lipid level information;
   obtain the retinal image from the testee, when the clinical information of the testee is within a predetermined range;
   obtain a cardiovascular disease diagnosis assistant information of the testee according to the retinal image, via a cardiovascular disease diagnosis assistant model including at least one convolutional neural network layer which obtains a diagnosis assistant information used for the diagnosis of the cardiovascular disease according to the retinal image, based on the retinal image, wherein the clinical information is included in the cardiovascular disease diagnosis assistant information; and
   output the cardiovascular disease diagnosis assistant information;
   wherein, the cardiovascular disease diagnosis assistant information includes recommendation for drug therapy or non-drug therapy to improve the testee's condition.

2. The cardiovascular disease diagnosis assistant device of claim 1, wherein:
   the cardiovascular disease diagnosis assistant information includes at least one of i) a grade information which includes a grade selected from a plurality of grades indicating an extent of risk of the cardiovascular disease, ii) a score information for determining a risk of the cardiovascular disease or iii) a risk information which indicates whether the testee is included in a risk group for the cardiovascular disease or not,
   the cardiovascular disease is a coronary artery disease, and
   the grade information is a coronary artery disease risk grade information which describes a risk for the coronary artery disease,
   the score information is a coronary artery disease calcium score information, and
   the risk information is a coronary artery disease risk information which indicates whether the testee is included in a high-risk group of the coronary artery disease.

3. The cardiovascular disease diagnosis assistant device of claim 1,
   wherein the at least one processor is further configured to obtain an eye disease diagnosis assistant information of the testee according to the retinal image, via the cardiovascular disease diagnosis assistant neural network model which obtains the eye disease diagnosis assistant information according to the retinal image, based on the retinal image, and
   wherein the at least one processor is further configured to output the eye disease diagnosis assistant information.

4. The cardiovascular disease diagnosis assistant device of claim 1,
   wherein the recommendation is determined by using at least one of a pre-stored cardiovascular disease diagnosis assistant information-recommendation relation or a neural network model.

5. The cardiovascular disease diagnosis assistant device of claim 1,
   wherein the drug therapy includes at least one of a hypertension drug, a hyperlipidemia drug, a diabetic drug or a hypertriglyceridemia drug.

6. The cardiovascular disease diagnosis assistant device of claim 1,
   wherein the blood lipid level information includes at least one of concentration of low-density lipoprotein (LDL-C), total serum cholesterol concentration, LDL cholesterol concentration, triglyceride concentration or HDL cholesterol concentration.

7. The cardiovascular disease diagnosis assistant device of claim 5,
   wherein the hypertension drug includes at least one of 1) angiotensin-converting enzyme inhibitors 2) angiotensin receptor blockers, 3) calcium channel blockers, 4) beta blockers, 5) alpha blockers, 6) diuretics, or 7) direct vasodilators.

8. The cardiovascular disease diagnosis assistant device of claim 5,
   wherein the hyperlipidemia drug includes at least one of 1) statins, 2) ezetimibes, 3) cholestyramines, 4) fibrates, 5) niacins, or 6) omega-3 acid ethyl esters.

* * * * *